United States Patent
Cheruvallath et al.

(10) Patent No.: US 12,428,403 B2
(45) Date of Patent: Sep. 30, 2025

(54) N-(HETEROCYCLYL AND HETEROCYCLYLALKYL) -3-BENZYLPYRIDIN-2-AMINE DERIVATIVES AS SSTR4 AGONISTS

(71) Applicant: Takeda Pharmaceutical Company Limited, Osaka (JP)

(72) Inventors: Zacharia Cheruvallath, San Diego, CA (US); Jason Green, San Diego, CA (US); Kristin Schleicher, San Diego, CA (US); Huikai Sun, San Diego, CA (US); Mingnam Tang, San Diego, CA (US)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 375 days.

(21) Appl. No.: 17/916,476

(22) PCT Filed: Mar. 31, 2021

(86) PCT No.: PCT/US2021/025225
§ 371 (c)(1),
(2) Date: Sep. 30, 2022

(87) PCT Pub. No.: WO2021/202775
PCT Pub. Date: Oct. 7, 2021

(65) Prior Publication Data
US 2023/0192659 A1  Jun. 22, 2023

Related U.S. Application Data

(60) Provisional application No. 63/002,623, filed on Mar. 31, 2020.

(51) Int. Cl.
| | |
|---|---|
| C07D 403/12 | (2006.01) |
| A61K 45/06 | (2006.01) |
| C07D 401/12 | (2006.01) |
| C07D 403/14 | (2006.01) |
| C07D 405/14 | (2006.01) |
| C07D 413/14 | (2006.01) |
| C07D 417/14 | (2006.01) |

(52) U.S. Cl.
CPC ............ *C07D 403/12* (2013.01); *A61K 45/06* (2013.01); *C07D 401/12* (2013.01); *C07D 403/14* (2013.01); *C07D 405/14* (2013.01); *C07D 413/14* (2013.01); *C07D 417/14* (2013.01); *C07B 2200/07* (2013.01)

(58) Field of Classification Search
None
See application file for complete search history.

(56) References Cited

U.S. PATENT DOCUMENTS

| | | | |
|---|---|---|---|
| 6,106,864 A | 8/2000 | Dolan et al. | |
| 8,183,371 B2 * | 5/2012 | Connolly | A61P 25/24 544/405 |
| 11,045,457 B2 | 6/2021 | Cheruvallath et al. | |
| 2023/0021834 A1 | 1/2023 | Cheruvallath et al. | |

FOREIGN PATENT DOCUMENTS

| | | |
|---|---|---|
| CL | 200702347 | 3/2008 |
| CL | 2022002690 A1 | 6/2023 |
| CN | 101277695 A | 10/2008 |
| CN | 110650951 A | 1/2020 |
| JP | 2001-519416 A | 10/2001 |
| JP | 2009-541421 A | 11/2009 |
| JP | 2013509424 A | 3/2013 |
| JP | 2016-518430 A | 6/2016 |

(Continued)

OTHER PUBLICATIONS

Schuelert, N. et al. European Journal of Pharmacology, 2015, 746, 274-281 (Year: 2015).*
Almarsson et al. Crystal engineering of the composition of pharmaceutical phases. Do pharmaceutical co-crystals represent a new path to improved medicines? Chem. Commun. 17:1889-1896 (2004).
Berge, Stephen M. et al. Pharmaceutical Salts. Journal of Pharmaceutical Sciences 66(1):1-19 (1977).
Bundgaard, Hans. Design of Prodrugs. Elsevier: 7-9, 21-24 (1985).
Busche, Marc Aurel. et al. Decreased amyloid-β and increased neuronal hyperactivity by immunotherapy in Alzheimer's models. Nat Neurosci 18(12):1725-1727 (2015).

(Continued)

*Primary Examiner* — Clinton A Brooks
*Assistant Examiner* — Nicola Maria Bauer
(74) *Attorney, Agent, or Firm* — WILSON SONSINI GOODRICH & ROSATI

(57) ABSTRACT

Disclosed are compounds of Formula (1), and pharmaceutically acceptable salts thereof, wherein n, $R^1$, $R^4$, $R^5$, $R^6$, $R^7$, $R^8$, $R^9$, $R^{10}$, $R^{11}$, $R^{14}$, $X^2$, $X^3$ and $X^{12}$ are defined in the specification. This disclosure also relates to materials and methods for preparing compounds of Formula (1), to pharmaceutical compositions which contain them, and to their use for treating diseases, disorders, and conditions associated with SSTR4.

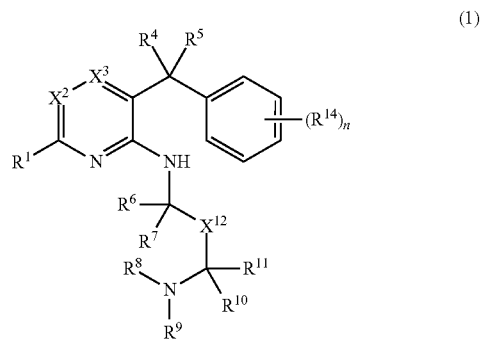

33 Claims, No Drawings

(56) References Cited

FOREIGN PATENT DOCUMENTS

| TW | I315305 B | 10/2009 | | |
|---|---|---|---|---|
| WO | WO-9111172 A1 | 8/1991 | | |
| WO | WO-9402518 A1 | 2/1994 | | |
| WO | WO-9855148 A1 | 12/1998 | | |
| WO | 2006128803 A1 | 12/2006 | | |
| WO | 2007014940 A2 | 2/2007 | | |
| WO | 2008000692 A2 | 1/2008 | | |
| WO | 2008019967 A2 | 2/2008 | | |
| WO | 2011053696 A1 | 5/2011 | | |
| WO | 2014184275 A1 | 11/2014 | | |
| WO | 2018170284 A1 | 9/2018 | | |
| WO | WO-2019169153 A1 | * | 9/2019 | ............ A61K 31/40 |
| WO | 2021202781 A1 | 10/2021 | | |
| WO | WO-2021202775 A1 | 10/2021 | | |

OTHER PUBLICATIONS

Eliel, Ernest L. et al. Stereochemistry of Organic Compounds. Wiley-Interscience (1994).
Finnin, Barrie C, and Timothy M. Morgan. Transdermal Penetration Enhancers: Applications, Limitations, And Potential. Journal of Pharmaceutical Sciences 88(10):955-958 (1999).
Gastambide, Francois et al. Hippocampal SSTR4 somatostatin receptors control the selection of memory strategies. 202(1-3):153-163 (2009).
Gennaro, Alfonso R. Remington: The Science and Practice of Pharmacy, 20th Edition. Lippincott Williams & Wilkins (2000).
Haleblian, John K. Characterization of Habits and Crystalline Modification of Solids and Their Pharmaceutical Applications. Journal of Pharmaceutical Sciences 64(8):1269-1288 (1975).
Higuchi, Takeru et al. Pro-Drugs as Novel Delivery Systems. ACS Symposium Series 14:1-129 (1975).
Larock, Richard C. et al. Comprehensive Organic Transformations: A Guide to Functional Group Preparations: Second Edition, Wiley-VCH 1-18 (1999).
Liang et al. Fast-dissolving intraoral drug delivery. Expert Opinion in Therapeutic Patents 11(6):981-986 (2001).
Lieberman, Herbert. et al. Pharmaceutical Dosage Forms. Marcel Decker $2^{nd}$ edition:209-214 (1990).
Meyer, Michael A. Highly Expressed Genes within Hippocampal Sector CA1: Implications for the Physiology of Memory. Neurol Int 6(2):5388, 1-4 (2014).
PCT/US2021/025225 International Search Report and Written Opinion dated Jun. 2, 2021.
Qiu, Cuie. et al. Somatostatin receptor subtype 4 couples to the M-current to regulate seizures. J Neurosci 28(14):3567-3576 (2008).
Roche, Edward B. Bioreversible Carriers In Drug Design: Theory And Application. American Pharmaceutical Association and Pergamon Press (1987).
Serrano-Pozo, Alberto. et al. Neuropathological alterations in Alzheimer disease. Cold Spring Harb Perspect Med 1(1):a006189, 1-23 (2011).
Squire, Larry R, and Adam J O Dede. Conscious and unconscious memory systems. Cold Spring Harb Perspect Biol 7(3):a021667, 1-14 (2015).
Stahl, P Heinrich, and Camille G. Wermuth. Handbook of Pharmaceutical Salts: Properties, Selection, and Use. Verlag Helvetica Chimica Acta and Wiley-VCH (2002).
Verma et al. Current Status of Drug Delivery Technologies and Future Directions. Pharmaceutical Technology On-line 25(2):1-14 (2001).
Yamamoto, Kaoru. et al. Chronic optogenetic activation augments αβ pathology in a mouse model of Alzheimer disease. Cell Rep 11(6):859-865 (2015).
Hassan, Seham Y.; et al., Synthesis of 3-benzyl-2-substituted quinoxalines as novel monoamine oxidase A inhibitors, Bioorganic & Medicinal Chemistry Letters, 2006, 16(6), 1753-1756.

* cited by examiner

N-(HETEROCYCLYL AND HETEROCYCLYLALKYL)-3-BENZYLPYRIDIN-2-AMINE DERIVATIVES AS SSTR4 AGONISTS

CROSS-REFERENCE TO RELATED APPLICATIONS

This application is a 35 USC § 371 National Stage filing of International Application No. PCT/US2021/025225, filed Mar. 31, 2021, which claims the benefit of priority to U.S. Provisional Application No. 63/002,623, filed Mar. 31, 2020. The entire contents of the aforementioned applications are incorporated herein by reference in their entireties.

FIELD OF THE INVENTION

This invention relates to N-(heterocyclyl and heterocyclylalkyl)-3-benzylpyridin-2-amine derivatives which are modulators of somatostatin receptor 4 (SSTR4), to pharmaceutical compositions which contain them, and to their use to treat diseases, disorders, and conditions associated with SSTR4, including Alzheimer's disease.

BACKGROUND OF THE INVENTION

Somatostatin receptor 4 (SSTR4) is a G-protein coupled receptor for the peptide somatostatin. SSTR4 is coupled with Gi, inhibitory G protein, which inhibits production of cyclic AMP. SSTR4 is abundantly expressed in the central nervous system (CNS) and to a lesser extent in the dorsal root ganglia and intestine. See M. A. Meyer, "Highly Expressed Genes within Hippocampal Sector CA1: Implications for the Physiology of Memory," *Neurology International* 6(2):5388 (2014). SSTR4 is highly conserved among different species. For example, human, mouse, and rat SSTR4 protein sequences share greater than 87% identity at the amino acid level. These factors—predominant expression in the brain and high degree of sequence homology across different species—suggest that SSTR4 has an important role in physiology.

Experiments using bacTRAP technology indicate SSTR4 has its strongest expression in the pyramidal neurons in the cortex and in the CA1 region of the hippocampus. This CNS expression is conserved in humans, non-human primates, and mice. The hippocampus is important for learning and memory. See L. R. Squire and A. J. Dede, "Conscious and Unconscious Memory Systems," *Cold Spring Harbor Perspectives in Biology* 7:a021667 (2015). Indeed, the CA1 region of the hippocampus is the last station in the trisynaptic circuit that governs learning. This circuit starts in the entorhinal cortex, which also contains SSTR4, extends into the dentate gyrus, then into CA3, and finally reaches the CA1 region of the hippocampus. CA1 projects out of the hippocampus through the subiculum. This circuit encodes all types of information from the external world in order to generate memories and to learn new knowledge.

Alzheimer's disease is characterized by degeneration of neurons within this circuitry, mainly in the entorhinal cortex and CA1 region of the hippocampus. See A. Serrano-Pozo et al., "Neuropathological Alterations in Alzheimer Disease," *Cold Spring Harbor Perspectives in Medicine* 1: a006189 (2011). In addition, hippocampal sst4 appears to selectively control the use of cognitive strategies by switching from hippocampus-based multiple associations to simple striatum-based behavioral responses. See F. Gastambide et al., "Hippocampal SSTR4 Somatostatin Receptors Control the Selection of Memory Strategies," *Psychopharmacology (Berl)* 202(1-3):153-63 (2009). This finding provides a strong basis for using SSTR4 agonists as a pharmacological approach to improve striatum-based learning. Id.

Moreover, recent studies also point to hyperactivity of the hippocampus as a main driver for disease progression as well as impairment of cognitive abilities in Alzheimer's patients. See M. A. Busche et al., "Decreased Amyloid-β and Increased Neuronal Hyperactivity by Immunotherapy in Alzheimer's Models," *Nature Neuroscience* 18(12):1725-27 (2015); see also K. Yamamoto et al., "Chronic Optogenetic Activation Augments Aβ Pathology in a Mouse Model of Alzheimer Disease," *Cell Reports* 11(6):859-65 (2015). Activation of SSTR4 receptor has been shown to play a role in controlling neuronal activity. See C. Qiu et al., "Somatostatin Receptor Subtype 4 Couples to the M-Current to Regulate Seizures," *Journal of Neuroscience* 28(14):3567-76 (2008). Thus, agonists for the receptor will likely represent good pharmacological tools to inhibit and control neuronal activity in the cortex and hippocampus.

SSTR4 agonists are expected to be useful for treating Alzheimer's disease and other CNS disorders such as epilepsy and depression.

SUMMARY OF THE INVENTION

This invention provides N-(heterocyclyl and heterocyclylalkyl)-3-benzylpyridin-2-amine derivatives and pharmaceutically acceptable salts thereof. This invention also provides pharmaceutical compositions that contain the N-(heterocyclyl and heterocyclylalkyl)-3-benzylpyridin-2-amine derivatives and provides for their use to treat diseases, disorders and conditions associated with SSTR4, including Alzheimer's disease and other CNS disorders.

One aspect of the invention provides compounds of Formula 1:

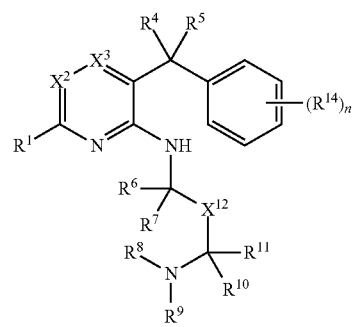

or a pharmaceutically acceptable salt thereof in which:
$X^2$ is $CR^2$ and $X^3$ is selected from N and $CR^3$, or
$X^2$ is N and $X^3$ is N;
$R^1$ and $R^2$ are each independently selected from hydrogen, halo, cyano,
  $R^a$, —$OR^b$, —$C(O)R^b$, —$C(O)OR^b$, —$C(O)N(R^c)R^b$ and —$C(O)N(R^c)OR^b$, or $R^1$ and $R^2$, together with the carbon atoms to which they are attached, form a benzene ring which is unsubstituted or substituted with from 1 to 4 optional substituents independently selected from halo, hydroxy, cyano, amino, and $C_{1-4}$ alkyl which at each occurrence is independently unsubstituted or substituted with from 1 to 3 optional substituents independently selected from halo; and
wherein:

$R^a$ is selected from $C_{1-4}$ alkyl, $C_{3-6}$ cycloalkyl, $C_{2-6}$ heterocyclyl and $C_{1-5}$ heteroaryl, each unsubstituted or substituted with from 1 to 3 optional substituents independently selected from halo, $C_{1-4}$ alkyl and $C_{1-4}$ alkoxy, wherein the $C_{1-4}$ alkyl and $C_{1-4}$ alkoxy optional substituents are each independently unsubstituted or substituted with from 1 to 3 optional substituents independently selected from halo;

$R^b$ is selected from hydrogen and from $C_{1-4}$ alkyl, $C_{3-6}$ cycloalkyl, $C_{2-6}$ heterocyclyl and $C_{1-5}$ heteroaryl, each unsubstituted or substituted with from 1 to 3 optional substituents independently selected from halo, $C_{1-4}$ alkyl and $C_{1-4}$ alkoxy, wherein the $C_{1-4}$ alkyl and $C_{1-4}$ alkoxy optional substituents are each independently unsubstituted or substituted with from 1 to 3 optional substituents independently selected from halo; and $R^c$ is selected from hydrogen and $C_{1-4}$ alkyl;

wherein for $R^a$ and $R^b$, the $C_{2-6}$ heterocyclyl substituent is a monocyclic ring with from 3 to 8 ring members in which 1 or 2 ring members are heteroatoms, each of the heteroatoms independently selected from N, O and S, and the $C_{1-5}$ heteroaryl substituent is a monocyclic ring with 5 or 6 ring members in which 1 to 4 ring members are heteroatoms, each of the heteroatoms independently selected from N, O, and S, provided no more than one of the ring members is O or S;

$R^3$ is selected from hydrogen, halo, cyano and $C_{1-4}$ alkyl which is unsubstituted or substituted with from 1 to 3 optional substituents independently selected from halo;

$R^4$ and $R^5$ are each independently selected from hydrogen, halo and $C_{1-4}$ alkyl which is unsubstituted or substituted with from 1 to 3 optional substituents independently selected from halo, or $R^4$ and $R^5$, together with the carbon atom to which they are both attached, form a $C_{3-5}$ cycloalkylidene;

$X^{12}$ is selected from a bond and $CR^{12}R^{13}$, and (a) $R^6$ is selected from hydrogen, halo and $C_{1-4}$ alkyl; $R^7$ and $R^8$, together with the carbon and nitrogen atoms to which they are respectively attached, form a $C_{3-5}$ heterocyclyl having 1 ring heteroatom; $R^9$ is selected from hydrogen and $C_{1-4}$ alkyl; and $R^{10}$, $R^{11}$, $R^{12}$ and $R^{13}$ are each independently selected from hydrogen, halo and $C_{1-4}$ alkyl; or (b) $R^6$ and $R^7$ are each independently selected from hydrogen, halo and $C_{1-4}$ alkyl, or $R^6$ and $R^7$, together with the carbon atom to which they are both attached, form a $C_{3-5}$ cycloalkylidene; $R^8$ and $R^9$, together with the nitrogen atom to which they are both attached, form a $C_{3-5}$ heterocyclyl which has 1 ring heteroatom and is unsubstituted or substituted with from 1 to 3 optional substituents independently selected from halo and $C_{1-4}$ alkyl; and $R^{10}$, $R^{11}$, $R^{12}$ and $R^{13}$ are each independently selected from hydrogen, halo and $C_{1-4}$ alkyl; or (c) $R^6$ and $R^7$ are each independently selected from hydrogen, halo and $C_{1-4}$ alkyl; $R^8$ is selected from hydrogen and $C_{1-4}$ alkyl; $R^9$ and $R^{10}$, together with the nitrogen and carbon atoms to which they are respectively attached, form a $C_{3-5}$ heterocyclyl which has 1 ring heteroatom and is unsubstituted or substituted with from 1 to 3 optional substituents independently selected from halo and $C_{1-4}$ alkyl; and $R^{11}$, $R^{12}$ and $R^{13}$ are each independently selected from hydrogen, halo and $C_{1-4}$ alkyl;

n is selected from 0, 1, 2, 3, 4 and 5; and each $R^{14}$ is independently selected from halo, $C_{1-4}$ alkyl and $C_{1-4}$ alkoxy, wherein the $C_{1-4}$ alkyl and $C_{1-4}$ alkoxy substituents are each independently unsubstituted or substituted with from 1 to 3 optional substituents independently selected from halo;

provided if $X^2$ is $CR^2$, $X^3$ is N, $X^{12}$ is a bond, n is 1, each of $R^1$, $R^4$, $R^5$, $R^6$, $R^7$, $R^8$, and $R^{11}$ is hydrogen, $R^9$ and $R^{10}$ together with the nitrogen and carbon atoms to which they are respectively attached form an unsubstituted pyrrolidin-2-yl, and $R^{14}$ is methoxy, then $R^2$ cannot be unsubstituted pyridin-3-yl or unsubstituted pyrimidin-5-yl.

Another aspect of the invention provides a compound which is selected from the group of compounds described in the examples and their pharmaceutically acceptable salts.

A further aspect of the invention provides a pharmaceutical composition which includes a compound of Formula 1 or a pharmaceutically acceptable salt thereof, or any one of the compounds or pharmaceutically acceptable salts defined in the preceding paragraph; and a pharmaceutically acceptable excipient.

An additional aspect of the invention provides a compound of Formula 1 or a pharmaceutically acceptable salt thereof, or any one of the compounds and pharmaceutically acceptable salts defined in the preceding paragraphs, for use as a medicament.

Another aspect of the invention provides a compound of Formula 1 or a pharmaceutically acceptable salt thereof, or any one of the compounds or pharmaceutically acceptable salts defined in the preceding paragraphs, for treatment of a disease, disorder or condition associated with SSTR4.

A further aspect of the invention provides a use of a compound of Formula 1 or a pharmaceutically acceptable salt thereof, or any one of the compounds or pharmaceutically acceptable salts defined in the preceding paragraphs, for the manufacture of a medicament for the treatment of a disease, disorder or condition associated with SSTR4.

An additional aspect of the invention provides a method of treating a disease, disorder or condition associated with SSTR4, the method comprising administering to the subject an effective amount of a compound of Formula 1 or a pharmaceutically acceptable salt thereof, or any one of the compounds or pharmaceutically acceptable salts defined in the preceding paragraphs.

Another aspect of the invention provides a method of treating a disease, disorder or condition in a subject, the method comprising administering to the subject an effective amount of a compound of Formula 1 or a pharmaceutically acceptable salt thereof, or any one of the compounds or pharmaceutically acceptable salts defined in the preceding paragraphs, wherein the disease, disorder or condition is selected from Alzheimer's disease, depression, anxiety, schizophrenia, bipolar disorder, autism, epilepsy, pain, and hyperactivity disorder.

A further aspect of the invention provides an effective amount of a compound of Formula 1 or a pharmaceutically acceptable salt thereof, or any one of the compounds or pharmaceutically acceptable salts defined in the preceding paragraphs; and at least one additional pharmacologically active agent.

DETAILED DESCRIPTION OF THE INVENTION

Unless otherwise indicated, this disclosure uses definitions provided below.

"Substituted," when used in connection with a chemical substituent or moiety (e.g., a $C_{1-6}$ alkyl group), means that one or more hydrogen atoms of the substituent or moiety have been replaced with one or more non-hydrogen atoms or groups, provided valence requirements are met and a chemically stable compound results from the substitution.

"About" or "approximately," when used in connection with a measurable numerical variable, refers to the indicated value of the variable and to all values of the variable that are within the experimental error of the indicated value or within ±10 percent of the indicated value, whichever is greater.

"Alkyl" refers to straight chain and branched saturated hydrocarbon groups, generally having a specified number of carbon atoms (e.g., $C_{1-4}$ alkyl refers to an alkyl group having 1 to 4 (i.e., 1, 2, 3 or 4) carbon atoms, $C_{1-6}$ alkyl refers to an alkyl group having 1 to 6 carbon atoms, and so on). Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alkanediyl" refers to divalent alkyl groups, where alkyl is defined above, and generally having a specified number of carbon atoms (e.g., $C_{1-4}$ alkanediyl refers to an alkanediyl group having 1 to 4 (i.e., 1, 2, 3 or 4) carbon atoms, $C_{1-6}$ alkanediyl refers to an alkanediyl group having 1 to 6 carbon atoms, and so on). Examples of alkanediyl groups include methylene, ethane-1,1-diyl, ethane-1,2-diyl, propane-1,3-diyl, propane-1,2-diyl, propane-1,1-diyl, propane-2,2-diyl, butane-1,4-diyl, butane-1,3-diyl, butane-1,2-diyl, butane-1,1-diyl, isobutane-1,3-diyl, isobutane-1,1-diyl, isobutane-1,2-diyl, and the like.

"Alkenyl" refers to straight chain and branched hydrocarbon groups having one or more carbon-carbon double bonds, and generally having a specified number of carbon atoms. Examples of alkenyl groups include ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Alkynyl" refers to straight chain or branched hydrocarbon groups having one or more triple carbon-carbon bonds, and generally having a specified number of carbon atoms. Examples of alkynyl groups include ethynyl, 1-propyn-1-yl, 2-propyn-1-yl, 1-butyn-1-yl, 3-butyn-1-yl, 3-butyn-2-yl, 2-butyn-1-yl, and the like.

"Halo," "halogen" and "halogeno" may be used interchangeably and refer to fluoro, chloro, bromo, and iodo.

"Haloalkyl," "haloalkenyl," and "haloalkynyl," refer, respectively, to alkyl, alkenyl, and alkynyl groups substituted with one or more halogen atoms, where alkyl, alkenyl, and alkynyl are defined above, and generally having a specified number of carbon atoms. Examples of haloalkyl groups include fluoromethyl, difluoromethyl, trifluoromethyl, chloromethyl, dichloromethyl, trichloromethyl, 1-fluoroethyl, 1,1-difluoroethyl, 1-chloroethyl, 1,1-dichloroethyl, 1-fluoro-1-methylethyl, 1-chloro-1-methylethyl, and the like.

"Cycloalkyl" refers to saturated monocyclic and bicyclic hydrocarbon groups, generally having a specified number of carbon atoms that comprise the ring or rings (e.g., $C_{3-8}$ cycloalkyl refers to a cycloalkyl group having 3 to 8 carbon atoms as ring members). Bicyclic hydrocarbon groups may include isolated rings (two rings sharing no carbon atoms), spiro rings (two rings sharing one carbon atom), fused rings (two rings sharing two carbon atoms and the bond between the two common carbon atoms), and bridged rings (two rings sharing two carbon atoms, but not a common bond). The cycloalkyl group may be attached through any ring atom unless such attachment would violate valence requirements, and where indicated, may optionally include one or more non-hydrogen substituents unless such substitution would violate valence requirements.

Examples of monocyclic cycloalkyl groups include cyclopropyl, cyclobutyl, cyclopentyl, cyclohexyl, and the like. Examples of fused bicyclic cycloalkyl groups include bicyclo[2.1.0]pentanyl (i.e., bicyclo[2.1.0]pentan-1-yl, bicyclo[2.1.0]pentan-2-yl, and bicyclo[2.1.0]pentan-5-yl), bicyclo[3.1.0]hexanyl, bicyclo[3.2.0]heptanyl, bicyclo[4.1.0]heptanyl, bicyclo[3.3.0]octanyl, bicyclo[4.2.0]octanyl, bicyclo[4.3.0]nonanyl, bicyclo[4.4.0]decanyl, and the like. Examples of bridged cycloalkyl groups include bicyclo[2.1.1]hexanyl, bicyclo[2.2.1]heptanyl, bicyclo[3.1.1]heptanyl, bicyclo[2.2.2]octanyl, bicyclo[3.2.1]octanyl, bicyclo[4.1.1]octanyl, bicyclo[3.3.1]nonanyl, bicyclo[4.2.1]nonanyl, bicyclo[3.3.2]decanyl, bicyclo[4.2.2]decanyl, bicyclo[4.3.1]decanyl, bicyclo[3.3.3]undecanyl, bicyclo[4.3.2]undecanyl, bicyclo[4.3.3]dodecanyl, and the like. Examples of spiro cycloalkyl groups include spiro[3.3]heptanyl, spiro[2.4]heptanyl, spiro[3.4]octanyl, spiro[2.5]octanyl, spiro[3.5]nonanyl, and the like. Examples of isolated bicyclic cycloalkyl groups include those derived from bi(cyclobutane), cyclobutanecyclopentane, bi(cyclopentane), cyclobutanecyclohexane, cyclopentanecyclohexane, bi(cyclohexane), etc.

"Cycloalkanediyl" refers to divalent cycloalkyl groups, where cycloalkyl is defined above, and generally having a specified number of carbon atoms (e.g., $C_{3-4}$ cycloalkanediyl refers to a cycloalkanediyl group having 3 to 4 (i.e., 3 or 4) carbon atoms, $C_{3-6}$ cycloalkanediyl refers to a cycloalkanediyl group having 3 to 6 carbon atoms, and so on). Examples of cycloalkanediyl groups include cyclopropan-1,1-diyl, cyclopropan-1,2-diyl, cyclobutan-1,1-diyl, cyclobutan-1,2-diyl, and the like.

"Cycloalkylidene" refers to divalent monocyclic cycloalkyl groups, where cycloalkyl is defined above, which are attached through a single carbon atom of the group, and generally having a specified number of carbon atoms that comprise the ring (e.g., $C_{3-6}$ cycloalkylidene refers to a cycloalkylidene group having 3 to 6 carbon atoms as ring members). Examples include cyclopropylidene, cyclobutylidene, cyclopentylidene, and cyclohexylidene.

"Cycloalkenyl" refers to partially unsaturated monocyclic and bicyclic hydrocarbon groups, generally having a specified number of carbon atoms that comprise the ring or rings. As with cycloalkyl groups, the bicyclic cycloalkenyl groups may include isolated, spiro, fused, or bridged rings. Similarly, the cycloalkenyl group may be attached through any ring atom, and where indicated, may optionally include one or more non-hydrogen substituents unless such attachment or substitution would violate valence requirements. Examples of cycloalkenyl groups include the partially unsaturated analogs of the cycloalkyl groups described above, such as cyclobutenyl (i.e., cyclobuten-1-yl and cyclobuten-3-yl), cyclopentenyl, cyclohexenyl, bicyclo[2.2.1]hept-2-enyl, and the like.

"Aryl" refers to fully unsaturated monocyclic aromatic hydrocarbons and to polycyclic hydrocarbons having at least one aromatic ring, both monocyclic and polycyclic aryl groups generally having a specified number of carbon atoms that comprise their ring members (e.g., $C_{6-14}$ aryl refers to an aryl group having 6 to 14 carbon atoms as ring members). The group may be attached through any ring atom, and where indicated, may optionally include one or more non-hydrogen substituents unless such attachment or substitution would violate valence requirements. Examples of aryl groups include phenyl, biphenyl, cyclobutabenzenyl, indenyl, naphthalenyl, benzocycloheptanyl, biphenylenyl, fluorenyl, groups derived from cycloheptatriene cation, and the like.

"Arylene" refers to divalent aryl groups, where aryl is defined above. Examples of arylene groups include o-phenylene (i.e., benzene-1,2-diyl).

"Heterocycle" and "heterocyclyl" may be used interchangeably and refer to saturated or partially unsaturated monocyclic or bicyclic groups having ring atoms composed of carbon atoms and 1 to 4 heteroatoms independently selected from nitrogen, oxygen, and sulfur. Both the monocyclic and bicyclic groups generally have a specified number of carbon atoms in their ring or rings (e.g., $C_{2-6}$ heterocyclyl refers to a heterocyclyl group having 2 to 6 carbon atoms and 1 to 4 heteroatoms as ring members). As with bicyclic cycloalkyl groups, bicyclic heterocyclyl groups may include isolated rings, spiro rings, fused rings, and bridged rings. The heterocyclyl group may be attached through any ring atom, and where indicated, may optionally include one or more non-hydrogen substituents unless such attachment or substitution would violate valence requirements or result in a chemically unstable compound. Examples of heterocyclyl groups include oxiranyl, thiiranyl, aziridinyl (e.g., aziridin-1-yl and aziridin-2-yl), oxetanyl, thietanyl, azetidinyl, tetrahydrofuranyl, tetrahydrothienyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 3,6-dihydro-2H-pyranyl, 2H-pyranyl, 1,2-dihydropyridinyl, 1,2,3,4-tetrahydropyridinyl, 1,2,5,6-tetrahydropyridinyl, 1,6-dihydropyrimidinyl, 1,2,3,4-tetrahydropyrimidinyl, and 1,2-dihydropyrazolo[1,5-d][1,2,4]triazinyl.

"Heterocycle-diyl" refers to heterocyclyl groups which are attached through two ring atoms of the group, where heterocyclyl is defined above. They generally have a specified number of carbon atoms in their ring or rings (e.g., $C_{2-6}$ heterocycle-diyl refers to a heterocycle-diyl group having 2 to 6 carbon atoms and 1 to 4 heteroatoms as ring members). Examples of heterocycle-diyl groups include the multivalent analogs of the heterocycle groups described above, such as morpholine-3,4-diyl, pyrrolidine-1,2-diyl, 1-pyrrolidinyl-2-ylidene, 1-pyridinyl-2-ylidene, 1-(4H)-pyrazolyl-5-ylidene, 1-(3H)-imidazolyl-2-ylidene, 3-oxazolyl-2-ylidene, 1-piperidinyl-2-ylidene, 1-piperazinyl-6-ylidene, and the like.

"Heteroaromatic" and "heteroaryl" may be used interchangeably and refer to unsaturated monocyclic aromatic groups and to polycyclic groups having at least one aromatic ring, each of the groups having ring atoms composed of carbon atoms and 1 to 4 heteroatoms independently selected from nitrogen, oxygen, and sulfur. Both the monocyclic and polycyclic groups generally have a specified number of carbon atoms as ring members (e.g., $C_{1-9}$ heteroaryl refers to a heteroaryl group having 1 to 9 carbon atoms and 1 to 4 heteroatoms as ring members) and may include any bicyclic group in which any of the above-listed monocyclic heterocycles are fused to a benzene ring. The heteroaryl group may be attached through any ring atom (or ring atoms for fused rings), and where indicated, may optionally include one or more non-hydrogen substituents unless such attachment or substitution would violate valence requirements or result in a chemically unstable compound. Examples of heteroaryl groups include monocyclic groups such as pyrrolyl (e.g., pyrrol-1-yl, pyrrol-2-yl, and pyrrol-3-yl), furanyl, thienyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, and pyrazinyl.

Examples of heteroaryl groups also include bicyclic groups such as benzofuranyl, isobenzofuranyl, benzothienyl, benzo[c]thienyl, 1H-indolyl, 3H-indolyl, isoindolyl, 1H-isoindolyl, indolinyl, isoindolinyl, benzimidazolyl, 1H-indazolyl, 2H-indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, 3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c]pyridinyl, 1H-pyrazolo[3,4-b]pyridinyl, 7H-purinyl, indolizinyl, imidazo[1,2-c]pyridinyl, imidazo[1,5-c]pyridinyl, pyrazolo[1,5-c]pyridinyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, pyrimido[4,5-d]pyrimidinyl, 1,2,3,4-tetrahydropyrido[2,3-b]pyrazinyl, 2,3-dihydrobenzo[b][1,4]dioxinyl, 3,4-dihydro-2H-pyrido[3,2-b][1,4]oxazinyl, 2,3-dihydro-1H-benzo[d]imidazolyl, benzo[d]thiazolyl, 2,3-dihydro-1H-pyrrolo[2,3-b]pyridinyl, [1,2,4]triazolo[1,5-a]pyridinyl, 2,3-dihydro-1H-imidazo[4,5-b]pyridinyl, tetrazolo[1,5-a]pyridinyl, 7H-pyrrolo[2,3-d]pyrimidinyl, pyrazolo[1,5-a]pyrimidinyl, imidazo[1,2-a]pyrimidinyl, 4,5-dihydro-1H-pyrazolo[3,4-d]pyrimidinyl, 2,3,6,7-tetrahydro-1H-purinyl, 5H-pyrrolo[2,3-b]pyrazinyl, imidazo[1,2-a]pyrazinyl, imidazo[1,2-b]pyridazinyl, and 4,5,6,7-tetrahydropyrazolo[1,5-a]pyrazinyl.

"Heteroarylene" refers to heteroaryl groups which are attached through two ring atoms of the group, where heteroaryl is defined above. They generally have a specified number of carbon atoms in their ring or rings (e.g., $C_{3-5}$ heteroarylene refers to a heteroarylene group having 3 to 5 carbon atoms and 1 to 4 heteroatoms as ring members). Examples of heteroarylene groups include the multivalent analogs of the heteroaryl groups described above, such as pyridine-2,3-diyl, pyridine-3,4-diyl, pyrazole-4,5-diyl, pyrazole-3,4-diyl, and the like.

"Oxo" refers to a double bonded oxygen (=O).

"Leaving group" refers to any group that leaves a molecule during a fragmentation process, including substitution reactions, elimination reactions, and addition-elimination reactions. Leaving groups may be nucleofugal, in which the group leaves with a pair of electrons that formerly served as the bond between the leaving group and the molecule, or may be electrofugal, in which the group leaves without the pair of electrons. The ability of a nucleofugal leaving group to leave depends on its base strength, with the strongest bases being the poorest leaving groups. Common nucleofugal leaving groups include nitrogen (e.g., from diazonium salts); sulfonates, including alkylsulfonates (e.g., mesylate), fluoroalkylsulfonates (e.g., triflate, hexaflate, nonaflate, and tresylate), and arylsulfonates (e.g., tosylate, brosylate, closylate, and nosylate). Others include carbonates, halide ions, carboxylate anions, phenolate ions, and alkoxides. Some stronger bases, such as $NH_2^-$ and $OH^-$ can be made better leaving groups by treatment with an acid. Common electrofugal leaving groups include the proton, $CO_2$, and metals.

"Opposite enantiomer" refers to a molecule that is a non-superimposable mirror image of a reference molecule, which may be obtained by inverting all stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

"Stereoisomer" and "stereoisomers" of a compound with given stereochemical configuration refer to the opposite enantiomer of the compound and to any diastereoisomers, including geometrical isomers (Z/E) of the compound. For example, if a compound has S,R,Z stereochemical configuration, its stereoisomers would include its opposite enantiomer having R,S,Z configuration, and its diastereomers having S,S,Z configuration, R,R,Z configuration, S,R,E configuration, R,S,E configuration, S,S,E configuration, and R,R,E configuration. If the stereochemical configuration of a compound is not specified, then "stereoisomer" refers to any one of the possible stereochemical configurations of the compound.

"Substantially pure stereoisomer" and variants thereof refer to a sample containing a compound having a specific stereochemical configuration and which comprises at least about 95% of the sample.

"Pure stereoisomer" and variants thereof refer to a sample containing a compound having a specific stereochemical configuration and which comprises at least about 99.5% of the sample.

"Subject" refers to a mammal, including a human.

"Pharmaceutically acceptable" substances refer to those substances which are suitable for administration to subjects.

"Treating" refers to reversing, alleviating, inhibiting the progress of, or preventing a disease, disorder or condition to which such term applies, or to reversing, alleviating, inhibiting the progress of, or preventing one or more symptoms of such disease, disorder or condition.

"Treatment" refers to the act of "treating," as defined immediately above.

"Drug," "drug substance," "active pharmaceutical ingredient," and the like, refer to a compound (e.g., compounds of Formula 1, including subgeneric compounds and compounds specifically named in the specification) that may be used for treating a subject in need of treatment.

"Effective amount" of a drug, "therapeutically effective amount" of a drug, and the like, refer to the quantity of the drug that may be used for treating a subject and may depend on the weight and age of the subject and the route of administration, among other things.

"Excipient" refers to any diluent or vehicle for a drug.

"Pharmaceutical composition" refers to the combination of one or more drug substances and one or more excipients.

"Drug product," "pharmaceutical dosage form," "dosage form," "final dosage form" and the like, refer to a pharmaceutical composition suitable for treating a subject in need of treatment and generally may be in the form of tablets, capsules, sachets containing powder or granules, liquid solutions or suspensions, patches, films, and the like.

"Condition associated with SSTR4" and similar phrases relate to a disease, disorder or condition in a subject for which activation of SSTR4 may provide a therapeutic or prophylactic benefit.

The following abbreviations may be used in the specification: Ac (acetyl); ACN (acetonitrile); AIBN (azo-bis-isobutyronitrile); API (active pharmaceutical ingredient); aq (aqueous); BINAP (2,2'-bis(diphenylphosphino)-1,1'-binaphthyl); Boc (tert-butoxycarbonyl); Cbz (carbobenzyloxy); dba (dibenzylideneacetone); DBU (1,8-diazabicyclo[5.4.0]undec-7-ene); DCC (1,3-dicyclohexylcarbodiimide); DCE (1,1-dichloroethane); DCM (dichloromethane); DEA (diethylamine); DIAD (diisopropyl azodicarboxylate); DIPEA (N,N-diisopropylethylamine, Hünig's Base); DMA (N,N-dimethylacetamide); DMAP (4-dimethylaminopyridine); DME (1,2-dimethoxyethane); DMF (N,N-dimethylformamide); DMP (Dess-Martin periodinane); DMSO (dimethylsulfoxide); dppf (1,1'-bis(diphenylphosphino)ferrocene); DTT (dithiothreitol); $EC_{50}$ (effective concentration at half maximal response); EDA (ethoxylated dodecyl alcohol, Brj®35); EDC (N-(3-dimethylaminopropyl)-N'-ethylcarbodiimide); EDTA (ethylenediaminetetraacetic acid); ee (enantiomeric excess); eq (equivalents); Et (ethyl); $Et_3N$ (triethylamine); EtOAc (ethyl acetate); EtOH (ethanol); HATU (2-(3H-[1,2,3]triazolo[4,5-b]pyridin-3-yl)-1,1,3,3-tetramethyluronium hexafluorophosphate(V)); HEPES (4-(2-hydroxyethyl)piperazine-1-ethanesulfonic acid); AcOH (acetic acid); HOBt (1H-benzo[d][1,2,3]triazol-1-ol); $IC_{50}$ (concentration at 50% inhibition); IPA (isopropanol); IPAc (isopropyl acetate); IPE (isopropylether); LDA (lithium diisopropylamide); LiHMDS (lithium bis(trimethylsilyl)amide); mCPBA (m-chloroperoxybenzoic acid); Me (methyl); MeOH (methanol); MTBE (methyl tert-butyl ether); mp (melting point); NaOt-Bu (sodium tertiary butoxide); NMM (N-methylmorpholine); NMP (N-methyl-pyrrolidone); OTf (triflate); PE (petroleum ether); Ph (phenyl); $pEC_{50}$ ($-\log_{10}(EC_{50})$, where $EC_{50}$ is given in molar (M) units); $pIC_{50}$ ($-\log_{10}(IC_{50})$, where $IC_{50}$ is given in molar (M) units); Pr (propyl); c-Pr (cyclopropyl), i-Pr (isopropyl); PTFE (polytetrafluoroethylene); PyBOP ((benzotriazol-1-yloxy)tripyrrolidinophosphonium hexafluorophosphate); PyBroP® (bromotripyrrolidinophosphonium hexafluorophosphate); RT (room temperature, approximately 20° C. to 25° C.); SFC (supercritical fluid chromatography); T3P (2,4,6-tripropyl-1,3,5,2,4,6-trioxatriphosphinane 2,4,6-trioxide); TCEP (tris(2-carboxyethyl)phosphine); TFA (trifluoroacetic acid); TFAA (2,2,2-trifluoroacetic anhydride); THF (tetrahydrofuran); TMS (trimethylsilyl); and Tris buffer (2-amino-2-hydroxymethyl-propane-1,3-diol buffer).

As described, below, this disclosure concerns compounds of Formula 1 and their pharmaceutically acceptable salts. This disclosure also concerns materials and methods for preparing compounds of Formula 1, pharmaceutical compositions which contain them, and the use of compounds of Formula 1 and their pharmaceutically acceptable salts (optionally in combination with other pharmacologically active agents) for treating diseases, disorders or conditions of the CNS, including Alzheimer's disease, and other diseases, disorders or conditions associated with SSTR4.

The compounds of Formula 1 include those in which:
(1) $X^2$ is $CR^2$ and $X^3$ is selected from N and $CR^3$, or $X^2$ is N and $X^3$ is N;

$R^1$ and $R^2$ are each independently selected from hydrogen, halo, cyano, $R^a$, $-OR^b$, $-C(O)R^b$, $-C(O)OR^b$, $-C(O)N(R^c)R^b$ and $-C(O)N(R^c)OR^b$, or $R^1$ and $R^2$, together with the carbon atoms to which they are attached, form a benzene ring which is unsubstituted or substituted with from 1 to 4 optional substituents independently selected from halo, hydroxy, cyano, amino, and $C_{1-4}$ alkyl which at each occurrence is independently unsubstituted or substituted with from 1 to 3 optional substituents independently selected from halo; and wherein:

$R^a$ is selected from $C_{1-4}$ alkyl, $C_{3-6}$ cycloalkyl, $C_{2-6}$ heterocyclyl and $C_{1-5}$ heteroaryl, each unsubstituted or substituted with from 1 to 3 optional substituents independently selected from halo, $C_{1-4}$ alkyl and $C_{1-4}$ alkoxy, wherein the $C_{1-4}$ alkyl and $C_{1-4}$ alkoxy optional substituents are each independently unsubstituted or substituted with from 1 to 3 optional substituents independently selected from halo;

$R^b$ is selected from hydrogen and from $C_{1-4}$ alkyl, $C_{3-6}$ cycloalkyl, $C_{2-6}$ heterocyclyl and $C_{1-5}$ heteroaryl, each unsubstituted or substituted with from 1 to 3 optional substituents independently selected from halo, $C_{1-4}$ alkyl and $C_{1-4}$ alkoxy, wherein the $C_{1-4}$ alkyl and $C_{1-4}$ alkoxy optional substituents are each independently unsubstituted or substituted with from 1 to 3 optional substituents independently selected from halo; and $R^c$ is selected from hydrogen and $C_{1-4}$ alkyl;

wherein for $R^a$ and $R^b$, the $C_{2-6}$ heterocyclyl substituent is a monocyclic ring with from 3 to 8 ring members in which 1 or 2 ring members are heteroatoms, each of the heteroatoms independently selected from N, O and S, and the $C_{1-5}$ heteroaryl substituent is a monocyclic ring with 5 or 6 ring members in which 1 to 4 ring members are heteroatoms, each of the heteroatoms independently selected from N, O, and S, provided no more than one of the ring members is O or S;

$R^3$ is selected from hydrogen, halo, cyano and $C_{1-4}$ alkyl which is unsubstituted or substituted with from 1 to 3 optional substituents independently selected from halo;

$R^4$ and $R^5$ are each independently selected from hydrogen, halo and $C_{1-4}$ alkyl which is unsubstituted or substituted with from 1 to 3 optional substituents independently selected from halo, or $R^4$ and $R^5$, together with the carbon atom to which they are both attached, form a $C_{3-5}$ cycloalkylidene;

$X^{12}$ is selected from a bond and $CR^{12}R^{13}$, and (a) $R^6$ is selected from hydrogen, halo and $C_{1-4}$ alkyl;
$R^7$ and $R^8$, together with the carbon and nitrogen atoms to which they are respectively attached, form a $C_{3-5}$ heterocyclyl having 1 ring heteroatom;
$R^9$ is selected from hydrogen and $C_{1-4}$ alkyl; and
$R^{10}$, $R^{11}$, $R^{12}$ and $R^{13}$ are each independently selected from hydrogen, halo and $C_{1-4}$ alkyl; or (b) $R^6$ and $R^7$ are each independently selected from hydrogen, halo and $C_{1-4}$ alkyl, or $R^6$ and $R^7$, together with the carbon atom to which they are both attached, form a $C_{3-5}$ cycloalkylidene;
$R^8$ and $R^9$, together with the nitrogen atom to which they are both attached, form a $C_{3-5}$ heterocyclyl which has 1 ring heteroatom and is unsubstituted or substituted with from 1 to 3 substituents independently selected from halo and $C_{1-4}$ alkyl; and
$R^{10}$, $R^{11}$, $R^{12}$ and $R^{13}$ are each independently selected from hydrogen, halo and $C_{1-4}$ alkyl; or (c) $R^6$ and $R^7$ are each independently selected from hydrogen, halo and $C_{1-4}$ alkyl;
$R^8$ is selected from hydrogen and $C_{1-4}$ alkyl;
$R^9$ and $R^{10}$, together with the nitrogen and carbon atoms to which they are respectively attached, form a $C_{3-5}$ heterocyclyl which has 1 ring heteroatom and is unsubstituted or substituted with from 1 to 3 substituents independently selected from halo and $C_{1-4}$ alkyl; and
$R^{11}$, $R^{12}$ and $R^{13}$ are each independently selected from hydrogen, halo and $C_{1-4}$ alkyl;

n is selected from 0, 1, 2, 3, 4 and 5; and each $R^{14}$ is independently selected from halo, $C_{1-4}$ alkyl and $C_{1-4}$ alkoxy, wherein the $C_{1-4}$ alkyl and $C_{1-4}$ alkoxy substituents are each independently unsubstituted or substituted with from 1 to 3 optional substituents independently selected from halo;

provided if $X^2$ is $CR^2$, $X^3$ is N, $X^{12}$ is a bond, n is 1, each of $R^1$, $R^4$, $R^5$, $R^6$, $R^7$, $R^8$, and $R^{11}$ is hydrogen, $R^9$ and $R^{10}$ together with the nitrogen and carbon atoms to which they are respectively attached form an unsubstituted pyrrolidin-2-yl, and $R^{14}$ is methoxy, then $R^2$ cannot be unsubstituted pyridin-3-yl or unsubstituted pyrimidin-5-yl.

In addition to embodiment (1) in the preceding paragraph, the compounds of Formula 1 include those in which:

(2) $R^1$ and $R^2$, together with the carbon atoms to which they are attached, form a benzene ring which is unsubstituted or substituted with from 1 to 4 optional substituents independently selected from halo, hydroxy, cyano, amino, and $C_{1-4}$ alkyl which at each occurrence is independently unsubstituted or substituted with from 1 to 3 optional substituents independently selected from halo.

In addition to embodiment (2) in the preceding paragraph, the compounds of Formula 1 include those in which $R^1$ and $R^2$, together with the carbon atoms to which they are attached, form a benzene ring which is unsubstituted or substituted with from 1 to 4 optional substituents independently selected from:

(3) halo, cyano, and $C_{1-4}$ alkyl which at each occurrence is independently unsubstituted or substituted with from 1 to 3 optional substituents independently selected from halo;

(4) halo and $C_{1-4}$ alkyl which at each occurrence is independently unsubstituted or substituted with from 1 to 3 optional substituents independently selected from halo;

(5) $C_{1-4}$ alkyl which at each occurrence is independently unsubstituted or substituted with from 1 to 3 optional substituents independently selected from halo;

(6) $C_{1-4}$ alkyl which at each occurrence is unsubstituted; or (7) methyl;

In addition to embodiments (1) to (7) in the preceding paragraphs, the compounds of Formula 1 include those in which $R^1$ and $R^2$, together with the carbon atoms to which they are attached, form a benzene ring which is unsubstituted or substituted with from:

(8) 1 to 3 optional substituents;
(9) 1 to 2 optional substituents;
(10) 1 optional substituent; or
(11) 0 optional substituents.

In addition to embodiment (1) above, the compounds of Formula 1 include those in which $R^1$ and $R^2$ are each independently selected from:

(12) hydrogen, halo, cyano, $R^a$, —$OR^b$, —$C(O)R^b$, —$C(O)OR^b$, —$C(O)N(R^c)R^b$ and —$C(O)N(R^c)OR^b$;

(13) hydrogen, cyano, $R^a$, —$OR^b$, —$C(O)R^b$, —$C(O)OR^b$, —$C(O)N(R^c)R^b$ and —$C(O)N(R^c)OR^b$;

(14) hydrogen, cyano, $R^a$, —$OR^b$, —$C(O)R^b$, —$C(O)OR^b$ and —$C(O)N(R^c)R^b$; or

(15) hydrogen, $R^a$, —$OR^b$, —$C(O)R^b$, —$C(O)OR^b$ and —$C(O)N(R^c)R^b$.

In addition to embodiments (12) to (15) in the preceding paragraph, the compounds of Formula 1 include those in which:

(16) $R^a$ is selected from $C_{1-4}$ alkyl, $C_{3-6}$ cycloalkyl, $C_{3-5}$ heterocyclyl and $C_{1-5}$ heteroaryl, each unsubstituted or substituted with from 1 to 3 optional substituents independently selected from halo, $C_{1-4}$ alkyl and $C_{1-4}$ alkoxy, wherein the $C_{1-4}$ alkyl and $C_{1-4}$ alkoxy optional substituents are each independently unsubstituted or substituted with from 1 to 3 optional substituents independently selected from halo;

$R^b$ is selected from hydrogen and from $C_{1-4}$ alkyl, $C_{3-6}$ cycloalkyl, $C_{3-5}$ heterocyclyl and $C_{1-5}$ heteroaryl, each unsubstituted or substituted with from 1 to 3 optional substituents independently selected from halo, $C_{1-4}$ alkyl and $C_{1-4}$ alkoxy, wherein the $C_{1-4}$ alkyl and $C_{1-4}$ alkoxy optional substituents are each independently unsubstituted or substituted with from 1 to 3 optional substituents independently selected from halo; and $R^c$ is selected from hydrogen and $C_{1-4}$ alkyl;

wherein for $R^a$ and $R^b$, the $C_{3-5}$ heterocyclyl substituent is a monocyclic ring with from 4 to 7 ring members in which 1 or 2 ring members are heteroatoms, each of the heteroatoms independently selected from N, O and S, and the $C_{1-5}$ heteroaryl substituent is a monocyclic ring with 5 or 6 ring members in which 1 to 4 ring members are heteroatoms, each of the heteroatoms independently selected from N, O, and S, provided no more than one of the ring members is O or S.

In addition to embodiment (16) in the preceding paragraph, the compounds of Formula 1 include those in which, for $R^a$ and $R^b$, the $C_{3-5}$ heterocyclyl substituent is a monocyclic ring having:

(17) from 4 to 6 ring members.

In addition to embodiments (15) and (16) in the preceding paragraphs, the compounds of Formula 1 include those in which, for $R^a$ and $R^b$, the $C_{3-5}$ heterocyclyl substituent is a monocyclic ring having:

(18) 1 or 2 ring members are heteroatoms, each of the heteroatoms independently selected from N and O.

In addition to embodiment (16) above, the compounds of Formula 1 include those in which, for $R^a$ and $R^b$, the $C_{3-5}$ heterocyclyl substituent is selected from:

(19) azetidinyl, pyrrolidinyl, piperidinyl, tetrahydrofuranyl, tetrahydropyranyl, and morpholinyl; or

(20) azetidin-1-yl, pyrrolidin-1-yl, piperidinyl, tetrahydrofuran-3-yl, tetrahydropyran-4-yl, and morpholin-4-yl; or In addition to embodiments (12) to (20) in the preceding paragraphs, the compounds of Formula 1 include those in which, for $R^a$ and $R^b$:

(21) the $C_{1-5}$ heteroaryl substituent is a monocyclic ring with 5 ring members in which 1 to 4 ring members are heteroatoms, each of the heteroatoms independently selected from N, O, and S, provided no more than one of the ring members is O or S.

In addition to embodiment (21) in the preceding paragraph, the compounds of Formula 1 include those in which, for $R^a$ and $R^b$, the $C_{1-5}$ heteroaryl substituent is selected from:

(22) pyrrolyl, furanyl, thienyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl and tetrazolyl;

(23) pyrazolyl, imidazolyl, isoxazolyl, oxazolyl, isothiazolyl and thiazolyl; or

(24) imidazol-2-yl, oxazol-2-yl and thiazol-2-yl;

In addition to embodiments (12) to (20) above, the compounds of Formula 1 include those in which, for $R^a$ and $R^b$, the $C_{1-5}$ heteroaryl substituent is selected from:

(25) pyrrolyl, furanyl, thienyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl and pyrazinyl.

In addition to embodiments (1) to (25) above, the compounds of Formula 1 include those in which:

(26) $X^2$ is $CR^2$ and $X^3$ is N.

In addition to embodiments (1) to (25) above, the compounds of Formula 1 include those in which:

(27) $X^2$ is $CR^2$ and $X^3$ is $CR^3$.

In addition to embodiment (27) in the preceding paragraph, the compounds of Formula 1 include those in which $R^3$ is selected from:

(28) hydrogen, halo, cyano and $C_{1-3}$ alkyl which is unsubstituted or substituted with from 1 to 3 optional substituents independently selected from halo;

(29) hydrogen, halo, cyano and methyl which is unsubstituted or substituted with from 1 to 3 optional substituents independently selected from halo;

(30) hydrogen, halo, cyano and methyl which is unsubstituted or substituted with from 1 to 3 optional substituents independently selected from fluoro;

(31) hydrogen, halo, cyano and methyl;

(32) hydrogen, halo and methyl;

(33) hydrogen and halo; or

(34) hydrogen.

In addition to embodiment (1) above, the compounds of Formula 1 include those in which:

(35) $X^2$ is N and $X^3$ is N.

In addition to embodiments (1) to (35) in the preceding paragraphs, the compounds of Formula 1 include those in which $R^1$ is selected from:

(36) hydrogen, $R^a$, —$OR^b$, —$C(O)R^b$, —$C(O)OR^b$ and —$C(O)N(R^c)R^b$, wherein:

$R^a$ is selected from $C_{1-4}$ alkyl and $C_{3-6}$ cycloalkyl, each unsubstituted or substituted with from 1 to 3 optional substituents independently selected from halo, $C_{1-4}$ alkyl and $C_{1-4}$ alkoxy, wherein the $C_{1-4}$ alkyl and $C_{1-4}$ alkoxy optional substituents are each independently unsubstituted or substituted with from 1 to 3 optional substituents independently selected from halo;

$R^b$ is selected from hydrogen and from $C_{1-4}$ alkyl and $C_{3-6}$ cycloalkyl, each unsubstituted or substituted with from 1 to 3 optional substituents independently selected from halo, $C_{1-4}$ alkyl and $C_{1-4}$ alkoxy, wherein the $C_{1-4}$ alkyl and $C_{1-4}$ alkoxy optional substituents are each independently unsubstituted or substituted with from 1 to 3 optional substituents independently selected from halo; and $R^c$ is selected from hydrogen and $C_{1-4}$ alkyl.

In addition to embodiment (36) in the preceding paragraph, the compounds of Formula 1 include those in which $R^1$ is selected from:

(37) hydrogen, $R^a$, $-OR^b$, $-C(O)R^b$, $-C(O)OR^b$ and $-C(O)N(R^c)R^b$; or

(38) hydrogen, $R^a$, $-OR^b$ and $-C(O)N(R^c)R^b$.

In addition to embodiments (36) to (38) in the preceding paragraphs, the compounds of Formula 1 include those in which for $R^1$:

(39) $R^a$ is selected from $C_{1-3}$ alkyl and $C_{3-5}$ cycloalkyl, each unsubstituted or substituted with from 1 to 3 optional substituents independently selected from halo, $C_{1-4}$ alkyl and $C_{1-4}$ alkoxy, wherein the $C_{1-4}$ alkyl and $C_{1-4}$ alkoxy optional substituents are each independently unsubstituted or substituted with from 1 to 3 optional substituents independently selected from halo;

$R^b$ is selected from hydrogen and from $C_{1-3}$ alkyl and $C_{3-5}$ cycloalkyl, each unsubstituted or substituted with from 1 to 3 optional substituents independently selected from halo, $C_{1-4}$ alkyl and $C_{1-4}$ alkoxy, wherein the $C_{1-4}$ alkyl and $C_{1-4}$ alkoxy optional substituents are each independently unsubstituted or substituted with from 1 to 3 optional substituents independently selected from halo; and $R^c$ is selected from hydrogen and $C_{1-3}$ alkyl.

In addition to embodiments (36) to (38) above, the compounds of Formula 1 include those in which for

(40) $R^a$ is selected from methyl, ethyl, propyl, isopropyl and cyclopropyl, each unsubstituted or substituted with from 1 to 3 optional substituents independently selected from halo, $C_{1-4}$ alkyl and $C_{1-4}$ alkoxy, wherein the $C_{1-4}$ alkyl and $C_{1-4}$ alkoxy optional substituents are each independently unsubstituted or substituted with from 1 to 3 optional substituents independently selected from halo;

$R^b$ is selected from hydrogen, methyl, ethyl, propyl, isopropyl and cyclopropyl, each unsubstituted or substituted with from 1 to 3 optional substituents independently selected from halo, $C_{1-4}$ alkyl and $C_{1-4}$ alkoxy, wherein the $C_{1-4}$ alkyl and $C_{1-4}$ alkoxy optional substituents are each independently unsubstituted or substituted with from 1 to 3 optional substituents independently selected from halo; and $R^c$ is selected from hydrogen and methyl.

In addition to embodiments (1) to (40) in the preceding paragraphs, the compounds of Formula 1 include those in which $R^4$ and $R^5$ are each independently selected from:

(41) hydrogen, halo and $C_{1-4}$ alkyl which is unsubstituted or substituted with from 1 to 3 optional substituents independently selected from halo;

(42) hydrogen, halo and $C_{1-3}$ alkyl which is unsubstituted or substituted with from 1 to 3 optional substituents independently selected from halo;

(43) hydrogen, halo and methyl which is unsubstituted or substituted with from 1 to 3 optional substituents independently selected from halo;

(44) hydrogen, halo and methyl; and

(45) hydrogen and methyl.

In addition to embodiments (1) to (40) above, the compounds of Formula 1 include those in which:

(46) $R^4$ is hydrogen and $R^5$ is methyl;

(47) $R^4$ and $R^5$ are each methyl; or

(48) $R^4$ and $R^5$ are each hydrogen.

In addition to embodiments (1) to (40) above, the compounds of Formula 1 include those in which:

(49) $R^4$ and $R^5$, together with the carbon atom to which they are both attached, form a $C_{3-5}$ cycloalkylidene; or

(50) $R^4$ and $R^5$, together with the carbon atom to which they are both attached, form a cyclopropylidene.

In addition to embodiments (1) to (50) in the preceding paragraphs, the compounds of Formula 1 include those in which:

(51)) $R^{12}$ is a bond and (a) $R^6$ is selected from hydrogen, halo and $C_{1-4}$ alkyl; $R^7$ and $R^8$, together with the carbon and nitrogen atoms to which they are respectively attached, form a $C_{3-5}$ heterocyclyl having 1 ring heteroatom; $R^9$ is selected from hydrogen and $C_{1-4}$ alkyl; and $R^{10}$ and $R^{11}$ are each independently selected from hydrogen, halo and $C_{1-4}$ alkyl; or (b) $R^6$ and $R^7$ are each independently selected from hydrogen, halo and $C_{1-4}$ alkyl, or $R^6$ and $R^7$, together with the carbon atom to which they are both attached, form a $C_{3-5}$ cycloalkylidene; $R^8$ and $R^9$, together with the nitrogen atom to which they are both attached, form a $C_{3-5}$ heterocyclyl which has 1 ring heteroatom and is unsubstituted or substituted with from 1 to 3 optional substituents independently selected from halo and $C_{1-4}$ alkyl; and $R^{10}$ and $R^{11}$ are each independently selected from hydrogen, halo and $C_{1-4}$ alkyl; or (c) $R^6$ and $R^7$ are each independently selected from hydrogen, halo and $C_{1-4}$ alkyl; $R^8$ is selected from hydrogen and $C_{1-4}$ alkyl; $R^9$ and $R^{10}$, together with the nitrogen and carbon atoms to which they are respectively attached, form a $C_{3-5}$ heterocyclyl which has 1 ring heteroatom and is unsubstituted or substituted with from 1 to 3 optional substituents independently selected from halo and $C_{1-4}$ alkyl; and $R^{11}$ is selected from hydrogen, halo and $C_{1-4}$ alkyl.

In addition to embodiments (1) to (50) above, the compounds of Formula 1 include those in which:

(52)) $X^{12}$ is a bond and (b) $R^6$ and $R^7$ are each independently selected from hydrogen, halo and $C_{1-4}$ alkyl, or $R^6$ and $R^7$, together with the carbon atom to which they are both attached, form a $C_{3-5}$ cycloalkylidene; $R^8$ and $R^9$, together with the nitrogen atom to which they are both attached, form a $C_{3-5}$ heterocyclyl which has 1 ring heteroatom and is unsubstituted or substituted with from 1 to 3 optional substituents independently selected from halo and $C_{1-4}$ alkyl; and $R^{10}$ and $R^{11}$ are each independently selected from hydrogen, halo and $C_{1-4}$ alkyl; or (c) $R^6$ and $R^7$ are each independently selected from hydrogen, halo and $C_{1-4}$ alkyl; $R^8$ is selected from hydrogen and $C_{1-4}$ alkyl; $R^9$ and $R^{10}$, together with the nitrogen and carbon atoms to which they are respectively attached, form a $C_{3-5}$ heterocyclyl which has 1 ring heteroatom and is unsubstituted or substituted with from 1 to 3 optional substituents independently selected from halo and $C_{1-4}$ alkyl; and $R^{11}$ is selected from hydrogen, halo and $C_{1-4}$ alkyl.

In addition to embodiments (1) to (50) above, the compounds of Formula 1 include those in which:
(53) $X^{12}$ is a bond and
$R^6$ and $R^7$ are each independently selected from hydrogen, halo and $C_{1-4}$ alkyl, or $R^6$ and $R^7$, together with the carbon atom to which they are both attached, form a $C_{3-5}$ cycloalkylidene;
$R^8$ and $R^9$, together with the nitrogen atom to which they are both attached, form a $C_{3-5}$ heterocyclyl which has 1 ring heteroatom and is unsubstituted or substituted with from 1 to 3 optional substituents independently selected from halo and $C_{1-4}$ alkyl; and
$R^{10}$ and $R^{11}$ are each independently selected from hydrogen, halo and $C_{1-4}$ alkyl.

In addition to embodiment (53) in the preceding paragraph, the compounds of Formula 1 include those in which $R^6$ and $R^7$ are each independently selected from:
(54) hydrogen, halo and $C_{1-4}$ alkyl, or $R^6$ and $R^7$, together with the carbon atom to which they are both attached, form a cyclopropylidene;
(55) hydrogen, halo and $C_{1-4}$ alkyl;
(56) hydrogen and $C_{1-4}$ alkyl;
(57) hydrogen and $C_{1-3}$ alkyl; or
(58) hydrogen and methyl.

In addition to embodiment (53) above, the compounds of Formula 1 include those in which:
(59) $R^6$ is methyl and $R^7$ is hydrogen;
(60) $R^6$ and $R^7$ are each methyl;
(61) $R^6$ and $R^7$ are each hydrogen; or
(62) $R^6$ and $R^7$, together with the carbon atom to which they are both attached, form a cyclopropylidene.

In addition to embodiments (53) to (62) in the preceding paragraphs, the compounds of Formula 1 include those in which $R^8$ and $R^9$, together with the nitrogen atom to which they are both attached, form a $C_{3-5}$ heterocyclyl which is:
(63) azetidinyl, which unsubstituted or substituted with from 1 to 3 optional substituents independently selected from halo and $C_{1-4}$ alkyl;
(64) pyrrolidinyl, which is unsubstituted or substituted with from 1 to 3 optional substituents independently selected from halo and $C_{1-4}$ alkyl; or
(65) piperidinyl, which is unsubstituted or substituted with from 1 to 3 optional substituents independently selected from halo and $C_{1-4}$ alkyl.

In addition to embodiments (53) to (65) in the preceding paragraphs, the compounds of Formula 1 include those in which the $C_{3-5}$ heterocyclyl formed by $R^8$ and $R^9$ and the nitrogen atom to which they are both attached is:
(66) unsubstituted or substituted with from 1 to 3 optional substituents independently selected from halo and $C_{1-3}$ alkyl;
(67) unsubstituted or substituted with from 1 to 3 optional substituents independently selected from halo and methyl;
(68) unsubstituted or substituted with from 1 to 3 optional substituents independently selected from halo;
(69) unsubstituted or substituted with from 1 to 3 optional substituents independently selected from fluoro; or
(70) unsubstituted.

In addition to embodiments (53) to (70) in the preceding paragraphs, the compounds of Formula 1 include those in which $R^{10}$ and $R^{11}$ are each independently selected from:
(71) hydrogen, halo and $C_{1-3}$ alkyl;
(72) hydrogen and $C_{1-3}$ alkyl;
(73) hydrogen and methyl;
(74) methyl; or
(75) hydrogen.

In addition to embodiments (1) to (50) above, the compounds of Formula 1 include those in which:
(76)) $X^{12}$ is a bond and
$R^6$ and $R^7$ are each independently selected from hydrogen, halo and $C_{1-4}$ alkyl;
$R^8$ is selected from hydrogen and $C_{1-4}$ alkyl;
$R^9$ and $R^{10}$, together with the nitrogen and carbon atoms to which they are respectively attached, form a $C_{3-5}$ heterocyclyl which has 1 ring heteroatom and is unsubstituted or substituted with from 1 to 3 optional substituents independently selected from halo and $C_{1-4}$ alkyl; and
$R^{11}$ is selected from hydrogen, halo and $C_{1-4}$ alkyl.

In addition to embodiment (76) in the preceding paragraph, the compounds of Formula 1 include those in which $R^6$ and $R^7$ are each independently selected from:
(77) hydrogen and $C_{1-4}$ alkyl;
(78) hydrogen and $C_{1-3}$ alkyl; or
(79) hydrogen and methyl.

In addition to embodiments (76) to (79) in the preceding paragraphs, the compounds of Formula 1 include those in which:
(80) $R^6$ is methyl and $R^7$ is hydrogen;
(81) $R^6$ and $R^7$ are each methyl; or
(82) $R^6$ and $R^7$ are each hydrogen.

In addition to embodiments (76) to (82) in the preceding paragraphs, the compounds of Formula 1 include those in which $R^8$ is selected from:
(83) hydrogen and $C_{1-3}$ alkyl;
(84) hydrogen and methyl;
(85) methyl; or
(86) hydrogen.

In addition to embodiments (76) to (86) in the preceding paragraphs, the compounds of Formula 1 include those in which $R^9$ and $R^{10}$, together with the nitrogen and carbon atoms to which they are respectively attached, form a $C_{3-5}$ heterocyclyl which is:
(87) azetidinyl, which is unsubstituted or substituted with from 1 to 3 optional substituents independently selected from halo and $C_{1-4}$ alkyl;
(88) pyrrolidinyl, which is unsubstituted or substituted with from 1 to 3 optional substituents independently selected from halo and $C_{1-4}$ alkyl; or
(89) piperidinyl, which is unsubstituted or substituted with from 1 to 3 optional substituents independently selected from halo and $C_{1-4}$ alkyl.

In addition to embodiments (76) to (89) in the preceding paragraphs, the compounds of Formula 1 include those in which the $C_{3-5}$ heterocyclyl formed by $R^9$ and $R^{10}$ and the nitrogen and carbon atoms to which they are respectively attached is:
(90) unsubstituted or substituted with from 1 to 3 optional substituents independently selected from halo and $C_{1-3}$ alkyl;
(91) unsubstituted or substituted with from 1 to 3 optional substituents independently selected from halo and methyl;
(92) unsubstituted or substituted with from 1 to 3 optional substituents independently selected from halo;
(93) unsubstituted or substituted with from 1 to 3 optional substituents independently selected from fluoro; or
(94) unsubstituted.

In addition to embodiments (76) to (94) in the preceding paragraphs, the compounds of Formula 1 include those in which $R^{11}$ is selected from:
(95) hydrogen, halo and $C_{1-3}$ alkyl;
(96) hydrogen and methyl;
(97) methyl; or
(98) hydrogen.

In addition to embodiments (1) to (50) above, the compounds of Formula 1 include those in which:
(99) $X^{12}$ is $CR^{12}R^{13}$ and
  (a) $R^6$ is selected from hydrogen, halo and $C_{1-4}$ alkyl;
    $R^7$ and $R^8$, together with the carbon and nitrogen atoms to which they are respectively attached, form a $C_{3-5}$ heterocyclyl having 1 ring heteroatom;
    $R^9$ is selected from hydrogen and $C_{1-4}$ alkyl; and
    $R^{10}$, $R^{11}$, $R^{12}$ and $R^{13}$ are each independently selected from hydrogen, halo and $C_{1-4}$ alkyl; or
  (b) $R^6$ and $R^7$ are each independently selected from hydrogen, halo and $C_{1-4}$ alkyl, or $R^6$ and $R^7$, together with the carbon atom to which they are both attached, form a $C_{3-5}$ cycloalkylidene;
    $R^8$ and $R^9$, together with the nitrogen atom to which they are both attached, form a $C_{3-5}$ heterocyclyl which has 1 ring heteroatom and is unsubstituted or substituted with from 1 to 3 optional substituents independently selected from halo and $C_{1-4}$ alkyl; and
    $R^{10}$, $R^{11}$, $R^{12}$ and $R^{13}$ are each independently selected from hydrogen, halo and $C_{1-4}$ alkyl; or
  (c) $R^6$ and $R^7$ are each independently selected from hydrogen, halo and $C_{1-4}$ alkyl;
    $R^8$ is selected from hydrogen and $C_{1-4}$ alkyl;
    $R^9$ and $R^{10}$, together with the nitrogen and carbon atoms to which they are respectively attached, form a $C_{3-5}$ heterocyclyl which has 1 ring heteroatom and is unsubstituted or substituted with from 1 to 3 optional substituents independently selected from halo and $C_{1-4}$ alkyl; and
    $R^{11}$, $R^{12}$ and $R^{13}$ are each independently selected from hydrogen, halo and $C_{1-4}$ alkyl.

In addition to embodiments (1) to (50) above, the compounds of Formula 1 include those in which:
(100) $X^{12}$ is $CR^{12}R^{13}$ and
  $R^6$ is selected from hydrogen, halo and $C_{1-4}$ alkyl;
  $R^7$ and $R^8$, together with the carbon and nitrogen atoms to which they are respectively attached, form a $C_{3-5}$ heterocyclyl having 1 ring heteroatom;
  $R^9$ is selected from hydrogen and $C_{1-4}$ alkyl; and
  $R^{10}$, $R^{11}$, $R^{12}$ and $R^{13}$ are each independently selected from hydrogen, halo and $C_{1-4}$ alkyl.

In addition to embodiment (100) in the preceding paragraph, the compounds of Formula 1 include those in which $R^6$ is selected from:
(101) hydrogen, halo and $C_{1-3}$ alkyl;
(102) hydrogen, halo and methyl;
(103) hydrogen and methyl; or
(104) hydrogen.

In addition to embodiments (100) to (104) in the preceding paragraphs, the compounds of Formula 1 include those in which $R^7$ and $R^8$, together with the carbon and nitrogen atoms to which they are respectively attached, form a $C_{3-5}$ heterocyclyl which is:
(105) azetidinyl;
(106) azetidin-2-yl;
(107) pyrrolidinyl;
(108) pyrrolidin-3-yl;
(109) piperidinyl; or
(110) piperidin-4-yl.

In addition to embodiments (100) to (110) in the preceding paragraphs, the compounds of Formula 1 include those in which:
(111) $R^9$ is selected from hydrogen and $C_{1-3}$ alkyl; and
$R^{10}$, $R^{11}$, $R^{12}$ and $R^{13}$ are each independently selected from hydrogen, halo and $C_{1-3}$ alkyl;
(112) $R^9$ is selected from hydrogen and methyl; and
$R^{10}$, $R^{11}$, $R^{12}$ and $R^{13}$ are each independently selected from hydrogen, halo and $C_{1-3}$ alkyl; or
(113) $R^9$ is selected from hydrogen and methyl; and
$R^{10}$, $R^{11}$, $R^{12}$ and $R^{13}$ are each independently selected from hydrogen, halo, methyl and ethyl.

In addition to embodiments (100) to (113) in the preceding paragraphs, the compounds of Formula 1 include those in which:
(114) $R^{10}$ and $R^{11}$ are each independently selected from hydrogen, halo and methyl;
(115) $R^{10}$ and $R^{11}$ are each independently selected from hydrogen, fluoro and methyl;
(116) $R^{10}$ and $R^{11}$ are each independently selected from hydrogen and methyl;
(117) $R^{10}$ is methyl and $R^{11}$ hydrogen;
(118) $R^{10}$ and $R^{11}$ are each methyl; or
(119) $R^{10}$ and $R^{11}$ are each hydrogen.

In addition to embodiments (100) to (119) in the preceding paragraphs, the compounds of Formula 1 include those in which:
(120) $R^{12}$ and $R^{13}$ are each independently selected from hydrogen, fluoro, methyl and ethyl;
(121) $R^{12}$ and $R^{13}$ are each independently selected from hydrogen, fluoro, methyl and ethyl;
(122) $R^{12}$ and $R^{13}$ are each independently selected from hydrogen and methyl;
(123) $R^{12}$ is methyl and $R^{13}$ is hydrogen;
(124) $R^{12}$ and $R^{13}$ are each methyl; or
(125) $R^{12}$ and $R^{13}$ are each hydrogen.

In addition to embodiments (1) to (125) in the preceding paragraphs, the compounds of Formula 1 include those in which each $R^{14}$ is independently selected from:
(126) halo, $C_{1-3}$ alkyl and $C_{1-3}$ alkoxy, wherein the $C_{1-3}$ alkyl and $C_{1-3}$ alkoxy substituents are each independently unsubstituted or substituted with from 1 to 3 optional substituents independently selected from halo;
(127) halo, methyl and methoxy, wherein the methyl and methoxy substituents are each independently unsubstituted or substituted with from 1 to 3 optional substituents independently selected from halo;
(128) fluoro, methyl and methoxy, wherein the methyl and methoxy substituents are each independently unsubstituted or substituted with from 1 to 3 optional substituents independently selected from fluoro;
(129) fluoro, methyl and methoxy, wherein the methyl and methoxy substituents are unsubstituted; or
(130) fluoro.

In addition to embodiments (126) to (130) in the preceding paragraphs, the compounds of Formula 1 include those in which n is selected from:
(131) 0, 1, 2 and 3;
(132) 0, 1 and 2; or
(133) 0 and 1.

In addition to embodiments (126) to (133) in the preceding paragraphs, the compounds of Formula 1 include those in which:
(134) n is 1.

In addition to embodiments (1) to (125) in the preceding paragraphs, the compounds of Formula 1 include those in which:
(135) n is 0.

Compounds of Formula 1 include embodiments (1) through (135) described in the preceding paragraphs and compounds specifically named in the examples, may exist as salts, complexes, solvates, hydrates, and liquid crystals.

Likewise, compounds of Formula 1 that are salts may exist as complexes, solvates, hydrates, and liquid crystals.

Compounds of Formula 1 may form pharmaceutically acceptable complexes, salts, solvates and hydrates. These salts include acid addition salts (including di-acids) and base salts. Pharmaceutically acceptable acid addition salts include salts derived from inorganic acids such as hydrochloric acid, nitric acid, phosphoric acid, sulfuric acid, hydrobromic acid, hydroiodic acid, hydrofluoric acid, and phosphorous acids, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

Pharmaceutically acceptable base salts include salts derived from bases, including metal cations, such as an alkali or alkaline earth metal cation, as well as amines. Examples of suitable metal cations include sodium, potassium, magnesium, calcium, zinc, and aluminum. Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2002).

Pharmaceutically acceptable salts may be prepared using various methods. For example, a compound of Formula 1 may be reacted with an appropriate acid or base to give the desired salt. Alternatively, a precursor of the compound of Formula 1 may be reacted with an acid or base to remove an acid- or base-labile protecting group or to open a lactone or lactam group of the precursor. Additionally, a salt of the compound of Formula 1 may be converted to another salt (or free form) through treatment with an appropriate acid or base or through contact with an ion exchange resin. Following reaction, the salt may be isolated by filtration if it precipitates from solution, or by evaporation to recover the salt. The degree of ionization of the salt may vary from completely ionized to almost non-ionized.

Compounds of Formula 1 may exist in a continuum of solid states ranging from fully amorphous to fully crystalline. The term "amorphous" refers to a state in which the material lacks long range order at the molecular level and, depending upon temperature, may exhibit the physical properties of a solid or a liquid. Typically, such materials do not give distinctive X-ray diffraction patterns and, while exhibiting the properties of a solid, are more formally described as a liquid. Upon heating, a change from solid to liquid properties occurs which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

Compounds of Formula 1 may also exist in unsolvated and solvated forms. The term "solvate" describes a molecular complex comprising the compound and one or more pharmaceutically acceptable solvent molecules (e.g., ethanol). The term "hydrate" is a solvate in which the solvent is water. Pharmaceutically acceptable solvates include those in which the solvent may be isotopically substituted (e.g., $D_2O$, acetone-$d_6$, DMSO-$d_6$).

A currently accepted classification system for solvates and hydrates of organic compounds is one that distinguishes between isolated site, channel, and metal-ion coordinated solvates and hydrates. See, e.g., K. R. Morris (H. G. Brittain ed.) *Polymorphism in Pharmaceutical Solids* (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Compounds of Formula 1 may also exist as multi-component complexes (other than salts and solvates) in which the compound (drug) and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions but could also be a complex of a neutral molecule with a salt. Co-crystals may be prepared by melt crystallization, by recrystallization from solvents, or by physically grinding the components together. See, e.g., O. Almarsson and M. J. Zaworotko, *Chem. Commun.* (2004) 17:1889-1896. For a general review of multi-component complexes, see J. K. Haleblian, *J. Pharm. Sci.* (1975) 64(8):1269-88.

When subjected to suitable conditions, compounds of Formula 1 may exist in a mesomorphic state (mesophase or liquid crystal). The mesomorphic state lies between the true crystalline state and the true liquid state (either melt or solution). Mesomorphism arising as the result of a change in temperature is described as "thermotropic" and mesomorphism resulting from the addition of a second component, such as water or another solvent, is described as "lyotropic." Compounds that have the potential to form lyotropic mesophases are described as "amphiphilic" and include molecules which possess a polar ionic moiety (e.g., $-COO^-Na^+$, $-COO^-K^+$, $-SO_3^-Na^+$) or polar non-ionic moiety (such as $-N^-N^+(CH_3)_3$). See, e.g., N. H. Hartshorne and A. Stuart, *Crystals and the Polarizing Microscope* (4th ed, 1970).

Each compound of Formula 1 may exist as polymorphs, stereoisomers, tautomers, or some combination thereof, may be isotopically-labeled, may result from the administration of a prodrug, or form a metabolite following administration.

"Prodrugs" refer to compounds having little or no pharmacological activity that can, when metabolized in vivo, undergo conversion to compounds having desired pharmacological activity. Prodrugs may be prepared by replacing appropriate functionalities present in pharmacologically active compounds with "pro-moieties" as described, for example, in H. Bundgaar, *Design of Prodrugs* (1985). Examples of prodrugs include ester, ether or amide derivatives of compounds of Formula 1 having carboxylic acid, hydroxy, or amino functional groups, respectively. For further discussions of prodrugs, see e.g., T. Higuchi and V. Stella "Pro-drugs as Novel Delivery Systems," *ACS Symposium Series* 14 (1975) and E. B. Roche ed., *Bioreversible Carriers in Drug Design* (1987).

"Metabolites" refer to compounds formed in vivo upon administration of pharmacologically active compounds. Examples include hydroxymethyl, hydroxy, secondary amino, primary amino, phenol, and carboxylic acid derivatives of compounds of Formula 1 having methyl, alkoxy, tertiary amino, secondary amino, phenyl, and amide groups, respectively.

Compounds of Formula 1 may exist as stereoisomers that result from the presence of one or more stereogenic centers, one or more double bonds, or both. The stereoisomers may be pure, substantially pure, or mixtures. Such stereoisomers may also result from acid addition or base salts in which the counter-ion is optically active, for example, when the counter-ion is D-lactate or L-lysine.

Compounds of Formula 1 may exist as tautomers, which are isomers resulting from tautomerization. Tautomeric isomerism includes, for example, imine-enamine, keto-enol, oxime-nitroso, and amide-imidic acid tautomerism.

Compounds of Formula 1 may exhibit more than one type of isomerism.

Geometrical (cis/trans) isomers may be separated by conventional techniques such as chromatography and fractional crystallization.

Conventional techniques for preparing or isolating a compound having a specific stereochemical configuration include chiral synthesis from a suitable optically pure precursor or resolution of the racemate (or the racemate of a salt or derivative) using, for example, chiral high-pressure liquid chromatography (HPLC). Alternatively, the racemate (or a racemic precursor) may be reacted with a suitable optically active compound, for example, an alcohol, or, in the case where the compound of Formula 1 contains an acidic or basic moiety, an acid or base such as tartaric acid or 1-phenylethylamine. The resulting diastereomeric mixture may be separated by chromatography, fractional crystallization, etc., and the appropriate diastereoisomer converted to the compound having the requisite stereochemical configuration. For a further discussion of techniques for separating stereoisomers, see E. L. Eliel and S. H. Wilen, *Stereochemistry of Organic Compounds* (1994).

Compounds of Formula 1 may possess isotopic variations, in which at least one atom is replaced by an atom having the same atomic number, but an atomic mass different from the atomic mass usually found in nature. Isotopes suitable for inclusion in compounds of Formula 1 include, for example, isotopes of hydrogen, such as $^2$H and $^3$H; isotopes of carbon, such as $^{11}$C, $^{13}$C and $^{14}$C; isotopes of nitrogen, such as $^{13}$N and $^{15}$N; isotopes of oxygen, such as $^{15}$O, $^{17}$O and $^{18}$O; isotopes of sulfur, such as $^{35}$S; isotopes of fluorine, such as $^{18}$F; isotopes of chlorine, such as $^{36}$Cl, and isotopes of iodine, such as $^{123}$I and $^{125}$I. Use of isotopic variations (e.g., deuterium, $^2$H) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^3$H, or $^{14}$C), which may be useful in drug and/or substrate tissue distribution studies. Substitution with positron emitting isotopes, such as $^{11}$C, $^{18}$F, $^{15}$O and $^{13}$N, may be useful in Positron Emission Topography (PET) studies for examining substrate receptor occupancy. Isotopically-labeled compounds may be prepared by processes analogous to those described elsewhere in the disclosure using an appropriate isotopically-labeled reagent in place of a non-labeled reagent.

The compounds of Formula 1 may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in several treatises, including Richard Larock, *Comprehensive Organic Transformations* (1999), and the multi-volume series edited by Michael B. Smith and others, *Compendium of Organic Synthetic Methods* (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a di-acid, etc.). In addition, in some instances, reaction intermediates may be used in subsequent steps without isolation or purification (i.e., in situ).

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry* (1999) and P. Kocienski, *Protective Groups* (2000).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure and claims to a stoichiometric range, a temperature range, a pH range, etc., whether expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane, cyclohexane, methylcyclohexane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methylethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

In the schemes, below, substituent identifiers (n, $R^1$, $R^4$, $R^5$, $R^6$, $R^7$, $R^8$, $R^9$, $R^{10}$, $R^{11}$, $R^{14}$, $X^2$, $X^3$ and $X^{12}$) are as defined above for Formula 1. As mentioned earlier, however, some of the starting materials and intermediates may include protecting groups, which are removed prior to the final product. In such cases, the substituent identifier refers to moieties defined in Formula 1 and to those moieties with appropriate protecting groups. For example, a starting material or intermediate in the schemes may include $R^2$ substituent having a potentially reactive amine. In such cases, $R^2$ would include the moiety with or without, say, a Boc or Cbz group attached to the amine.

Schemes A and B show general methods for preparing compounds of Formula 1. In accordance with Scheme A, a heteroaryl halide (A1, Y=Cl, Br, I) is reacted with a primary amine (A2) in the presence of a non-nucleophilic base (e.g., DIPEA, Et$_3$N, CsF, K$_2$CO$_3$, etc.) and a polar aprotic solvent (e.g., dioxane, DMSO, DMF, THF, etc.). The S$_N$Ar reaction may be carried out at room temperature or above (e.g. 25-130° C.) and gives the compound of Formula 1 directly or indirectly, for example, after removal of protecting groups, further elaboration of functional groups, etc.

Scheme A

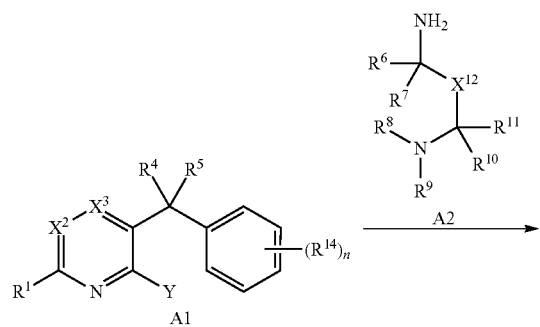

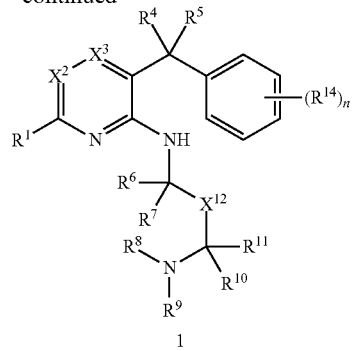

Scheme B shows a general method for preparing compounds of Formula 1 when $R^4$ is methyl and $R^5$ is hydrogen (Formula 1A) or when $R^4$ and $R^5$ are each hydrogen (Formula 1B). In accordance with Scheme B, a heteroaromatic dihalide (B1, Y=Cl, Br, I) is reacted with a primary amine (A2) in the presence of a non-nucleophilic base (e.g., DIPEA, Et$_3$N, CsF, K$_2$CO$_3$, etc.) and a polar aprotic solvent (e.g., dioxane, DMSO, DMF, THF, etc.) to give a heteroaromatic amine (B2). The amine (B2) is reacted with a 2-(trimethylsilyl)vinyl boronic acid or ester (B3 in which, e.g., each $R^{15}$ is H or $C_{1-4}$ alkyl) in the presence of a palladium catalyst (e.g., RuPhos Pd G3, Pd(dppf)Cl$_2$, PdCl$_2$(dtbpf), etc.), base (e.g., K$_2$CO$_3$, Na$_2$CO$_3$, KF, Et$_3$N, etc.) and one or more polar solvents (e.g., dioxane, DMF, water, etc.). The palladium catalyzed cross-coupling reaction is carried out at elevated temperature (e.g., 75-110° C.) and gives an ethene-1,1-diyldiaryl intermediate (B4). The ethene moiety is subsequently reduced (via e.g., catalytic hydrogenation) to give the compound of Formula 1A. Alternatively, the amine (B2) may be reacted with a benzyl boronic acid or ester (B5) in the presence of a palladium catalyst, base and one or more polar solvents to give the compound of Formula 1B.

The methods depicted in the schemes may be varied as desired. For example, protecting groups may be added or removed and products may be further elaborated via, for example, alkylation, acylation, hydrolysis, oxidation, reduction, amidation, sulfonation, alkynation, and the like to give the desired final product. Furthermore, any intermediate or final product which comprises mixture of stereoisomers may be optionally purified by chiral column chromatography (e.g., supercritical fluid chromatography) or by derivatization with optically-pure reagents as described above to give a desired stereoisomer.

Compounds of Formula 1, which include compounds named above, and their pharmaceutically acceptable complexes, salts, solvates and hydrates, should be assessed for their biopharmaceutical properties, such as solubility and solution stability across pH, permeability, and the like, to select an appropriate dosage form and route of administration. Compounds that are intended for pharmaceutical use may be administered as crystalline or amorphous products, and may be obtained, for example, as solid plugs, powders, or films by methods such as precipitation, crystallization, freeze drying, spray drying, evaporative drying, microwave drying, or radio frequency drying.

Scheme B

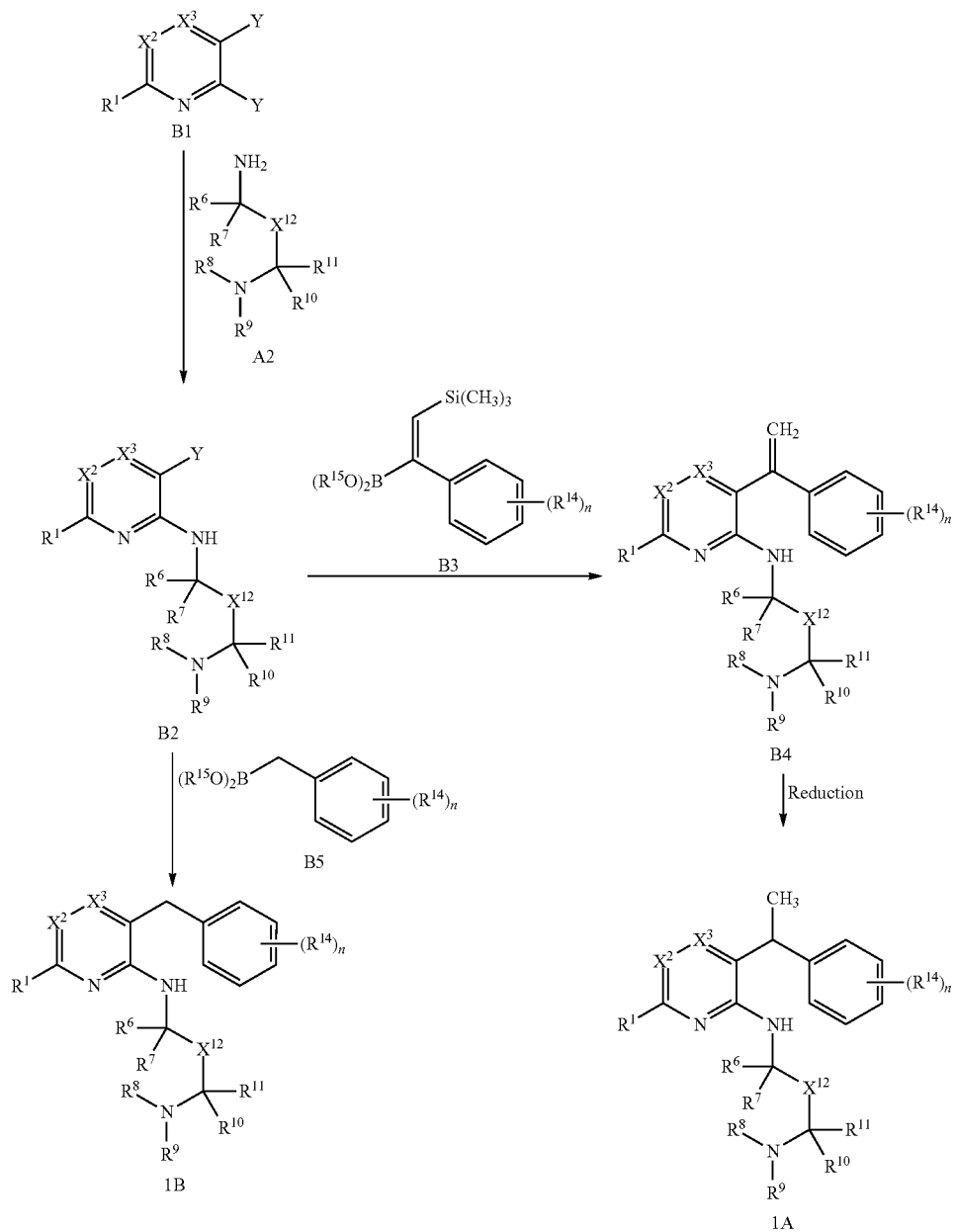

Compounds of Formula 1 may be administered alone or in combination with one another or with one or more pharmacologically active compounds which are different than the compounds of Formula 1. Generally, one or more of these compounds are administered as a pharmaceutical composition (a formulation) in association with one or more pharmaceutically acceptable excipients. The choice of excipients depends on the mode of administration, the effect of the excipient on solubility and stability, and the nature of the dosage form, among other things. Useful pharmaceutical compositions and methods for their preparation may be found, for example, in A. R. Gennaro (ed.), *Remington: The Science and Practice of Pharmacy* (20th ed., 2000).

Compounds of Formula 1 may be administered orally. Oral administration may involve swallowing in which case the compound enters the bloodstream via the gastrointestinal tract. Alternatively or additionally, oral administration may involve mucosal administration (e.g., buccal, sublingual, supralingual administration) such that the compound enters the bloodstream through the oral mucosa.

Formulations suitable for oral administration include solid, semi-solid and liquid systems such as tablets; soft or hard capsules containing multi- or nano-particulates, liquids, or powders; lozenges which may be liquid-filled; chews; gels; fast dispersing dosage forms; films; ovules; sprays; and buccal or mucoadhesive patches. Liquid formulations include suspensions, solutions, syrups and elixirs. Such formulations may be employed as fillers in soft or hard capsules (made, e.g., from gelatin or hydroxypropylmethylcellulose) and typically comprise a carrier (e.g., water, ethanol, polyethylene glycol, propylene glycol, methylcellulose, or a suitable oil) and one or more emulsifying agents, suspending agents or both. Liquid formulations may also be prepared by the reconstitution of a solid (e.g., from a sachet).

Compounds of Formula 1 may also be used in fast-dissolving, fast-disintegrating dosage forms such as those described in Liang and Chen, *Expert Opinion in Therapeutic Patents* (2001) 11(6):981-986.

For tablet dosage forms, depending on dose, the active pharmaceutical ingredient (API) may comprise from about 1 wt % to about 80 wt % of the dosage form or more typically from about 5 wt % to about 60 wt % of the dosage form. In addition to the API, tablets may include one or more disintegrants, binders, diluents, surfactants, glidants, lubricants, anti-oxidants, colorants, flavoring agents, preservatives, and taste-masking agents. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, $C_{1-6}$ alkyl-substituted hydroxypropylcellulose, starch, pregelatinized starch, and sodium alginate. Generally, the disintegrant will comprise from about 1 wt % to about 25 wt % or from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropylcellulose and hydroxypropylmethylcellulose. Tablets may also contain diluents, such as lactose (monohydrate, spray-dried monohydrate, anhydrous), mannitol, xylitol, dextrose, sucrose, sorbitol, microcrystalline cellulose, starch and dibasic calcium phosphate dihydrate.

Tablets may also include surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets may also contain lubricants such as magnesium stearate, calcium stearate, zinc stearate, sodium stearyl fumarate, and mixtures of magnesium stearate with sodium lauryl sulfate. Lubricants may comprise from about 0.25 wt % to about 10 wt % or from about 0.5 wt % to about 3 wt % of the tablet.

Tablet blends may be compressed directly or by roller compaction to form tablets. Tablet blends or portions of blends may alternatively be wet-, dry-, or melt-granulated, melt congealed, or extruded before tableting. If desired, prior to blending one or more of the components may be sized by screening or milling or both. The final dosage form may comprise one or more layers and may be coated, uncoated, or encapsulated. Exemplary tablets may contain up to about 80 wt % of API, from about 10 wt % to about 90 wt % of binder, from about 0 wt % to about 85 wt % of diluent, from about 2 wt % to about 10 wt % of disintegrant, and from about 0.25 wt % to about 10 wt % of lubricant. For a discussion of blending, granulation, milling, screening, tableting, coating, as well as a description of alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets*, Vol. 1-3 (2d ed., 1990); and D. K. Parikh & C. K. Parikh, *Handbook of Pharmaceutical Granulation Technology*, Vol. 81 (1997).

Consumable oral films for human or veterinary use are pliable water-soluble or water-swellable thin film dosage forms which may be rapidly dissolving or mucoadhesive. In addition to the API, a typical film includes one or more film-forming polymers, binders, solvents, humectants, plasticizers, stabilizers or emulsifiers, viscosity-modifying agents, and solvents. Other film ingredients may include anti-oxidants, colorants, flavorants and flavor enhancers, preservatives, salivary stimulating agents, cooling agents, co-solvents (including oils), emollients, bulking agents, anti-foaming agents, surfactants, and taste-masking agents. Some components of the formulation may perform more than one function.

In addition to dosing requirements, the amount of API in the film may depend on its solubility. If water soluble, the API would typically comprise from about 1 wt % to about 80 wt % of the non-solvent components (solutes) in the film or from about 20 wt % to about 50 wt % of the solutes in the film. A less soluble API may comprise a greater proportion of the composition, typically up to about 88 wt % of the non-solvent components in the film.

The film-forming polymer may be selected from natural polysaccharides, proteins, or synthetic hydrocolloids and typically comprises from about 0.01 wt % to about 99 wt % or from about 30 wt % to about 80 wt % of the film.

Film dosage forms are typically prepared by evaporative drying of thin aqueous films coated onto a peelable backing support or paper, which may be carried out in a drying oven or tunnel (e.g., in a combined coating-drying apparatus), in lyophilization equipment, or in a vacuum oven.

Useful solid formulations for oral administration may include immediate release formulations and modified release formulations. Modified release formulations include delayed-, sustained-, pulsed-, controlled-, targeted-, and programmed-release. For a general description of suitable modified release formulations, see U.S. Pat. No. 6,106,864. For details of other useful release technologies, such as high energy dispersions and osmotic and coated particles, see Verma et al, *Pharmaceutical Technology On-line* (2001) 25(2):1-14.

Compounds of Formula 1 may also be administered directly into the blood stream, muscle, or an internal organ of the subject. Suitable techniques for parenteral administration include intravenous, intraarterial, intraperitoneal, intrathecal, intraventricular, intraurethral, intrasternal, intracranial, intramuscular, intrasynovial, and subcutaneous administration. Suitable devices for parenteral administration include needle injectors, including microneedle injectors, needle-free injectors, and infusion devices.

Parenteral formulations are typically aqueous solutions which may contain excipients such as salts, carbohydrates and buffering agents (e.g., pH of from about 3 to about 9). For some applications, however, compounds of Formula 1 may be more suitably formulated as a sterile non-aqueous solution or as a dried form to be used in conjunction with a suitable vehicle such as sterile, pyrogen-free water. The preparation of parenteral formulations under sterile conditions (e.g., by lyophilization) may be readily accomplished using standard pharmaceutical techniques.

The solubility of compounds which are used in the preparation of parenteral solutions may be increased through appropriate formulation techniques, such as the incorporation of solubility-enhancing agents. Formulations for parenteral administration may be formulated to be immediate or modified release. Modified release formulations include delayed, sustained, pulsed, controlled, targeted, and programmed release. Thus, compounds of Formula 1 may be formulated as a suspension, a solid, a semi-solid, or a thixotropic liquid for administration as an implanted depot providing modified release of the active compound. Examples of such formulations include drug-coated stents and semi-solids and suspensions comprising drug-loaded poly(DL-lactic-coglycolic)acid (PGLA) microspheres.

Compounds of Formula 1 may also be administered topically, intradermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers may include alcohol, water, mineral oil, liquid petrolatum, white petrolatum, glycerin, polyethylene glycol and propylene glycol. Topical formulations may also include penetration enhancers. See, e.g., Finnin and Morgan, *J. Pharm. Sci.* 88(10): 955-958 (1999).

Other means of topical administration include delivery by electroporation, iontophoresis, phonophoresis, sonophoresis and microneedle or needle-free (e.g. Powderject™ and Bioject™) injection. Formulations for topical administration may be formulated to be immediate or modified release as described above.

Compounds of Formula 1 may also be administered intranasally or by inhalation, typically in the form of a dry powder, an aerosol spray, or nasal drops. An inhaler may be used to administer the dry powder, which comprises the API alone, a powder blend of the API and a diluent, such as lactose, or a mixed component particle that includes the API and a phospholipid, such as phosphatidylcholine. For intranasal use, the powder may include a bioadhesive agent, e.g., chitosan or cyclodextrin. A pressurized container, pump, sprayer, atomizer, or nebulizer, may be used to generate the aerosol spray from a solution or suspension comprising the API, one or more agents for dispersing, solubilizing, or extending the release of the API (e.g., EtOH with or without water), one or more solvents (e.g., 1,1,1,2-tetrafluoroethane or 1,1,1,2,3,3,3-heptafluoropropane) which serve as a propellant, and an optional surfactant, such as sorbitan trioleate, oleic acid, or an oligolactic acid. An atomizer using electrohydrodynamics may be used to produce a fine mist.

Prior to use in a dry powder or suspension formulation, the drug product is usually comminuted to a particle size suitable for delivery by inhalation (typically 90% of the particles, based on volume, having a largest dimension less than 5 microns). This may be achieved by any appropriate size reduction method, such as spiral jet milling, fluid bed jet milling, supercritical fluid processing, high pressure homogenization, or spray drying.

Capsules, blisters and cartridges (made, for example, from gelatin or hydroxypropylmethyl cellulose) for use in an inhaler or insufflator may be formulated to contain a powder mixture of the active compound, a suitable powder base such as lactose or starch, and a performance modifier such as L-leucine, mannitol, or magnesium stearate. The lactose may be anhydrous or monohydrated. Other suitable excipients include dextran, glucose, maltose, sorbitol, xylitol, fructose, sucrose, and trehalose.

A suitable solution formulation for use in an atomizer using electrohydrodynamics to produce a fine mist may contain from about 1 µg to about 20 mg of the API per actuation and the actuation volume may vary from about 1 µL to about 100 µL. A typical formulation may comprise one or more compounds of Formula 1, propylene glycol, sterile water, EtOH, and NaCl. Alternative solvents, which may be used instead of propylene glycol, include glycerol and polyethylene glycol.

Formulations for inhaled administration, intranasal administration, or both, may be formulated to be immediate or modified release using, for example, PGLA. Suitable flavors, such as menthol and levomenthol, or sweeteners, such as saccharin or sodium saccharin, may be added to formulations intended for inhaled/intranasal administration.

In the case of dry powder inhalers and aerosols, the dosage unit is determined by means of a valve that delivers a metered amount. Units are typically arranged to administer a metered dose or "puff" containing from about 10 µg to about 1000 µg of the API. The overall daily dose will typically range from about 100 µg to about 10 mg which may be administered in a single dose or, more usually, as divided doses throughout the day.

The active compounds may be administered rectally or vaginally, e.g., in the form of a suppository, pessary, or enema. Cocoa butter is a traditional suppository base, but various alternatives may be used as appropriate. Formulations for rectal or vaginal administration may be formulated to be immediate or modified release as described above.

Compounds of Formula 1 may also be administered directly to the eye or ear, typically in the form of drops of a micronized suspension or solution in isotonic, pH-adjusted, sterile saline. Other formulations suitable for ocular and aural administration include ointments, gels, biodegradable implants (e.g. absorbable gel sponges, collagen), non-biodegradable implants (e.g. silicone), wafers, lenses, and particulate or vesicular systems, such as niosomes or liposomes. The formulation may include one or more polymers and a preservative, such as benzalkonium chloride. Typical polymers include crossed-linked polyacrylic acid, polyvinyl alcohol, hyaluronic acid, cellulosic polymers (e.g., hydroxypropylmethylcellulose, hydroxyethylcellulose, methyl cellulose), and heteropolysaccharide polymers (e.g., gelan gum). Such formulations may also be delivered by iontophoresis. Formulations for ocular or aural administration may be formulated to be immediate or modified release as described above.

To improve their solubility, dissolution rate, taste-masking, bioavailability, or stability, compounds of Formula 1 may be combined with soluble macromolecular entities, including cyclodextrin and its derivatives and polyethylene glycol-containing polymers. For example, API-cyclodextrin complexes are generally useful for most dosage forms and routes of administration. Both inclusion and non-inclusion complexes may be used. As an alternative to direct complexation with the API, the cyclodextrin may be used as an auxiliary additive, i.e. as a carrier, diluent, or solubilizer. Alpha-, beta- and gamma-cyclodextrins are commonly used for these purposes. See, e.g., WO 91/11172, WO 94/02518, and WO 98/55148.

As noted above, one or more compounds of Formula 1, including compounds specifically named above, and their pharmaceutically active complexes, salts, solvates and hydrates, may be combined with each other or with one or more other active pharmaceutically active compounds to treat various diseases, conditions and disorders. In such cases, the active compounds may be combined in a single dosage form as described above or may be provided in the form of a kit which is suitable for coadministration of the compositions. The kit comprises (1) two or more different pharmaceutical compositions, at least one of which contains a compound of Formula 1; and (2) a device for separately retaining the two pharmaceutical compositions, such as a divided bottle or a divided foil packet. An example of such a kit is the familiar blister pack used for the packaging of tablets or capsules. The kit is suitable for administering different types of dosage forms (e.g., oral and parenteral) or for administering different pharmaceutical compositions at separate dosing intervals, or for titrating the different pharmaceutical compositions against one another. To assist with patient compliance, the kit typically comprises directions for administration and may be provided with a memory aid.

For administration to human patients, the total daily dose of the claimed and disclosed compounds is typically in the range of about 0.1 mg to about 3000 mg depending on the route of administration. For example, oral administration may require a total daily dose of from about 1 mg to about 3000 mg, while an intravenous dose may only require a total daily dose of from about 0.1 mg to about 300 mg. The total daily dose may be administered in single or divided doses and, at the physician's discretion, may fall outside of the typical ranges given above. Although these dosages are based on an average human subject having a mass of about 60 kg to about 70 kg, the physician will be able to determine the appropriate dose for a patient (e.g., an infant) whose mass falls outside of this weight range.

As noted above, the compounds of Formula 1 may be used to treat diseases, disorders, and conditions for which activation of SSTR4 is indicated. Such diseases, disorders, and conditions generally relate to any unhealthy or abnormal state in a subject for which the activation of SSTR4 provides a therapeutic benefit. More particularly, the compounds of Formula 1 may be used to treat CNS diseases, disorders or conditions, including Alzheimer's disease, and other forms of dementia (i.e., major or mild neurocognitive disorders) associated with one or more medical conditions, including frontotemporal lobar degeneration, Lewy body disease, vascular disease, traumatic brain injury, substance or medication use, HIV infection, prion disease, Parkinson's disease, and Huntington's disease. The compounds of Formula 1 may also be used to treat major or mild neurocognitive disorders associated with depression, schizophrenia, bipolar disorder, and autism. In addition, the compounds of Formula 1 may be used to treat anxiety and to treat epilepsy.

The claimed and disclosed compounds may be combined with one or more other pharmacologically active compounds or therapies to treat one or more disorders, diseases or conditions for which SSTR4 is indicated. Such combinations may offer significant therapeutic advantages, including fewer side effects, improved ability to treat underserved patient populations, or synergistic activity. For example, compounds of Formula 1, which include compounds specifically named above, and their pharmaceutically acceptable complexes, salts, solvates and hydrates, may be administered simultaneously, sequentially or separately in combination with one or more compounds or therapies for treating Alzheimer's disease, including beta-secretase inhibitors, gamma-secretase inhibitors, HMG-CoA reductase inhibitors, nonsteroidal anti-inflammatory drugs (NSAIDs, such as apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone, piroxicam, choline and magnesium salicylates, salsalate, and sulindac), vitamin E, and anti-amyloid antibodies. Specific examples of compounds used to treat Alzheimer's disease include donepezil, rivastigmine, memantine, and galantamine.

In addition to drugs used to improve cognition, the compounds of Formula 1 may be combined with sedatives, hypnotics, anxiolytics, antipsychotics, tranquilizers, and other medications that are used in the treatment of Alzheimer's disease. For example, the compounds of Formula 1 may be combined with one or more agents for treating depression (antidepressants) and/or schizophrenia (atypical or typical antipsychotics) including amitriptyline, amoxapine, aripiprazole, asenapine, bupropion, chlordiazepoxide, citalopram, chlorpromazine, clozapine, desipramine, desvenlafaxine, doxepin, duloxetine, escitalopram, fluoxetine, fluoxetine, fluphenazine, haloperidol, iloperidone, imipramine, isocarboxazid, lamotrigine, levomilnacipran, lurasidone, mirtazapine, nefazodone, nortriptyline, olanzapine, paliperidone, paroxetine, perphenazine, phenelzine, protriptyline, quetiapine, risperidone, selegiline, sertraline, tranylcypromine, trazodone, trimipramine, venlafaxine, vilazodone, and vortioxetine, and ziprasidone.

Likewise, the compounds of Formula 1 may be combined with one or more agents for treating anxiety (anxiolytics) including benzodiazepines (alprazolam, chlordiazepoxide, clobazepam, clonazepam, clorazepate, diazepam, estazolam, flurazepam, lorazepam, midazolam, oxazepam, prazepam, quazepam, temazepam, and triazolam), antihistamines (hydroxyzine), non-benzodiazepines (eszopiclone, zaleplon, zolpidem, and zopiclone) and buspirone.

The compounds of Formula 1 may also be combined with one or more agents for treating epilepsy (antiepileptics or anticonvulsants) including acetazolamide, carbamazepine, clobazam, clonazepam, eslicarbazepine acetate, ethosuximide, gabapentin, lacosamide, lamotrigine, levetiracetam, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, and zonisamide.

Biological Activity

The biological activity of the compound of Formula 1 with respect to SSTR4 may be determined using the following in vitro and in vivo methods.

Inhibition of Forskolin Stimulated cAMP in Cells Overexpressing SSTR4

This cell-based assay measures the ability of compounds to inhibit forskolin stimulated cAMP in CHO-K1 cells overexpressing SSTR4. CHO-K1 cells overexpressing SSTR4 (CHO-SSTR4) are purchased from DiscoveRx (product code 95-0059C2). The CHO-SSTR4 cells are maintained in F12K media with 10% Fetal Bovine Serum (Hyclone), 1% Pen/Strep (Life Technologies), and 800 µg/mL G418 (Life Technologies). To perform the assay, 3000 cells are plated per well in white 384-well plate (Corning 3570) in 50 complete media and the cells are allowed to attach for 16 hours in a 37° C., 5% $CO_2$ incubator. The next day, the culture media is removed from the cells and the cells are washed (added then removed) with Krebs Ringer Buffer (ZenBio, KRB-1000 mL). Test compounds are suspended in DMSO and diluted in stimulation buffer: Krebs Ringer Buffer plus 0.5% BSA (Roche), 300 µM IBMX (Sigma), and 350 nM forskolin (Sigma). The cells are incubated in 10 µL compound/stimulation buffer for 30 minutes at room temperature. Cellular cAMP levels are detected with a HTRF LANCE Ultra cAMP kit (Perkin Elmer, catalog number TRF0264).

The assay is performed in accordance with the manufacturer's instructions. Five µL of diluted Eu-W8044 labeled streptavidin (dilution: 1:50 in cAMP Detection Buffer) is added to each well. Then 5 µL of diluted biotin cAMP (dilution: 1:150 in cAMP Detection Buffer) is added to each well. The plates are covered and allowed to incubate for 60 minutes at room temperature on a shaker. HTRF (665 nm/615 nm) is read on a Perkin Elmer ENVISION plate reader. The $pEC_{50}$ values are generated using Activity Base for Screening Data Management.

SSTR4 I-125 Somatostatin Competition Binding Assay

This membrane-based assay measures the ability of compounds to competitively inhibit binding of I-125 labeled somatostatin to SSTR4 in membranes from CHO-K1 that overexpress SSTR4. Membranes from CHO-K1 cells overexpressing SSTR4 are purchased from Perkin Elmer (catalog number ES-524-M400UA). Test compounds are suspended in DMSO and then diluted in assay buffer (25 mM HEPES pH 7.4, 10 mM $MgCl_2$, 1 mM $CaCl_2$, 0.5% BSA) plus 0.2 nM I-125 labeled somatostatin (Perkin Elmer catalog number NEX389). Fifty μL of compound/I-125 somatostatin in assay buffer are added per well to 96-well poly-propylene plate. Then 1 μg of SSTR4 membranes in 50 μL assay buffer are added per well. The Plate is incubated for 60 minutes at room temperature. FilterMat A filters (Perkin Elmer catalog number 1450-421) are pre-soaked in 0.5% PEI (Sigma catalog number P3143). The contents of the assay plate are transferred to filters with a TomTech harvester and washed 5 times with 20 mM HEPES, 100 mM NaCl. The filters are dried in a microwave oven then transferred to sample bag containing a scintillator sheet (Perkin Elmer catalog number 1450-441). The scintillator sheets are melted to filters using a heat block. The filters are then read in a MicroBeta scintillation counter. Binding Ki curves are generated using Activity Base for Screening Data Management and the results are reported as $pIC_{50}$.

SSTR1 I-125 Somatostatin Competition Binding Assay for Selectivity Versus SSTR1

This membrane-based assay measures the ability of compounds to competitively inhibit binding of I-125 labeled somatostatin to SSTR1 in membranes from CHO-K1 that overexpress SSTR1. Membranes from CHO-K1 cells overexpressing SSTR1 are purchased from Perkin Elmer (catalog number ES-520-M400UA). Test compounds are suspended in DMSO and then diluted in assay buffer (25 mM HEPES pH 7.4, 10 mM $MgCl_2$, 1 mM $CaCl_2$, 0.5% BSA) plus 0.4 nM I-125 labeled somatostatin (Perkin Elmer catalog number NEX389). Fifty μL of compound/I-125 somatostatin in assay buffer are added per well to 96-well poly-propylene plate. Then 10 μg of SSTR1 membranes in 50 μL assay buffer are added per well. The plate is incubated for 60 minutes at room temperature. FilterMat A filters (Perkin Elmer catalog number 1450-421) are pre-soaked in 0.5% PEI (Sigma catalog number P3143). The contents of the assay plate are transferred to filters with a TomTech harvester and washed 5 times with 20 mM HEPES, 100 mM NaCl. The filters are dried in a microwave oven then transferred to sample bag containing a scintillator sheet (Perkin Elmer catalog number 1450-441). The scintillator sheets are melted to the filters using a heat block. The filters are then read in a MicroBeta scintillation counter. Binding Ki curves are generated using Activity Base for Screening Data Management and the results are reported as $pIC_{50}$.

In vivo Screening Using Subcutaneous Pentylenetetrazole (PTZ)

Swiss-Webster mice, 6-8 weeks old are used in the subcutaneous PTZ model of seizures. PTZ is a GABAergic agent that blocks GABA receptors, thereby disinhibiting all CNS systems and inducing seizures in animals. Seizures can be assessed and quantified by observation of the animals in the study. Thus, this model provides a screening model to test compounds with anti-convulsant activity in mice, which is derived from the activity of the compound on the inhibitory receptor SSTR4. In accordance with the method, Swiss-Webster mice which are 6 to 8 weeks old are acclimatized to the study room prior to start the experiment (1 hour). Animals (n=6/group) are then blindly dosed with vehicle or test compound, and 15 minutes later are dosed subcutaneously with PTZ. Animals are scored based on the time it takes them to get a seizure that impairs their capacity to stand. The time is scored as latency to seizure. Number and degree of seizures are also scored, but not used in the final data.

EXAMPLES

The following examples are intended to be illustrative and non-limiting and represent specific embodiments of the present invention.

$^1$H Nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: $CDCl_3$ (deuterochloroform), DMSO-$d_6$ (deuterodimethylsulfoxide), $CD_3OD$ (deuteromethanol), $CD_3CN$ (deuteroacetonitrile), and THF-$d_8$ (deuterotetrahydrofuran). The mass spectra (m/z for $[M+H]^+$) were recorded using either electrospray ionization (ESI-MS) or atmospheric pressure chemical ionization (APCI-MS) mass spectrometry.

Where indicated, products of certain preparations and examples are purified by mass-triggered HPLC, flash chromatography, preparative TLC or SFC. Reverse phase chromatography is typically carried out on a column (e.g., Gemini™ 5 μm C18 110 Å, Axia™ 30×75 mm, 5 μm) under acidic conditions ("acid mode") eluting with ACN and water mobile phases containing 0.035% and 0.05% trifluoroacetic acid (TFA), respectively, or under basic conditions ("basic mode") eluting with water and 20/80 (v/v) water/acetonitrile mobile phases, both containing 10 mM $NH_4HCO_3$. Preparative TLC is typically carried out on silica gel 60 $F_{254}$ plates. The preparations and examples may employ SFC to separate enantiomers. After isolation by chromatography, the solvent is removed and the product is obtained by drying in a centrifugal evaporator (e.g., GeneVac™), rotary evaporator, evacuated flask, etc. Reactions in an inert (e.g., nitrogen) or reactive (e.g., $H_2$) atmosphere are typically carried out at a pressure of about 1 atmosphere (14.7 psi).

Preparation 1: methyl 5,6-dichloropyrazine-2-carboxylate

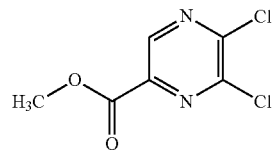

Step A: methyl 5-hydroxypyrazine-2-carboxylate

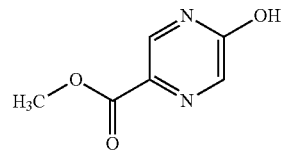

To a solution of 5-hydroxypyrazine-2-carboxylic acid (200 g, 1.43 mol) in MeOH (1.5 L) was added SOCl$_2$ (339.68 g, 2.86 mol, 207.12 mL) dropwise at 0° C. The mixture was stirred at 70° C. for 16 hours and then concentrated under reduced pressure. The resulting residue was triturated with EtOAc (500 mL) and filtered to give the title compound as a black-brown solid (229 g, 98.9% yield, 95% purity). $^1$H NMR (400 MHz, CD$_3$OD) δ ppm 3.90 (s, 3H), 8.04 (s, 1H), 8.19 (s, 1H), 8.87 (s, 1H).

Step B: methyl 6-bromo-5-hydroxypyrazine-2-carboxylate

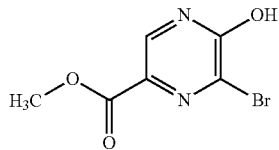

To a solution of methyl 5-hydroxypyrazine-2-carboxylate (114 g, 739.67 mmol) in DMF (1.1 L) was added NBS (138.23 g, 776.65 mmol) portion-wise at 0° C. The mixture was stirred at 20° C. for 16 hours and was then diluted with water (1 L) and extracted with EtOAc (1 L×6). The combined organic layers were washed with brine (500 mL), dried over Na$_2$SO$_4$, filtered and concentrated under reduced pressure to give the title compound as a red gum (195 g, contains 36% DMF). $^1$H NMR (400 MHz, CD$_3$OD) δ ppm 3.89 (s, 3H), 8.17 (s, 1H).

Step C: methyl 5,6-dichloropyrazine-2-carboxylate

To methyl 6-bromo-5-hydroxypyrazine-2-carboxylate (100 g, 429.15 mmol) was added SOCl$_2$ (445.18 mL, 6.14 mol). The mixture was stirred at 80° C. for 16 hours at which time TLC (petroleum ether/EtOAc=5/1) indicated the reaction was complete. The reaction mixture was concentrated under reduced pressure to give a residue, which was diluted with EtOAc (1000 mL×2) followed by slow addition of water (500 mL). The combined organic layers were washed with saturated aq NaHCO$_3$ (1000 mL) and then with brine (300 mL). The organic layer was dried over anhydrous Na$_2$SO$_4$, filtered and concentrated under reduced pressure to give a residue, which was purified by column chromatography (SiO$_2$) using a gradient of petroleum ether/EtOAc (100:1 to 10:1) to give the title compound as a light-yellow solid (22.2 g, 24.3% yield, 97% purity). $^1$H NMR (400 MHz, CDCl$_3$) δ ppm 4.02 (s, 3H), 8.98 (s, 1H); ESI-MS m/z [M+H]$^+$ 207.0.

Preparation 2: (Z)-(2-(4-fluorophenyl)-2-(4,4,5,5-tetramethyl-1,3,2-dioxaborolan-2-yl)vinyl)trimethylsilane

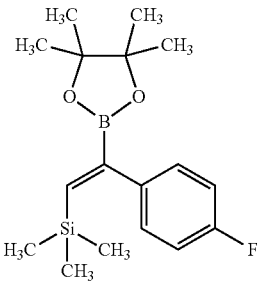 [SMILES: CC1(C)OB(/C(=C/[Si](C)(C)C)c2ccc(F)cc2)OC1(C)C]

A mixture of CuCl (514.8 mg, 5.20 mmol, 124.35 μL), t-BuONa (2 g, 20.80 mmol) and Xantphos (3.61 g, 6.24 mmol) in THF (50 mL) was stirred at 25° C. for 0.5 hours. A solution of 4,4,4',4',5,5,5',5'-octamethyl-2,2'-bi(1,3,2-dioxaborolane) (15.85 g, 62.40 mmol) in THF (30 mL) was added to the mixture, which was stirred for an additional 0.5 hours at 25° C. To the resulting dark brown solution was added ((4-fluorophenyl)ethynyl)trimethylsilane (10 g, 52.00 mmol) in THF (30 mL) followed by MeOH (4.21 mL). The mixture was stirred at 50° C. for another 16 hours and then diluted with THF (50 mL) and filtered through a pad of Celite®. The filtrate was concentrated in vacuo and the solid phase was triturated with petroleum ether (50 mL) for 0.5 hours. The filter cake was discarded. The filtrate was concentrated in vacuo and purified by flash silica gel chromatography, using EtOAc/petroleum ether as eluent. The product-containing fractions were concentrated to afford the title compound as light-yellow solid (10.8 g, 64%). $^1$H NMR (400 MHz, CDCl$_3$) δ ppm 0.00 (s, 9H), 1.38 (s, 12H), 6.96 (s, 1H), 7.06-7.10 (m, 2H), 7.20-7.24 (m, 2H).

Preparation 3: 6-chloro-5-(1-(4-fluorophenyl)vinyl) pyrazine-2-carboxylic acid

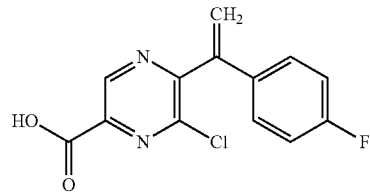 [SMILES: C=C(c1ccc(F)cc1)c1ncc(C(=O)O)nc1Cl]

Step A: methyl (E)-6-chloro-5-(1-(4-fluorophenyl)-2-(trimethylsilyl)vinyl)pyrazine-2-carboxylate

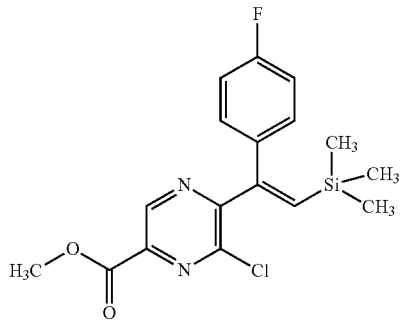

To a round bottom flask containing methyl 5,6-dichloropyrazine-2-carboxylate (1.0 g, 4.83 mmol) and (Z)-(2-(4-fluorophenyl)-2-(4,4,5,5-tetramethyl-1,3,2-dioxaborolan-2-yl)vinyl)trimethylsilane (1.62 g, 5.07 mmol) in THF (3 mL) and water (0.5 mL) were added PdCl$_2$(dppf)·CH$_2$Cl$_2$ (394.48 mg, 483.06 µmol) and Na$_2$CO$_3$ (1.02 g, 9.66 mmol). The reaction mixture was stirred at 50° C. for 3 hours under N$_2$ and was then diluted with water (50 mL) and extracted with EtOAc (100 mL×2). The combined organic phases were washed with water (50 mL) and with brine (50 mL), dried over anhydrous Na$_2$SO$_4$, filtered and concentrated under reduced pressure. The concentrate was purified by silica gel column chromatography, using a gradient of petroleum ether/EtOAc (1:0 to 9:1) to give the title compound as a yellow solid (1.47 g, 57.1%). $^1$H NMR (400 MHz, DMSO-d$_6$) δ ppm 0.00 (s, 9H), 3.93 (s, 3H), 6.41 (s, 1H), 7.20-7.31 (m, 4H), 9.15 (s, 1H); ESI-MS m/z [M+H]$^+$ 364.8.

Step B: methyl 6-chloro-5-(1-(4-fluorophenyl)vinyl)pyrazine-2-carboxylate

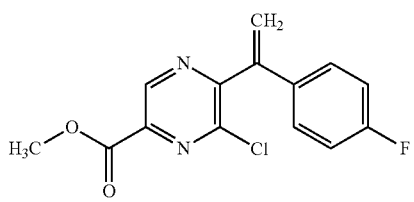 [SMILES: C=C(c1ccc(F)cc1)c1ncc(C(=O)OC)nc1Cl]

A mixture of methyl (E)-6-chloro-5-(1-(4-fluorophenyl)-2-(trimethylsilyl)vinyl)pyrazine-2-carboxylate (650 mg, 1.78 mmol, 1.0 equiv.) in TFA (7 mL) was stirred at 50° C. for 20 hours and then concentrated under reduced pressure. The resulting residue was dissolved in EtOAc (30 mL) and the mixture adjusted to pH 8 by addition of saturated aq Na$_2$CO$_3$. The organic layers were separated, dried over anhydrous Na$_2$SO$_4$, filtered and concentrated under reduced pressure. The concentrate was purified by silica gel column chromatography, using a gradient of petroleum ether/EtOAc (1:0 to 8:1) to give the title compound as a light-yellow solid (440 mg, 82.7%). $^1$H NMR (400 MHz, CDCl$_3$) δ ppm 4.06 (s, 3H), 5.69 (s, 1H), 5.99 (s, 1H), 6.99-7.09 (m, 2H), 7.16-7.24 (m, 2H), 9.25 (s, 1H); ESI-MS m/z [M+H]$^+$ 293.1.

Step C: 6-chloro-5-(1-(4-fluorophenyl)vinyl)pyrazine-2-carboxylic acid

A solution of LiOH·H$_2$O (118.01 mg, 2.81 mmol) in water (1.25 mL) was added to a solution of methyl 6-chloro-5-(1-(4-fluorophenyl)vinyl)pyrazine-2-carboxylate (420 mg, 1.41 mmol) in THF (5 mL). The mixture was stirred at 30° C. for 1 hour and was then acidified to pH 3 by addition of 1.0 N HCl and extracted with EtOAc (60 mL×2). The organic layers were dried over anhydrous Na$_2$SO$_4$, filtered and concentrated under reduced pressure to give the title compound as a white solid (370 mg, 94.4%). $^1$H NMR (400 MHz, DMSO-d$_6$) δ ppm 5.65 (s, 1H), 6.17 (s, 1H), 7.07-7.26 (m, 2H), 7.30-7.43 (m, 2H), 9.20 (s, 1H), 13.63-14.42 (m, 1H); ESI-MS m/z [M+H]$^+$ 279.1.

Preparation 4: 6-(1-(4-fluorophenyl)ethyl)-5-(((R)-1-methylpyrrolidin-3-yl)amino)pyrazine-2-carboxylic acid

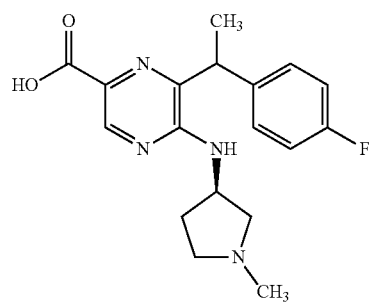 [SMILES: CC(c1ccc(F)cc1)c1nc(C(=O)O)cnc1N[C@@H]1CCN(C)C1]

Step A: methyl (R)-6-chloro-5-((1-methylpyrrolidin-3-yl)amino)pyrazine-2-carboxylate

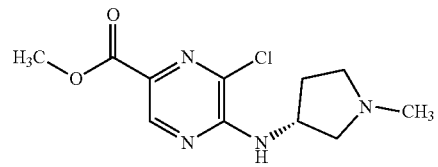

To a solution of methyl 5,6-dichloropyrazine-2-carboxylate (1 g, 4.83 mmol) in dioxane (48.3 mL) was added DIPEA (1.266 mL, 7.25 mmol) and (R)-1-methylpyrrolidin-3-amine (0.629 g, 6.28 mmol). The solution was stirred at room temperature for 16 hours and then purified by silica gel column chromatography (ISCO® NH column) to give the title compound as a yellow solid (570 mg, 43.6%).

Step B: methyl (R)-6-(1-(4-fluorophenyl)vinyl)-5-((1-methylpyrrolidin-3-yl)amino)pyrazine-2-carboxylate

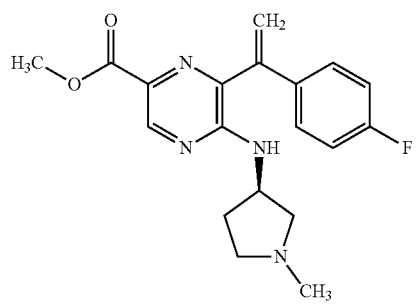 [SMILES: C=C(c1ccc(F)cc1)c1nc(C(=O)OC)cnc1N[C@@H]1CCN(C)C1]

A mixture of methyl (R)-6-chloro-5-((1-methylpyrrolidin-3-yl)amino)pyrazine-2-carboxylate (370 mg, 1.367 mmol), 2-(1-(4-fluorophenyl)vinyl)-4,4,5,5-tetramethyl-1,3,2-dioxaborolane (576 mg, 2.323 mmol), Pd(dppf)Cl₂ (100 mg, 0.137 mmol) and Na₂CO₃ (1367 µL, 2.73 mmol) in dioxane (6834 µL) was degassed with N₂ for 5 minutes and then heated in a sealed tube at 110° C. for 16 hours. Following reaction, the mixture was purified by silica gel column chromatography (ISCO® NH column) to give the title compound as a brown oil (170 mg, 34.9%).

Step C: methyl 6-(1-(4-fluorophenyl)ethyl)-5-(((R)-1-methylpyrrolidin-3-yl)amino)pyrazine-2-carboxylate

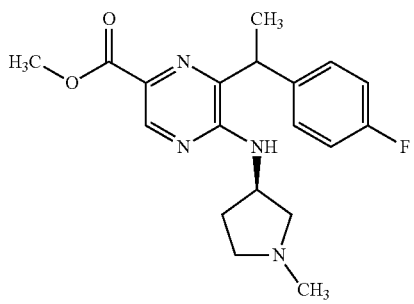

A mixture of methyl (R)-6-(1-(4-fluorophenyl)vinyl)-5-((1-methylpyrrolidin-3-yl)amino)pyrazine-2-carboxylate (170 mg, 0.477 mmol) and palladium on carbon (15.23 mg, 0.143 mmol, 10%) in EtOAc (4.8 mL) was stirred under H₂ at room temperature for 5 hours. Following reaction, the mixture was filtered and concentrated to give the title compound as a yellow oil, which was used without further purification.

Step D: 6-(1-(4-fluorophenyl)ethyl)-5-(((R)-1-methylpyrrolidin-3-yl)amino)pyrazine-2-carboxylic acid To a solution of methyl 6-(1-(4-fluorophenyl)ethyl)-5-(((R)-1-methylpyrrolidin-3-yl)amino)pyrazine-2-carboxylate (171 mg, 0.477 mmol) in dioxane (3.2 mL) and MeOH (1590 µL) was added a solution of KOH (716 µL, 1.431 mmol). The mixture was stirred at room temperature overnight and then adjusted to pH 5 by adding 1.0 M HCl. The solvent was removed to give the title compound as a light-yellow solid (280 mg, 99%).

Preparation 5: 6-(1-(4-fluorophenyl)ethyl)-5-((2-(pyrrolidin-1-yl)ethyl)amino)pyrazine-2-carboxylic acid

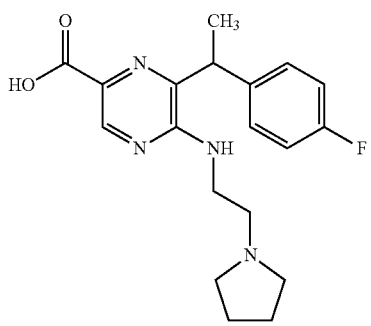

Step A: methyl 6-chloro-5-((2-(pyrrolidin-1-yl)ethyl)amino)pyrazine-2-carboxylate

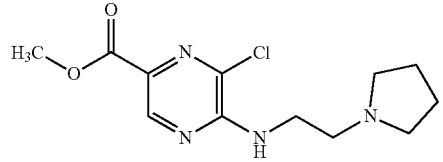 [SMILES: COC(=O)c1cnc(NCCN2CCCC2)c(Cl)n1]

To a mixture of methyl 5,6-dichloropyrazine-2-carboxylate (57 g, 275.34 mmol) in dioxane (1.3 L) were added dropwise DIPEA (72 mL, 53.42 g, 413.36 mmol) and 2-pyrrolidin-1-ylethanamine (32.38 g, 283.60 mmol) in dioxane (130 mL) at 25° C. The mixture was stirred at 25° C. for 72 hours and then concentrated to dryness. The product was triturated with petroleum ether/EtOAc (3:1, 500 mL) at 25° C. for 10 minutes. The resulting solid was filtered, dissolved in EtOAc (1000 mL) and washed with saturated aq NaHCO₃ (500 mL). The aqueous layer was extracted with EtOAc (1000 mL×2). The combined organic phase was washed with brine (500 mL×2), dried over Na₂SO₄, and concentrated to give the title compound as a brown oil (71 g, 88%). ¹H NMR (400 MHz, CDCl₃) δ ppm 1.82 (dt, J=6.9, 3.3 Hz, 4H), 2.55-2.61 (m, 4H), 2.77 (t, J=6.1 Hz, 2H), 3.55-3.64 (m, 2H), 3.95 (s, 3H), 6.52 (br s, 1H), 8.73 (s, 1H); ESI-MS m/z [M+H]⁺ 285.1.

Step B: methyl 6-(1-(4-fluorophenyl)vinyl)-5-((2-(pyrrolidin-1-yl)ethyl)amino)pyrazine-2-carboxylate

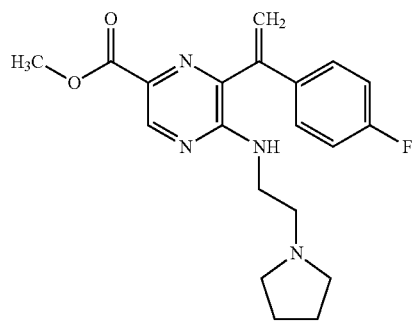 [SMILES: C=C(c1ccc(F)cc1)c1nc(C(=O)OC)cnc1NCCN1CCCC1]

To a stirred mixture of methyl 6-chloro-5-(2-pyrrolidin-1-ylethylamino)pyrazine-2-carboxylate (50 g, 175.60 mmol) in dioxane (1500 mL) and water (230 mL), were added 2-(1-(4-fluorophenyl)vinyl)-4,4,5,5-tetramethyl-1,3,2-dioxaborolane (52.28 g, 210.72 mmol), PdCl₂(dppf)·CH₂Cl₂ (11.47 g, 14.05 mmol) and Et₃N (195.53 mL, 1.40 mol). The mixture was degassed and purged with N₂ (3×) and then stirred at 110° C. for 16 hours under N₂. The reaction mixture was purified by silica gel column chromatography, using a gradient of petroleum ether/EtOAc (10:1 to 0:1) and then triturated with petroleum ether/EtOAc (3:1, 80 mL) at 25° C. for 10 minutes to give the title compound as light-yellow solid (36 g, 55%). ¹H NMR (400 MHz, CDCl₃) δ ppm 1.63 (br s, 4H), 2.30 (br s, 4H), 2.50 (br t, J=5.7 Hz, 2H), 3.30-3.46 (m, 2H), 3.93 (s, 3H), 5.67 (s, 2H), 5.85 (s, 1H), 7.00 (br t, J=8.5 Hz, 2H), 7.19-7.37 (m, 2H), 8.80 (s, 1H); ESI-MS m/z [M+H]⁺ 371.2.

Step C: methyl 6-(1-(4-fluorophenyl)ethyl)-5-((2-(pyrrolidin-1-yl)ethyl)amino)pyrazine-2-carboxylate

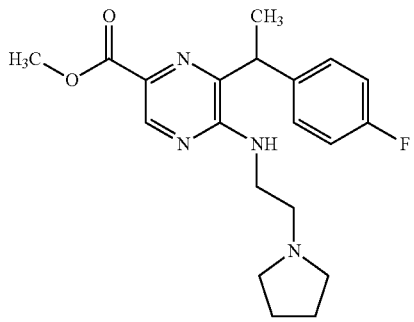

To a round bottom flask containing methyl 6-(1-(4-fluorophenyl)vinyl)-5-((2-(pyrrolidin-1-yl)ethyl)amino)pyrazine-2-carboxylate (12 g, 32.40 mmol) in MeOH (100 mL) was added Pd/C (2 g, 10%, wet basis). The suspension was degassed under vacuum and purged with $H_2$ several times. The mixture was stirred at 25° C. for 16 hours under $H_2$ (15 psi) and then diluted with MeOH (100 mL) and filtered through a pad of Celite®. The filtrate was concentrated in vacuo to give the title compound as a red gum (12 g, 92.5%). $^1$H NMR (400 MHz, CDCl$_3$) δ ppm 1.70 (br d, J=6.8 Hz, 4H), 1.76 (br s, 3H), 2.32-2.55 (m, 4H), 2.61-2.74 (m, 1H), 3.29-3.48 (m, 2H), 3.50 (s, 1H), 3.96 (s, 3H), 4.10 (q, J=7.0 Hz, 1H), 5.79 (br s, 1H), 6.90-7.03 (m, 2H), 7.13-7.23 (m, 2H), 8.72 (s, 1H); ESI-MS m/z [M+H]$^+$ 373.2.

Step D: 6-(1-(4-fluorophenyl)ethyl)-5-((2-(pyrrolidin-1-yl)ethyl)amino)pyrazine-2-carboxylic acid To a solution of methyl 6-(1-(4-fluorophenyl)ethyl)-5-((2-(pyrrolidin-1-yl)ethyl)amino)pyrazine-2-carboxylate (5.3 g, 14.23 mmol) in THF (50 mL) was added a solution of LiOH·H$_2$O (895.68 mg, 21.35 mmol) in water (10 mL). The mixture was stirred at 25° C. for 16 hours and then washed with MTBE (20×3 mL). The aqueous phase was acidified to pH 5 by addition of 1 M HCl and then extracted with EtOAc (100 mL×3). The combined organic layers were concentrated in vacuo to give the title compound as a light-yellow solid (3 g, 56%). $^1$H NMR (400 MHz, CD$_3$OD) δ ppm 1.68 (dd, J=6.7, 2.1 Hz, 3H), 2.01 (br d, J=2.3 Hz, 4H), 3.21 (br s, 2H), 3.33-3.46 (m, 4H), 3.80 (br s, 2H), 4.31 (br d, J=7.3 Hz, 1H), 6.94-7.05 (m, 2H), 7.33 (br t, J=6.0 Hz, 2H), 8.66 (s, 1H); ESI-MS m/z [M+H]$^+$ 359.2.

Preparation 6: methyl (S)-6-(1-(4-fluorophenyl)ethyl)-5-((2-(pyrrolidin-1-yl)ethyl)amino)pyrazine-2-carboxylate

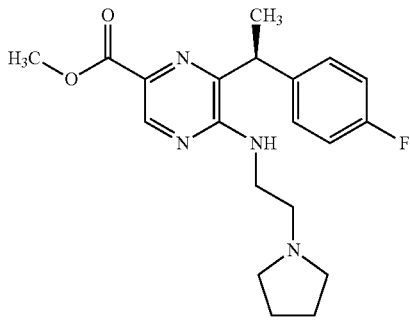 [SMILES: COC(=O)c1cnc(NCCN2CCCC2)c([C@@H](C)c2ccc(F)cc2)n1]

Preparation 7: methyl (R)-6-(1-(4-fluorophenyl)ethyl)-5-((2-(pyrrolidin-1-yl)ethyl)amino)pyrazine-2-carboxylate

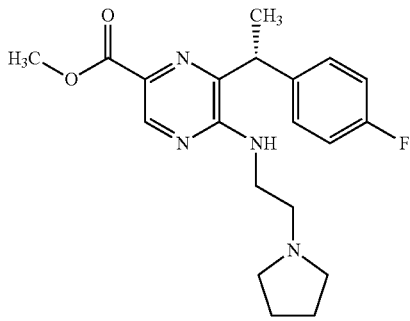 [SMILES: COC(=O)c1cnc(NCCN2CCCC2)c([C@H](C)c2ccc(F)cc2)n1]

and

Methyl 6-(1-(4-fluorophenyl)ethyl)-5-((2-(pyrrolidin-1-yl)ethyl)amino)pyrazine-2-carboxylate (7.3 g, 19.60 µmol) was separated by SFC (Chiralpak® IC-H, 5 µm, 30 mm ID×250 mm) using H$_2$O (0.1% NH$_3$)/MeOH (55:45) to give two enantiomers. The early-eluting enantiomer was assigned as S-stereochemical configuration and was isolated as a red gum (3 g, 46.2%). $^1$H NMR (400 MHz, CDCl$_3$) δ ppm 1.71 (d, J=7.1 Hz, 3H), 1.75 (dt, J=6.4, 3.1 Hz, 4H), 2.30-2.37 (m, 2H), 2.38-2.51 (m, 3H), 2.64 (ddd, J=12.2, 7.7, 4.9 Hz, 1H), 3.28-3.47 (m, 2H), 3.73 (q, J=7.1 Hz, 1H), 3.96 (s, 3H), 5.73 (br s, 1H), 6.93-7.02 (m, 2H), 7.15-7.21 (m, 2H), 8.72 (s, 1H); ESI-MS m/z [M+H]$^+$ 373.1. The later-eluting enantiomer was assigned R-stereochemical configuration and was isolated as a red gum (3.5 g, 53.8%). $^1$H NMR (400 MHz, CDCl$_3$) δ ppm 1.71 (d, J=7.1 Hz, 3H), 1.76 (dt, J=6.3, 3.1 Hz, 4H), 2.32-2.39 (m, 2H), 2.40-2.52 (m, 3H), 2.66 (ddd, J=12.1, 7.6, 4.6 Hz, 1H), 3.29-3.48 (m, 2H), 3.73 (q, J=6.9 Hz, 1H), 3.96 (s, 3H), 5.76 (br s, 1H), 6.93-7.00 (m, 2H), 7.15-7.22 (m, 2H), 8.72 (s, 1H); ESI-MS m/z [M+H]$^+$ 373.1.

Preparation 8: (S)-6-(1-(4-fluorophenyl)ethyl)-5-((2-(pyrrolidin-1-yl)ethyl)amino)pyrazine-2-carboxylic acid

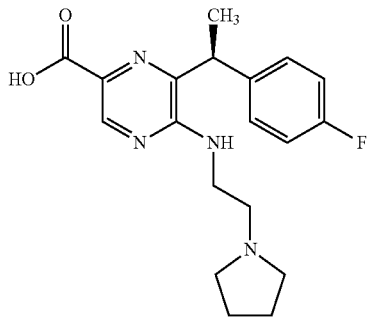 [SMILES: C[C@@H](c1ccc(F)cc1)c1nc(C(=O)O)cnc1NCCN1CCCC1]

To a solution of methyl (S)-6-(1-(4-fluorophenyl)ethyl)-5-((2-(pyrrolidin-1-yl)ethyl)amino)pyrazine-2-carboxylate (0.2 g, 537.01 μmol) in THF (2 mL) was added a solution of LiOH·H$_2$O (45.07 mg, 1.07 mmol) in water (0.5 mL). The mixture was stirred at 25° C. for 16 hours and was then washed with MTBE (3 mL×3). The aqueous phase was acidified to pH 6~7 using 1.0 N HCl and was subsequently concentrated under reduced pressure to give the title compound as a light-yellow gum (220 mg, containing 10% LiCl). $^1$H NMR (400 MHz, CD$_3$OD) δ ppm 1.67 (br d, J=6.0 Hz, 3H), 1.92-2.00 (m, 6H), 3.21 (br s, 4H), 3.75 (t, J=5.4 Hz, 2H), 4.29 (br d, J=6.4 Hz, 1H), 6.96 (t, J=8.7 Hz, 2H), 7.34 (br dd, J=8.3, 5.6 Hz, 2H), 8.59 (s, 1H).

Preparation 9: (R)-6-(1-(4-fluorophenyl)ethyl)-5-((2-(pyrrolidin-1-yl)ethyl)amino)pyrazine-2-carboxylic acid

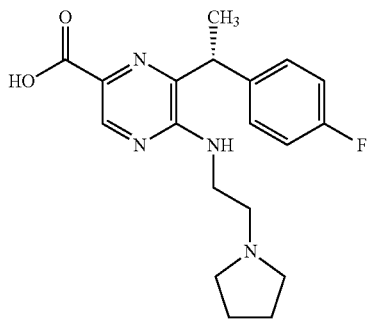 [SMILES: C[C@H](c1ccc(F)cc1)c1nc(C(=O)O)cnc1NCCN1CCCC1]

To a solution of methyl (R)-6-(1-(4-fluorophenyl)ethyl)-5-((2-(pyrrolidin-1-yl)ethyl)amino)pyrazine-2-carboxylate (2.9 g, 7.79 mmol) in THF (30 mL) and water (6 mL) was added LiOH·H$_2$O (653.51 mg, 15.57 mmol) at 25° C. The reaction mixture was stirred at 25° C. for 16 hours and then diluted with water (20 mL) and washed with EtOAc (10 mL×2). The aqueous layer was acidified to pH~6 by addition of 1.0 N HCl, forming a precipitate which was collected by filtration. The filter cake was washed with water (4 mL×2) and dried with toluene and EtOAc in vacuo to give the title compound as a light-yellow solid (1.55 g, 55.5%). $^1$H NMR (400 MHz, CD$_3$OD) δ ppm 1.65 (d, J=7.1 Hz, 3H), 1.96-2.01 (m, 4H), 3.18-3.29 (m, 4H), 3.31-3.38 (m, 2H), 3.74 (t, J=5.7 Hz, 2H), 4.23 (q, J=7.1 Hz, 1H), 6.94 (t, J=8.8 Hz, 2H), 7.25-7.40 (m, 2H), 8.56 (s, 1H); ESI-MS m/z [M+H]$^+$ 359.2.

Preparation 10: 6-(4-fluorobenzyl)-3-methyl-5-((2-(pyrrolidin-1-yl)ethyl)amino)pyrazine-2-carboxylic acid

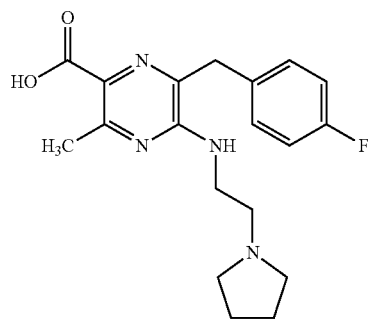 [SMILES: Cc1nc(NCCN2CCCC2)c(Cc2ccc(F)cc2)nc1C(=O)O]

Step A: methyl 6-chloro-3-methyl-5-((2-(pyrrolidin-1-yl)ethyl)amino)pyrazine-2-carboxylate

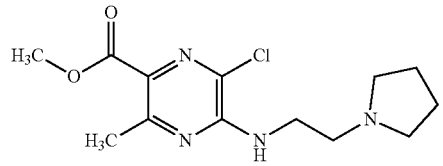 [SMILES: COC(=O)c1nc(Cl)c(NCCN2CCCC2)nc1C]

To a solution of methyl 5,6-dichloro-3-methylpyrazine-2-carboxylate (1.0 g, 4.52 mmol) in dioxane (30.2 mL) were added DIPEA (1.185 mL, 6.79 mmol) and 2-(pyrrolidin-1-yl)ethanamine (0.672 g, 5.88 mmol). The solution was stirred at room temperature for 16 hours and then purified by silica gel chromatography (NH column) to give the title compound as a yellow solid (1 g, 74%). ESI-MS m/z [M+H]$^+$ 299.1.

Step B: methyl 6-(4-fluorobenzyl)-3-methyl-5-((2-(pyrrolidin-1-yl)ethyl)amino)pyrazine-2-carboxylate

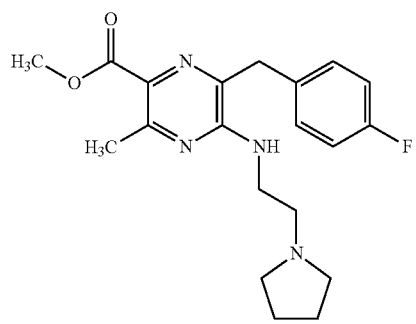 [SMILES: COC(=O)c1nc(Cc2ccc(F)cc2)c(NCCN2CCCC2)nc1C]

A mixture of methyl 6-chloro-3-methyl-5-((2-(pyrrolidin-1-yl)ethyl)amino)pyrazine-2-carboxylate (300 mg, 1.004 mmol), 2-(4-fluorobenzyl)-4,4,5,5-tetramethyl-1,3,2-dioxaborolane (427 mg, 1.807 mmol), Na$_2$CO$_3$ (1004 µL, 2.008 mmol) and PdCl$_2$(dppf) (73.5 mg, 0.100 mmol) in dioxane (5.0 mL) was degassed with N$_2$ for 5 minutes and then heated at 110° C. for 16 hours. The mixture was purified by silica gel chromatography (NH column) using a gradient of 10-50% EtOAc in heptane to give the title compound as a yellow solid (210 mg, 56.2%). ESI-MS m/z [M+H]$^+$ 373.2.

Step C: 6-(4-fluorobenzyl)-3-methyl-5-((2-(pyrrolidin-1-yl)ethyl)amino)pyrazine-2-carboxylic acid To a solution of methyl 6-(4-fluorobenzyl)-3-methyl-5-((2-(pyrrolidin-1-yl)ethyl)amino)pyrazine-2-carboxylate (210 mg, 0.564 mmol) in dioxane (3.6 mL) and MeOH (1.9 mL) was added an aq solution of 2.0 N KOH (564 µL, 1.128 mmol). The reaction mixture was stirred at room temperature overnight and then adjusted to pH 7 by the addition of 1.0 M HCl. After removal of solvent, water (10 mL) was added and the aqueous solution was washed with EtOAc (10 mL×2). The aqueous solution was dried to give the title compound as a yellow solid (205 mg, 80% purity) in a mixture with NaCl. The product was used without further purification. ESI-MS m/z [M+H]$^+$ 359.2.

Preparation 11: 6-(1-(4-fluorophenyl)ethyl)-3-methyl-5-((2-(pyrrolidin-1-yl)ethyl)amino)pyrazine-2-carboxylic acid

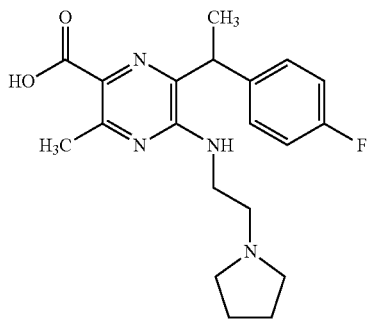 [SMILES: Cc1nc(NCCN2CCCC2)c(C(C)c2ccc(F)cc2)nc1C(=O)O]

Step A: methyl 6-(1-(4-fluorophenyl)vinyl)-3-methyl-5-((2-(pyrrolidin-1-yl)ethyl)amino)pyrazine-2-carboxylate

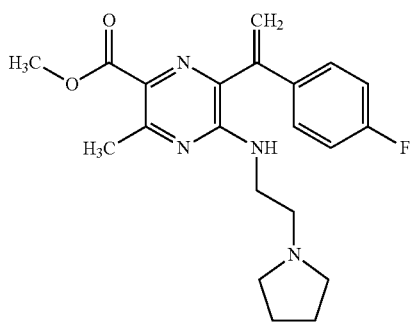 [SMILES: C=C(c1ccc(F)cc1)c1nc(C(=O)OC)c(C)nc1NCCN1CCCC1]

A mixture of methyl 6-chloro-3-methyl-5-((2-(pyrrolidin-1-yl)ethyl)amino)pyrazine-2-carboxylate (120 mg, 0.402 mmol), 2-(1-(4-fluorophenyl)vinyl)-4,4,5,5-tetramethyl-1,3,2-dioxaborolane (179 mg, 0.723 mmol), Na$_2$CO$_3$ (446 µL, 0.803 mmol) and PdCl$_2$(dppf) (29.4 mg, 0.040 mmol) in dioxane (2.0 mL) was degassed with N$_2$ for 5 minutes, and then heated at 110° C. for 16 hours. The reaction mixture was purified by silica gel chromatography (NH column) using a gradient of 10-50% EtOAc in heptane to give the title compound as a light-yellow oil (112 mg, 72.5%).

Step B: methyl 6-(1-(4-fluorophenyl)ethyl)-3-methyl-5-((2-(pyrrolidin-1-yl)ethyl)amino)pyrazine-2-carboxylate

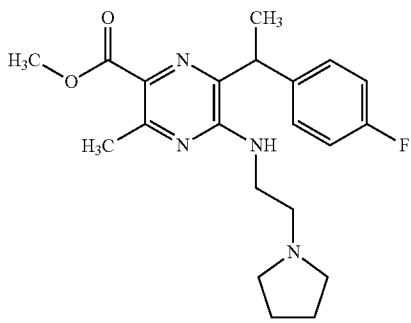 [SMILES: COC(=O)c1nc(C(C)c2ccc(F)cc2)c(NCCN2CCCC2)nc1C]

A mixture of methyl 6-(1-(4-fluorophenyl)vinyl)-3-methyl-5-((2-(pyrrolidin-1-yl)ethyl)amino)pyrazine-2-carboxylate (112 mg, 0.291 mmol) and dry 10% Pd/C (11 mg) in EtOAc (2.9 mL) was stirred under H$_2$ at room temperature overnight. The solvent was removed under vacuum to give the title compound as a light-yellow solid, which was used without further purification. ESI-MS m/z [M+H]$^+$ 387.1.

Step C: 6-(1-(4-fluorophenyl)ethyl)-3-methyl-5-((2-(pyrrolidin-1-yl)ethyl)amino)pyrazine-2-carboxylic acid To a solution of methyl 6-(1-(4-fluorophenyl)ethyl)-3-methyl-5-((2-(pyrrolidin-1-yl)ethyl)amino)pyrazine-2-carboxylate (108 mg, 0.279 mmol) in dioxane (1.9 mL) and MeOH (0.9 mL) was added an aq solution of 2.0 N KOH (279 µL, 0.559 mmol). The reaction mixture was stirred at room temperature overnight and then adjusted to pH 7 by adding 1.0 N HCl. Solvent was removed to give the title compound (125 mg, 100%) in a mixture with NaCl (17%), which was used without further purification. ESI-MS m/z [M+H]$^+$ 373.2.

Preparation 12: 4,4,5,5-tetramethyl-2-(3-methylbenzyl)-1,3,2-dioxaborolane

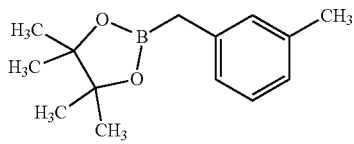

A mixture of 1-(chloromethyl)-3-methyl-benzene (6.00 g, 42.7 mmol), 4,4,5,5-tetramethyl-1,3,2-dioxaborolane (8.19 g, 64.0 mmol), DIPEA (22.35 mL, 128.0 mmol) and Pd(PPh$_3$)$_2$Cl$_2$ (1.50 g, 2.13 mmol) in DCE (200 mL) was stirred at 80° C. for 48 hours under N$_2$ and then concentrated under reduced pressure. The resulting residue was dissolved in EtOAc (100 mL), washed with saturated aq NaCl (20 mL×3), dried over Na$_2$SO$_4$, filtered and concentrated under reduced pressure. The crude residue was purified by flash silica column chromatography, using a gradient of petroleum ether/EtOAc (1000:1 to 30:1) to give the title compound as a light-yellow oil (4.50 g, 45%). $^1$H NMR (400 MHz, CDCl$_3$) δ ppm 1.25 (s, 12H), 2.27 (s, 2H), 2.31 (s, 3H), 6.91-7.04 (m, 3H), 7.09-7.17 (m, 1H).

Preparation 13: 3-methyl-6-(3-methylbenzyl)-5-((2-(pyrrolidin-1-yl)ethyl)amino)pyrazine-2-carboxylic acid

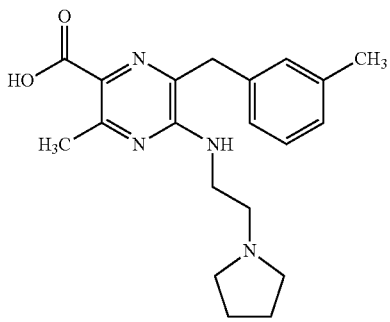 [SMILES: Cc1cccc(Cc2nc(C(=O)O)c(C)nc2NCCN2CCCC2)c1]

Step A: methyl 3-methyl-6-(3-methylbenzyl)-5-((2-(pyrrolidin-1-yl)ethyl)amino)pyrazine-2-carboxylate

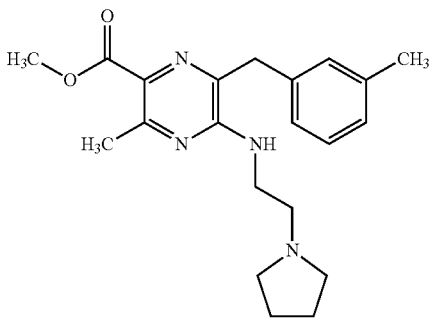

A mixture of methyl 6-chloro-3-methyl-5-((2-(pyrrolidin-1-yl)ethyl)amino)pyrazine-2-carboxylate (260 mg, 0.870 mmol), 4,4,5,5-tetramethyl-2-(3-methylbenzyl)-1,3,2-dioxaborolane (364 mg, 1.566 mmol), Na$_2$CO$_3$ (967 μL, 1.740 mmol) and PdCl$_2$(dppf)$_2$ (63.7 mg, 0.087 mmol) in dioxane (4.35 mL) was degassed with N$_2$ for 5 minutes and then heated at 110° C. for 16 hours. The reaction mixture was purified by silica gel chromatography (NH column) using a gradient of 10-50% EtOAc in heptane to give the title compound as a yellow solid (168 mg, 52.4%). ESI-MS m/z [M+H]$^+$ 369.1.

Step B: 3-methyl-6-(3-methylbenzyl)-5-((2-(pyrrolidin-1-yl)ethyl)amino)pyrazine-2-carboxylic acid To a solution of methyl 3-methyl-6-(3-methylbenzyl)-5-((2-(pyrrolidin-1-yl)ethyl)amino)pyrazine-2-carboxylate (168 mg, 0.456 mmol) in dioxane (3.0 mL) and MeOH (1.5 mL) was added a solution of KOH (456 μL, 0.912 mmol). The reaction mixture was stirred at room temperature overnight and then adjusted to pH 7 by addition of 1.0 N HCl. The organic solvent was removed, and the aqueous phase concentrated in vacuo to give the title compound as a yellow solid containing NaCl salt (about 70% purity based on calculation). The product was used without further purification. ESI-MS m/z [M+H]$^+$ 355.1.

Preparation 14: 5-((trans-1,3-dimethylpiperidin-4-yl)amino)-6-(4-fluorobenzyl)-3-methylpyrazine-2-carboxylic acid

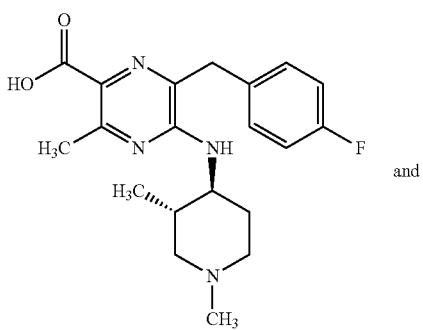

and

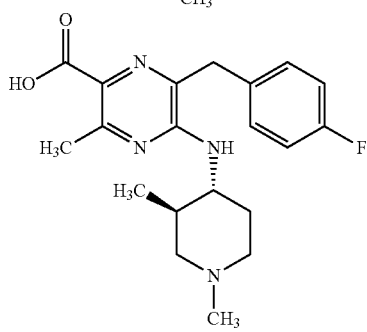

Step A: methyl 5-((trans-1-(tert-butoxycarbonyl)-3-methylpiperidin-4-yl)amino)-6-chloro-3-methylpyrazine-2-carboxylate

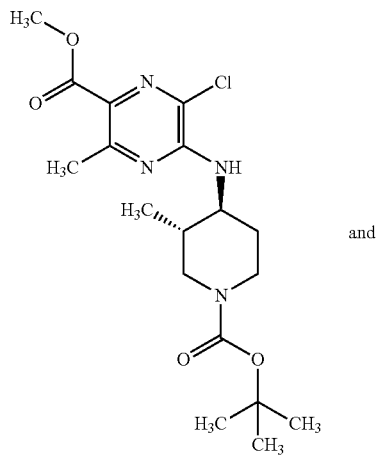

and

-continued

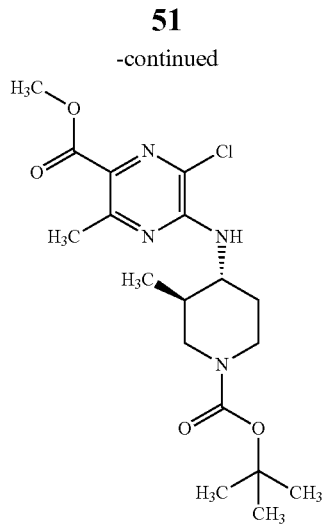

To a solution of methyl 5,6-dichloro-3-methylpyrazine-2-carboxylate (105 mg, 0.474 mmol) in dioxane (4.74 mL) were added DIPEA (132 µL, 0.758 mmol) and tert-butyl (3R,4R)-4-amino-3-methylpiperidine-1-carboxylate (132 mg, 0.616 mmol). The solution was stirred at room temperature for 16 hours and then purified by silica gel chromatography (NH column) to give the title compound as a yellow solid (128 mg, 67.7%). ESI-MS m/z [M-55]+ 343.00.

Step B: methyl 5-((trans-1-(tert-butoxycarbonyl)-3-methylpiperidin-4-yl)amino)-6-(4-fluorobenzyl)-3-methylpyrazine-2-carboxylate

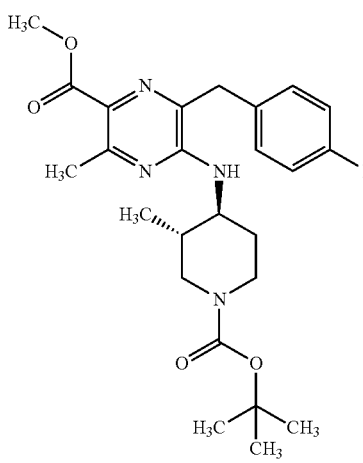

and

-continued

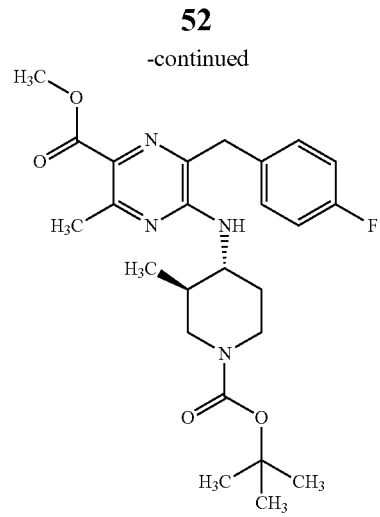

A mixture of methyl 5-((trans-1-(tert-butoxycarbonyl)-3-methylpiperidin-4-yl)amino)-6-chloro-3-methylpyrazine-2-carboxylate (78 mg, 0.196 mmol), 2-(4-fluorobenzyl)-4,4,5,5-tetramethyl-1,3,2-dioxaborolane (92 mg, 0.391 mmol), Na$_2$CO$_3$ (196 µL, 0.391 mmol) and PdCl$_2$(dppf) (14.31 mg, 0.020 mmol) in dioxane (2.0 mL) was degassed with N$_2$ for 5 minutes and then heated at 110° C. for 16 hours. The mixture was purified by silica gel chromatography (NH column) using a gradient of 10-50% EtOAc in heptane to give the title compound as a colorless oil (67 mg, 72.5%). ESI-MS m/z [M+H]+ 473.10.

Step C: methyl 6-(4-fluorobenzyl)-3-methyl-5-((trans-3-methylpiperidin-4-yl)amino)pyrazine-2-carboxylate

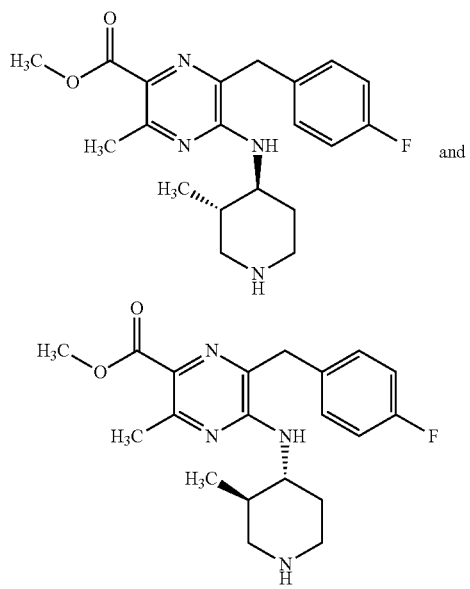

To a solution of methyl 5-((trans-1-(tert-butoxycarbonyl)-3-methylpiperidin-4-yl)amino)-6-(4-fluorobenzyl)-3-methylpyrazine-2-carboxylate (67 mg, 0.142 mmol) in DCM (3.0 mL) was added TFA (1.5 mL). The solution was stirred at room temperature for 1 hour and then the solvent was removed to give a TFA salt of the title compound as a sticky oil (69 mg, 100%), which was used without further purification.

Step D: methyl 5-((trans-1,3-dimethylpiperidin-4-yl)amino)-6-(4-fluorobenzyl)-3-methylpyrazine-2-carboxylate

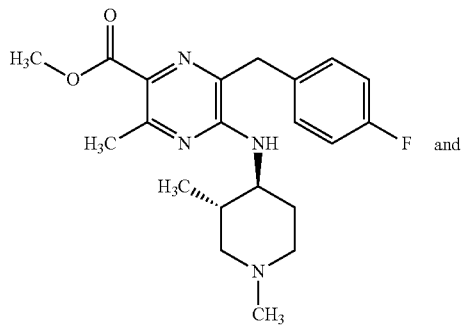

and

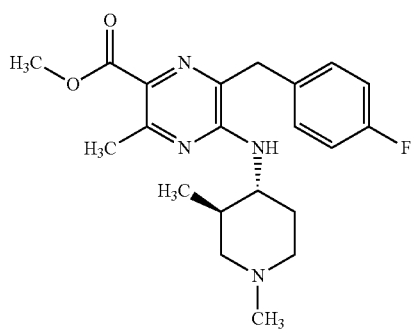

A mixture of a TFA salt of methyl 6-(4-fluorobenzyl)-3-methyl-5-((trans-3-methylpiperidin-4-yl)amino)pyrazine-2-carboxylate (69 mg, 0.142 mmol), DIPEA (37.2 µL, 0.213 mmol), paraformaldehyde (12.78 mg, 0.426 mmol) and sodium triacetoxyborohydride (135 mg, 0.638 mmol) in DCM (1.4 mL) was stirred at room temperature for 2 days. LC/MS indicated the reaction was complete. Ethyl acetate (10 mL) was added, followed by saturated aq NaHCO₃ (8 mL). The resulting mixture was vigorously stirred for 2 hours. The organic layer was separated, washed with brine, dried over anhydrous Na₂SO₄ and concentrated in vacuo to give the title compound as a light-yellow oil (49 mg, 89%), which was used without further purification. ESI-MS m/z [M+H]⁺ 387.15.

Step E: 5-((trans-1,3-dimethylpiperidin-4-yl)amino)-6-(4-fluorobenzyl)-3-methylpyrazine-2-carboxylic acid A mixture of methyl 5-((trans-1,3-dimethylpiperidin-4-yl)amino)-6-(4-fluorobenzyl)-3-methylpyrazine-2-carboxylate (49 mg, 0.127 mmol) and 2.0 N KOH (190 µL, 0.380 mmol) in MeOH (282 µL) and dioxane (564 µL) was stirred at room temperature for 24 hours and then quenched by the addition of 1.0 N HCl (0.38 mL). The solvent was removed in vacuo to give the title compound (70 mg, 60% purity by calculation) in a mixture with KCl. ESI-MS m/z [M+H]⁺ 373.10.

Preparation 15: 6-(1-(4-fluorophenyl)ethyl)-3-(methoxymethyl)-5-((2-(pyrrolidin-1-yl)ethyl)amino)pyrazine-2-carboxylic acid

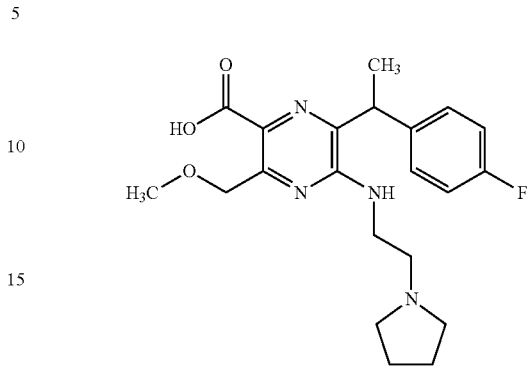

Step A: methyl 6-chloro-3-(methoxymethyl)-5-((2-(pyrrolidin-1-yl)ethyl)amino)pyrazine-2-carboxylate

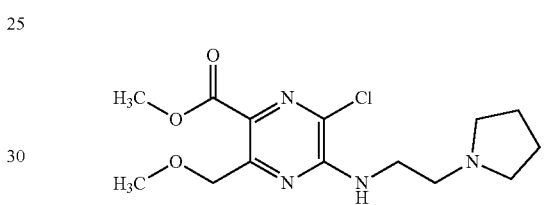

To a solution of methyl 5,6-dichloro-3-(methoxymethyl)pyrazine-2-carboxylate (100 mg, 0.398 mmol) and DIPEA (104 µL, 0.597 mmol) in dioxane (1992 µL) was added 2-(pyrrolidin-1-yl)ethan-1-amine (54.6 mg, 0.478 mmol, 1.2 equiv.). The solution was stirred at room temperature for 3 days and then purified by silica gel column chromatography (NH column) using a gradient of 10-80% EtOAc in heptane to give the title compound as a yellow oil (95 mg, 72.5%). ESI-MS m/z [M+H]⁺ 329.05.

Step B: methyl 6-(1-(4-fluorophenyl)vinyl)-3-(methoxymethyl)-5-((2-(pyrrolidin-1-yl)ethyl)amino)pyrazine-2-carboxylate

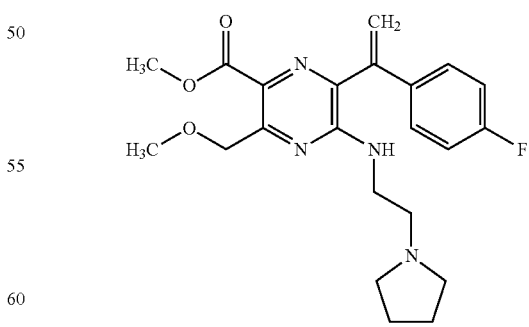

A mixture of methyl 6-chloro-3-(methoxymethyl)-5-((2-(pyrrolidin-1-yl)ethyl)amino)pyrazine-2-carboxylate (95 mg, 0.289 mmol), 2-(1-(4-fluorophenyl)vinyl)-4,4,5,5-tetramethyl-1,3,2-dioxaborolane (129 mg, 0.520 mmol), Pd(dppf)Cl₂·CH₂Cl₂ (21.14 mg, 0.029 mmol) and Na₂CO₃

(321 µL, 0.578 mmol) in dioxane (1.5 mL) was degassed with N₂, and then heated in a sealed tube at 110° C. for 16 hours. Following reaction, the mixture was purified by preparative HPLC (Phenomenex Gemini® C18, 5 µm, 30 mm ID×150 mm) using a gradient of 10-50% ACN (0.035% TFA) in water (0.05% TFA) to give a TFA salt of the title compound as a yellow solid (74 mg, 48.5%).

Step C: methyl 6-(1-(4-fluorophenyl)ethyl)-3-(methoxymethyl)-5-((2-(pyrrolidin-1-yl)ethyl)amino)pyrazine-2-carboxylate

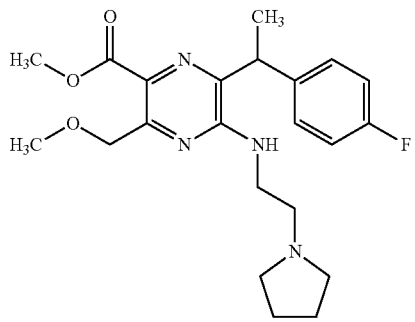 [SMILES: COCc1nc(NCCN2CCCC2)c(C(C)c2ccc(F)cc2)nc1C(=O)OC]

A mixture of a TFA salt of methyl 6-(1-(4-fluorophenyl)vinyl)-3-(methoxymethyl)-5-((2-(pyrrolidin-1-yl)ethyl)amino)pyrazine-2-carboxylate (74 mg, 0.140 mmol), 10% Pd/C (10 mg) and DIPEA (36.7 µL, 0.210 mmol) in MeOH (1.4 mL) was stirred under H₂ atmosphere (balloon) at room temperature for 6 hours. Following reaction, the mixture was filtered, and the filtrate was concentrated under vacuum to give the title compound as a light-yellow oil (59 mg). ESI-MS m/z [M+H]⁺ 417.1

Step D: 6-(1-(4-fluorophenyl)ethyl)-3-(methoxymethyl)-5-((2-(pyrrolidin-1-yl)ethyl)amino)pyrazine-2-carboxylic acid To a solution of methyl 6-(1-(4-fluorophenyl)ethyl)-3-(methoxymethyl)-5-((2-(pyrrolidin-1-yl)ethyl)amino)pyrazine-2-carboxylate (59 mg, 0.142 mmol) in dioxane (0.95 mL) and MeOH (0.47 mL) was added 2 M KOH (0.14 mL, 0.283 mmol). The solution was stirred at room temperature for 16 hours. The reaction was quenched with HCL (0.35 mL) and the mixture was concentrated under reduced pressure give the title compound (57% purity) as a mixture with KCl. The product was used without further purification.

Preparation 16:
3-(4-fluorobenzyl)-5,6-dimethylpyrazin-2-ol

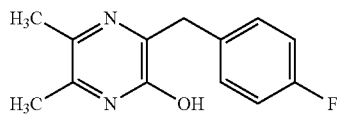

Step A: tert-butyl (1-((4-chloro-3-oxobutan-2-yl)amino)-3-(4-fluorophenyl)-1-oxopropan-2-yl)carbamate

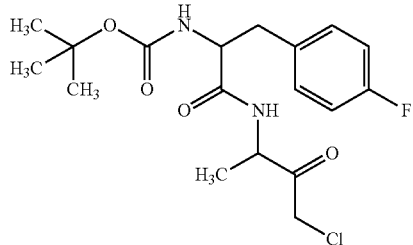 [SMILES: CC(NC(=O)C(Cc1ccc(F)cc1)NC(=O)OC(C)(C)C)C(=O)CCl]

A solution of 2-((tert-butoxycarbonyl)amino)-3-(4-fluorophenyl)propanoic acid (0.702 g, 2.48 mmol) and Et₃N (0.377 mL, 2.70 mmol) in THF (22.5 mL) was cooled to 0° C. Isobutyl chloroformate (0.324 mL, 2.48 mmol) was added and the mixture was stirred for 25 minutes. A solution of 3-amino-1-chlorobutan-2-one hydrochloride (0.356 g, 2.25 mmol) pre-treated with Et₃N (0.377 mL, 2.70 mmol) in DMF (22.5 mL) was added, and the reaction mixture was stirred for 3 hours while slowly warming to room temperature. The reaction mixture was concentrated partway under reduced pressure, then poured into EtOAc. The organic phase was washed with water, dried over Na₂SO₄, filtered, and concentrated under reduced pressure. The resulting residue was purified by automated flash silica column chromatography, using a gradient of 0-50% EtOAc in heptanes. The product-containing fractions were evaporated to give the title compound as a white solid (363.8 mg, 42%). ESI-MS m/z [M+H]⁺ 387.3.

Step B: 2-amino-N-(4-chloro-3-oxobutan-2-yl)-3-(4-fluorophenyl)propanamide

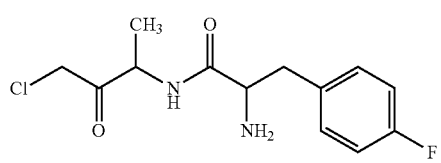 [SMILES: CC(NC(=O)C(N)Cc1ccc(F)cc1)C(=O)CCl]

To a solution of tert-butyl (1-((4-chloro-3-oxobutan-2-yl)amino)-3-(4-fluorophenyl)-1-oxopropan-2-yl)carbamate (363.8 mg, 0.940 mmol) in dioxane (940 µL) was added HCl (4 M in dioxane, 2.35 mL, 9.40 mmol) dropwise. The reaction mixture was stirred for 30 minutes at room temperature. The solvent was removed under reduced pressure. Diethyl ether was added and removed under reduced pressure to give an HCl salt of the title compound (304 mg, assumed quantitative) which was used without further purification. ESI-MS m/z [M+H]⁺ 287.1.

Step C: 3-(4-fluorobenzyl)-5,6-dimethylpyrazin-2-ol

A solution of 2-amino-N-(4-chloro-3-oxobutan-2-yl)-3-(4-fluorophenyl)propanamide hydrochloride (304 mg, 0.940 mmol) was taken up in MeOH (9.40 mL) and stirred at 65° C. for 2 hours. The reaction mixture was concentrated under reduced pressure. The resulting residue was extracted with CHCl₃, washed with water, dried over Na₂SO₄, filtered, and concentrated under reduced pressure to give the title compound as an off-white solid (176.3 mg, 81%). ESI-MS m/z [M+H]$^+$ 233.1.

Preparation 17: 3-chloro-5,6-dimethyl-N-(1-methylpiperidin-4-yl)pyrazin-2-amine

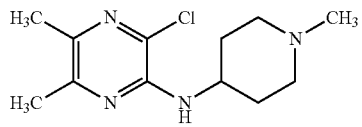

A solution of 2,3-dichloro-5,6-dimethylpyrazine (250 mg, 1.412 mmol), 1-methylpiperidin-4-amine (242 mg, 2.118 mmol) and DIPEA (740 µL, 4.24 mmol) in dioxane (2.8 mL) was heated at 130° C. for 16 hours. The mixture was purified by silica gel column chromatography (NH column) to give the title compound as a colorless oil (60 mg, 17%). ESI-MS m/z [M+H]$^+$ 255.1.

Preparation 18: 3-chloro-5,6-dimethyl-N-(2-(pyrrolidin-1-yl)ethyl)pyrazin-2-amine

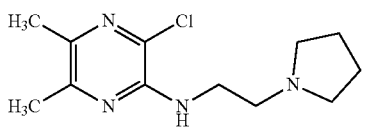 [SMILES: Cc1nc(Cl)c(NCCN2CCCC2)nc1C]

The title compound was prepared like PREPARATION 17, using 2,3-dichloro-5,6-dimethylpyrazine (150 mg, 0.847 mmol) and 2-(pyrrolidin-1-yl)ethanamine (145 mg, 1.271 mmol), and was isolated as a light-yellow oil (99 mg, 45.9%). ESI-MS m/z [M+H]$^+$ 255.15.

Preparation 19: (R)-3-chloro-5,6-dimethyl-N-(1-methylpyrrolidin-3-yl)pyrazin-2-amine

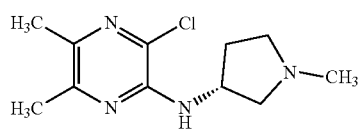

The title compound was prepared like PREPARATION 17, using 2,3-dichloro-5,6-dimethylpyrazine (250 mg, 1.412 mmol) and (R)-1-methylpyrrolidin-3-amine (212 mg, 2.12 mmol), and was isolated as a colorless oil (40 mg, 12%). ESI-MS m/z [M+H]$^+$ 241.1.

Preparation 20: 6-isopropyl-3-(3-methylbenzyl)pyrazin-2(1H-one

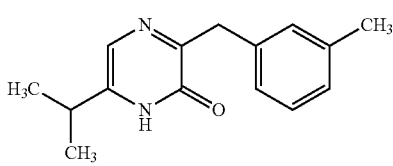 [SMILES: Cc1cccc(Cc2ncc(C(C)C)[nH]c2=O)c1]

Step A: tert-butyl (1-(methoxy(methyl)amino)-3-methyl-1-oxobutan-2-yl)carbamate

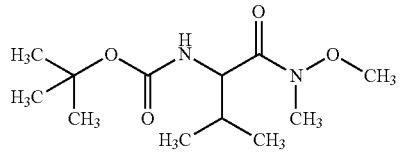 [SMILES: CON(C)C(=O)C(NC(=O)OC(C)(C)C)C(C)C]

To a solution of 2-((tert-butoxycarbonyl)amino)-3-methylbutanoic acid) (1 g, 4.60 mmol) and N,O-dimethylhydroxylamine hydrochloride (0.47 g, 4.86 mmol) in DCM (20 mL) at 0° C. was added DMAP (0.843, 6.90 mmol) and a solution of DCC (1 g, 5.06 mmol) in DCM (50 mL). The reaction mixture was stirred at room temperature overnight. An insoluble urea byproduct was filtered off, and the filtrate was washed with 5% sodium hydrogen sulfate solution (100 mL×3). The organic layer was dried over Na$_2$SO$_4$, filtered and concentrated under reduced pressure to give the title compound as a white solid (1.19 g, 99.9%). ESI-MS [M+H]$^+$ 261.2.

Step B: 2-amino-N-methoxy-N,3-dimethylbutanamide

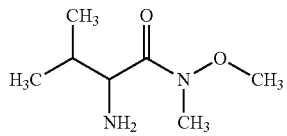

To a 100 mL round bottomed flask containing with tert-butyl (1-(methoxy(methyl)amino)-3-methyl-1-oxobutan-2-yl)carbamate (1.19 g, 4.57 mmol) was added a 4.0 M solution of HCl in dioxane. The reaction mixture was stirred overnight, concentrated and diluted with EtOAc. The organic layer was washed with saturated brine, dried over anhydrous Na$_2$SO$_4$, filtered and concentrated under reduced pressure. The crude product was purified by flash silica gel column chromatography, using a gradient of 0-100% EtOAc in heptane to give the title compound as an off-white solid (460 mg g, 63%). ESI-MS [M+H]$^+$ 161.3.

Step C: tert-butyl (1-((1-(methoxy(methyl)amino)-3-methyl-1-oxobutan-2-yl)amino)-1-oxo-3-(m-tolyl)propan-2-yl)carbamate

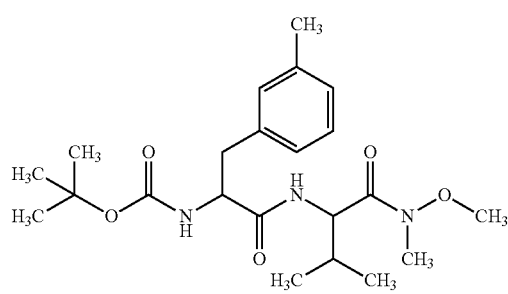 [SMILES: CON(C)C(=O)C(NC(=O)C(Cc1cccc(C)c1)NC(=O)OC(C)(C)C)C(C)C]

To a round bottomed flask containing 2-((tert-butoxycarbonyl)amino)-3-(m-tolyl)propanoic acid (0.80 g, 2.87 mmol) in THF (5 mL) at 0° C. was added Et₃N (0.63 g, 6.32 mmol) followed by isobutyl carbonochloridate (0.431 g, 3.16 mmol). The reaction mixture was stirred for 30 minutes. Next, 2-amino-N-methoxy-N,3-dimethylbutanamide (460 mg g, 2.87 mmol) was added and the reaction mixture was stirred at room temperature overnight. Following reaction, the mixture was diluted with EtOAc, washed with saturated brine, dried over Na₂SO₄, filtered and concentrated to an oil. The crude product was purified by flash silica gel column chromatography, using a gradient of 0-100% EtOAc in heptane to give the title compound as a clear oil (1.21 g, quantitative yield). ESI-MS [M+H]⁺ 422.4.

Step D: tert-butyl (1-((3-methyl-1-oxobutan-2-yl)amino)-1-oxo-3-(m-tolyl)propan-2-yl)carbamate

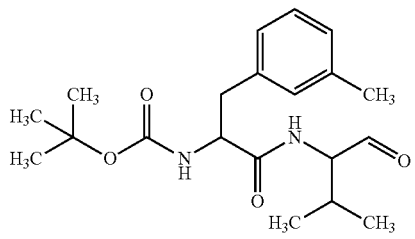 [SMILES: Cc1cccc(CC(NC(=O)OC(C)(C)C)C(=O)NC(C=O)C(C)C)c1]

To tert-butyl (1-((1-(methoxy(methyl)amino)-3-methyl-1-oxobutan-2-yl)amino)-1-oxo-3-(m-tolyl)propan-2-yl)carbamate (1.22 g, 2.89 mmol) in THF (6 mL) at 0° C. was added a 2.0 N solution of LiAlH₄ (4.34 mL, 8.68 mmol). Upon completion (~1 hour), the reaction was quenched by dropwise addition of EtOAc (20 mL). After stirring for about 15 minutes, water (15 mL) was added to the reaction mixture and stirring was continued for another 30 minutes. The organic layer was separated, and the aqueous layer was extracted with EtOAc (20 mL×3). The combined organic extracts were dried over Na₂SO₄, filtered, and concentrated to an oil. The crude product was purified by flash silica gel column chromatography, using a gradient of 0-100% EtOAc in heptane to give the title compound as an oil (1.02 g, 97%). ESI-MS [M+H]⁺ 363.3.

Step E: 6-isopropyl-3-(3-methylbenzyl)pyrazin-2(1H)-one

To a solution of tert-butyl (1-((3-methyl-1-oxobutan-2-yl)amino)-1-oxo-3-(m-tolyl)propan-2-yl)carbamate (1 g, 2.76 mmol) in DCM (10 mL) was added a 4 N solution of HCl in dioxane (6.90 mL, 27.6 mmol). Within a few minutes, the clear solution became warm and turned pale yellow. The reaction mixture was stirred at room temperature overnight, and then concentrated under reduced pressure, diluted with water (75 mL) and adjusted to pH >12 with 50% NaOH. The reaction mixture was extracted with EtOAc and the combined organic extracts were dried over Na₂SO₄, filtered, and concentrated to an oil. The oil was diluted with acetonitrile (5 mL), stirred at room temperature overnight and then concentrated to an oil, which was purified by flash silica gel column chromatography, using a gradient of 0-100% EtOAc in heptane to give the title compound as an oil (0.125 g, 18.70%). ESI-MS [M+H]⁺ 243.1.

Preparation 21: 3-chloro-5-isopropyl-2-(3-methylbenzyl)pyrazine

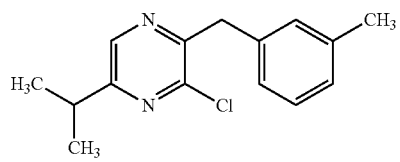 [SMILES: Cc1cccc(Cc2ncc(C(C)C)nc2Cl)c1]

To a 100 mL round bottomed flask containing 6-isopropyl-3-(3-methylbenzyl)pyrazin-2(1H)-one (0.125 g, 0.516 mmol) was added POCl₃ (0.475 g, 3.10 mmol). The solution was heated at 100° C. until its color changed from clear to light brown. Excess POCl₃ was removed under reduced pressure and the crude product was purified by flash silica gel column chromatography, using a gradient of 0-100% EtOAc in heptane to give the title compound as a semi-solid (28 mg, 21%). ESI-MS [M+H]⁺ 261.1.

Preparation 22: N-(2-(azetidin-1-yl)ethyl)-6-chloro-3-(3-methylbenzyl)pyrazin-2-amine

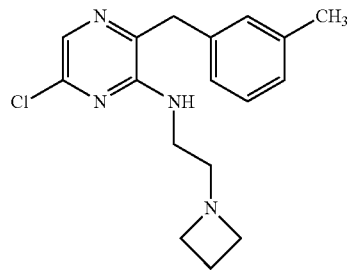 [SMILES: Cc1cccc(Cc2ncc(Cl)nc2NCCN2CCC2)c1]

Step A: (3,5-dichloropyrazin-2-yl)(m-tolyl)methanol

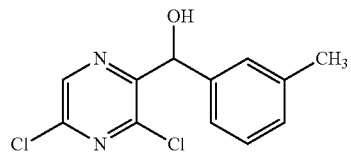 [SMILES: Cc1cccc(C(O)c2ncc(Cl)nc2Cl)c1]

A solution of n-BuLi (2.5 M in hexane, 6.44 mL) in THF (12 mL) was added dropwise to 2,2,6,6-tetramethylpiperidine (2.27 g, 16.10 mmol, 2.74 mL) in THF at −20° C. The resulting mixture was warmed to 0° C. and stirred for 30 minutes. The reaction mixture was then cooled to −78° C. and a solution of 2,6-dichloropyrazine (2 g, 13.42 mmol) in THF (4 mL) was added dropwise. The reaction mixture was stirred at −78° C. for 1 hour. A solution of 3-methylbenzaldehyde (2.42 g, 20.13 mmol) in THF (4 mL) was added dropwise at −78° C. The reaction mixture was stirred for 1 hour and then poured into ice-cold NH₄Cl solution (50 mL) and extracted with EtOAc (20 mL×2). The combined organic layers were dried over Na₂SO₄, filtered, and concentrated in vacuo. The crude product was purified by flash silica gel column chromatography, using a gradient of petroleum ether/EtOAc(100:1 to 5:1) to give the title compound as a yellow oil (1.1 g, 29%). $^1$H NMR (400 MHz, CDCl$_3$) δ ppm 2.34 (s, 3H), 4.18 (d, J=8.00 Hz, 1H), 6.00 (d, J=8.40 Hz, 1H), 7.71-7.27 (m, 4H), 8.58 (s, 1H).

Step B: 3,5-dichloro-2-(3-methylbenzyl)pyrazine

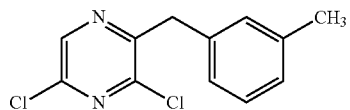 [SMILES: Cc1cccc(Cc2ncc(Cl)nc2Cl)c1]

A mixture of TMSCl (1.45 g, 13.38 mmol, 1.69 mL) and NaI (2.01 g, 13.38 mmol) in ACN (10 mL) was stirred at 20° C. for 10 minutes. Then a solution of (3,5-dichloropyrazin-2-yl)(m-tolyl)methanol (600 mg, 2.23 mmol) in ACN (8 mL) was added and the reaction mixture was heated at 80° C. for 4 hours. The mixture was cooled to room temperature and poured onto a mixture of saturated Na$_2$S$_2$O$_3$ solution (20 mL) and saturated NaHCO$_3$ solution (20 mL) and then extracted with EtOAc (10 mL×3). The combined organic layers were dried over Na$_2$SO$_4$, filtered and concentrated in vacuo. The crude product was purified by flash column chromatography on silica gel, using a gradient of petroleum ether/EtOAc=(1:0 to 20:1) to give the title compound as a yellow oil (400.0 mg, 29%). $^1$H NMR (400 MHz, CDCl$_3$) δ ppm 2.33 (s, 3H), 4.21-4.31 (m, 2H), 7.06-7.23 (m, 4H), 8.47 (s, 1H); ESI-MS m/z [M+H]$^+$ 253.0.

Step C: N-(2-(azetidin-1-yl)ethyl)-6-chloro-3-(3-methylbenzyl)pyrazin-2-amine hydrogen chloride To a mixture of 3,5-dichloro-2-(3-methylbenzyl)pyrazine (350 mg, 1.38 mmol) and 2-(azetidin-1-yl)ethanamine (207.33 mg, 2.07 mmol) in DMSO (4 mL) was added CsF (628.87 mg, 4.14 mmol, 152.64 µL) at 20° C. The mixture was stirred at 50° C. for 2 hours and was then diluted with EtOAc (20 mL) and with saturated NH$_4$Cl solution (20 mL). The aqueous layer was separated and extracted with EtOAc (15 mL×3). The combined organic layers were dried over Na$_2$SO$_4$, filtered and concentrated in vacuo. The crude product was purified by preparative HPLC (Phenomenex Synergi™ C18, 4 µm, ID 21.2 mm×250 mm) using a gradient of 22-52% ACN in water (0.05% HCl) to give an HCl salt of the title compound as a yellow oil (63.0 mg, 94%). $^1$H NMR (400 MHz, CDCl$_3$) δ ppm 1.99-2.06 (m, 2H), 2.33 (s, 3H), 2.51-2.54 (m, 2H), 3.06-3.10 (m, 4H), 3.21-3.25 (m, 2H), 4.01 (s, 2H), 5.33 (s, 1H), 7.06-7.08 (m, 3H), 7.20-7.24 (m, 1H), 7.75 (s, 1H); ESI-MS m/z [M+H]$^+$ 317.0.

Preparation 23: 3-benzyl-6-ethylpyrazin-2-yl trifluoromethanesulfonate

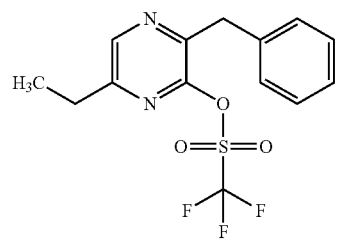 [SMILES: CCc1cnc(Cc2ccccc2)c(OS(=O)(=O)C(F)(F)F)n1]

Step A: 3-benzyl-6-ethylpyrazin-2(1H)-one

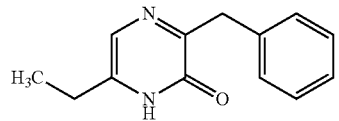 [SMILES: CCc1cnc(Cc2ccccc2)c(=O)[nH]1]

The title compound was prepared like PREPARATION 20, starting with 2-(tert-butoxycarbonylamino)butanoic acid (5 g, 24.60 mmol), and was obtained as a light brown solid (180.0 mg). $^1$H NMR (400 MHz, CDCl$_3$) δ ppm 1.31 (t, J=7.5 Hz, 3H), 2.61 (q, J=7.5 Hz, 2H), 4.13 (s, 2H), 7.20-7.25 (m, 1H), 7.28-7.33 (m, 2H), 7.35-7.40 (m, 2H), 7.42 (s, 1H); ESI-MS m/z [M+H]$^+$ 214.8.

Step B: 3-benzyl-6-ethylpyrazin-2-yl trifluoromethanesulfonate

To a solution of 3-benzyl-6-ethylpyrazin-2(1H)-one (40 mg, 168.02 µmol) in DCM (3 mL) was added Et$_3$N (26.58 mg, 262.68 µmol, 36.41 µL) and trifluoromethylsulfonyl trifluoromethanesulfonate (94.81 mg, 336.04 µmol, 55.44 µL) at 0° C. The reaction mixture was stirred at 20° C. for 2 hours and then concentrated in vacuo. The product was purified by silica gel column chromatography, using a gradient of petroleum ether/EtOAc 6 (20:1 to 10:1) to give the title compound as a yellow oil (30.0 mg, 51%). ESI-MS m/z [M+H]$^+$ 346.9.

Preparation 24: tert-butyl trans-4-((3-chloro-5-(trifluoromethyl)pyrazin-2-yl)amino)-3-ethylpiperidine-1-carboxylate

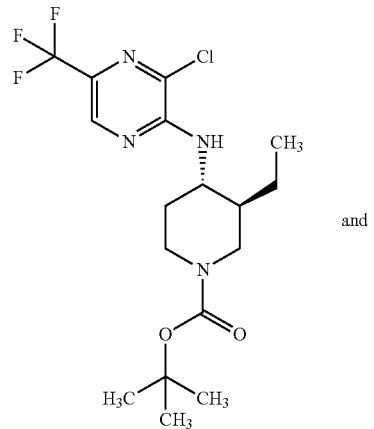

and

-continued

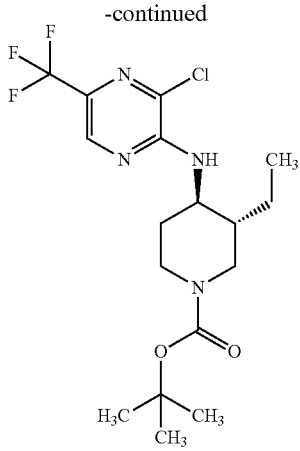

Step A: 1-(tert-butyl) 4-ethyl 5-(((trifluoromethyl)sulfonyl)oxy)-3,6-dihydropyridine-1,4(2H)-dicarboxylate

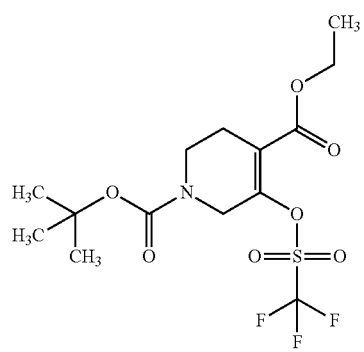 [SMILES: CCOC(=O)C1=C(OS(=O)(=O)C(F)(F)F)CN(C(=O)OC(C)(C)C)CC1]

To a 250 mL round-bottomed flask were added 1-(tert-butyl) 4-ethyl 3-oxopiperidine-1,4-dicarboxylate (5.7 g, 21.01 mmol), 1,1,1-trifluoro-N-phenyl-N-((trifluoromethyl)sulfonyl)methanesulfonamide (11.26 g, 31.5 mmol) and THF (80 mL) to give a colorless solution. Next, NaH (1.260 g, 31.5 mmol) was added at 0° C. and the reaction mixture was stirred at 0° C. for 1 hour, and then warmed to room temperature and stirred overnight. The mixture was concentrated to ½ volume, quenched with 10% $Na_2CO_3$ and extracted with EtOAc. The organic layers were washed with brine, dried over anhydrous $MgSO_4$, and concentrated. The residue was purified by silica gel column chromatography (120 g column) using a gradient of hexane/EtOAc (1:0 to 4:1) to give the title compound as a light brown syrup (8.56 g, 87%). ESI-MS m/z $[M+H]^+$ 404.4.

Step B: 1-(tert-butyl) 4-ethyl 5-vinyl-3,6-dihydropyridine-1,4(2H)-dicarboxylate

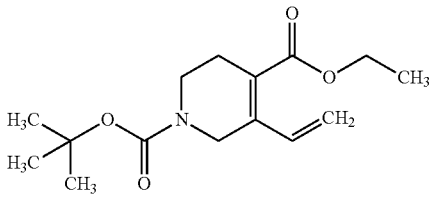 [SMILES: C=CC1=C(C(=O)OCC)CCN(C(=O)OC(C)(C)C)C1]

To a 250 mL round-bottomed flask were added 1-(tert-butyl) 4-ethyl 5-(((trifluoromethyl)sulfonyl)oxy)-3,6-dihydropyridine-1,4(2H)-dicarboxylate (4.7 g, 11.65 mmol), 4,4,5,5-tetramethyl-2-vinyl-1,3,2-dioxaborolane (2.372 mL, 13.98 mmol), RuPhos Pd G3 (0.455 g, 0.583 mmol), $Cs_2CO_3$ (7.59 g, 23.30 mmol) and dioxane (78 mL) to give a white suspension. Nitrogen was bubbled through the mixture for 5 minutes and then the reaction mixture was heated at 75° C. overnight. The mixture was then filtered, and the filtrate was concentrated under reduced pressure. The resulting residue was purified by silica gel column chromatography (120 g column) using hexane/EtOAc (9:1) to give the title compound as a light brown syrup (2.52 g, 77%). ESI-MS m/z $[M+H]^+$ 282.1.

Step C: 1-(tert-butyl) 4-ethyl 3-ethylpiperidine-1,4-dicarboxylate

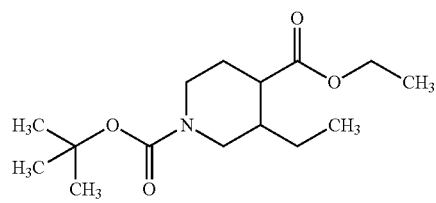 [SMILES: CCOC(=O)C1CCN(C(=O)OC(C)(C)C)CC1CC]

To a 250 mL round-bottomed flask were added 1-(tert-butyl) 4-ethyl 5-vinyl-3,6-dihydropyridine-1,4(2H)-dicarboxylate (2.52 g, 8.96 mmol) and dihydroxypalladium on carbon (0.314 g, 0.448 mmol) in EtOH (30 mL) and THF (30.0 mL) to give a black suspension. The flask was evacuated and back-filled with hydrogen (3×). The reaction mixture was then stirred at room temperature under hydrogen (50 psi) for 10 days. The catalyst was filtered off and the filtrate was concentrated to give the title compound as a colorless syrup (2.52 g, 99%) which was used without further purification. ESI-MS m/z $[M+H]^+$ 286.4.

Step D: 1-(tert-butyl) 4-ethyl trans-3-ethylpiperidine-1,4-dicarboxylate

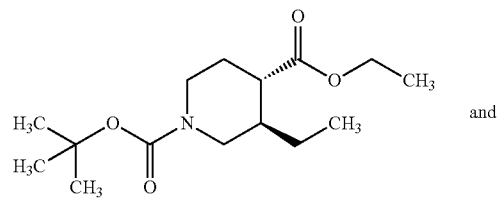

and

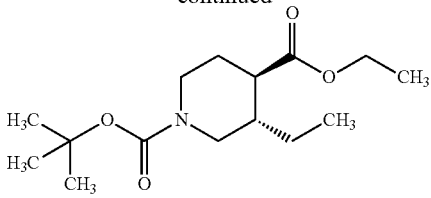

Sodium (0.406 g, 17.66 mmol) was added to ethanol (53.0 mL) in a 250 mL round-bottomed flask. When the sodium was completely dissolved, a solution of 1-(tert-butyl) 4-ethyl 3-ethylpiperidine-1,4-dicarboxylate (2.52 g, 8.83 mmol) in ethanol (35.3 mL) was added. The resulting mixture was heated at 85° C. overnight and then concentrated to ½ its original volume, quenched with water, and extracted with EtOAc. The combined organic layers were washed with brine, dried over anhydrous MgSO$_4$ and concentrated to give the title compound as a tan syrup (2.11 g, 84%). ESI-MS m/z [M+H]$^+$ 286.4.

Step E: trans-1-(tert-butoxycarbonyl)-3-ethylpiperidine-4-carboxylic acid

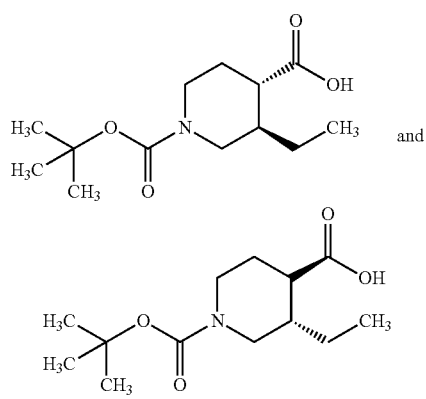

To a 250 mL round-bottomed flask were added 1-(tert-butyl) 4-ethyl trans-3-ethylpiperidine-1,4-dicarboxylate (2.11 g, 7.39 mmol), lithium hydroxide (14.79 mL, 29.6 mmol) and dioxane (30 mL) to give a tan solution. The mixture was stirred at room temperature overnight, and then heated at 50° C. overnight, concentrated under reduced pressure, and extracted with ether. The aqueous phase was acidified with 1 N HCl to pH 5 and extracted with EtOAc. The organic layers were dried over anhydrous MgSO$_4$ and concentrated under reduced pressure to give the title compound as a tan syrup. ESI-MS m/z [M+H]$^+$ 258.3.

Step F: tert-butyl trans-4-amino-3-ethylpiperidine-1-carboxylate

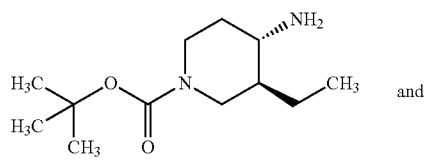

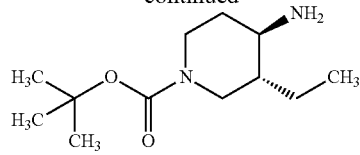

To a 250 mL round-bottomed flask were added trans-1-(tert-butoxycarbonyl)-3-ethylpiperidine-4-carboxylic acid (1.902 g, 7.39 mmol), diphenyl phosphorazidite (2.408 mL, 11.82 mmol), Et$_3$N (1.545 mL, 11.09 mmol) and toluene (49.3 mL) to give a brown solution. The solution was heated at 100° C. for 1 hour and then cooled to room temperature. Next, NaOH (7.39 mL, 73.9 mmol) was added. The mixture was stirred at room temperature for 3 hours and then concentrated under reduced pressure. The residue was suspended in EtOAc and filtered through a pad of Celite®. The filtrate was concentrated and purified by silica gel column chromatography (120 g NH column) using a gradient of hexane/EtOAc (3:2 to 1:4) to give the title compound as a colorless syrup (1.11 g; 65.8%). ESI-MS m/z [M+H]$^+$ 229.3.

Step G: tert-butyl trans-4-((3-chloro-5-(trifluoromethyl)pyrazin-2-yl)amino)-3-ethylpiperidine-1-carboxylate To a 40 mL vial were added 2,3-dichloro-5-(trifluoromethyl)pyrazine (0.1 g, 0.461 mmol), tert-butyl trans-4-amino-3-ethylpiperidine-1-carboxylate (0.137 g, 0.599 mmol), DIPEA (0.120 mL, 0.691 mmol) and dioxane (3 mL) to give a colorless solution. The solution was stirred at 75° C. for 3 days, and then quenched with water and extracted with EtOAc. The combined organic layers were washed with brine, dried over anhydrous MgSO$_4$ and concentrated to give the title compound as a colorless film. ESI-MS m/z [M+H]$^+$ 409.8.

Preparation 25: tert-butyl 4-((3-chloro-5-(trifluoromethyl)pyrazin-2-yl)amino)-3-methylpiperidine-1-carboxylate

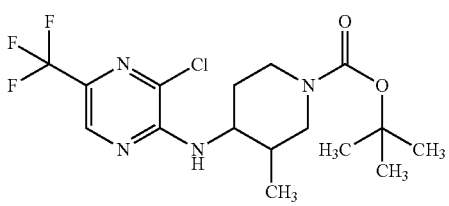 [SMILES: CC1CN(C(=O)OC(C)(C)C)CCC1Nc1ncc(C(F)(F)F)nc1Cl]

To a 40 mL vial were added 2,3-dichloro-5-(trifluoromethyl)pyrazine (0.1 g, 0.461 mmol), tert-butyl 4-amino-3-methylpiperidine-1-carboxylate hydrogen chloride (0.150 g, 0.599 mmol), DIPEA (0.120 mL, 0.691 mmol) and dioxane (3 mL) to give a white suspension. The resulting mixture was stirred at 75° C. for 3 days. The mixture was treated with water and extracted with EtOAc. The organic layers were washed with brine, dried over anhydrous MgSO$_4$, and concentrated to give the title compound as a brown film which was used without further purification. ESI-MS m/z [M+H]$^+$ 395.4.

Preparation 26: 3-chloro-2-(4-fluorobenzyl)-5-(trifluoromethyl)pyrazine

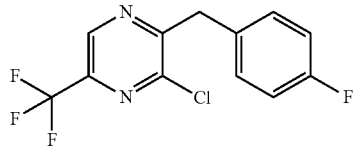 [SMILES: Fc1ccc(Cc2ncc(C(F)(F)F)nc2Cl)cc1]

To a 100 mL round-bottomed flask were added 2,3-dichloro-5-(trifluoromethyl)pyrazine (0.43 g, 1.982 mmol), 2-(4-fluorobenzyl)-4,4,5,5-tetramethyl-1,3,2-dioxaborolane (0.842 g, 3.57 mmol), (dppf)$_2$PdCl$_2$ (0.145 g, 0.198 mmol), Na$_2$CO$_3$ (1.982 mL, 3.96 mmol) and dioxane (19.8 mL) to give an orange suspension. The suspension was degassed with N$_2$ and heated at 110° C. overnight. The mixture was then quenched with water and extracted with EtOAc. The organic layers were washed with brine, dried over anhydrous MgSO$_4$, and concentrated under reduced pressure. The resulting residue was purified by silica gel column chromatography, using a gradient of hexane/EtOAc (4:1 to 1:1) to give the title compound (0.349 g, 60.6%). ESI-MS m/z [M+H]$^+$ 291.3.

Preparation 27:
5,6-dichloro-3-methylpyrazine-2-carbonitrile

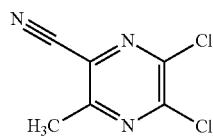

Step A:
5-amino-6-chloro-3-methylpyrazine-2-carbonitrile

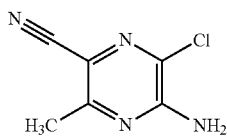

A solution of 5-amino-3-methylpyrazine-2-carbonitrile (2.91 g, 21.7 mmol) and NCS (3.19 g, 23.9 mmol) in ACN (108 mL) was slowly heated to 75° C. over 3 hours. The reaction mixture was allowed to cool to room temperature and diluted with EtOAc. The organic phase was washed with saturated aq NaHCO$_3$ (3×) then dried over Na$_2$SO$_4$, filtered, and concentrated under reduced pressure to give the title compound as an orange solid (3.66 g, quantitative) which was used without further purification. ESI-MS m/z [M+H]$^+$ 168.9.

Step B:
5,6-dichloro-3-methylpyrazine-2-carbonitrile

To a solution of CuCl (6.23 g, 62.9 mmol), CuCl$_2$ (8.46 g, 62.9 mmol) and 5-amino-6-chloro-3-methylpyrazine-2-carbonitrile (3.66 g, 21.7 mmol) in ACN (108 mL) at 0° C. was added tert-butyl nitrite (5.59 g, 54.2 mmol) dropwise. The reaction mixture was stirred for 30 minutes at room temperature and then heated to 65° C. for 45 minutes and allowed to cool to room temperature. The mixture was diluted with DCM, filtered through a pad of Celite® and concentrated under reduced pressure to afford a viscous brown liquid, which was adsorbed onto silica and purified by automated flash column chromatography, using a gradient of EtOAc in heptanes. Fractions containing the desired product were evaporated to give the title compound as a white solid (2.14 g, 52%). $^1$H NMR (500 MHz, DMSO-d$_6$) δ ppm 2.68 (d, J=2.0 Hz, 3H). The compound did not ionize by ESI-MS.

Preparation 28: 5-((2-(azetidin-1-yl)ethyl)amino)-6-chloro-3-methylpyrazine-2-carbonitrile

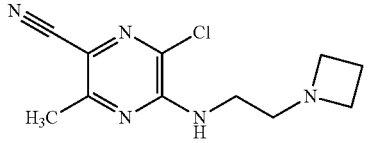 [SMILES: Cc1nc(NCCN2CCC2)c(Cl)nc1C#N]

A solution of 5,6-dichloro-3-methylpyrazine-2-carbonitrile (0.300 g, 1.60 mmol) in dioxane (10 mL) (PREPARATION 27) was treated with 2-(azetidin-1-yl)ethanamine (0.160 g, 1.60 mmol) and DIPEA (0.557 mL, 3.19 mmol). The reaction mixture was stirred at room temperature overnight and then concentrated under reduced pressure. The residue was taken up in MeOH and filtered through a hydrophilic PTFE 0.45 μm Millipore® filter. The filter was rinsed with MeOH and the filtrate was purified by preparative HPLC (Phenomenex Gemini® C18, 5 μm, 30 mm IDx150 mm) using a gradient of 10-100% aq ACN (80%, 10 mM NH$_4$HCO$_3$) in water (10 mM NH$_4$HCO$_3$). Fractions containing the desired product were evaporated and dried under vacuum to give the title compound as a pale yellow solid (157.9 mg, 39.3%). ESI-MS m/z [M+H]$^+$ 252.10.

Preparation 29: (R)-6-chloro-3-methyl-5-((1-methylpyrrolidin-3-yl)amino)pyrazine-2-carbonitrile

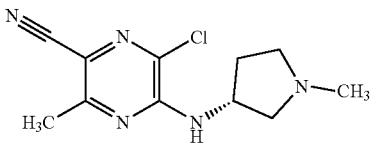 [SMILES: Cc1nc(N[C@@H]2CCN(C)C2)c(Cl)nc1C#N]

To a solution of 5,6-dichloro-3-methylpyrazine-2-carbonitrile (315 mg, 1.67 mmol) in DCM (8.37 mL) at 0° C. were added DIPEA (0.585 mL, 3.35 mmol) and (R)-1-methylpyrrolidin-3-amine (184 mg, 1.84 mmol). The reaction mixture was stirred overnight, while gradually warming to room temperature. The mixture was then diluted with water and extracted with DCM. The organic phase was dried over Na$_2$SO$_4$, filtered, and concentrated under reduced pressure. The residue was partially purified by automated flash silica column chromatography. Fractions containing the desired product were evaporated to give the title compound as an orange solid (170.1 mg, 40%) which was used without additional purification. ESI-MS m/z [M+H]$^+$ 252.10.

Preparation 30: 2-chloro-3-(4-fluorobenzyl)pyrazine

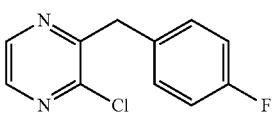 [SMILES: Fc1ccc(Cc2nccnc2Cl)cc1]

A mixture of 2,3-dichloropyrazine (1.3 g, 8.73 mmol), 2-(4-fluorobenzyl)-4,4,5,5-tetramethyl-1,3,2-dioxaborolane (2.08 g, 8.81 mmol), Na$_2$CO$_3$ (2 M, 9.82 mL) and PdCl$_2$(dppf)·CH$_2$Cl$_2$ (712.61 mg, 872.61 μmol) in dioxane (40 mL) was stirred at 105° C. for 16 hours and then diluted with EtOAc (100 mL) and washed with water (100 mL×3). The organic layers were dried over anhydrous Na$_2$SO$_4$, filtered and concentrated under reduced pressure. The residue was purified by silica gel column chromatography, using petroleum ether/EtOAc (10:1) to give the title compound (1 g, 51.4%). $^1$H NMR (400 MHz, CDCl$_3$) δ ppm 4.27 (s, 2H), 6.97 (t, J=8.71 Hz, 2H), 7.21-7.28 (m, 2H), 8.23 (d, J=2.43 Hz, 1H), 8.43 (d, J=2.43 Hz, 1H); ESI-MS m/z [M+H]$^+$ 223.1.

Preparation 31: 2-chloro-3-(1-(4-fluorophenyl)ethyl)pyrazine

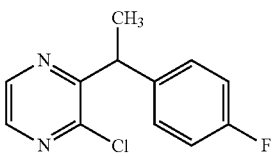 [SMILES: CC(c1ccc(F)cc1)c1nccnc1Cl]

Step A: (E)-2-chloro-3-(1-(4-fluorophenyl)-2-(trimethylsilyl)vinyl)pyrazine

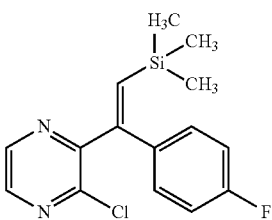 [SMILES: C[Si](C)(C)/C=C(\c1ccc(F)cc1)c1nccnc1Cl]

The title compound was prepared like STEP A of PREPARATION 3, using 2,3-dichloropyrazine (500 mg, 3.36 mmol), (Z)-(2-(4-fluorophenyl)-2-(4,4,5,5-tetramethyl-1,3,2-dioxaborolan-2-yl)vinyl)trimethylsilane (1.18 g, 3.69 mmol), PdCl$_2$(dppf) (245.57 mg, 335.62 μmol) and Na$_2$CO$_3$ (4 M, 2.10 mL) in dioxane (8 mL), and was obtained as a yellow oil (797 mg, 77.3%). ESI-MS m/z [M+H]$^+$ 307.1.

Step B: 2-chloro-3-(1-(4-fluorophenyl)vinyl)pyrazine

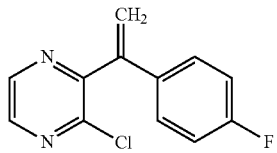

The title compound was prepared like STEP B of PREPARATION 3, using (E)-2-chloro-3-(1-(4-fluorophenyl)-2-(trimethylsilyl)vinyl)pyrazine (780 mg, 2.54 mmol) in TFA (16 mL, 216.10 mmol), and was obtained as a yellow oil (290 mg, 48.7%). ESI-MS m/z [M+H]$^+$ 235.1.

Step C: 2-chloro-3-(1-(4-fluorophenyl)ethyl)pyrazine

To a solution of 2-chloro-3-(1-(4-fluorophenyl)vinyl)pyrazine (290 mg, 1.236 mmol) in EtOAc (5 mL) was added PtO$_2$ (90 mg). The suspension was degassed under vacuum, purged with H$_2$ several times, stirred under H$_2$ (15 psi) at 20° C. for 16 hours and then filtered through a pad of Celite®. The filtrate was concentrated in vacuo and purified by silica gel column chromatography, using a gradient of petroleum ether/EtOAc (1:0 to 10:1) to give the title compound as a yellow oil (125 mg, 42.7%). $^1$H NMR (400 MHz, CDCl$_3$) δ ppm 1.68 (d, J=7.1 Hz, 3H), 4.70 (d, J=7.1 Hz, 1H), 6.94-7.02 (m, 2H), 7.27-7.32 (m, 2H), 8.23 (d, J=2.4 Hz, 1H), 8.51 (d, J=2.4 Hz, 1H); ESI-MS m/z [M+H]$^+$ 237.1.

Preparation 32: 3-chloro-N-(2-(pyrrolidin-1-yl)ethyl)pyrazin-2-amine

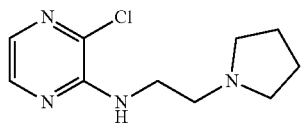 [SMILES: Clc1nccnc1NCCN1CCCC1]

To a solution of 2,3-dichloropyrazine (500 mg, 3.36 mmol) in dioxane (22.4 mL) was added 2-(pyrrolidin-1-yl)ethan-1-amine (498 mg, 4.36 mmol) followed by DIPEA (879 μL, 5.03 mmol). The solution was heated at 80° C. overnight and purified by silica gel column chromatography (NH column) using a gradient of 10-100% EtOAc in heptane to give the title compound as a yellow oil (450 mg, 59.1%). $^1$H NMR (400 MHz, CDCl$_3$) δ ppm 1.82 (dt, J=6.88, 3.26 Hz, 4H), 2.54-2.64 (m, 4H), 2.77 (t, J=6.14 Hz, 2H), 3.43-3.66 (m, 2H), 5.86 (br s, 1H), 7.56 (d, J=2.75 Hz, 1H), 7.95 (d, J=2.75 Hz, 1H).

Preparation 33: 3-chloro-2-(1-(4-fluorophenyl)ethyl)-5-(trifluoromethyl)pyrazine

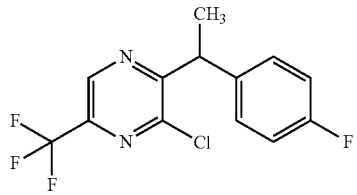 [SMILES: CC(c1ccc(F)cc1)c1ncc(C(F)(F)F)nc1Cl]

Step A: 3-chloro-2-(1-(4-fluorophenyl)vinyl)-5-(trifluoromethyl)pyrazine

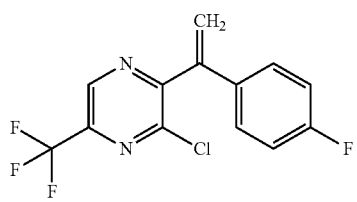 [SMILES: C=C(c1ccc(F)cc1)c1ncc(C(F)(F)F)nc1Cl]

To a 250 mL round-bottomed flask were added 2,3-dichloro-5-(trifluoromethyl)pyrazine (0.36 g, 1.659 mmol), 2-(1-(4-fluorophenyl)vinyl)-4,4,5,5-tetramethyl-1,3,2-dioxaborolane (0.617 g, 2.489 mmol), PdCl$_2$(dppf)$_2$ (0.121 g, 0.166 mmol), Na$_2$CO$_3$ (1.659 mL, 3.32 mmol) and dioxane (16.59 mL) to give an orange suspension. The suspension was degassed with N$_2$ and then heated at 110° C. overnight. The reaction mixture was treated with water and extracted with EtOAc. The organic layers were washed with brine, dried over anhydrous MgSO$_4$, concentrated under reduced pressure and purified by silica gel column chromatography, using a gradient of hexane/EtOAc (1:0 to 9:1) to give the title compound (0.216 g, 43%). ESI-MS m/z [M+H]$^+$ 303.1.

Step B: 3-chloro-2-(1-(4-fluorophenyl)ethyl)-5-(trifluoromethyl)pyrazine

To a 250 mL round-bottomed flask were added 3-chloro-2-(1-(4-fluorophenyl)vinyl)-5-(trifluoromethyl)pyrazine (0.502 g, 1.659 mmol), platinum (0.065 g, 0.017 mmol) and MeOH (20 mL) to give a black suspension. The flask was evacuated and back-filled with hydrogen (3×) and the suspension was stirred at room temperature under hydrogen atmosphere (balloon) overnight. The reaction mixture was filtered, and the filtrate was concentrated under reduced pressure to give the title compound (487 mg) which was used without further purification. ESI-MS m/z [M+H]$^+$ 305.1.

Preparation 34: 5-(4-fluorobenzyl)-6-((2-(pyrrolidin-1-yl)ethyl)amino)nicotinic acid

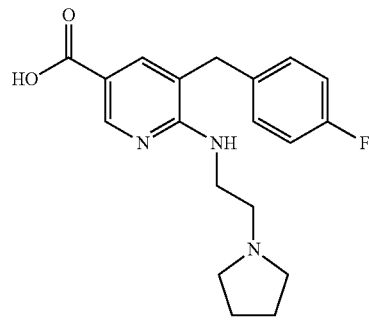 [SMILES: O=C(O)c1cnc(NCCN2CCCC2)c(Cc2ccc(F)cc2)c1]

Step A: methyl 6-chloro-5-(4-fluorobenzyl)nicotinate

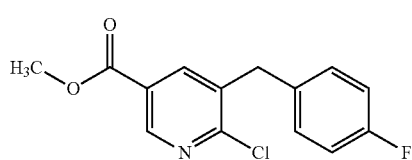 [SMILES: COC(=O)c1cnc(Cl)c(Cc2ccc(F)cc2)c1]

To a 250 mL round-bottomed flask were added methyl 5-bromo-6-chloronicotinate (1.0 g, 3.99 mmol), 2-(4-fluorobenzyl)-4,4,5,5-tetramethyl-1,3,2-dioxaborolane (1.414 g, 5.99 mmol), PdCl$_2$(dppf)$_2$ (0.584 g, 0.798 mmol), and Na$_2$CO$_3$ (1.269 g, 11.98 mmol) in dioxane (30 mL) and water (7.50 mL) to give an orange suspension. The suspension was sparged with nitrogen for 5 minutes and then heated at 100° C. for 2 hours and filtered. The filtrate was treated with water and extracted with EtOAc. The organic phase was dried over anhydrous MgSO$_4$ and purified via Biotage® column chromatography (40 g column) using a gradient of hexane/EtOAc (4:1 to 1:1) to give the title compound as a light-yellow syrup (0.516 g, 46.2%). ESI-MS m/z [M+H]$^+$ 280.3.

Step B: methyl 5-(4-fluorobenzyl)-6-((2-(pyrrolidin-1-yl)ethyl)amino)nicotinate

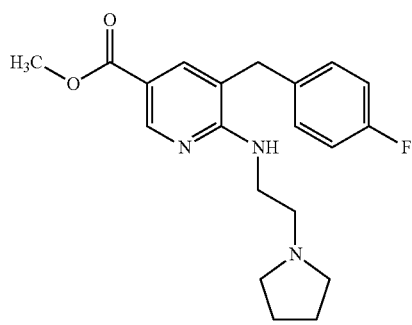 [SMILES: COC(=O)c1cnc(NCCN2CCCC2)c(Cc2ccc(F)cc2)c1]

To a 40 mL vial were added methyl 6-chloro-5-(4-fluorobenzyl)nicotinate (0.15 g, 0.536 mmol), 2-(pyrrolidin-1- yl)ethan-1-amine (0.067 g, 0.590 mmol), (R)-2,2'-bis(diphenylphosphanyl)-1,1'-binaphthalene (0.033 g, 0.054 mmol), Pd$_2$(dba)$_3$ (0.049 g, 0.054 mmol) and Cs$_2$CO$_3$ (0.349 g, 1.073 mmol) in toluene (4 mL) to give a tan suspension. The suspension was degassed and then heated at 90° C. overnight. The reaction mixture was treated with water and extracted with EtOAc. The organic layer was dried over anhydrous MgSO$_4$ and concentrated to give a tan film (0.192 g) which was used without further purification. ESI-MS m/z [M+H]$^+$ 358.4.

Step C: 5-(4-fluorobenzyl)-6-((2-(pyrrolidin-1-yl)ethyl)amino)nicotinic acid

To a 125 mL pear flask were added methyl 5-(4-fluorobenzyl)-6-((2-(pyrrolidin-1-yl)ethyl)amino)nicotinate (0.192 g, 0.536 mmol) and lithium hydroxide (1.072 mL, 2.144 mmol) in dioxane (3 mL) to give a tan solution. The solution was stirred at room temperature overnight and then treated with diluted HCl and extracted with EtOAc. The aqueous phase was concentrated under reduced pressure to give a brown film, which was used without further purification. ESI-MS m/z [M+H]$^+$ 344.4.

Preparation 35: 6-((1,3-dimethylpiperidin-4-yl)amino)-5-(4-fluorobenzyl)nicotinic acid

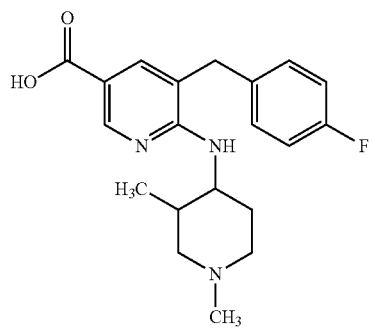 [SMILES: CC1CN(C)CCC1Nc1ncc(C(=O)O)cc1Cc1ccc(F)cc1]

Step A: methyl 5-bromo-6-((1-(tert-butoxycarbonyl)-3-methylpiperidin-4-yl)amino)nicotinate

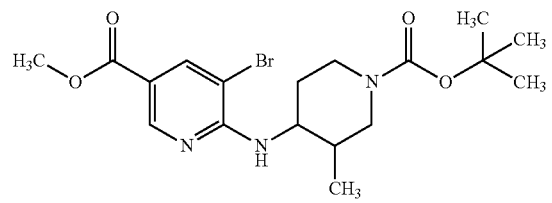 [SMILES: COC(=O)c1cnc(NC2CCN(C(=O)OC(C)(C)C)CC2C)c(Br)c1]

To a 40 mL vial were added methyl 5-bromo-6-chloronicotinate (0.188 g, 0.751 mmol), tert-butyl 4-amino-3-methylpiperidine-1-carboxylate, HCl (0.188 g, 0.751 mmol) and DIPEA (0.392 mL, 2.252 mmol) in dioxane (4 mL) to give a white suspension. The suspension was stirred at 80° C. for 2 days and then heated at 100° C. for 1 week. About 50% conversion was observed. The reaction mixture was treated with water and extracted with EtOAc. The organic layers were washed with brine, dried over anhydrous MgSO$_4$ and concentrated. The resulting residue was purified by Biotage® column chromatography (40 g column) using a gradient of hexane/EtOAc (4:1 to 1:1) to give the title compound as a tan film (50.0 mg, 15.6%). ESI-MS m/z [M+H]$^+$ 428.3.

Step B: methyl 6-((1-(tert-butoxycarbonyl)-3-methylpiperidin-4-yl)amino)-5-(4-fluorobenzyl)nicotinate

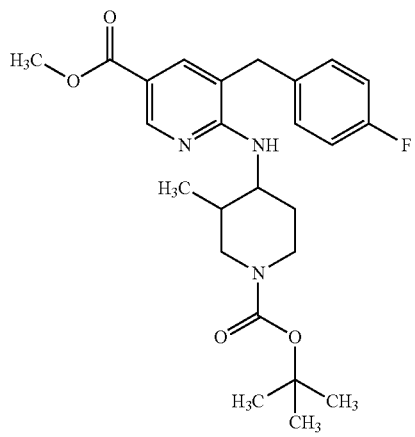 [SMILES: COC(=O)c1cnc(NC2CCN(C(=O)OC(C)(C)C)CC2C)c(Cc2ccc(F)cc2)c1]

To a 100 mL round-bottomed flask were added methyl 5-bromo-6-((1-(tert-butoxycarbonyl)-3-methylpiperidin-4-yl)amino)nicotinate (0.050 g, 0.117 mmol), 2-(4-fluorobenzyl)-4,4,5,5-tetramethyl-1,3,2-dioxaborolane (0.050 g, 0.210 mmol), (dppf)$_2$PdCl$_2$ (8.54 mg, 0.012 mmol) and Na$_2$CO$_3$ (0.025 g, 0.233 mmol) in dioxane (3 mL) and water (0.750 mL) to give an orange solution. The solution was degassed with N$_2$ and then heated at 110° C. overnight. After cooling down to room temperature, the reaction mixture was treated with water and extracted with EtOAc. The organic layers were washed with brine, dried over anhydrous MgSO$_4$ and concentrated to give the title compound as a tan film, which was used without further purification. ESI-MS m/z [M+H]$^+$ 458.5.

Step C: methyl 5-(4-fluorobenzyl)-6-((3-methylpiperidin-4-yl)amino)nicotinate

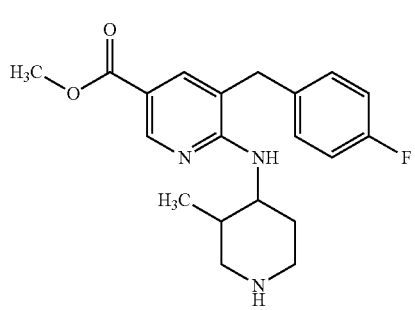 [SMILES: COC(=O)c1cnc(NC2CCNCC2C)c(Cc2ccc(F)cc2)c1]

To a 125 mL pear flask were added methyl 6-((1-(tert-butoxycarbonyl)-3-methylpiperidin-4-yl)amino)-5-(4-fluorobenzyl)nicotinate (0.054 g, 0.117 mmol) and hydrogen chloride (0.117 mL, 0.468 mmol) in dioxane (3 mL) to give a brown solution. The solution was stirred at 50° C. for 3 hours and then concentrated to give the title compound as a tan solid, which was used without further purification. ESI-MS m/z [M+H]+ 358.4.

Step D: methyl 6-((1,3-dimethylpiperidin-4-yl)amino)-5-(4-fluorobenzyl)nicotinate

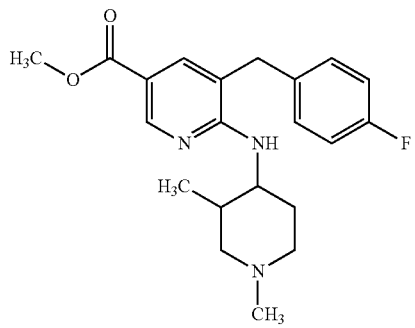 [SMILES: COC(=O)c1cnc(NC2CCN(C)CC2C)c(Cc2ccc(F)cc2)c1]

To a 125 mL pear flask were added methyl 5-(4-fluorobenzyl)-6-((3-methylpiperidin-4-yl)amino)nicotinate (0.042 g, 0.117 mmol) and formaldehyde (0.018 mL, 0.232 mmol) in methanol (3 mL) to give a tan solution. Sodium cyanotrihydroborate (0.015 g, 0.232 mmol) was added, and the reaction mixture was stirred at room temperature for 3 hours and then treated with water and extracted with EtOAc. The organic layers were washed with brine, dried over anhydrous MgSO4 and concentrated under reduced pressure to give the title compound as a tan film, which was used without further purification. ESI-MS m/z [M+H]+ 372.4.

Step E: 6-((1,3-dimethylpiperidin-4-yl)amino)-5-(4-fluorobenzyl)nicotinic acid

To a 100 mL round-bottomed flask were added methyl 6-((1,3-dimethylpiperidin-4-yl)amino)-5-(4-fluorobenzyl)nicotinate (0.043 g, 0.117 mmol) and lithium hydroxide (0.234 mL, 0.468 mmol) in dioxane (3 mL) to give a tan solution. The solution was stirred at room temperature for 3 days. The reaction mixture was adjusted to pH 4 by treatment with 1.0 N HCl and was extracted with EtOAc. The aqueous phase was concentrated, and the resulting residue was re-dissolved in ethanol. A precipitate was filtered off and the filtrate was concentrated under reduced pressure to give the title compound as a brown film, which was used without further purification. ESI-MS m/z [M+H]+358.4.

Preparation 36: 3-bromo-N-(2-(pyrrolidin-1-yl)ethyl)-6-(trifluoromethyl)pyridin-2-amine

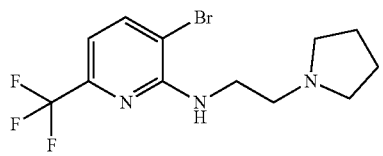 [SMILES: FC(F)(F)c1ccc(Br)c(NCCN2CCCC2)n1]

To a 125 mL round-bottomed flask were added 3-bromo-2-chloro-6-(trifluoromethyl)pyridine (1.0 g, 3.84 mmol), 2-(pyrrolidin-1-yl)ethan-1-amine (0.482 g, 4.22 mmol) and potassium carbonate (1.061 g, 7.68 mmol) in DMF (8 mL) to give a white suspension. The suspension was heated at 100° C. overnight and then treated with water and extracted with EtOAc. The organic layers were washed with brine, dried over anhydrous MgSO4 and concentrated to give the title compound as a tan syrup (1.37 g, 94%) which was used without further purification. ESI-MS m/z [M+H]+ 339.3.

Preparation 37: 6-(1-(4-fluorophenyl)ethyl)-N-(2-oxopropyl)-5-((2-(pyrrolidin-1-yl)ethyl)amino)pyrazine-2-carboxamide

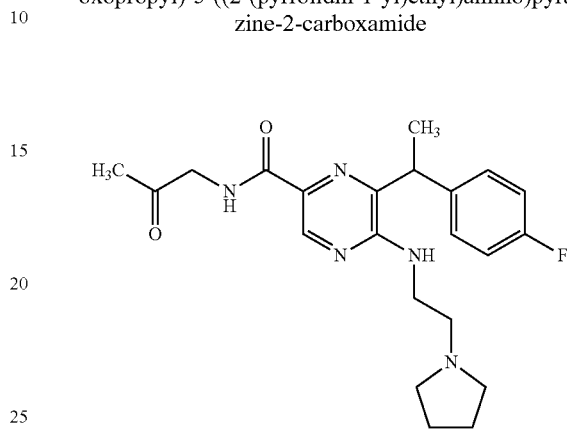

Step A: 6-(1-(4-fluorophenyl)ethyl)-N-(2-hydroxypropyl)-5-((2-(pyrrolidin-1-yl)ethyl)amino)pyrazine-2-carboxamide

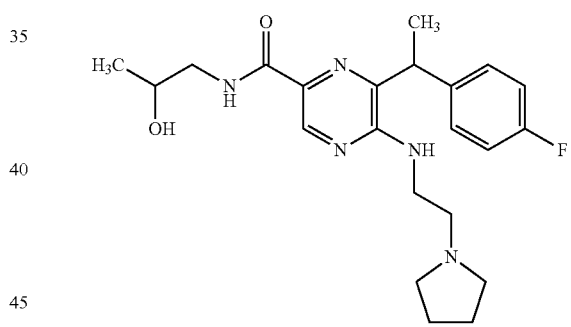

To a round bottom flask containing 6-(1-(4-fluorophenyl)ethyl)-5-((2-(pyrrolidin-1-yl)ethyl)amino)pyrazine-2-carboxylic acid (0.5 g, 1.40 mmol) and 1-aminopropan-2-ol (157.17 mg, 2.09 mmol, 163.89 μL) in DMF (5 mL) were added DIPEA (728.96 μL, 540.89 mg, 4.19 mmol) and HATU (1.06 g, 2.79 mmol). The reaction mixture was stirred at 25° C. for 16 hours and then purified by silica gel column chromatography, using a gradient of 0-10% MeOH in DCM to give the title compound as a yellow gum (0.2 g, 32.7%). ESI-MS m/z [M+H]+ 416.3.

Step B: 6-(1-(4-fluorophenyl)ethyl)-N-(2-oxopropyl)-5-((2-(pyrrolidin-1-yl)ethyl)amino)pyrazine-2-carboxamide To a round bottom flask containing 6-(1-(4-fluorophenyl)ethyl)-N-(2-hydroxypropyl)-5-((2-(pyrrolidin-1-yl)ethyl)amino)pyrazine-2-carboxamide (0.2 g, 481.34 μmol) in DCM (2 mL) was added DMP (223.53 μL, 722.02 μmol) at 0° C. The reaction mixture was stirred at 25° C. for 16 hours and then purified by silica gel column chromatography, using a 0-10% gradient of MeOH in DCM to give the title compound as a yellow gum (0.18 g, 83.2%). ESI-MS m/z [M+H]⁺ 414.3.

Preparation 38: 6-(1-(4-fluorophenyl)ethyl)-3-methyl-N-(2-oxopropyl)-5-((2-(pyrrolidin-1-yl)ethyl)amino)pyrazine-2-carboxamide

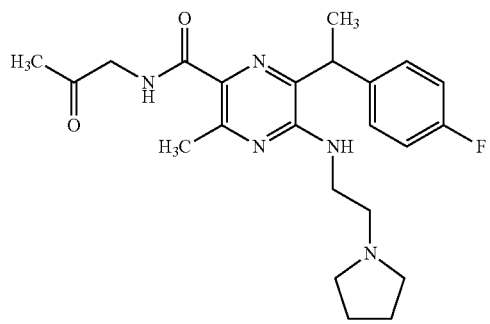 [SMILES: CC(=O)CNC(=O)c1nc(C(C)c2ccc(F)cc2)c(NCCN2CCCC2)nc1C]

Step A: 6-(1-(4-fluorophenyl)ethyl)-N-(2-hydroxypropyl)-3-methyl-5-((2-(pyrrolidin-1-yl)ethyl)amino)pyrazine-2-carboxamide

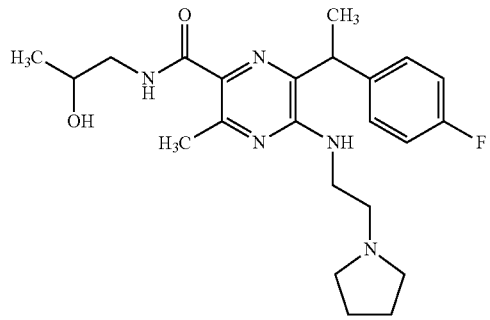 [SMILES: Cc1nc(NCCN2CCCC2)c(C(C)c2ccc(F)cc2)nc1C(=O)NCC(C)O]

To a solution of 6-(1-(4-fluorophenyl)ethyl)-3-methyl-5-((2-(pyrrolidin-1-yl)ethyl)amino)pyrazine-2-carboxylic acid (300 mg, 0.532 mmol) and HATU (202 mg, 0.532 mmol) in DMF (5.3 mL) was added DIPEA (206 mg, 1.595 mmol). The solution was stirred at room temperature for 10 minutes and then 1-aminopropan-2-ol (43.9 mg, 0.585 mmol) was added. The reaction mixture was stirred at room temperature for 6 hours and then purified by silica gel column chromatography (NH column) using a gradient of 0-10% MeOH in DCM to give the title compound as a colorless oil (174 mg, 0.405 mmol, 76%). ESI-MS m/z [M+H]⁺ 430.20.

Step B: 6-(1-(4-fluorophenyl)ethyl)-3-methyl-N-(2-oxopropyl)-5-((2-(pyrrolidin-1-yl)ethyl)amino)pyrazine-2-carboxamide A solution of 6-(1-(4-fluorophenyl)ethyl)-N-(2-hydroxypropyl)-3-methyl-5-((2-(pyrrolidin-1-yl)ethyl)amino)pyrazine-2-carboxamide (170 mg, 0.396 mmol) and Dess-Martin periodinane (218 mg, 0.515 mmol) in DCM (4.0 mL) was stirred at room temperature for 4 hours and then diluted with saturated aq Na₂S₂O₃ (3 mL) and NaHCO₃ (3 mL). The mixture was stirred vigorously for 1 hour and then purified by silica gel column chromatography, using a gradient of 15-100% EtOAc in heptane to give the title compound as a colorless oil (52 mg, 30.7%). ESI-MS m/z [M+H]⁺ 428.15.

Preparation 39: 3-chloro-6-(3-methylbenzyl)-5-(methylthio)-1,2,4-triazine

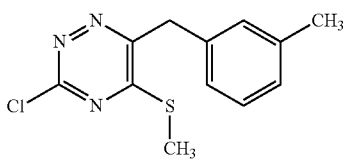 [SMILES: CSc1nc(Cl)nnc1Cc1cccc(C)c1]

Step A: 6-iodo-1,2,4-triazine-3,5(2H,4H)-dione

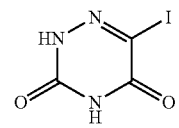

To a mixture of 2H-1,2,4-triazine-3,5-dione (17.00 g, 150.4 mmol) in water (530 mL) were added KI (79.87 g, 481.1 mmol), NaOH (24.06 g, 601.4 mmol) and I2 (114.48 g, 451.05 mmol) at 20° C. The reaction mixture was stirred at 120° C. for 24 hours and then quenched with saturated aq Na₂S₂O₃ (250 mL), acidified to pH 2-3 with aqueous 4 M HCl and extracted with EtOAc (500 mL×3). The combined organic layers were dried, filtered and concentrated in vacuo to afford a light-yellow solid (14.0 g, 60% purity). The solid was purified by flash silica column chromatography, using DCM/EtOH/HCO₂H (100:2:1) to give the title compound as a light-yellow solid (10.0 g, 22% yield, 80% purity). ¹H NMR (400 MHz, DMSO-d₆) δ ppm 7.38 12.14 (br s, 1H), 12.59 (br s, 1H).

Step B: 6-(3-methylbenzyl)-1,2,4-triazine-3,5(2H,4H)-dione

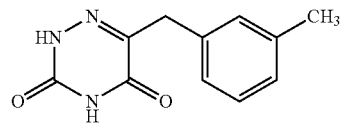 [SMILES: Cc1cccc(Cc2n[nH]c(=O)[nH]c2=O)c1]

A mixture of 4,4,5,5-tetramethyl-2-(3-methylbenzyl)-1,3,2-dioxaborolane (2.80 g, 12.0 mmol), 6-iodo-1,2,4-triazine-3,5(2H,4H)-dione (3.00 g, 10.0 mmol), Pd(dppf)Cl₂ (514.4 mg, 702.8 μmol) and aqueous Na₂CO₃ (2.5 M, 11.32 mL, 28.2 mmol) in dioxane (50 mL) was stirred at 100° C. for 24 hours. The reaction was quenched with water (100 mL) and the reaction mixture was acidified to pH 2-3 with aqueous 2 M HCl (2 M) and extracted with EtOAc (100 mL 3×). The combined organic layers were dried over Na₂SO₄, filtered and concentrated under reduced pressure. The crude product was purified by flash silica column chromatography, using petroleum ether/EtOAc/MeOH (50:50:1) to give a light brown gum (3 g). The gum was purified by preparative HPLC (Phenomenex Synergi Max-RP 10 μm, ID 50 mm×250 mm) using a gradient of 5-55% ACN in water (0.225% FA) to give the title compound as an off-white solid (900 mg, 41%). $^1$H NMR (400 MHz, DMSO-d$_6$) δ ppm 2.26 (s, 3H), 3.73 (s, 2H), 6.97-7.07 (m, 3H), 7.12-7.20 (m, 1H), 11.94 (br s, 1H), 12.10 (s, 1H); ESI-MS m/z [M+H]$^+$ 218.2.

Step C:
3,5-dichloro-6-(3-methylbenzyl)-1,2,4-triazine

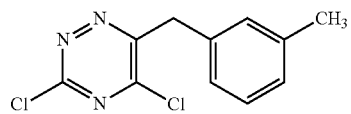 [SMILES: Cc1cccc(Cc2nnc(Cl)nc2Cl)c1]

A mixture of 6-(3-methylbenzyl)-1,2,4-triazine-3,5(2H,4H)-dione (850 mg, 3.91 mmol) in POCl$_3$ (20.0 mL) was stirred at 110° C. for 24 hours and then cooled and concentrated under reduced pressure. The resulting residue was diluted with DCM (50 mL) and the mixture was carefully added to ice water (100 mL). The organic phase was dried over anhydrous Na$_2$SO$_4$, filtered, and concentrated under reduced pressure to afford crude product, which was purified by flash silica column chromatography, using a gradient of petroleum ether/EtOAc (30:1 to 10:1). The title compound was obtained as a light-yellow oil (700 mg, 67%). $^1$H NMR (400 MHz, CDCl$_3$) δ ppm 2.33 (s, 3H), 4.43 (s, 2H), 7.04-7.14 (m, 3H), 7.17-7.25 (m, 1H).

Step D: 3-chloro-6-(3-methylbenzyl)-5-(methylthio)-1,2,4-triazine

To a solution of 3,5-dichloro-6-(3-methylbenzyl)-1,2,4-triazine (700 mg, 2.75 mmol) in THF (25.0 mL) was carefully added an aqueous solution of NaSMe (20%, 1.00 mL, 3.14 mmol) at 0° C. The mixture was stirred at 15° C. for 16 hours and then diluted with water (20 mL) and extracted with EtOAc (20 mL×2). The combined organic layers were washed with saturated aq NaCl (15 mL×3), dried, filtered and concentrated under reduced pressure. The resulting residue was purified by flash silica column chromatography, using petroleum ether/EtOAc (10:1) to give the title compound as a yellow solid (190 mg, 24%). $^1$H NMR (400 MHz, CDCl$_3$) δ ppm 2.32 (s, 3H), 2.56 (s, 3H), 4.23 (s, 2H), 7.04-7.14 (m, 3H), 7.17-7.23 (m, 1H); ESI-MS m/z [M+H]$^+$ 265.9.

Preparation 40: 3-ethyl-6-(3-methylbenzyl)-5-(methylthio)-1,2,4-triazine

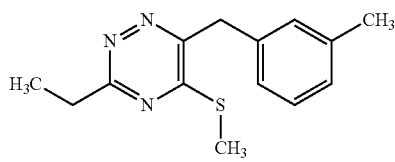 [SMILES: CCc1nnc(Cc2cccc(C)c2)c(SC)n1]

To a mixture of 3-chloro-6-(3-methylbenzyl)-5-(methylthio)-1,2,4-triazine (40.0 mg, 140 μmol) and Pd(dppf)Cl$_2$·CH$_2$Cl$_2$ (11.4 mg, 14.0 μmol) in dioxane (1.50 mL) was added 1 M diethylzinc in toluene (200 μL, 200 μmol) at 0° C. The reaction mixture was stirred at 85° C. for 1.5 hours under N$_2$ and then quenched with water (2 mL) and extracted with EtOAc (15 mL×3). The combined organic layers were dried, filtered and concentrated under reduced pressure. The resulting residue was purified by preparative TLC, using petroleum ether/EtOAc (3:1) to give the title compound as a light-yellow oil (30.0 mg, 78%). ESI-MS m/z [M+H]$^+$ 260.0.

Preparation 41: 3-methyl-6-(3-methylbenzyl)-5-(methylthio)-1,2,4-triazine

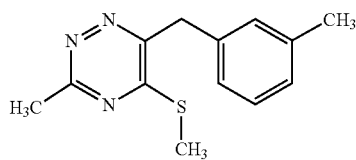

To a mixture of 3-chloro-6-(3-methylbenzyl)-5-(methylthio)-1,2,4-triazine (40.0 mg, 140 μmol) and Pd(PPh$_3$)$_4$ (16.2 mg, 14.0 μmol) in THF (1.20 mL) was added 2 M trimethylaluminum in toluene solution (200 μL, 400 μmol) at 0° C. The mixture was stirred at 70° C. for 16 hours under N$_2$ and then quenched with water (2 mL), acidified to pH 3-4 by addition of 1 N HCl aq solution and extracted with EtOAc (15 mL 3×). The combined organic layers were dried, filtered and concentrated under reduced pressure. The resulting residue was purified by preparative TLC, using petroleum ether/EtOAc (2:1) to give the title compound as a light-yellow oil (28.0 mg, 78%). ESI-MS m/z [M+H]$^+$ 246.1.

Preparation 42: 3-methyl-6-(1-phenylethyl)-1,2,4-triazin-5(4H)-one

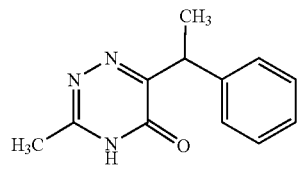 [SMILES: Cc1nnc(C(C)c2ccccc2)c(=O)[nH]1]

Step A: 2-oxo-3-phenylbutanoic acid

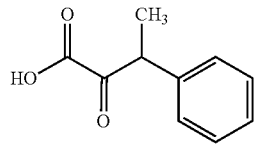

Starting material (Z)-2-hydroxy-3-phenylacrylic acid (7.917 g, 48.2 mmol) was dissolved in a heated solution of 1.0 M NaOH (101 mL, 101 mmol) and allowed to cool to room temperature. Next, MeI (3.00 mL, 48.2 mmol) was added. The reaction mixture was stirred at room temperature for 3 days and then acidified with 1N HCl until the solution remained white. The mixture was extracted with Et$_2$O, dried over anhydrous Na$_2$SO$_4$, filtered and concentrated in vacuo.

The resulting residue was purified by a silica gel column chromatography, using a gradient of 25-30% EtOAc in heptanes to give the title compound (3.502 g, 40.8%). $^1$H NMR (500 MHz, DMSO-d$_6$) δ ppm 1.34 (d, J=6.83 Hz, 3H), 4.43-4.54 (m, 1H), 7.18-7.23 (m, 2H), 7.24-7.30 (m, 1H), 7.32-7.37 (m, 2H).

Step B: 3-methyl-6-(1-phenylethyl)-1,2,4-triazin-5(4H)-one

To a vial containing a solution of acetimidamide HCl (0.532 g, 5.63 mmol) in EtOH (2.84 mL) was added hydrazine hydrate (0.282 g, 5.63 mmol) in EtOH (2.84 mL). The mixture was stirred at room temperature for 10 minutes. Next, 2-oxo-3-phenylbutanoic acid (0.912 g, 5.12 mmol) in EtOH (2.84 mL) was added, and the mixture was stirred at room temperature for 1 hour. The vial was heated to 150° C. for 5 minutes. The solution was filtered and concentrated in vacuo. The crude material was taken up in DMF and MeOH, filtered and purified by preparative HPLC (Phenomenex Gemini® 30 mm ID×100 mm) using a gradient of 10-100% aq ACN (80%, 10 mM NH$_4$HCO$_3$) in water (10 mM NH$_4$HCO$_3$) to give the title compound (0.539 g, 48.9%). $^1$H NMR (500 MHz, DMSO-d$_6$) δ ppm 1.44 (d, J=6.83 Hz, 3H), 2.21-2.28 (m, 3H), 4.36 (d, J=6.35 Hz, 1H), 7.15-7.21 (m, 1H), 7.22-7.30 (m, 4H), 13.55 (br s, 1H).

Preparation 43: 6-(1-(4-fluorophenyl)ethyl)-3-methyl-1,2,4-triazin-5(4H)-one

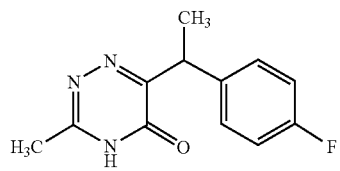 [SMILES: Cc1nnc(C(C)c2ccc(F)cc2)c(=O)[nH]1]

Step A: 3-(4-fluorophenyl)-2-oxobutanoic acid

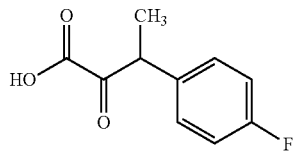

To a solution of (Z)-3-(4-fluorophenyl)-2-hydroxyacrylic acid (2.469 g, 13.55 mmol) dissolved in NaOH aq (28.5 mL, 28.5 mmol) was added iodomethane (0.844 mL, 13.55 mmol). The resulting solution was stirred at room temperature for 6 days and then acidified with 1.0 N HCl until the solution remained white. The mixture was extracted with EtOAc. The organic layer was dried over Na$_2$SO$_4$, filtered and concentrated in vacuo to afford a dark red viscous oil. The crude product was purified by a silica gel column chromatography, using 40% EtOAc in heptanes to give the title compound (1.5287 g, 57.5%). ESI-MS m/z [M+H]$^+$ 197.1.

Step B: 6-(1-(4-fluorophenyl)ethyl)-3-methyl-1,2,4-triazin-5(4H)-one

To a vial containing a solution of acetimidamide HCl (0.814 g, 8.61 mmol) in EtOH (4.02 mL) was added hydrazine hydrate(0.431 g, 8.61 mmol). The solution was stirred for 1 hour at room temperature. Next, a solution of 3-(4-fluorophenyl)-2-oxobutanoic acid (1.536 g, 7.83 mmol) in EtOH (4.02 mL) was added and the reaction mixture was stirred for 1 hour. The vial was sealed, and the reaction mixture was heated to 150° C. in a microwave reactor for 5 minutes. Ethyl acetate (5 mL) was added slowly to the stirred solution. The solids were filtered off, washing the filter cake with EtOAc. The filtrate and EtOAc wash were combined, concentrated under reduced pressure, taken up into DMF and MeOH, filtered, and purified by preparative HPLC (Phenomenex Gemini® C18, 5 μm, 30 mm ID×150 mm) using a gradient of 30-90% aq ACN (80%, 10 mM NH$_4$HCO$_3$) in water (10 mM NH$_4$HCO$_3$) to give the title compound (0.484 g, 26.5%).

Preparation 44: 3-chloro-6-(4-fluorobenzyl)-5-(methylthio)-1,2,4-triazine

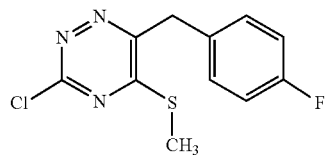 [SMILES: CSc1nc(Cl)nnc1Cc1ccc(F)cc1]

Step A: 6-(4-fluorobenzyl)-1,2,4-triazine-3,5(2H,4H)-dione

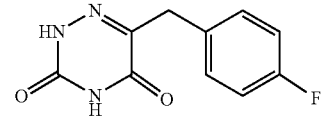 [SMILES: O=c1[nH]nc(Cc2ccc(F)cc2)c(=O)[nH]1]

To a mixture of 3-(4-fluorophenyl)-2-oxo-propanoic acid (16 g, 87.84 mmol) and aminourea hydrogen chloride (11 g, 98.63 mmol) in water (130 mL) was added 1 N NaOH (400 mL) at 80° C. The mixture was stirred at 80° C. for 16 hours and then cooled to 0° C. and acidified to pH 3~4 by addition of 12 N HCl aq. The precipitate was collected by filtration to give a light-yellow solid, which was dissolved in EtOAc (500 mL) and washed with brine (50 mL×2). The organic layer was dried over Na$_2$SO$_4$, filtered and concentrated in vacuo to give the title compound as a light-yellow solid (14.8 g, 76%). $^1$H NMR (400 MHz, DMSO-d$_6$) δ ppm 3.76 (s, 2H), 7.02-7.17 (m, 2H), 7.23-7.31 (m, 2H), 11.96 (br s, 1H), 12.12 (s, 1H).

Step B: 3,5-dichloro-6-(4-fluorobenzyl)-1,2,4-triazine

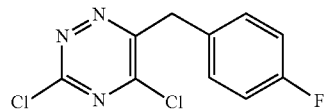 [SMILES: Fc1ccc(Cc2nnc(Cl)nc2Cl)cc1]

A mixture of 6-(4-fluorobenzyl)-1,2,4-triazine-3,5(2H,4H)-dione (10 g, 45.21 mmol) in POCl$_3$ (210 mL) was stirred at 110° C. for 8 hours. The reaction mixture was cooled to room temperature and concentrated in vacuo. The residue was diluted with EtOAc (200 mL) and the mixture was carefully added to ice water (400 mL). The organic layer was separated, washed with brine (20 mL×2), dried over Na$_2$SO$_4$, filtered and concentrated in vacuo. The product was purified by silica gel flash column chromatography, using petroleum ether/EtOAc (10:1) to give the title compound as a yellow oil (7.3 g, 63%). $^1$H NMR (400 MHz, CDCl$_3$) δ ppm 4.44 (s, 2H), 6.98-7.06 (m, 2H), 7.29 (dd, J=8.5, 5.5 Hz, 2H); ESI-MS m/z [M+H]$^+$ 257.9.

Step C: 3-chloro-6-(4-fluorobenzyl)-5-(methylthio)-1,2,4-triazine

To a solution of 3,5-dichloro-6-(4-fluorobenzyl)-1,2,4-triazine (7.3 g, 28.29 mmol) in THF (70 mL) was carefully added a solution of 20% NaSMe aq (14.87 g, 42.44 mmol) at 0° C. The mixture was stirred at 0° C. for 30 minutes and then diluted with water (100 mL) and extracted with EtOAc (300 mL×2). The combined organic layers were washed with brine (100 mL×3), dried over Na$_2$SO$_4$, filtered and concentrated in vacuo. The product was purified by flash silica gel column chromatography, using a gradient of EtOAc/petroleum ether (0:100 to 10:90) to give the title compound as a light-yellow solid (5.2 g, 68%). $^1$H NMR (400 MHz, CDCl$_3$) δ ppm 2.57 (s, 3H), 4.23 (s, 2H), 7.00 (t, J=8.5 Hz, 2H), 7.23-7.32 (m, 2H).

Preparation 45: 6-(4-fluorobenzyl)-3-methyl-5-(methylthio)-1,2,4-triazine

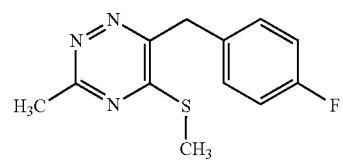 [SMILES: CSc1nc(C)nnc1Cc1ccc(F)cc1]

To a mixture of 3-chloro-6-(4-fluorobenzyl)-5-(methylthio)-1,2,4-triazine (4 g, 14.83 mmol) and Pd(PPh$_3$)$_4$ (1.71 g, 1.48 mmol) in THF (40 mL) was added a 2 M solution of trimethylaluminum in toluene (18.54 mL, 37.08 mmol) at 0° C. The reaction mixture was heated to 70° C. for 6 hours under N$_2$ and then quenched with water (50 mL), acidified to pH 3~4 with 4.0 N HCl aq solution and extracted with EtOAc (300 mL×2). The combined organic layers were dried over Na$_2$SO$_4$, filtered and concentrated in vacuo. The product was purified by flash silica gel column chromatography (ISCO® 40 g SepaFlash® column) using a gradient of EtOAc/petroleum ether (0:100 to 10:90) to give the title compound as a yellow solid (3.1 g, 52%). $^1$H NMR (400 MHz, CDCl$_3$) δ ppm 2.52 (s, 3H), 2.74 (s, 3H), 4.22 (s, 2H), 6.94-7.01 (m, 2H), 7.27-7.31 (m, 2H); ESI-MS m/z [M+H]$^+$ 250.2.

Preparation 46: 6-(1-(4-fluorophenyl)ethyl)-3-methyl-5-(methylthio)-1,2,4-triazine

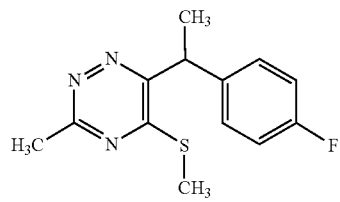 [SMILES: CSc1nc(C)nnc1C(C)c1ccc(F)cc1]

To a solution of 6-(4-fluorobenzyl)-3-methyl-5-(methylthio)-1,2,4-triazine (2.85 g, 11.43 mmol) in THF (60 mL) was added 1 M LiHMDS in THF (13.72 mL, 13.72 mmol) dropwise at −78° C. The solution was stirred for 30 minutes at −78° C. Next, iodomethane (3.24 g, 22.86 mmol, 1.42 mL) was added. The reaction mixture was stirred at −78° C. for 2 hours and then quenched by carefully adding saturated NH$_4$Cl (40 mL) and extracted with EtOAc (500 mL). The combined organic layers were washed with brine, dried over Na$_2$SO$_4$, filtered and concentrated in vacuo. The product was purified by flash silica gel chromatography (ISCO® 40 g SepaFlash® column) using a gradient of EtOAc/petroleum ether (0:100 to 10:90) to give the title compound as a red oil (1.3 g, 43%). $^1$H NMR (400 MHz, CDCl$_3$) δ ppm 1.76 (d, J=7.1 Hz, 3H), 2.49 (s, 3H), 2.73 (s, 3H), 4.33 (q, J=6.9 Hz, 1H), 6.97 (t, J=8.7 Hz, 2H), 7.29 (dd, 5.5 Hz, 2H).

Preparation 47: 3-cyclopropyl-6-(4-fluorobenzyl)-5-(methylthio)-1,2,4-triazine

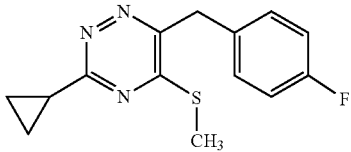 [SMILES: CSc1nc(C2CC2)nnc1Cc1ccc(F)cc1]

A mixture of 3-chloro-6-(4-fluorobenzyl)-5-(methylthio)-1,2,4-triazine (100 mg, 344.79 µmol), cyclopropylboronic acid (44.43 mg, 517.19 µmol), PdCl$_2$(dppf)·CH$_2$Cl$_2$ (28.16 mg, 34.48 µmol) and Cs$_2$CO$_3$ (1 M, 1.03 mL) in toluene (7 mL) was stirred at 80° C. for 16 hours. The reaction mixture was quenched with water (2 mL) and extracted with EtOAc (15 mL×3). The combined organic layers were dried over Na$_2$SO$_4$, filtered and concentrated in vacuo. The product was purified by flash silica gel column chromatography (ISCO® 4 g SepaFlash® column) using a gradient of EtOAc/petroleum ether (0:100 to 15:85) to give the title compound as an off-white solid (30.0 mg, 30%). $^1$H NMR (400 MHz, CDCl$_3$) δ ppm 1.06-1.20 (m, 4H), 2.37 (br s, 1H), 2.47 (s, 3H), 4.19 (s, 2H), 6.97 (t, J=8.4 Hz, 2H), 7.29 (br s, 2H); ESI-MS m/z [M+H]$^+$ 276.0.

Preparation 48: 3-ethyl-6-(4-fluorobenzyl)-5-(methylthio)-1,2,4-triazine

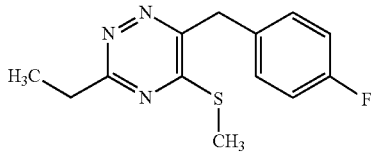 [SMILES: CCc1nnc(Cc2ccc(F)cc2)c(SC)n1]

To a mixture of 3-chloro-6-(4-fluorobenzyl)-5-(methylthio)-1,2,4-triazine (250 mg, 926.85 µmol) and PdCl$_2$(dppf)·CH$_2$Cl$_2$ (75.69 mg, 92.69 µmol) in dioxane (7 mL) was added 1 M diethylzinc in toluene (926.9 µL, 926.9 µmol) at 25° C. The mixture was heated to 60° C. for 2 hours under N$_2$ and then quenched with water (20 mL) and extracted with EtOAc (50 mL×3). The combined organic layers were dried over Na$_2$SO$_4$, filtered and concentrated in vacuo. The product was purified by flash silica gel column chromatography (ISCO® 12 g SepaFlash® column) using a gradient of EtOAc/petroleum ether (0:100 to 10:90) to give the title compound as a light-yellow oil (160.0 mg, 65%). $^1$H NMR (400 MHz, CDCl$_3$) δ ppm 1.40 (t, J=7.6 Hz, 3H), 2.54 (s, 3H), 3.03 (q, J=7.6 Hz, 2H), 4.22 (s, 2H), 6.96-7.02 (m, 2H), 7.28-7.34 (m, 2H).

Example 1

3-benzyl-N-(2-(pyrrolidin-1-yl)ethyl)quinoxalin-2-amine

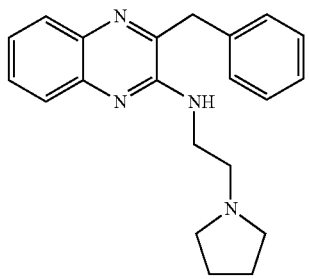 [SMILES: c1ccc(Cc2nc3ccccc3nc2NCCN2CCCC2)cc1]

To 10 mL microwave vial were added 2-benzyl-3-chloroquinoxaline (0.065 g, 0.255 mmol) and 2-(pyrrolidin-1-yl)ethanamine (0.087 g, 0.766 mmol) in NMP (3 mL). The mixture was heated at 150° C. for 2 hours in a Biotage® microwave reactor and then filtered and purified by preparative HPLC (Waters SunFire® C18, 5 µm, 30 mm ID×75 mm column) using a gradient of 10-35% ACN (0.035% TFA) in water (0.05% TFA). The pure fractions were combined and lyophilized to give the title compound as an off-white solid (0.063 g, 74%). $^1$H NMR (400 MHz, CD$_3$OD) δ ppm 1.90-2.16 (m, 4H), 3.02 (br s, 2H), 3.45-3.53 (m, 2H), 3.67 (br s, 2H), 3.86-3.92 (m, 2H), 4.27-4.33 (m, 2H), 7.20-7.34 (m, 5H), 7.44 (ddd, J=8.34, 6.95, 1.39 Hz, 1H), 7.56-7.64 (m, 1H), 7.66-7.71 (m, 1H), 7.85 (dd, J=8.34, 1.01 Hz, 1H); ESI-MS m/z [M+H]$^+$ 333.2.

Example 2

N-(2-(azetidin-1-yl)ethyl)-3-benzyl-8-methylquinoxalin-2-amine

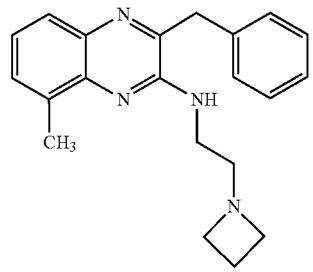 [SMILES: Cc1cccc2nc(Cc3ccccc3)c(NCCN3CCC3)nc12]

and

Example 3

N-(2-(azetidin-1-yl)ethyl)-3-benzyl-5-methylquinoxalin-2-amine

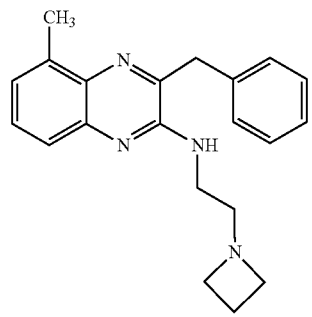 [SMILES: Cc1cccc2nc(NCCN3CCC3)c(Cc3ccccc3)nc12]

Step A: 3-benzyl-8-methylquinoxalin-2(1H)-one and 3-benzyl-5-methylquinoxalin-2(1H)-one

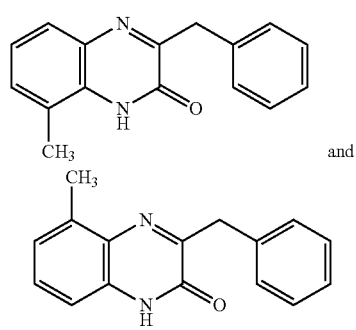

A mixture of 3-methylbenzene-1,2-diamine (3 g, 24.56 mmol) and 2-oxo-3-phenylpropanoic acid (4.03 g, 24.56 mmol) in ethanol (70 mL) was refluxed overnight and then cooled to 0° C. A solid precipitate was filtered, washed with cold ethanol, and dried to give a mixture of the title compounds as an off-white solid (5.1 g, 83%) which was used without further purification.

Step B: 2-benzyl-3-chloro-5-methylquinoxaline and 3-benzyl-2-chloro-5-methylquinoxaline

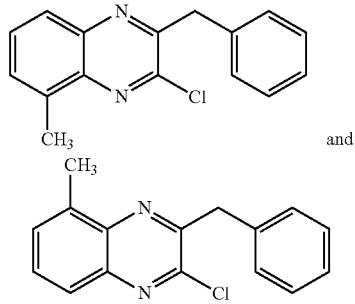

and

To a mixture of 3-benzyl-8-methylquinoxalin-2(1H)-one and 3-benzyl-5-methylquinoxalin-2(1H)-one (1 g, 4 mmol) was added POCl$_3$ (6.13 g, 40 mmol). The resulting solution was heated at 120° C. for 3 hours and then cooled to 0° C. Cold water was added dropwise and a grey solid precipitate was filtered, washed with water, and dried to give a mixture of the title compounds (0.2 g, 19%) which was used without further purification.

Step C: N-(2-(azetidin-1-yl)ethyl)-3-benzyl-8-methylquinoxalin-2-amine and N-(2-(azetidin-1-yl)ethyl)-3-benzyl-5-methylquinoxalin-2-amine To a 10 mL microwave vial were added a mixture of 2-benzyl-3-chloro-5-methylquinoxaline and 3-benzyl-2-chloro-5-methylquinoxaline (40 mg, 0.149 mmol) and 2-(azetidin-1-yl)ethanamine (0.045 g, 0.447 mmol) in DMSO (3 mL). The mixture was heated at 100° C. for 4 hours in a Biotage® microwave reactor and then filtered and purified by preparative HPLC (Waters SunFire® C18, 5 μm, 30 mm ID×75 mm column) using a gradient of 10-35% ACN (0.035% TFA) in water (0.05% TFA) to give two regioisomers. The early-eluting regioisomer was assigned as the TFA salt of N-(2-(azetidin-1-yl)ethyl)-3-benzyl-8-methylquinoxalin-2-amine and was obtained as a light brown oil (11 mg, 22%). $^1$H NMR (400 MHz, CD$_3$OD) δ ppm 2.28 (dtt, J=11.87, 9.47, 9.47, 4.93, 4.93 Hz, 1H), 2.40-2.54 (m, 1H), 2.65 (s, 3H), 3.54 (t, J=5.68 Hz, 2H), 3.79 (t, J=5.68 Hz, 2H), 3.91-4.08 (m, 4H), 4.27-4.31 (m, 2H), 7.19-7.36 (m, 6H), 7.44-7.49 (m, 1H), 7.67-7.72 (m, 1H); ESI-MS m/z [M+H]$^+$ 333.2. The later-eluting regioisomer was assigned as the TFA salt of N-(2-(azetidin-1-yl)ethyl)-3-benzyl-5-methylquinoxalin-2-amine and was obtained as a light brown oil (14 mg, 28%). $^1$H NMR (400 MHz, CD$_3$OD) δ ppm 2.30-2.58 (m, 2H), 2.63 (s, 3H), 3.44-3.51 (m, 2H), 3.72-3.80 (m, 2H), 3.96-4.10 (m, 2H), 4.12-4.24 (m, 2H), 4.27 (s, 2H), 7.17-7.35 (m, 6H), 7.42-7.49 (m, 1H), 7.50-7.56 (m, 1H); ESI-MS m/z [M+H]$^+$ 333.2.

Example 4

N-(2-(azetidin-1-yl)ethyl)-3-(3-methoxybenzyl)-8-methylquinoxalin-2-amine

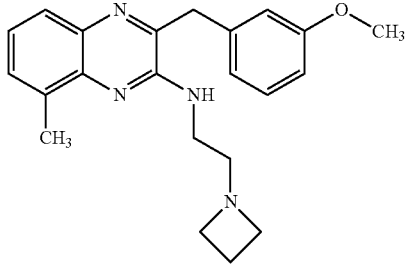 [SMILES: COc1cccc(Cc2nc3cccc(C)c3nc2NCCN2CCC2)c1]

and

Example 5

N-(2-(azetidin-1-yl)ethyl)-3-(3-methoxybenzyl)-5-methylquinoxalin-2-amine

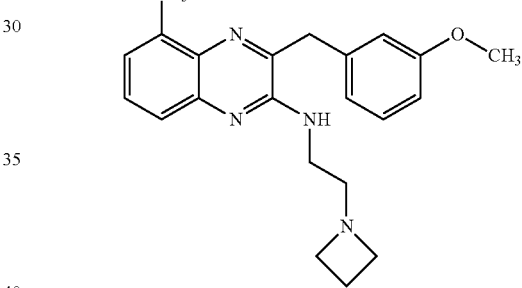

The title compounds were prepared like EXAMPLE 2 and EXAMPLE 3, using 3-(3-methoxyphenyl)-2-oxopropanoic acid in step A instead of 2-oxo-3-phenylpropanoic acid. The products were purified by preparative HPLC (Waters SunFire® C18, 5 μm, 30 mm ID×75 mm column) using a gradient of 10-35% ACN (0.035% TFA) in water (0.05% TFA) to give two regioisomers. The earlier-eluting regioisomer was assigned as the TFA salt of N-(2-(azetidin-1-yl)ethyl)-3-(3-methoxybenzyl)-8-methylquinoxalin-2-amine and was obtained as a light brown oil. $^1$H NMR (400 MHz, CD$_3$OD) δ ppm 2.29 (dtt, J=11.87, 9.44, 9.44, 4.83, 4.83 Hz, 1H), 2.48 (dquin, J=11.87, 9.28, 9.28, 9.28, 9.28 Hz, 1H), 2.65 (s, 3H), 3.54 (t, J=5.68 Hz, 2H), 3.72-3.75 (m, 3H), 3.79 (t, J=5.68 Hz, 2H), 3.92-4.10 (m, 4H), 4.23-4.28 (m, 2H), 6.76-6.85 (m, 3H), 7.20 (t, J=7.96 Hz, 1H), 7.34 (dd, J=8.21, 7.20 Hz, 1H), 7.44-7.50 (m, 1H), 7.70 (dd, J=8.34, 0.76 Hz, 1H); ESI-MS m/z [M+H]$^+$ 363.5. The later-eluting regioisomer was assigned as the TFA salt of N-(2-(azetidin-1-yl)ethyl)-3-(3-methoxybenzyl)-5-methylquinoxalin-2-amine and was obtained as a brown oil. $^1$H NMR (400 MHz, CD$_3$OD) δ ppm 2.29-2.43 (m, 1H), 2.45-2.58 (m, 1H), 2.65 (s, 3H), 3.45-3.51 (m, 2H), 3.73-3.79 (m, 5H), 4.03 (q, J=9.85 Hz, 2H), 4.15-4.23 (m, 2H), 4.25 (s, 2H), 6.79 (dd, J=7.96, 2.15 Hz, 1H), 6.83-6.90 (m, 2H), 7.20 (t, J=7.83 Hz, 1H), 7.26-7.30 (m, 1H), 7.43-7.49 (m, 1H), 7.51-7.56 (m, 1H); ESI-MS m/z [M+H]$^+$ 363.5.

Example 6

N-(2-(azetidin-1-yl)ethyl)-8-methyl-3-(3-methylbenzyl)quinoxalin-2-amine

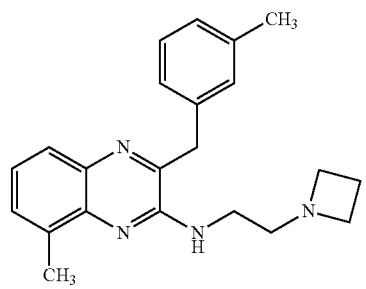 [SMILES: Cc1cccc(Cc2nc3cccc(C)c3nc2NCCN2CCC2)c1]

The title compound was prepared like EXAMPLE 2 and EXAMPLE 3, using 2-oxo-3-(m-tolyl)propanoic acid in step A instead of 2-oxo-3-phenylpropanoic acid. Purification by preparative HPLC gave only one pure isomer, which was assigned as the TFA salt of N-(2-(azetidin-1-yl)ethyl)-8-methyl-3-(3-methylbenzyl)quinoxalin-2-amine and was obtained as a brown oil. $^1$H NMR (400 MHz, CD$_3$OD) δ ppm 2.25-2.33 (m, 4H), 2.42-2.51 (m, 1H), 2.64-2.67 (m, 3H), 3.34 (s, 2H), 3.53 (t, J=5.68 Hz, 2H), 3.79 (t, J=5.68 Hz, 2H), 3.91-4.06 (m, 4H), 4.25 (s, 2H), 6.99-7.08 (m, 3H), 7.14-7.21 (m, 1H), 7.30-7.37 (m, 1H), 7.47 (d, J=6.82 Hz, 1H), 7.68-7.72 (m, 1H).

Example 7

8-methyl-3-(3-methylbenzyl)-N-(2-(pyrrolidin-1-yl)ethyl)quinolin-2-amine

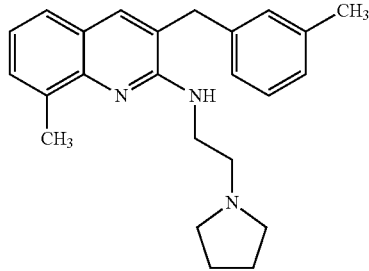 [SMILES: Cc1cccc(Cc2cc3cccc(C)c3nc2NCCN2CCCC2)c1]

Step A: 3-(m-tolyl)-N-(o-tolyl)propanamide

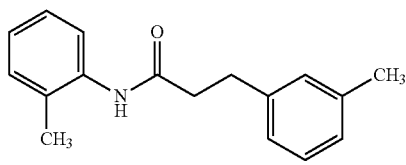 [SMILES: Cc1cccc(CCC(=O)Nc2ccccc2C)c1]

A mixture of the 3-(m-tolyl)propanoic acid (0.589 g, 3.59 mmol), o-toluidine (0.461 g, 4.30 mmol) and DIPEA (1.867 mL, 1.391 g, 10.76 mmol) in DMF was treated with T3P (1.712 g, 5.38 mmol). The reaction mixture was stirred at room temperature overnight, and then diluted with EtOAc, washed with saturated NaHCO$_3$ and brine, dried over Na$_2$SO$_4$, filtered and concentrated. The resulting oil was purified by flash column chromatography, using a gradient of 0-100% EtOAc in heptane to give the title compound as an oil (0.487 g, 53.6%). ESI-MS m/z [M+H]$^+$ 254.2.

Step B: 2-chloro-8-methyl-3-(3-methylbenzyl)quinoline

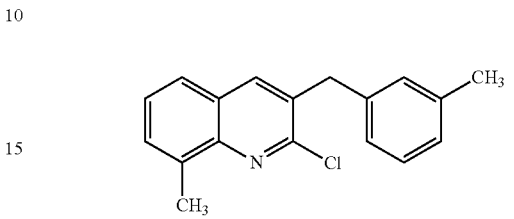

To a 100 mL round bottom flask containing DMF (0.447 mL) at 0° C. was added POCl$_3$ dropwise. Next, 3-(m-tolyl)-N-(o-tolyl)propanamide was added to the flask in one portion at room temperature. The resulting viscous oil was heated at 80° C. overnight. Excess POCl$_3$ was removed on a rotary evaporator and the product purified by flash column chromatography, using a gradient of 0-100% EtOAc in heptanes to give the title compound (9 mg, 2%). ESI-MS m/z [M+H]$^+$ 282.3.

Step C: 8-methyl-3-(3-methylbenzyl)-N-(2-(pyrrolidin-1-yl)ethyl)quinolin-2-amine To 2-chloro-8-methyl-3-(3-methylbenzyl)quinoline (9 mg, 0.032 mmol) in NMP (3 mL) was added 2-(pyrrolidin-1-yl)ethanamine (10.94 mg, 0.096 mmol). The solution was heated in a microwave reactor at 150° C. for 1 hour, and then filtered and purified by preparative HPLC (Waters SunFire® C18, 5 μm, 30 mm ID×75 mm column) using a gradient of 25-50% ACN (0.035% TFA) in water (0.05% TFA) to give the title compound as a clear film (2 mg, 18%). $^1$H NMR (400 MHz, CD$_3$OD) δ ppm 1.76-1.83 (m, 4H), 2.30 (s, 3H), 2.56-2.63 (m, 7H), 2.79 (t, J=6.69 Hz, 2H), 3.34 (s, 1H), 3.73 (t, J=6.69 Hz, 2H), 3.93 (s, 2H), 7.00-7.08 (m, 4H), 7.17-7.23 (m, 1H), 7.33 (dd, J=14.27, 7.45 Hz, 2H), 7.48 (s, 1H); ESI-MS m/z [M+H]$^+$ 360.3.

Example 8

(R)-(6-(1-(4-fluorophenyl)ethyl)-5-((2-(pyrrolidin-1-yl)ethyl)amino)pyrazin-2-yl)(pyrrolidin-1-yl)methanone

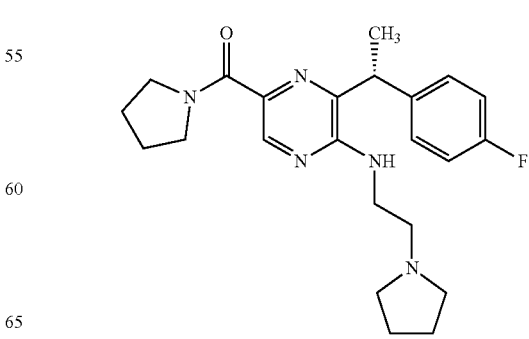

To a solution of (R)-6-(1-(4-fluorophenyl)ethyl)-5-((2-(pyrrolidin-1-yl)ethyl)amino)pyrazine-2-carboxylic acid (15 mg, 0.042 mmol) and HATU (15.91 mg, 0.042 mmol) in DMF (419 μL) was added DIPEA (14.62 μL, 0.084 mmol). The reaction mixture was stirred at room temperature for 5 minutes. Next, pyrrolidine (4.46 mg, 0.063 mmol) was added. The reaction mixture was stirred at room temperature for 2 hours and then purified by preparative HPLC (Phenomenex Gemini® C18, 5 μm, 30 mm ID×150 mm) using a gradient of 10-50% ACN (0.035% TFA) in water (0.05% TFA) to give a TFA salt of the title compound as a white film (18 mg, 82%). $^1$H NMR (400 MHz, CD$_3$OD) δ ppm 1.66 (d, J=6.88 Hz, 3H), 1.89-2.01 (m, 6H), 2.11 (br dd, J=6.42, 2.57 Hz, 2H), 2.95-3.12 (m, 2H), 3.38-3.47 (m, 2H), 3.61-3.71 (m, 4H), 3.72-3.84 (m, 2H), 3.86-3.92 (m, 2H), 4.34 (q, J=6.88 Hz, 1H), 7.00-7.09 (m, 2H), 7.24-7.32 (m, 2H), 8.54 (s, 1H); ESI-MS m/z [M+H]$^+$ 412.1.

Example 9

(R)-N-cyclobutyl-6-(1-(4-fluorophenyl)ethyl)-5-((2-(pyrrolidin-1-yl)ethyl)amino)pyrazine-2-carboxamide

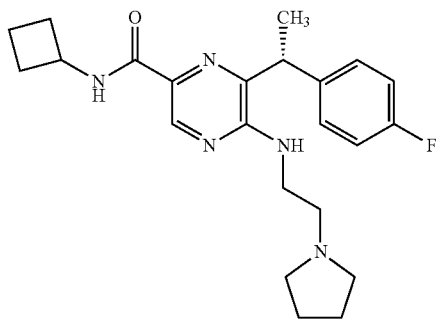 [SMILES: C[C@H](c1ccc(F)cc1)c1nc(C(=O)NC2CCC2)cnc1NCCN1CCCC1]

A TFA salt of the title compound was prepared like EXAMPLE 8, using (R)-6-(1-(4-fluorophenyl)ethyl)-5-((2-(pyrrolidin-1-yl)ethyl)amino)pyrazine-2-carboxylic acid (15 mg, 0.042 mmol) and cyclobutanamine (4.46 mg, 0.063 mmol), and was obtained as a white film (16 mg, 72.7%). $^1$H NMR (400 MHz, CD$_3$OD) δ ppm 1.72 (d, J=6.97 Hz, 3H), 1.80-1.89 (m, 2H), 1.94-2.04 (m, 2H), 2.07-2.21 (m, 4H), 2.36-2.46 (m, 2H), 2.95-3.11 (m, 2H), 3.40 (td, J=5.89, 1.97 Hz, 2H), 3.58-3.69 (m, 2H), 3.74-3.89 (m, 2H), 4.33 (q, J=6.97 Hz, 1H), 4.53 (quin, J=8.30 Hz, 1H), 7.00-7.12 (m, 2H), 7.27-7.37 (m, 2H), 8.62 (s, 1H); ESI-MS m/z [M+H]$^+$ 412.1.

Example 10

(6-((R)-1-(4-fluorophenyl)ethyl)-5-((2-(pyrrolidin-1-yl)ethyl)amino)pyrazin-2-yl)((S)-3-methoxypyrrolidin-1-yl)methanone

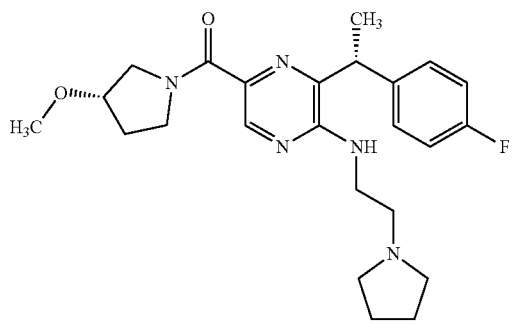 [SMILES: CO[C@H]1CCN(C(=O)c2cnc(NCCN3CCCC3)c([C@H](C)c3ccc(F)cc3)n2)C1]

A TFA salt of the title compound was prepared like EXAMPLE 8, using (R)-6-(1-(4-fluorophenyl)ethyl)-5-((2-(pyrrolidin-1-yl)ethyl)amino)pyrazine-2-carboxylic acid (15 mg, 0.042 mmol) and (S)-3-methoxypyrrolidine (6.35 mg, 0.063 mmol), and was obtained as a colorless film (5.4 mg, 23.2%). $^1$H NMR (400 MHz, CD$_3$OD) δ ppm 1.54 (dd, J=6.88, 3.30 Hz, 3H), 1.77-1.91 (m, 3H), 1.94-2.10 (m, 3H), 2.80-3.03 (m, 2H), 3.18 (s, 1H), 3.27 (s, 1H), 3.28-3.36 (m, 2H), 3.45-3.60 (m, 3H), 3.62-3.74 (m, 3H), 3.75-3.87 (m, 2H), 3.89-3.99 (m, 1H), 4.24 (dq, J=9.65, 6.93 Hz, 1H), 6.85-6.98 (m, 2H), 7.09-7.23 (m, 2H), 8.43 (d, J=3.85 Hz, 1H); ESI-MS m/z [M+H]$^+$ 442.1.

Example 11

(6-((R)-1-(4-fluorophenyl)ethyl)-5-((2-(pyrrolidin-1-yl)ethyl)amino)pyrazin-2-yl)((R)-3-methoxypyrrolidin-1-yl)methanone

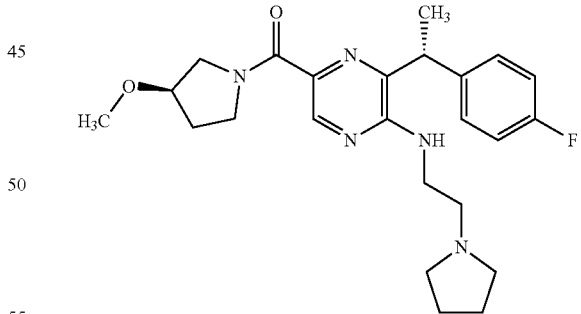

A TFA salt of the title compound was prepared like EXAMPLE 8, using (R)-6-(1-(4-fluorophenyl)ethyl)-5-((2-(pyrrolidin-1-yl)ethyl)amino)pyrazine-2-carboxylic acid (15 mg, 0.042 mmol) and (R)-3-methoxypyrrolidine (6.35 mg, 0.063 mmol), and was obtained as a colorless film (5.8 mg, 24.9%). $^1$H NMR (400 MHz, CD$_3$OD) δ ppm 1.67 (t, J=6.46 Hz, 3H), 1.88-2.05 (m, 3H), 2.07-2.23 (m, 3H), 2.90-3.17 (m, 2H), 3.38-3.46 (m, 3H), 3.56-3.72 (m, 3H), 3.74-3.91 (m, 3H), 3.93-4.13 (m, 3H), 4.30-4.43 (m, 1H), 7.03 (t, J=8.76 Hz, 2H), 7.23-7.31 (m, 2H), 8.56 (d, J=3.94 Hz, 1H); ESI-MS m/z [M+H]$^+$ 442.1.

Example 12

6-((R)-1-(4-fluorophenyl)ethyl)-5-((2-(pyrrolidin-1-yl)ethyl)amino)-N-((S)-tetrahydrofuran-3-yl)pyrazine-2-carboxamide

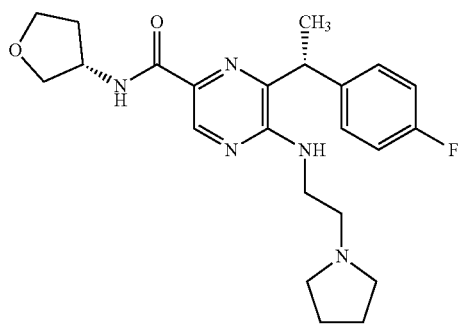 [SMILES: C[C@H](c1ccc(F)cc1)c1nc(C(=O)N[C@H]2CCOC2)cnc1NCCN1CCCC1]

A TFA salt of the title compound was prepared like EXAMPLE 8, using (R)-6-(1-(4-fluorophenyl)ethyl)-5-((2-(pyrrolidin-1-yl)ethyl)amino)pyrazine-2-carboxylic acid (15 mg, 0.042 mmol) and (S)-tetrahydrofuran-3-amine (4.74 mg, 0.054 mmol), and was obtained as a white solid (5.8 mg, 25.6%). $^1$H NMR (400 MHz, CD$_3$OD) δ ppm 1.69 (d, J=6.97 Hz, 3H), 1.91-2.03 (m, 3H), 2.06-2.19 (m, 2H), 2.28-2.45 (m, 1H), 2.87-3.13 (m, 2H), 3.41 (td, J=5.75, 3.26 Hz, 2H), 3.53-3.70 (m, 2H), 3.73-3.90 (m, 4H), 3.93-4.07 (m, 2H), 4.33 (q, J=6.85 Hz, 1H), 4.57-4.65 (m, 1H), 7.05 (t, J=8.71 Hz, 2H), 7.30 (dd, J=8.53, 5.41 Hz, 2H), 8.63 (s, 1H); ESI-MS m/z [M+H]$^+$ 428.1.

Example 13

6-((R)-1-(4-fluorophenyl)ethyl)-5-((2-(pyrrolidin-1-yl)ethyl)amino)-N-((R)-tetrahydrofuran-3-yl)pyrazine-2-carboxamide

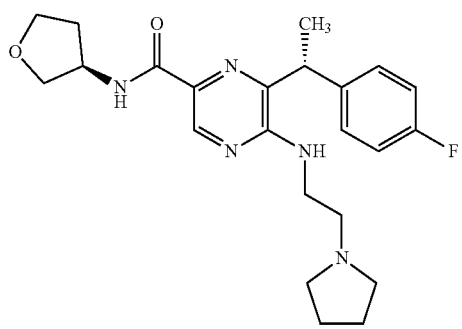 [SMILES: C[C@H](c1ccc(F)cc1)c1nc(C(=O)N[C@@H]2CCOC2)cnc1NCCN1CCCC1]

A TFA salt of the title compound was prepared like EXAMPLE 8, using (R)-6-(1-(4-fluorophenyl)ethyl)-5-((2-(pyrrolidin-1-yl)ethyl)amino)pyrazine-2-carboxylic acid (15 mg, 0.042 mmol) and (R)-tetrahydrofuran-3-amine (4.74 mg, 0.054 mmol), and was obtain as a white film (6.3 mg, 27.8%). $^1$H NMR (400 MHz, CD$_3$OD) δ ppm 1.69 (d, J=6.97 Hz, 3H), 1.90-2.02 (m, 3H), 2.11 (br d, J=2.75 Hz, 2H), 2.36 (dq, J=13.11, 7.55 Hz, 1H), 2.91-3.13 (m, 2H), 3.41 (td, J=5.89, 3.07 Hz, 2H), 3.57-3.72 (m, 2H), 3.73-3.91 (m, 4H), 3.92-4.04 (m, 2H), 4.33 (q, J=6.91 Hz, 1H), 4.62 (ddt, J=7.45, 5.69, 3.75, 3.75 Hz, 1H), 6.99-7.13 (m, 2H), 7.26-7.35 (m, 2H), 8.63 (s, 1H).

Example 14

6-((R)-1-(4-fluorophenyl)ethyl)-N-(cis-3-methoxycyclobutyl)-5-((2-(pyrrolidin-1-yl)ethyl)amino)pyrazine-2-carboxamide

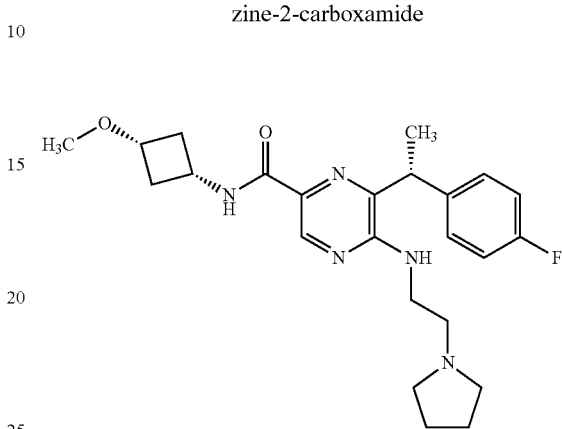

and

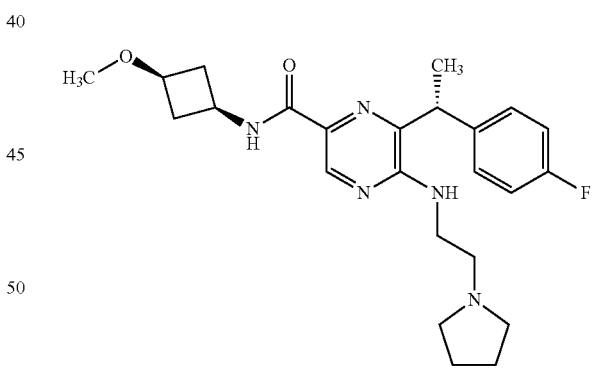

A TFA salt of the title compound was prepared like EXAMPLE 8, using (R)-6-(1-(4-fluorophenyl)ethyl)-5-((2-(pyrrolidin-1-yl)ethyl)amino)pyrazine-2-carboxylic acid (15 mg, 0.042 mmol) and cis-3-methoxycyclobutan-1-amine hydrochloride (5.76 mg, 0.042 mmol), and was obtained as a white film (8 mg, 34.4%). $^1$H NMR (400 MHz, CD$_3$OD) δ ppm 1.72 (d, J=6.88 Hz, 3H), 1.92-2.04 (m, 4H), 2.10 (br d, J=3.03 Hz, 2H), 2.75-2.86 (m, 2H), 2.91-3.09 (m, 2H), 3.30 (s, 3H), 3.37-3.47 (m, 2H), 3.55-3.71 (m, 2H), 3.74-3.91 (m, 3H), 4.11-4.22 (m, 1H), 4.33 (q, J=6.82 Hz, 1H), 7.00-7.11 (m, 2H), 7.28-7.37 (m, 2H), 8.61 (s, 1H); ESI-MS m/z [M+H]$^+$ 442.1.

Example 15

6-((R)-1-(4-fluorophenyl)ethyl)-N-(trans-3-methoxy-cyclobutyl)-5-((2-(pyrrolidin-1-yl)ethyl)amino)pyrazine-2-carboxamide 2,2,2-trifluoroacetate

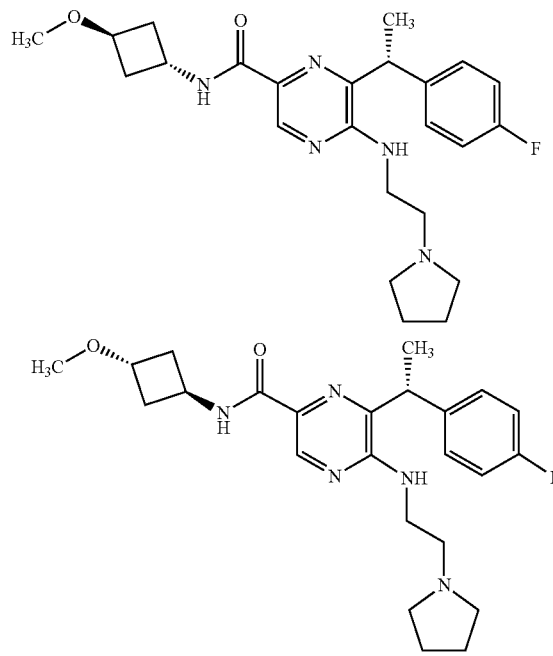

and

A TFA salt of the title compound was prepared like EXAMPLE 8, using (R)-6-(1-(4-fluorophenyl)ethyl)-5-((2-(pyrrolidin-1-yl)ethyl)amino)pyrazine-2-carboxylic acid (15 mg, 0.042 mmol) and trans-3-methoxycyclobutan-1-amine hydrochloride (8.06 mg, 0.059 mmol), and was obtained as a colorless film (6.8 mg, 29.2%). $^1$H NMR (400 MHz, CD$_3$OD) δ ppm 1.72 (d, J=6.88 Hz, 3H), 1.88-2.01 (m, 2H), 2.04-2.19 (m, 2H), 2.29-2.41 (m, 2H), 2.42-2.52 (m, 2H), 2.90-3.12 (m, 2H), 3.30 (s, 2H), 3.38-3.48 (m, 2H), 3.51-3.69 (m, 2H), 3.72-3.97 (m, 2H), 4.10 (tt, J=6.76, 3.60 Hz, 1H), 4.34 (q, J=6.88 Hz, 1H), 4.53-4.68 (m, 1H), 6.94-7.16 (m, 2H), 7.26-7.41 (m, 2H), 8.61 (s, 1H); ESI-MS m/z [M+H]$^+$ 442.1.

Example 16

(R)-(6-(1-(4-fluorophenyl)ethyl)-5-((2-(pyrrolidin-1-yl)ethyl)amino)pyrazin-2-yl)(morpholino)methanone

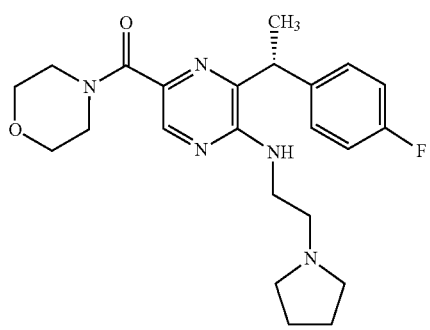 [SMILES: C[C@H](c1ccc(F)cc1)c1nc(C(=O)N2CCOCC2)cnc1NCCN1CCCC1]

The title compound was prepared like EXAMPLE 8, using (R)-6-(1-(4-fluorophenyl)ethyl)-5-((2-(pyrrolidin-1-yl)ethyl)amino)pyrazine-2-carboxylic acid (15 mg, 0.042 mmol) and morpholine (5.5 mg, 0.059 mmol), and was obtained as a light-yellow oil. $^1$H NMR (400 MHz, CDCl$_3$) δ ppm 1.58 (d, J=6.8 Hz, 3H), 1.71-1.74 (m, 4H), 2.28-2.36 (m, 2H), 2.39-2.51 (m, 3H), 2.63-2.71 (m, 1H), 3.26-3.45 (m, 2H), 3.72-4.05 (m, 9H), 5.55 (br s, 1H), 6.92-7.00 (m, 2H), 7.06-7.15 (m, 2H), 8.52 (s, 1H); ESI-MS m/z [M+H]$^+$ 428.3.

Example 17

(R)-N-cyclopropyl-6-(1-(4-fluorophenyl)ethyl)-N-methyl-5-((2-(pyrrolidin-1-yl)ethyl)amino)pyrazine-2-carboxamide

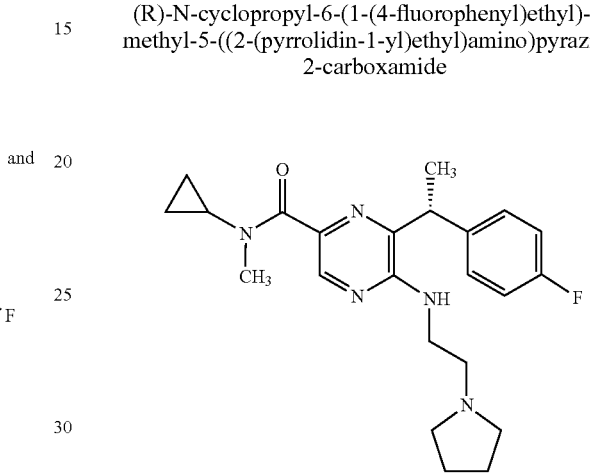

The title compound was prepared like EXAMPLE 8, using (R)-6-(1-(4-fluorophenyl)ethyl)-5-((2-(pyrrolidin-1-yl)ethyl)amino)pyrazine-2-carboxylic acid (15 mg, 0.042 mmol) and N-methylcyclopropanamine (4.1 mg, 0.059 mmol), and was obtained as a white solid. $^1$H NMR (400 MHz, CDCl$_3$) δ ppm 0.38-0.74 (m, 4H), 1.58 (br d, J=7.1 Hz, 3H), 1.66-1.77 (m, 4H), 2.23-2.34 (m, 2H), 2.35-2.48 (m, 3H), 2.62-2.73 (m, 1H), 3.14 (br s, 3H), 3.29 (td, J=8.4, 4.0 Hz, 2H), 3.33-3.44 (m, 1H), 3.92-4.04 (m, 1H), 5.45 (br s, 1H), 6.94 (br t, J=8.6 Hz, 2H), 7.04-7.17 (m, 2H), 8.41 (br d, J=0.9 Hz, 1H); ESI-MS m/z [M+H]$^+$ 412.1.

Example 18

(R)-6-(1-(4-fluorophenyl)ethyl)-5-((2-(pyrrolidin-1-yl)ethyl)amino)-N-(tetrahydro-2H-pyran-4-yl)pyrazine-2-carboxamide

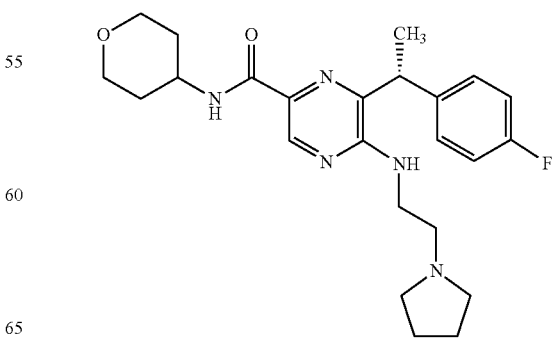

The title compound was prepared like EXAMPLE 8, using (R)-6-(1-(4-fluorophenyl)ethyl)-5-((2-(pyrrolidin-1-yl)ethyl)amino)pyrazine-2-carboxylic acid (15 mg, 0.042 mmol) and tetrahydro-2H-pyran-4-amine (6.0 mg, 0.059 mmol), and was obtained as a white solid. $^1$H NMR (400 MHz, CDCl$_3$) δ ppm 1.64 (br s, 5H), 1.68-1.76 (m, 4H), 1.95-2.07 (m, 2H), 2.24-2.33 (m, 2H), 2.36-2.47 (m, 3H), 2.64 (ddd, J=12.2, 7.8, 4.7 Hz, 1H), 3.22-3.44 (m, 2H), 3.50-3.63 (m, 2H), 3.99 (br d, J=7.3 Hz, 3H), 4.12-4.26 (m, 1H), 5.59 (br s, 1H), 6.90-7.01 (m, 2H), 7.04-7.17 (m, 2H), 7.53 (br d, J=7.9 Hz, 1H), 8.74 (s, 1H); ESI-MS m/z [M+H]$^+$ 442.2.

Example 19

6-(1-(4-fluorophenyl)ethyl)-5-((2-(pyrrolidin-1-yl)ethyl)amino)pyrazine-2-carboxamide

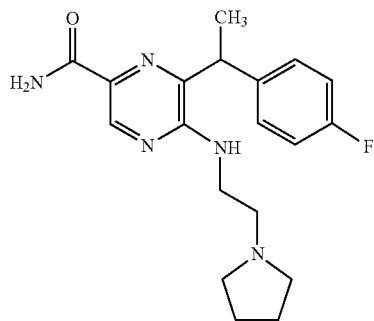

A TFA salt of the title compound was prepared like EXAMPLE 8, using 6-(1-(4-fluorophenyl)ethyl)-5-((2-(pyrrolidin-1-yl)ethyl)amino)pyrazine-2-carboxylic acid (30 mg, 0.065 mmol) and ammonium hydroxide (3.81 μL, 0.098 mmol) as a white solid. $^1$H NMR (500 MHz, CD$_3$OD) δ ppm 1.69 (d, J=6.83 Hz, 3H), 1.86-1.99 (m, 2H), 2.08 (tq, J=7.83, 4.06 Hz, 2H), 2.87-2.96 (m, 1H), 2.98-3.09 (m, 1H), 3.34-3.45 (m, 2H), 3.53-3.67 (m, 2H), 3.71-3.88 (m, 2H), 4.29 (q, J=6.83 Hz, 1H), 6.94-7.06 (m, 2H), 7.24-7.37 (m, 2H), 8.64 (s, 1H); ESI-MS m/z [M+H]$^+$ 358.1.

Example 20

(S)-6-(1-(4-fluorophenyl)ethyl)-5-((2-(pyrrolidin-1-yl)ethyl)amino)pyrazine-2-carboxamide

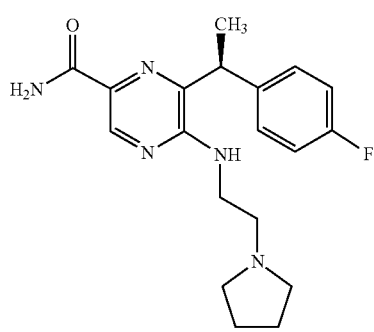 [SMILES: C[C@@H](c1ccc(F)cc1)c1nc(C(N)=O)cnc1NCCN1CCCC1]

and

Example 21

(R)-6-(1-(4-fluorophenyl)ethyl)-5-((2-(pyrrolidin-1-yl)ethyl)amino)pyrazine-2-carboxamide

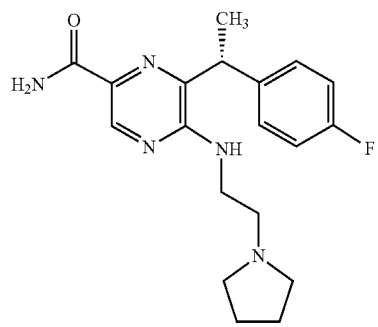 [SMILES: C[C@H](c1ccc(F)cc1)c1nc(C(N)=O)cnc1NCCN1CCCC1]

Racemate 6-(1-(4-fluorophenyl)ethyl)-5-((2-(pyrrolidin-1-yl)ethyl)amino)pyrazine-2-carboxamide 2,2,2-trifluoroacetate (21 mg) was resolved by chiral SFC separation (AD-H column, 25% MeOH+20 mM NH$_4$OH) to give two enantiomers. The earlier-eluting enantiomer was (S)-6-(1-(4-fluorophenyl)ethyl)-5-((2-(pyrrolidin-1-yl)ethyl)amino)pyrazine-2-carboxamide (8.0 mg, 40%). $^1$H NMR (500 MHz, CD$_3$OD) δ ppm 1.66 (d, J=6.83 Hz, 3H), 1.76 (br t, J=6.22 Hz, 4H), 2.40-2.50 (m, 4H), 2.56 (dt, J=12.33, 6.28 Hz, 1H), 2.62-2.74 (m, 1H), 3.54 (td, J=6.47, 1.46 Hz, 2H), 4.26 (q, J=6.83 Hz, 1H), 6.94-7.07 (m, 2H), 7.20-7.31 (m, 2H), 8.58 (s, 1H); ESI-MS m/z [M+H]$^+$ 358.1. The later-eluting enantiomer was (R)-6-(1-(4-fluorophenyl)ethyl)-5-((2-(pyrrolidin-1-yl)ethyl)amino)pyrazine-2-carboxamide (3.2 mg, 16%). $^1$H NMR (500 MHz, CD$_3$OD) δ ppm 1.66 (d, J=6.83 Hz, 3H), 1.77 (br t, J=6.10 Hz, 4H), 2.41-2.50 (m, 4H), 2.53-2.60 (m, 1H), 2.67 (dt, J=12.45, 6.47 Hz, 1H), 3.54 (td, J=6.47, 1.22 Hz, 2H), 4.26 (q, J=6.75 Hz, 1H), 6.90-7.06 (m, 2H), 7.20-7.30 (m, 2H), 8.58 (s, 1H); ESI-MS m/z [M+H]$^+$ 358.1.

Example 22

6-(1-(4-fluorophenyl)ethyl)-N-methyl-5-((2-(pyrrolidin-1-yl)ethyl)amino)pyrazine-2-carboxamide

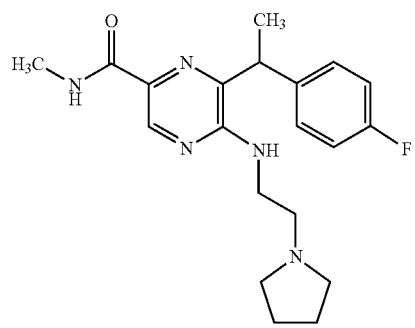 [SMILES: CNC(=O)c1cnc(NCCN2CCCC2)c(C(C)c2ccc(F)cc2)n1]

The title compound was prepared like EXAMPLE 8, using 6-(1-(4-fluorophenyl)ethyl)-5-((2-(pyrrolidin-1-yl)ethyl)amino)pyrazine-2-carboxylic acid (30 mg, 0.065 mmol) and methanamine (12.19 μL, 0.098 mmol). The product was purified by preparative HPLC (Phenomenex Gemini® C18, 5 µm, 30 mm ID×150 mm) using a gradient of 10-50% ACN (0.035% TFA) in water (0.05% TFA) to give a TFA salt of the title compound as a white solid (19 mg, 59.9%). ¹H NMR (500 MHz, CD₃OD) δ ppm 1.70 (d, J=6.83 Hz, 3H), 1.85-1.98 (m, 2H), 2.00-2.15 (m, 2H), 2.86-2.96 (m, 1H), 2.97-3.10 (m, 4H), 3.34-3.47 (m, 2H), 3.52-3.68 (m, 2H), 3.69-3.87 (m, 2H), 4.28 (q, J=6.83 Hz, 1H), 6.97-7.05 (m, 2H), 7.24-7.34 (m, 2H), 8.61 (s, 1H); ESI-MS m/z [M+H]⁺ 372.1.

Example 23

(S)-6-(1-(4-fluorophenyl)ethyl)-N-methyl-5-((2-(pyrrolidin-1-yl)ethyl)amino)pyrazine-2-carboxamide

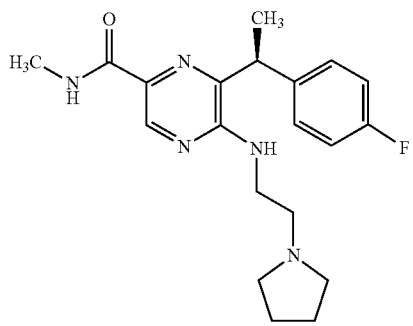 [SMILES: CNC(=O)c1cnc(NCCN2CCCC2)c([C@@H](C)c2ccc(F)cc2)n1]

and

Example 24

(R)-6-(1-(4-fluorophenyl)ethyl)-N-methyl-5-((2-(pyrrolidin-1-yl)ethyl)amino)pyrazine-2-carboxamide

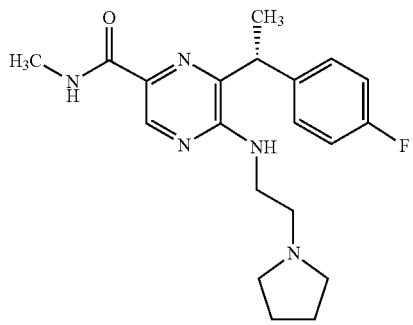 [SMILES: CNC(=O)c1cnc(NCCN2CCCC2)c([C@H](C)c2ccc(F)cc2)n1]

Racemate 6-(1-(4-fluorophenyl)ethyl)-N-methyl-5-((2-(pyrrolidin-1-yl)ethyl)amino)pyrazine-2-carboxamide 2,2,2-trifluoroacetate (19 mg) was resolved by chiral SFC separation (AD-H column, 17% MeOH+20 mM NH₄OH) to give two enantiomers. The earlier-eluting enantiomer was (S)-6-(1-(4-fluorophenyl)ethyl)-N-methyl-5-((2-(pyrrolidin-1-yl)ethyl)amino)pyrazine-2-carboxamide (5.1 mg, 26.8%). ¹H NMR (500 MHz, CD₃OD) δ ppm 1.67 (d, J=6.83 Hz, 3H), 1.74-1.81 (m, 4H), 2.40-2.49 (m, 4H), 2.54 (dt, J=12.14, 6.25 Hz, 1H), 2.63-2.74 (m, 1H), 2.97 (s, 3H), 3.49-3.56 (m, 2H), 4.25 (q, J=6.83 Hz, 1H), 6.96-7.06 (m, 2H), 7.24-7.31 (m, 2H), 8.55 (s, 1H); ESI-MS m/z [M+H]⁺ 372.1. The later-eluting enantiomer was (R)-6-(1-(4-fluorophenyl)ethyl)-N-methyl-5-((2-(pyrrolidin-1-yl)ethyl)amino)pyrazine-2-carboxamide (3.7 mg, 19.5%). ¹H NMR (500 MHz, CD₃OD) δ ppm 1.66 (d, J=6.83 Hz, 3H), 1.77 (br t, J=6.10 Hz, 4H), 2.42-2.50 (m, 4H), 2.55 (dt, J=12.26, 6.19 Hz, 1H), 2.67 (dt, J=12.45, 6.47 Hz, 1H), 3.54 (td, J=6.47, 1.22 Hz, 2H), 4.26 (q, J=6.75 Hz, 1H), 7.01 (t, J=8.66 Hz, 2H), 7.20-7.30 (m, 2H), 8.58 (s, 1H); ESI-MS m/z [M+H]⁺ 372.1.

Example 25

6-(1-(4-fluorophenyl)ethyl)-N,N-dimethyl-5-((2-(pyrrolidin-1-yl)ethyl)amino)pyrazine-2-carboxamide

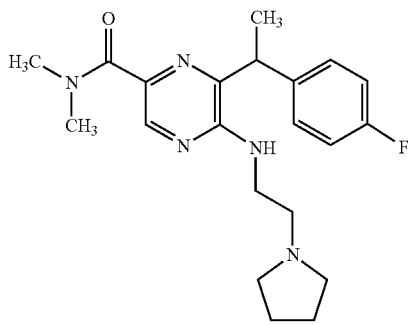 [SMILES: CC(c1ccc(F)cc1)c1nc(C(=O)N(C)C)cnc1NCCN1CCCC1]

The title compound was prepared like EXAMPLE 8, using 6-(1-(4-fluorophenyl)ethyl)-5-((2-(pyrrolidin-1-yl)ethyl)amino)pyrazine-2-carboxylic acid (30 mg, 0.065 mmol) and dimethylamine (32.6 µL, 0.065 mmol). The product was purified by preparative HPLC (Phenomenex Gemini® C18, 5 µm, 30 mm ID×150 mm) using a gradient of 10-50% ACN (0.035% TFA) in water (0.05% TFA) to give a TFA salt of the title compound as a white solid (19 mg, 58.3%). ¹H NMR (500 MHz, CD₃OD) δ ppm 1.63 (d, J=6.83 Hz, 3H), 1.89-2.00 (m, 2H), 2.03-2.14 (m, 2H), 2.88-2.98 (m, 1H), 3.00-3.06 (m, 1H), 3.12 (s, 3H), 3.23 (s, 3H), 3.36-3.43 (m, 2H), 3.56-3.69 (m, 2H), 3.70-3.86 (m, 2H), 4.30 (q, J=6.83 Hz, 1H), 6.93-7.05 (m, 2H), 7.18-7.31 (m, 2H), 8.34 (s, 1H); ESI-MS m/z [M+H]⁺ 386.1.

Example 26

(S)-6-(1-(4-fluorophenyl)ethyl)-N,N-dimethyl-5-((2-(pyrrolidin-1-yl)ethyl)amino)pyrazine-2-carboxamide

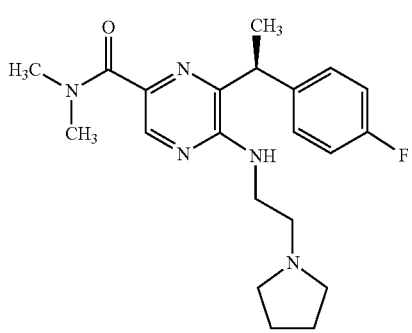 [SMILES: C[C@@H](c1ccc(F)cc1)c1nc(C(=O)N(C)C)cnc1NCCN1CCCC1]

and

Example 27

(R)-6-(1-(4-fluorophenyl)ethyl)-N,N-dimethyl-5-((2-(pyrrolidin-1-yl)ethyl)amino)pyrazine-2-carboxamide

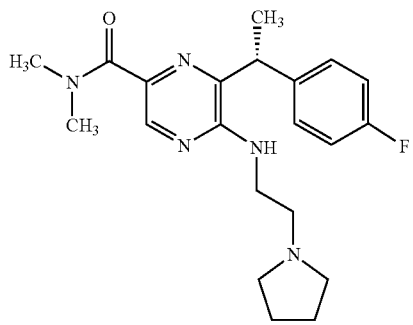

Racemate 6-(1-(4-fluorophenyl)ethyl)-N,N-dimethyl-5-((2-(pyrrolidin-1-yl)ethyl)amino)pyrazine-2-carboxamide (19 mg NH$_4$OH hydroxide) to give two enantiomers. The earlier-eluting enantiomer was ((S)-6-(1-(4-fluorophenyl)ethyl)-N,N-dimethyl-5-((2-(pyrrolidin-1-yl)ethyl)amino)pyrazine-2-carboxamide (3.8 mg, 20%). $^1$H NMR (500 MHz, CD$_3$OD) δ ppm 1.61 (d, J=6.83 Hz, 3H), 1.59-1.63 (m, 1H), 1.77 (br t, J=6.22 Hz, 4H), 2.45-2.53 (m, 4H), 2.56-2.63 (m, 1H), 2.70 (dt, J=12.26, 6.44 Hz, 1H), 3.11 (s, 3H), 3.25 (s, 3H), 3.53 (td, J=6.53, 2.32 Hz, 2H), 4.27 (q, J=6.83 Hz, 1H), 7.00 (t, J=8.66 Hz, 2H), 7.21-7.29 (m, 2H), 8.30 (s, 1H); ESI-MS m/z [M+H]$^+$ 386.1. The later-eluting enantiomer was (R)-6-(1-(4-fluorophenyl)ethyl)-N,N-dimethyl-5-((2-(pyrrolidin-1-yl)ethyl)amino)pyrazine-2-carboxamide (3.5 mg, 18%). $^1$H NMR (500 MHz, CD$_3$OD) δ ppm 1.61 (d, J=7.08 Hz, 4H), 1.77 (br t, J=6.22 Hz, 4H), 2.43-2.52 (m, 4H), 2.57 (dt, J=12.33, 6.28 Hz, 1H), 2.64-2.72 (m, 1H), 3.11 (s, 4H), 3.26 (s, 3H), 3.53 (td, J=6.53, 2.07 Hz, 2H), 4.27 (q, J=6.83 Hz, 1H), 6.96-7.05 (m, 2H), 7.18-7.28 (m, 2H), 8.30 (s, 1H); ESI-MS m/z [M+H]$^+$ 386.1.

Example 28

5-(1-(4-fluorophenyl)ethyl)-N,N-dimethyl-6-((2-((pyrrolidin-1-yl)ethyl)amino)pyrazine-2-carboxamide

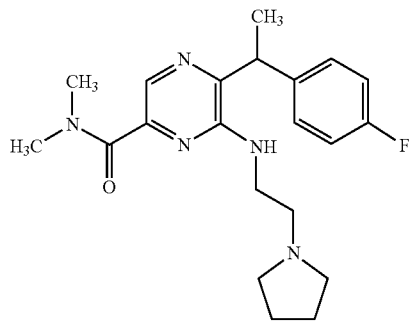 [SMILES: CC(c1ccc(F)cc1)c1ncc(C(=O)N(C)C)nc1NCCN1CCCC1]

The title compound was prepared like EXAMPLE 8, using 6-chloro-5-(1-(4-fluorophenyl)vinyl)pyrazine-2-carboxylic acid (80 mg, 287.08 μmol) and N-methylmethanamine hydrogen chloride (52.61 μL, 46.82 mg, 574.16 μmol), which was obtained as a light-yellow oil (15.1 mg, 74.5%). $^1$H NMR (400 MHz, CD$_3$OD) δ ppm 1.63 (d, J=7.03 Hz, 3H), 1.80 (br s, 4H), 2.52 (br s, 4H), 2.70 (br d, J=5.77 Hz, 2H), 3.12 (d, J=2.51 Hz, 6H), 3.45-3.56 (m, 2H), 4.29 (d, J=6.78 Hz, 1H), 7.02 (t, J=8.78 Hz, 2H), 7.27 (dd, J=8.53, 5.52 Hz, 2H), 7.98 (s, 1H); ESI-MS m/z [M+H]$^+$ 386.2.

Example 29 methyl (R)-6-(1-(4-fluorophenyl)ethyl)-5-((2-(pyrrolidin-1-yl)ethyl)amino)pyrazine-2-carboxylate

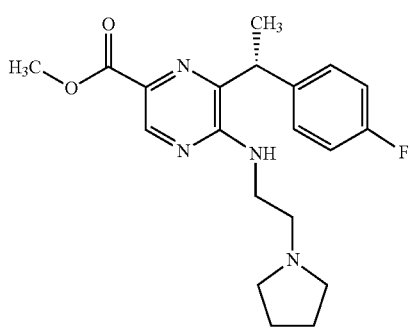 [SMILES: COC(=O)c1cnc(NCCN2CCCC2)c([C@H](C)c2ccc(F)cc2)n1]

To a solution of (R)-6-(1-(4-fluorophenyl)ethyl)-5-((2-(pyrrolidin-1-yl)ethyl)amino)pyrazine-2-carboxylic acid (51 mg, 0.142 mmol) in MeOH (2 mL) at 0° C. was added thionyl chloride (0.031 mL, 0.427 mmol) dropwise. The reaction mixture was allowed to warm to room temperature and then stirred for 8 hours. The solvent was removed in vacuo and the residue was re-dissolved in EtOAc (10 mL), washed with saturated aq NaHCO$_3$ and brine, and purified by silica gel column chromatography (NH column) using a gradient of 10-80% EtOAc in heptane to give the title compound as a colorless oil (33 mg, 62.3%). ESI-MS m/z [M+H]$^+$ 373.3.

Example 30

6-((R)-1-(4-fluorophenyl)ethyl)-5-(((R)-1-methylpyrrolidin-3-yl)amino)pyrazine-2-carboxamide

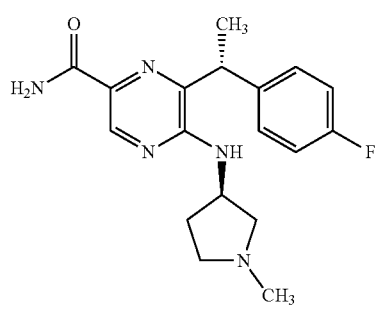 [SMILES: C[C@H](c1ccc(F)cc1)c1nc(C(N)=O)cnc1N[C@@H]1CCN(C)C1]

and

Example 31

6-((S)-1-(4-fluorophenyl)ethyl)-5-(((R)-1-methylpyrrolidin-3-yl)amino)pyrazine-2-carboxamide

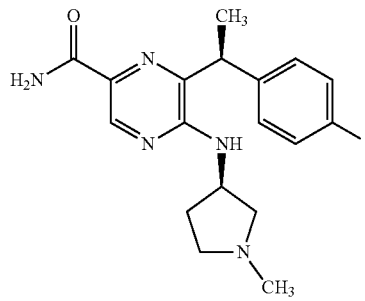

To a solution of 6-(1-(4-fluorophenyl)ethyl)-5-(((R)-1-methylpyrrolidin-3-yl)amino)pyrazine-2-carboxylic acid (45 mg, 0.076 mmol) in DMF (379 μL) was added HATU (28.8 mg, 0.076 mmol) and DIPEA (39.7 μL, 0.227 mmol). The solution was stirred at room temperature for 5 minutes. Next, ammonium hydroxide (8.85 μL, 0.227 mmol) was added. The reaction mixture was stirred at room temperature for 4 hours and then purified by preparative HPLC (Phenomenex Gemini® C18, 5 μm, 30 mm ID×150 mm) using a gradient of 10-50% ACN (0.035% TFA) in water (0.05% TFA). Each of title compounds (diastereoisomers) was obtained as a TFA salt with arbitrarily assigned stereochemical configuration. EXAMPLE 30 (7.7 mg, 30%): $^1$H NMR (400 MHz, CD$_3$OD) δ ppm 1.69 (br d, J=6.60 Hz, 3H), 2.04-2.21 (m, 1H), 2.42-2.65 (m, 1H), 2.77 (br s, 1H), 2.97 (br s, 3H), 3.10-3.28 (m, 1H), 3.38-3.49 (m, 1H), 3.58-3.78 (m, 1H), 3.82-4.02 (m, 1H), 4.33-4.50 (m, 1H), 4.62-4.73 (m, 1H), 7.03 (br t, J=7.70 Hz, 2H), 7.31 (dd, J=8.34, 5.50 Hz, 2H), 8.67 (s, 1H), 8.72 (s, 1H); ESI-MS m/z [M+H]$^+$ 344.1. EXAMPLE 31 (12 mg, 38%): $^1$H NMR (400 MHz, CD$_3$OD) δ ppm 1.69 (br d, J=6.88 Hz, 3H), 2.07-2.22 (m, 1H), 2.27-2.63 (m, 1H), 2.29-2.45 (m, 1H), 2.49-2.49 (m, 1H), 2.98 (s, 3H), 3.06-3.23 (m, 1H), 3.39 (br dd, J=11.37, 9.08 Hz, 1H), 3.62-3.78 (m, 1H), 3.82-4.18 (m, 1H), 4.28-4.52 (m, 1H), 4.62-4.74 (m, 1H), 7.03 (br t, J=8.67 Hz, 2H), 7.31 (dd, J=8.53, 5.41 Hz, 2H), 8.66 (s, 1H); ESI-MS m/z [M+H]$^+$ 344.1.

Example 32

6-((S)-1-(4-fluorophenyl)ethyl)-N,N-dimethyl-5-(((R)-1-methylpyrrolidin-3-yl)amino)pyrazine-2-carboxamide

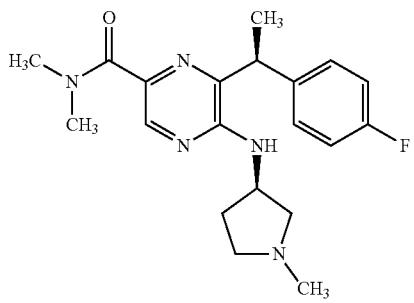 [SMILES: C[C@@H](c1ccc(F)cc1)c1nc(C(=O)N(C)C)cnc1N[C@@H]1CCN(C)C1]

Example 33

6-((R)-1-(4-fluorophenyl)ethyl)-N,N-dimethyl-5-(((R)-1-methylpyrrolidin-3-yl)amino)pyrazine-2-carboxamide

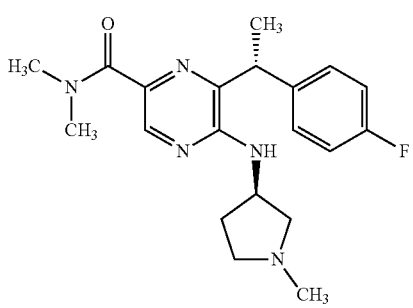 [SMILES: C[C@H](c1ccc(F)cc1)c1nc(C(=O)N(C)C)cnc1N[C@@H]1CCN(C)C1]

To a solution of 6-(1-(4-fluorophenyl)ethyl)-5-(((R)-1-methylpyrrolidin-3-yl)amino)pyrazine-2-carboxylic acid (45 mg, 0.076 mmol) in DMF (379 μL) was added HATU (28.8 mg, 0.076 mmol) and DIPEA (39.7 μL, 0.227 mmol). The solution was stirred at room temperature for 5 minutes. Next, dimethylamine (76 μL, 0.152 mmol) was added. The reaction mixture was stirred at room temperature for 4 hours and then purified by preparative HPLC (Phenomenex Gemini® C18, 5 μm, 30 mm ID×150 mm) using a gradient of 10-50% ACN (0.035% TFA) in water (0.05% TFA). Each of title compounds (diastereoisomers) was obtained as a TFA salt with arbitrarily assigned stereochemical configuration. EXAMPLE 32 (5.0 mg, 10%): $^1$H NMR (400 MHz, CD$_3$OD) δ ppm 1.64 (br d, J=6.88 Hz, 3H), 2.09-2.27 (m, 1H), 2.34-2.62 (m, 1H), 2.98 (s, 3H), 3.13 (s, 4H), 3.22 (s, 3H), 3.39 (br dd, J=11.60, 8.57 Hz, 1H), 3.68 (br d, J=11.28 Hz, 1H), 3.86-4.18 (m, 1H), 4.30-4.48 (m, 1H), 4.61-4.70 (m, 1H), 7.02 (br t, J=8.57 Hz, 2H), 7.24-7.33 (m, 2H), 8.31-8.40 (m, 1H); ESI-MS m/z [M+H]$^+$ 372.1. EXAMPLE 33 (5.7 mg, 12%). $^1$H NMR (400 MHz, CD$_3$OD) δ ppm 1.64 (br d, J=6.60 Hz, 3H), 2.09-2.38 (m, 1H), 2.43-2.61 (m, 1H), 2.97 (s, 3H), 3.14 (s, 4H), 3.22 (br s, 3H), 3.40-3.50 (m, 1H), 3.63-3.79 (m, 1H), 3.81-4.03 (m, 1H), 4.34-4.51 (m, 1H), 4.59-4.70 (m, 1H), 6.96-7.11 (m, 2H), 7.23-7.32 (m, 2H), 8.37 (s, 1H); ESI-MS m/z [M+H]$^+$ 372.1.

Example 34

6-((S)-1-(4-fluorophenyl)ethyl)-N-methyl-5-(((R)-1-methylpyrrolidin-3-yl)amino)pyrazine-2-carboxamide

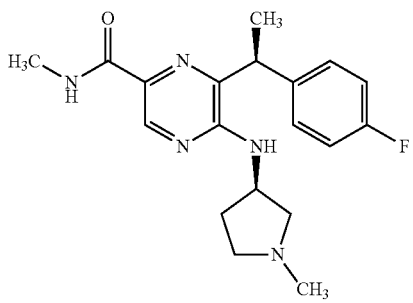 [SMILES: CNC(=O)c1cnc(N[C@@H]2CCN(C)C2)c([C@@H](C)c2ccc(F)cc2)n1]

Example 35

6-((R)-1-(4-fluorophenyl)ethyl)-N-methyl-5-(((R)-1-methylpyrrolidin-3-yl)amino)pyrazine-2-carboxamide

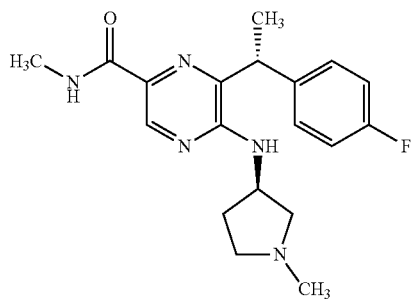 [SMILES: CNC(=O)c1cnc(N[C@@H]2CCN(C)C2)c([C@H](C)c2ccc(F)cc2)n1]

To a solution of 6-(1-(4-fluorophenyl)ethyl)-5-(((R)-1-methylpyrrolidin-3-yl)amino)pyrazine-2-carboxylic acid (45 mg, 0.076 mmol) in DMF (0.38 mL) was added HATU (28.8 mg, 0.076 mmol) and DIPEA (39.7 µL, 0.227 mmol). The solution was stirred at room temperature for 5 minutes. Next, methanamine (7.06 mg, 0.227 mmol) was added. The reaction mixture was stirred at room temperature for 4 hours and then purified by preparative HPLC (Phenomenex Gemini® C18, 5 µm, 30 mm ID×150 mm) using a gradient of 10-50% ACN (0.035% TFA) in water (0.05% TFA). Each of title compounds (diastereoisomers) was obtained as a TFA salt with arbitrarily assigned stereochemical configuration. EXAMPLE 34 (4 mg, 9%): $^1$H NMR (400 MHz, CD$_3$OD) δ ppm 1.71 (br d, J=6.79 Hz, 3H), 2.06-2.23 (m, 1H), 2.43-2.64 (m, 1H), 3.07-3.21 (m, 1H), 3.62-3.79 (m, 1H), 3.83-4.16 (m, 1H), 4.29-4.50 (m, 1H), 4.59-4.73 (m, 1H), 7.02 (br t, J=8.62 Hz, 2H), 7.31 (dd, J=8.53, 5.50 Hz, 2H), 8.54-8.69 (m, 1H); ESI-MS m/z [M+H]$^+$ 358.1. EXAMPLE 35 (4 mg, 9%): $^1$H NMR (400 MHz, CD$_3$OD) δ ppm 1.71 (br d, J=6.60 Hz, 3H), 2.07-2.20 (m, 1H), 2.41-2.58 (m, 1H), 2.92-3.04 (m, 6H), 3.11-3.25 (m, 1H), 3.38-3.49 (m, 1H), 3.59-3.78 (m, 1H), 3.80-4.01 (m, 1H), 4.28-4.49 (m, 1H), 4.58-4.70 (m, 1H), 6.94-7.10 (m, 2H), 7.31 (dd, J=8.39, 5.55 Hz, 2H), 8.57-8.70 (m, 1H). ESI-MS m/z [M+H]$^+$ 358.1.

Example 36

5-((trans-3-ethyl-1-methylpiperidin-4-yl)amino)-6-(4-fluorobenzyl)-N-methylpyrazine-2-carboxamide

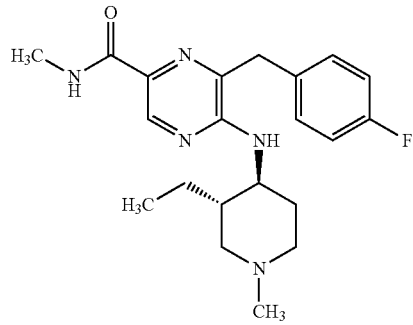

and

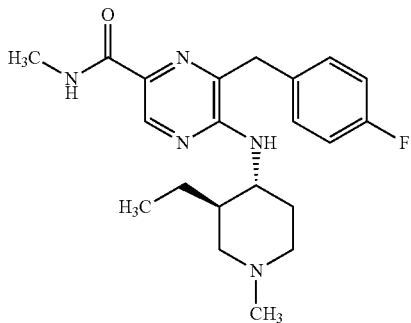

Step A: methyl 5-((trans-1-(tert-butoxycarbonyl)-3-ethylpiperidin-4-yl)amino)-6-chloropyrazine-2-carboxylate

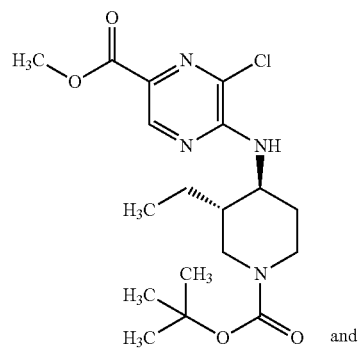

and

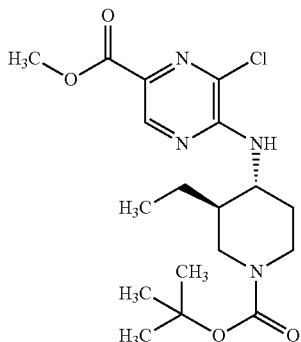

To a solution of methyl 5,6-dichloropyrazine-2-carboxylate (127 mg, 0.613 mmol) in dioxane (6.1 mL) were added DIPEA (321 µL, 1.839 mmol) and tert-butyl trans-4-amino-3-ethylpiperidine-1-carboxylate (200 mg, 0.613 mmol). The solution was stirred at room temperature overnight and then concentrated. The resulting residue was purified by silica gel column chromatography, using a gradient of hexane/EtOAc (4:1 to 1:1) to give the title compound (0.120 g, 49.1%). ESI-MS m/z [M+H]$^+$ 399.3.

Step B: methyl 5-((trans-1-(tert-butoxycarbonyl)-3-ethylpiperidin-4-yl)amino)-6-(4-fluorobenzyl)pyrazine-2-carboxylate

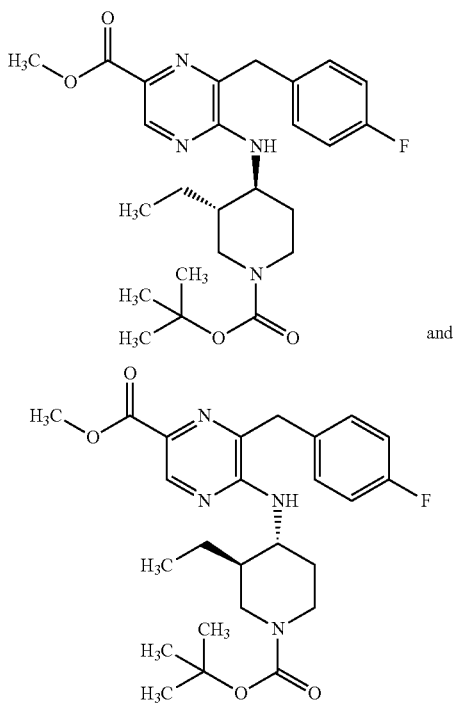

and

A mixture of methyl 5-((trans-1-(tert-butoxycarbonyl)-3-ethylpiperidin-4-yl)amino)-6-chloropyrazine-2-carboxylate (120 mg, 0.301 mmol), 2-(4-fluorobenzyl)-4,4,5,5-tetramethyl-1,3,2-dioxaborolane (128 mg, 0.542 mmol), Pd(dppf)Cl$_2$ (22.01 mg, 0.030 mmol) and Na$_2$CO$_3$ (334 μL, 0.602 mmol) in dioxane (3.0 mL) was degassed with nitrogen and then heated in a sealed tube at 110° C. for 16 hours. The mixture was filtered. The filtrate was concentrated under reduced pressure and the residue was purified by preparative HPLC (Phenomenex Gemini® C18, 5 μm, 30 mm ID×150 mm) using a gradient of 10-50% ACN (0.035% TFA) in water (0.05% TFA) to give a TFA salt of the title compound (77 mg, 43.6%). ESI-MS m/z [M+H]$^+$ 473.3.

Step C: methyl 5-((trans-3-ethylpiperidin-4-yl)amino)-6-(4-fluorobenzyl)pyrazine-2-carboxylate

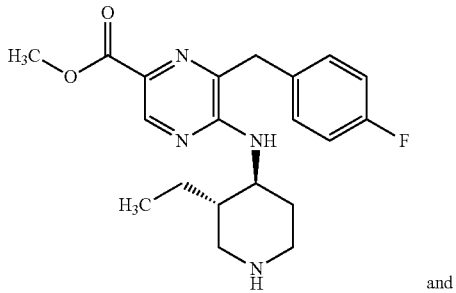

and

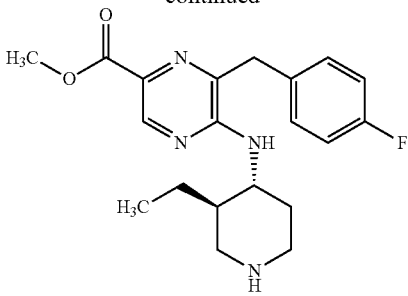

To a 75 mL round-bottomed flask were added methyl 5-((trans-1-(tert-butoxycarbonyl)-3-ethylpiperidin-4-yl)amino)-6-(4-fluorobenzyl)pyrazine-2-carboxylate 2,2,2-trifluoroacetate (77 mg, 0.131 mmol), hydrogen chloride (0.131 mL, 0.525 mmol) and dioxane (3 mL). The resulting colorless solution was stirred at 50° C. for 1 hour and then concentrated under reduced pressure to give the title compound as a solid, which was used without further purification. ESI-MS m/z [M+H]$^+$ 373.4.

Step D: methyl 5-((trans-3-ethyl-1-methylpiperidin-4-yl)amino)-6-(4-fluorobenzyl)pyrazine-2-carboxylate

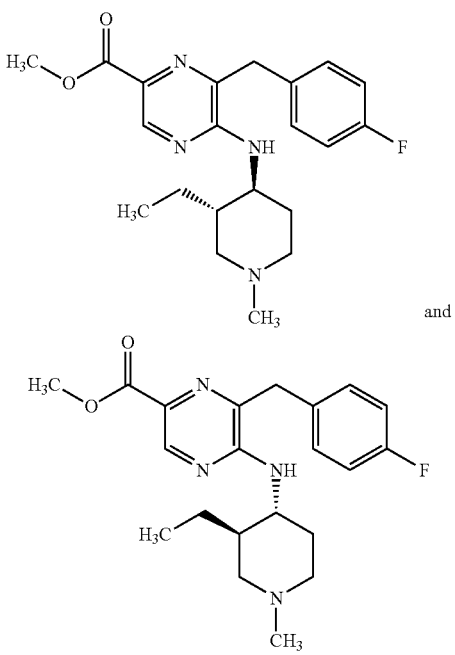

and

To a 50 mL round-bottomed flask were added methyl 5-((trans-3-ethylpiperidin-4-yl)amino)-6-(4-fluorobenzyl)pyrazine-2-carboxylate (0.049 g, 0.131 mmol), formaldehyde (0.020 mL, 0.259 mmol) and methanol (3 mL) to give a colorless solution. Next, sodium cyanotrihydroborate (8.23 mg, 0.131 mmol) was added. The reaction mixture was stirred at room temperature overnight and then treated with water and extracted with EtOAc. The organic layers were dried over anhydrous MgSO$_4$ and concentrated to give the title compound, which was used without further purification. ESI-MS m/z [M+H]$^+$ 387.4.

Step E: 5-((trans-3-ethyl-1-methylpiperidin-4-yl)amino)-6-(4-fluorobenzyl)pyrazine-2-carboxylic acid

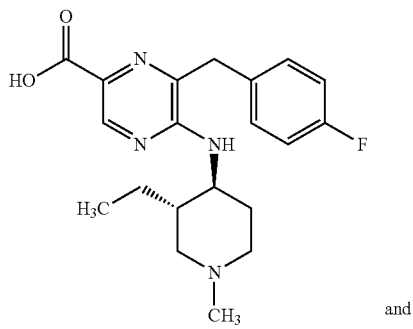

and

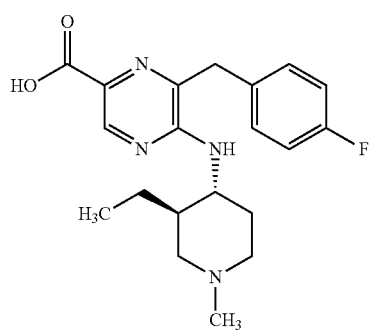

To a 125 mL pear flask were added methyl 5-((trans-3-ethyl-1-methylpiperidin-4-yl)amino)-6-(4-fluorobenzyl)pyrazine-2-carboxylate (0.051 g, 0.131 mmol), lithium hydroxide (0.262 mL, 0.524 mmol) and dioxane (3 mL). The resulting colorless solution was stirred at room temperature overnight, and then was concentrated to dryness to give the title compound, which was used without further purification. ESI-MS m/z [M+H]$^+$ 373.4.

Step F: 5-((trans-3-ethyl-1-methylpiperidin-4-yl)amino)-6-(4-fluorobenzyl)-N-methylpyrazine-2-carboxamide To an 8 mL vial were added 5-((trans-3-ethyl-1-methylpiperidin-4-yl)amino)-6-(4-fluorobenzyl)pyrazine-2-carboxylic acid (16.02 mg, 0.043 mmol), methanamine (0.043 mL, 0.086 mmol), HATU (16.35 mg, 0.043 mmol), DIPEA (0.022 mL, 0.129 mmol) and DMF (2 mL). The resulting yellow solution was stirred at room temperature overnight and then purified by preparative HPLC (Phenomenex Gemini® C18, 5 μm, 30 mm ID×150 mm) using a gradient of 40-90% aq ACN (80%, 10 mM NH$_4$HCO$_3$) in water (10 mM NH$_4$HCO$_3$) to give the title compound (7.6 mg, 45.8%). $^1$H NMR (400 MHz, CD$_3$OD) δ ppm 0.66-0.78 (m, 3H), 0.80-0.93 (m, 1H), 1.10-1.24 (m, 1H), 1.43-1.59 (m, 2H), 1.76 (s, 2H), 1.87-1.97 (m, 1H), 2.05-2.14 (m, 1H), 2.28 (s, 3H), 2.77-2.88 (m, 1H), 2.92 (s, 3H), 3.67-3.84 (m, 1H), 4.11-4.17 (m, 2H), 6.97-7.14 (m, 2H), 7.21-7.33 (m, 2H), 8.46-8.65 (m, 1H); ESI-MS m/z [M+H]$^+$ 386.4.

Example 37

5-(1-(4-fluorophenyl)ethyl)-6-((2-(pyrrolidin-1-yl)ethyl)amino)pyrazine-2-carboxamide

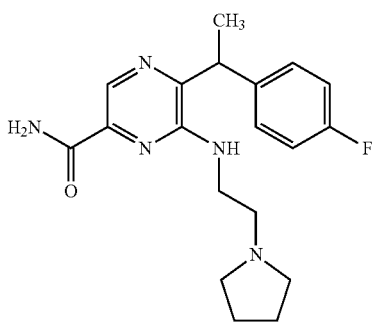 [SMILES: CC(c1ccc(F)cc1)c1ncc(C(N)=O)nc1NCCN1CCCC1]

Step A: 6-chloro-5-(1-(4-fluorophenyl)vinyl)pyrazine-2-carboxamide

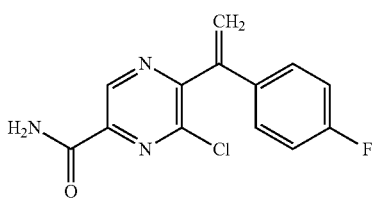 [SMILES: C=C(c1ccc(F)cc1)c1ncc(C(N)=O)nc1Cl]

A mixture of 6-chloro-5-(1-(4-fluorophenyl)vinyl)pyrazine-2-carboxylic acid (100 mg, 358.85 μmol), NH$_4$Cl (38.39 mg, 717.71 μmol, 25.09 HATU (204.67 mg, 538.28 μmol) and DIPEA (185.51 mg, 1.44 mmol, 250.02 μL) in DMF (2 mL) was stirred at 30° C. for 16 hours. The mixture was then diluted with water (10 mL×2) and extracted with EtOAc (15 mL×2). The organic layers were separated, washed with saturated aq NaCl (20 mL×2), dried, filtered and concentrated under reduce pressure. The product was purified by preparative TLC (SiO$_2$) using petroleum ether/EtOAc (1:1) to give the title compound as a yellow solid (130 mg). $^1$H NMR (400 MHz, CDCl$_3$) δ ppm 5.68 (s, 2H), 5.99 (s, 1H), 6.99-7.08 (m, 2H), 7.17-7.23 (m, 2H), 7.40-7.52 (m, 1H), 9.35 (s, 1H).

Step B: 6-chloro-5-(1-(4-fluorophenyl)ethyl)pyrazine-2-carboxamide

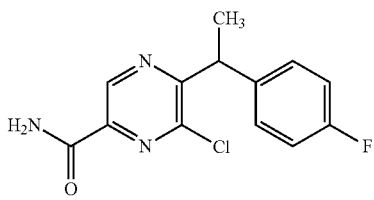 [SMILES: CC(c1ccc(F)cc1)c1ncc(C(N)=O)nc1Cl]

To a solution of 6-chloro-5-(1-(4-fluorophenyl)vinyl)pyrazine-2-carboxamide (130 mg, 468.16 μmol) in EtOH (10 mL) was added Raney-Ni (46.45 mg). The suspension was degassed under vacuum, purged with $H_2$ (3×) and stirred at 50° C. for 16 hours under $H_2$ (15 psi). The mixture was then diluted with EtOH (5 mL) and filtered through a pad of Celite®. The filtrate was concentrated under reduced pressure to give the title compound as a yellow solid (100 mg). ESI-MS m/z $[M+H]^+$ 280.1.

Step C: 5-(1-(4-fluorophenyl)ethyl)-6-((2-(pyrrolidin-1-yl)ethyl)amino)pyrazine carboxamide To a solution of 6-chloro-5-(1-(4-fluorophenyl)ethyl) pyrazine-2-carboxamide (100 mg, 357.53 μmol) in DMSO (1.5 mL) were added 2-pyrrolidin-1-ylethanamine (262.51 mg, 2.30 mmol) and DIPEA (262.54 mg, 2.03 mmol, 353.8 μL). The mixture was stirred at 80° C. for 16 hours and then purified by preparative HPLC (Phenomenex Gemini® C18, 10 μm, 25 mm ID×150 mm) using a gradient of 15-45% ACN in water (0.05% HCl) to give an HCl salt of the title compound as a light-yellow solid (28.6 mg, 19.9%). $^1$H NMR (400 MHz, $CD_3OD$) δ ppm 1.66 (d, J=6.8 Hz, 3H), 2.03 (br d, J=5.6 Hz, 4H), 2.83-3.04 (m, 2H), 3.38 (br d, J=4.6 Hz, 2H), 3.53-3.68 (m, 2H), 3.85 (br t, J=5.1 Hz, 2H), 4.51 (br d, J=6.6 Hz, 1H), 7.02 (t, J=8.6 Hz, 2H), 7.31 (dd, J=8.3, 5.3 Hz, 2H), 8.45 (s, 1H); ESI-MS m/z $[M+H]^+$ 358.2.

Example 38

5-(1-(4-fluorophenyl)ethyl)-N-methyl-6-((2-(pyrrolidin-1-yl)ethyl)amino)pyrazine-2-carboxamide

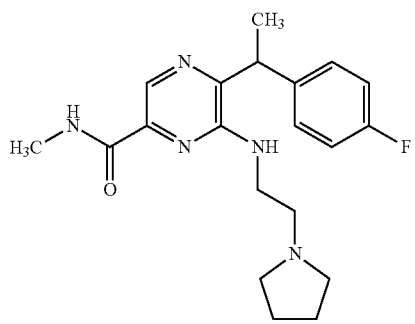 [SMILES: CNC(=O)c1cnc(C(C)c2ccc(F)cc2)c(NCCN2CCCC2)n1]

An HCl salt of the title compound was prepared like EXAMPLE 37, starting with 6-chloro-5-(1-(4-fluorophenyl) vinyl)pyrazine-2-carboxylic acid (100 mg, 358.85 μmol) and $MeNH_2HCl$ (48.46 mg, 717.71 μmol), and was obtained as a light-yellow solid (25.2 mg, 51.8% last step). $^1$H NMR (400 MHz, $CD_3OD$) δ ppm 1.64 (d, J=6.85 Hz, 3H), 1.92-2.08 (m, 4H), 2.95 (s, 5H), 3.35 (q, J=5.54 Hz, 2H), 3.59 (br dd, J=9.54, 4.16 Hz, 2H), 3.85 (dt, J=10.52, 5.26 Hz, 2H), 4.43 (d, J=6.85 Hz, 1H), 7.00 (t, J=8.68 Hz, 2H), 7.28 (dd, J=8.56, 5.38 Hz, 2H), 8.44 (s, 1H); ESI-MS m/z $[M+H]^+$ 372.3.

Example 39

N,N,3-trimethyl-6-(3-methylbenzyl)-5-((2-(pyrrolidin-1-yl)ethyl)amino)pyrazine-2-carboxamide

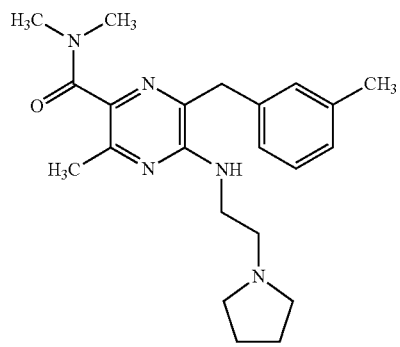

To a solution of 3-methyl-6-(3-methylbenzyl)-5-((2-(pyrrolidin-1-yl)ethyl)amino)pyrazine-2-carboxylic acid (33 mg, 0.065 mmol) and HATU (24.78 mg, 0.065 mmol) in DMF (0.65 mL) was added DIPEA (39.8 μL, 0.228 mmol). The solution was stirred at room temperature for 5 minutes. Next, dimethylamine (65.2 μL, 0.130 mmol) was added and the resulting solution was stirred at room temperature for 3 hours. The reaction mixture was then purified by preparative HPLC (Phenomenex Gemini® C18, 5 μm, 30 mm ID×150 mm) using a gradient of 10-50% ACN (0.035% TFA) in water (0.05% TFA) to give a TFA salt of the title compound as a colorless oil (16 mg, 49.5%). $^1$H NMR (400 MHz, $CD_3OD$) δ ppm 1.90-1.99 (m, 2H), 2.05-2.14 (m, 2H), 2.27 (s, 3H), 2.35 (s, 3H), 2.91 (s, 3H), 2.98-3.06 (m, 2H), 3.11 (s, 3H), 3.41 (t, J=5.86 Hz, 2H), 3.61-3.68 (m, 2H), 3.78 (t, J=5.86 Hz, 2H), 4.02 (s, 2H), 6.98-7.06 (m, 3H), 7.12-7.18 (m, 1H); ESI-MS m/z $[M+H]^+$ 382.1.

Example 40

N,3-dimethyl-6-(3-methylbenzyl)-5-((2-(pyrrolidin-1-yl)ethyl)amino)pyrazine-2-carboxamide

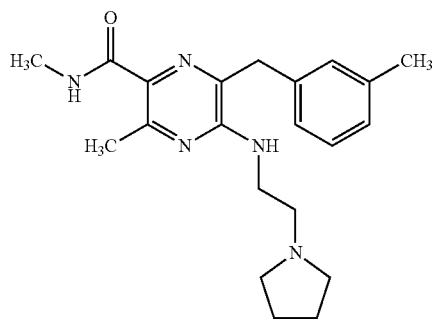

A TFA salt of the title compound was prepared like EXAMPLE 39, using 3-methyl-6-(3-methylbenzyl)-5-((2-(pyrrolidin-1-yl)ethyl)amino)pyrazine-2-carboxylic acid (33 mg, 0.093 mmol) and methanamine (17.5 mg, 0.186 mmol), and was obtained as a colorless oil (14 mg, 31%). $^1$H NMR (400 MHz, $CD_3OD$) δ ppm 1.94 (dd, J=7.08, 5.13 Hz, 2H), 2.03-2.13 (m, 2H), 2.29 (s, 3H), 2.73 (s, 3H), 2.87 (s, 3H), 2.95-3.03 (m, 2H), 3.41 (t, J=5.61 Hz, 2H), 3.59-3.68 (m, 2H), 3.81 (t, J=5.61 Hz, 2H), 4.06 (s, 2H), 6.97-7.09 (m, 3H), 7.13-7.20 (m, 1H); ESI-MS m/z [M+H]⁺ 368.1.

Example 41

3-methyl-6-(3-methylbenzyl)-5-((2-(pyrrolidin-1-yl)ethyl)amino)pyrazine-2-carboxamide

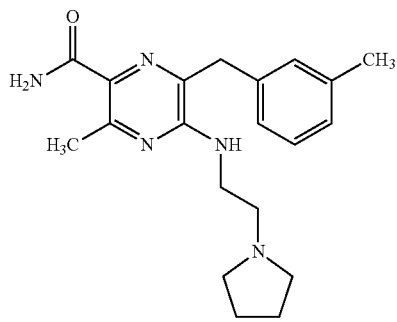 [SMILES: Cc1cccc(Cc2nc(C(N)=O)c(C)nc2NCCN2CCCC2)c1]

A TFA salt of the title compound was prepared like EXAMPLE 39, using 3-methyl-6-(3-methylbenzyl)-5-((2-(pyrrolidin-1-yl)ethyl)amino)pyrazine-2-carboxylic acid (33 mg, 0.093 mmol) and ammonium hydroxide (5.08 μL, 0.130 mmol), and was obtained as a white solid (19 mg, 62%). ¹H NMR (400 MHz, CD₃OD) δ ppm 1.95 (dd, J=7.57, 5.13 Hz, 2H), 2.05-2.19 (m, 2H), 2.29 (s, 3H), 2.72 (s, 3H), 2.97-3.08 (m, 2H), 3.43 (t, J=5.61 Hz, 2H), 3.65 (d, J=4.88 Hz, 2H), 3.83 (t, J=5.61 Hz, 2H), 4.04 (s, 2H), 6.97-7.08 (m, 3H), 7.10-7.24 (m, 1H); ESI-MS m/z [M+H]⁺ 354.1.

Example 42

6-(4-fluorobenzyl)-N,N,3-trimethyl-5-((2-(pyrrolidin-1-yl)ethyl)amino)pyrazine-2-carboxamide

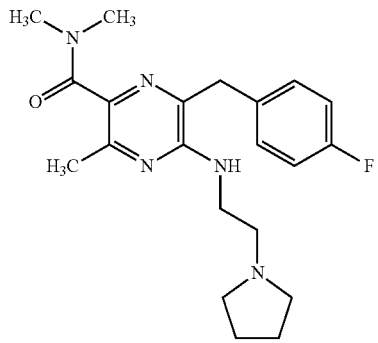 [SMILES: Cc1nc(NCCN2CCCC2)c(Cc2ccc(F)cc2)nc1C(=O)N(C)C]

To a solution of 6-(4-fluorobenzyl)-3-methyl-5-((2-(pyrrolidin-1-yl)ethyl)amino)pyrazine-2-carboxylic acid (33 mg, 0.074 mmol based on 80% purity) and HATU (28.0 mg, 0.074 mmol) in DMF (0.74 mL) was added DIPEA (32.2 μL, 0.184 mmol). The solution was stirred at room temperature for 5 minutes. Next, dimethylamine (73.7 μL, 0.147 mmol) was added. The resulting solution was stirred for 3 hours and then purified by preparative HPLC (Phenomenex Gemini® C18, 5 μm, 30 mm ID×150 mm) using a gradient of 10-50% ACN (0.035% TFA) in water (0.05% TFA) to give a TFA salt of the title compound as a colorless oil (17 mg, 46.2%). ¹H NMR (400 MHz, CD₃OD) δ ppm 1.89-2.02 (m, 2H), 2.14 (t, J=7.32 Hz, 2H), 2.35 (s, 3H), 2.88 (s, 3H), 3.00-3.15 (m, 5H), 3.43 (t, J=5.86 Hz, 2H), 3.61-3.74 (m, 2H), 3.80 (t, J=5.86 Hz, 2H), 4.03 (s, 2H), 6.95-7.09 (m, 2H), 7.18-7.28 (m, 2H); ESI-MS m/z [M+H]⁺ 386.3.

Example 43

6-(4-fluorobenzyl)-N,3-dimethyl-5-((2-(pyrrolidin-1-yl)ethyl)amino)pyrazine-2-carboxamide

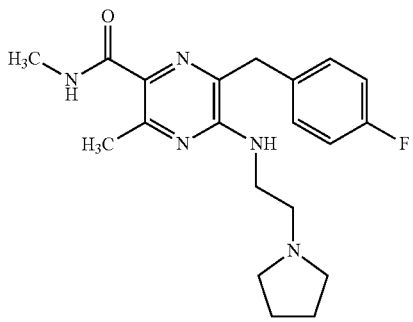 [SMILES: CNC(=O)c1nc(Cc2ccc(F)cc2)c(NCCN2CCCC2)nc1C]

A TFA salt of the title compound was prepared like EXAMPLE 42, using 6-(4-fluorobenzyl)-3-methyl-5-((2-(pyrrolidin-1-yl)ethyl)amino)pyrazine-2-carboxylic acid (33 mg, 0.074 mmol based on 80% purity) and methanamine (13.9 μL, 0.147 mmol), and was obtained as a white film (21 mg, 58.7%). ¹H NMR (400 MHz, CD₃OD) δ ppm 1.87-2.05 (m, 2H), 2.08-2.21 (m, 2H), 2.73 (s, 3H), 2.87 (s, 3H), 3.01-3.13 (m, 2H), 3.42 (t, J=5.86 Hz, 2H), 3.70 (d, J=5.37 Hz, 2H), 3.82 (t, J=5.61 Hz, 2H), 4.07 (s, 2H), 6.96-7.14 (m, 2H), 7.21-7.35 (m, 2H); ESI-MS m/z [M+H]⁺ 372.2.

Example 44

6-(4-fluorobenzyl)-N,3-dimethyl-5-((2-(pyrrolidin-1-yl)ethyl)amino)pyrazine-2-carboxamide

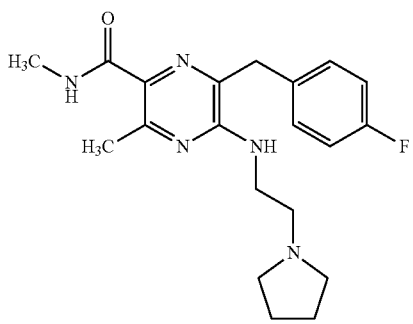 [SMILES: CNC(=O)c1nc(Cc2ccc(F)cc2)c(NCCN2CCCC2)nc1C]

A TFA salt of the title compound was prepared like EXAMPLE 42, using 6-(4-fluorobenzyl)-3-methyl-5-((2-(pyrrolidin-1-yl)ethyl)amino)pyrazine-2-carboxylic acid (30 mg, 0.074 mmol based on 80% purity) and ammonium hydroxide (5.2 μL, 0.134 mmol), and was obtained as a white film (11 mg, 32%). ¹H NMR (400 MHz, CD₃OD) δ ppm 1.91-2.03 (m, 2H), 2.07-2.20 (m, 2H), 2.72 (s, 3H), 3.03-3.17 (m, 3H), 3.44 (t, J=5.61 Hz, 2H), 3.72 (d, J=5.37 Hz, 2H), 3.84 (t, J=5.86 Hz, 2H), 4.05 (s, 2H), 6.98-7.08 (m, 2H), 7.15-7.34 (m, 2H).

Example 45

5-((trans-1,3-dimethylpiperidin-4-yl)amino)-6-(4-fluorobenzyl)-3-methylpyrazine-2-carboxamide

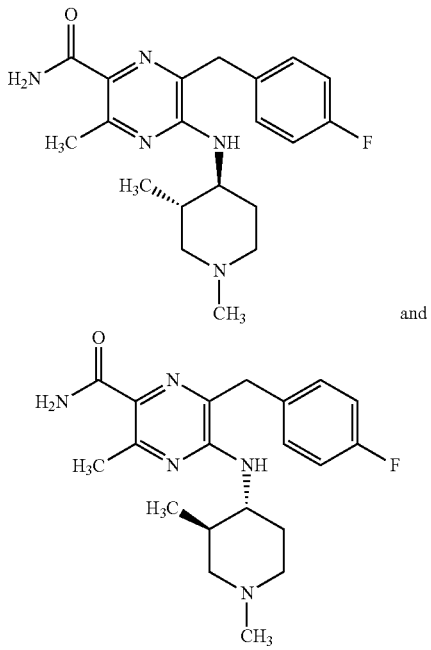

and

A TFA salt of the title compound was prepared like EXAMPLE 42, using 5-((trans-1,3-dimethylpiperidin-4-yl)amino)-6-(4-fluorobenzyl)-3-methylpyrazine-2-carboxylic acid (20 mg, 0.032 mmol) and ammonium hydroxide (2.5 µL, 0.064 mmol), and was obtained as a pale-green solid (10 mg, 63.9%). $^1$H NMR (400 MHz, CD$_3$OD) δ ppm 0.81 (d, J=6.59 Hz, 3H), 1.71-1.83 (m, 1H), 2.02-2.15 (m, 1H), 2.19-2.26 (m, 1H), 2.68 (s, 3H), 2.84-2.94 (m, 4H), 3.16 (td, J=13.12, 2.81 Hz, 1H), 3.46-3.58 (m, 2H), 4.04-4.17 (m, 3H), 7.02 (t, J=8.66 Hz, 2H), 7.24 (dd, J=8.30, 5.61 Hz, 2H); ESI-MS m/z [M+H]$^+$ 373.1.

Example 46

5-((trans-1,3-dimethylpiperidin-4-yl)amino)-6-(4-fluorobenzyl)-N,3-dimethylpyrazine-2-carboxamide

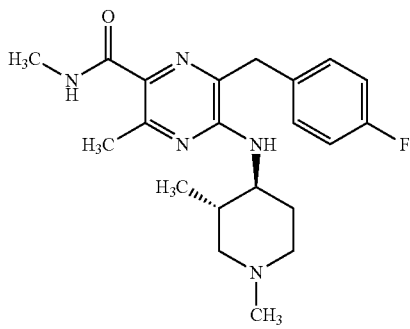

and

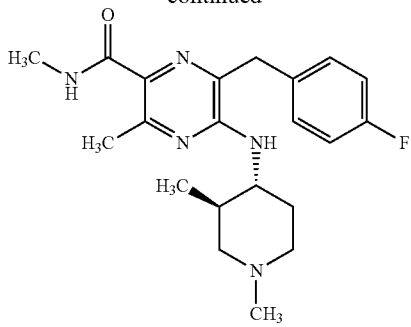

A TFA salt of the title compound was prepared like EXAMPLE 42, using 5-((trans-1,3-dimethylpiperidin-4-yl)amino)-6-(4-fluorobenzyl)-3-methylpyrazine-2-carboxylic acid (20 mg, 0.032 mmol) and methanamine (8.0 µL, 0.064 mmol), and was obtained as a white solid (8 mg, 49.7%). $^1$H NMR (400 MHz, CD$_3$OD) δ ppm 0.78 (d, J=6.59 Hz, 3H), 1.67-1.81 (m, 1H), 2.00-2.13 (m, 1H), 2.17-2.26 (m, 1H), 2.68 (s, 3H), 2.87 (d, J=2.93 Hz, 7H), 3.15 (td, J=13.06, 2.93 Hz, 1H), 3.43-3.57 (m, 2H), 4.04-4.16 (m, 3H), 7.01 (t, J=8.66 Hz, 2H), 7.23 (dd, J=8.30, 5.61 Hz, 2H); ESI-MS m/z [M+H]$^+$ 386.2.

Example 47

5-((trans-1,3-dimethylpiperidin-4-yl)amino)-6-(4-fluorobenzyl)-N,N,3-trimethylpyrazine-2-carboxamide

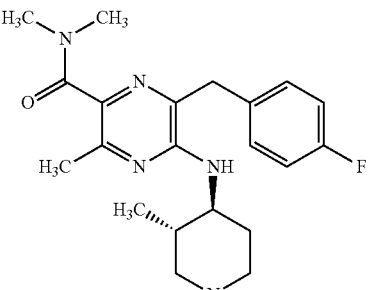

and

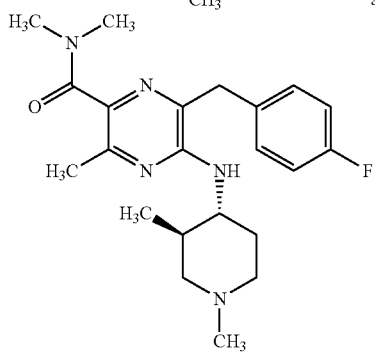

A TFA salt of the title compound was prepared like EXAMPLE 42, using 5-((trans-1,3-dimethylpiperidin-4-yl)amino)-6-(4-fluorobenzyl)-3-methylpyrazine-2-carboxylic acid (20 mg, 0.032 mmol) and dimethylamine (32.0 µL, 0.064 mmol), and was obtained as a white solid (6 mg, 36.3%). $^1$H NMR (400 MHz, CD$_3$OD) δ ppm 0.79 (d, J=6.59 Hz, 3H), 1.67-1.78 (m, 1H), 1.99-2.10 (m, 1H), 2.23 (br dd, J=14.28, 2.81 Hz, 1H), 2.31 (s, 3H), 2.89 (d, J=18.31 Hz, 7H), 3.07-3.19 (m, 4H), 3.45-3.56 (m, 2H), 3.99-4.12 (m, 3H), 7.00 (t, J=8.42 Hz, 2H), 7.21 (dd, J=8.18, 5.74 Hz, 2H); ESI-MS m/z [M+H]$^+$ 400.2.

Example 48

6-(1-(4-fluorophenyl)ethyl)-N,N,3-trimethyl-5-((2-(pyrrolidin-1-yl)ethyl)amino)pyrazine-2-carboxamide

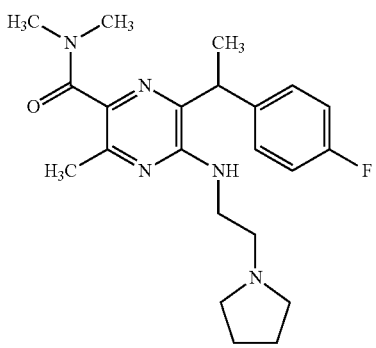 [SMILES: Cc1nc(NCCN2CCCC2)c(C(C)c2ccc(F)cc2)nc1C(=O)N(C)C]

A TFA salt of the title compound was prepared like EXAMPLE 42, using 6-(1-(4-fluorophenyl)ethyl)-3-methyl-5-((2-(pyrrolidin-1-yl)ethyl)amino)pyrazine-2-carboxylic acid (25 mg, 0.056 mmol) and dimethylamine (41.8 μL, 0.084 mmol), and was obtained as a white solid (24 mg, 84%). $^1$H NMR (400 MHz, CD$_3$OD) δ ppm 1.60 (d, J=6.83 Hz, 3H), 1.89-2.01 (m, 2H), 2.06-2.17 (m, 2H), 2.36 (s, 3H), 2.94-3.00 (m, 4H), 3.01-3.09 (m, 1H), 3.14 (s, 3H), 3.36-3.41 (m, 2H), 3.58-3.70 (m, 2H), 3.71-3.81 (m, 2H), 4.25 (q, J=6.83 Hz, 1H), 6.96-7.03 (m, 2H), 7.23-7.30 (m, 2H); ESI-MS m/z [M+H]$^+$ 400.1.

Example 49

6-(1-(4-fluorophenyl)ethyl)-N,3-dimethyl-5-((2-(pyrrolidin-1-yl)ethyl)amino)pyrazine-2-carboxamide

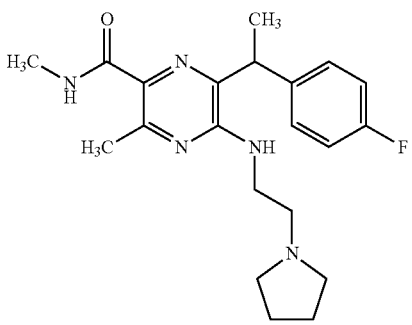 [SMILES: CNC(=O)c1nc(C(C)c2ccc(F)cc2)c(NCCN2CCCC2)nc1C]

A TFA salt of the title compound was prepared like EXAMPLE 42, using 6-(1-(4-fluorophenyl)ethyl)-3-methyl-5-((2-(pyrrolidin-1-yl)ethyl)amino)pyrazine-2-carboxylic acid (25 mg, 0.056 mmol) and methanamine (9.3 μL, 0.084 mmol), and was obtained as a white film (18 mg, 64.7%). $^1$H NMR (400 MHz, CD$_3$OD) δ ppm 1.67 (d, J=6.83 Hz, 3H), 1.90-2.01 (m, 2H), 2.05-2.15 (m, 2H), 2.73 (s, 3H), 2.90-2.97 (m, 4H), 3.00-3.11 (m, 1H), 3.34-3.43 (m, 2H), 3.56-3.69 (m, 2H), 3.71-3.85 (m, 2H), 4.24 (q, J=6.83 Hz, 1H), 6.93-7.05 (m, 2H), 7.21-7.34 (m, 2H); ESI-MS m/z [M+H]$^+$ 386.1.

Example 50

6-(1-(4-fluorophenyl)ethyl)-3-methyl-5-((2-(pyrrolidin-1-yl)ethyl)amino)pyrazine-2-carboxamide

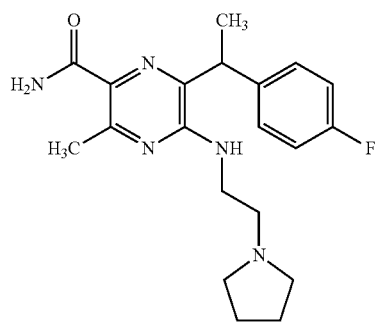 [SMILES: Cc1nc(NCCN2CCCC2)c(C(C)c2ccc(F)cc2)nc1C(N)=O]

A TFA salt of the title compound was prepared like EXAMPLE 42, using 6-(1-(4-fluorophenyl)ethyl)-3-methyl-5-((2-(pyrrolidin-1-yl)ethyl)amino)pyrazine-2-carboxylic acid (25 mg, 0.056 mmol) and ammonium hydroxide (4.3 μL, 0.111 mmol), and was obtained as a white solid (16 mg, 59.2%). $^1$H NMR (400 MHz, CD$_3$OD) δ ppm 1.66 (d, J=6.83 Hz, 3H), 1.90-2.02 (m, 2H), 2.04-2.16 (m, 2H), 2.73 (s, 3H), 2.92-2.99 (m, 1H), 3.01-3.10 (m, 1H), 3.38 (td, J=5.80, 3.05 Hz, 2H), 3.58-3.70 (m, 2H), 3.71-3.86 (m, 2H), 4.25 (q, J=6.83 Hz, 1H), 6.97-7.05 (m, 2H), 7.22-7.31 (m, 2H; ESI-MS m/z [M+H]$^+$ 372.10.

Example 51

N-(2-fluoroethyl)-6-(1-(4-fluorophenyl)ethyl)-3-methyl-5-((2-(pyrrolidin-1-yl)ethyl)amino)pyrazine-2-carboxamide

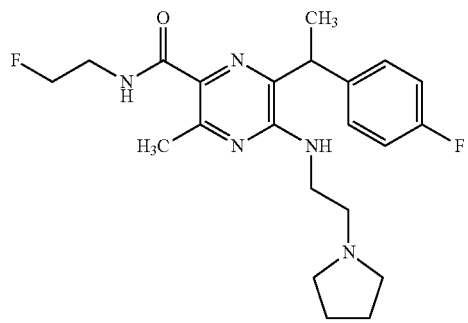 [SMILES: Cc1nc(NCCN2CCCC2)c(C(C)c2ccc(F)cc2)nc1C(=O)NCCF]

A TFA salt of the title compound was prepared like EXAMPLE 42, using 6-(1-(4-fluorophenyl)ethyl)-3-methyl-5-((2-(pyrrolidin-1-yl)ethyl)amino)pyrazine-2-carboxylic acid (12.5 mg, 0.028 mmol) and 2-fluoroethan-1-amine hydrogen chloride (5.6 mg, 0.056 mmol), and was obtained as a colorless oil (5 mg, 33.8%). ¹H NMR (400 MHz, CD₃OD) δ ppm 1.66 (d, J=6.83 Hz, 3H), 1.90-1.99 (m, 2H), 2.02-2.13 (m, 2H), 2.73 (s, 3H), 2.90-2.98 (m, 1H), 3.00-3.09 (m, 1H), 3.36-3.43 (m, 2H), 3.57-3.63 (m, 1H), 3.63-3.69 (m, 2H), 3.70-3.73 (m, 1H), 3.76-3.85 (m, 2H), 4.26 (q, J=6.83 Hz, 1H), 4.51 (t, J=5.13 Hz, 1H), 4.60 (t, J=5.00 Hz, 1H), 7.01 (t, J=8.79 Hz, 2H), 7.21-7.34 (m, 2H); ESI-MS m/z [M+H]⁺ 418.0.

Example 52

6-(1-(4-fluorophenyl)ethyl)-N-(2-methoxyethyl)-3-methyl-5-((2-(pyrrolidin-1-yl)ethyl)amino)pyrazine-2-carboxamide

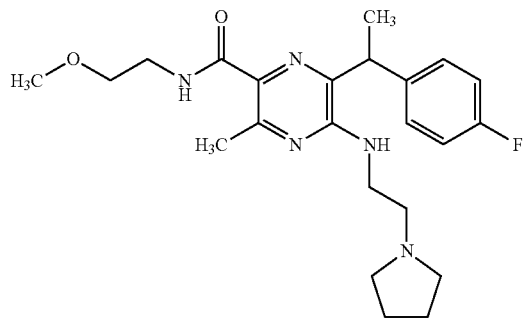 [SMILES: COCCNC(=O)c1nc(C(C)c2ccc(F)cc2)c(NCCN2CCCC2)nc1C]

A TFA salt of the title compound was prepared like EXAMPLE 42, using 6-(1-(4-fluorophenyl)ethyl)-3-methyl-5-((2-(pyrrolidin-1-yl)ethyl)amino)pyrazine-2-carboxylic acid (12.5 mg, 0.028 mmol) and 2-methoxyethan-1-amine (3.1 mg, 0.041 mmol), and was obtained as a colorless oil (5 mg, 33.6%). ¹H NMR (400 MHz, CD₃OD) δ ppm 1.65 (d, J=7.08 Hz, 3H), 1.89-2.00 (m, 2H), 2.06-2.14 (m, 2H), 2.73 (s, 3H), 2.90-3.00 (m, 1H), 3.02-3.08 (m, 1H), 3.34-3.44 (m, 5H), 3.56 (s, 4H), 3.61 (ddd, J=11.04, 7.38, 4.03 Hz, 1H), 3.67 (ddd, J=11.47, 7.57, 3.91 Hz, 1H), 3.73-3.86 (m, 2H), 4.27 (q, J=6.83 Hz, 1H), 6.98-7.04 (m, 2H), 7.22-7.31 (m, 2H); ESI-MS m/z [M+H]⁺ 430.2.

Example 53

6-(1-(4-fluorophenyl)ethyl)-3-methyl-5-((2-(pyrrolidin-1-yl)ethyl)amino)-N-(tetrahydro-2H-pyran-4-yl)pyrazine-2-carboxamide

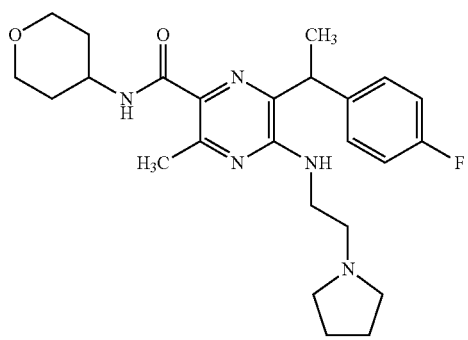 [SMILES: Cc1nc(NCCN2CCCC2)c(C(C)c2ccc(F)cc2)nc1C(=O)NC1CCOCC1]

A TFA salt of the title compound was prepared like EXAMPLE 42, using 6-(1-(4-fluorophenyl)ethyl)-3-methyl-5-((2-(pyrrolidin-1-yl)ethyl)amino)pyrazine-2-carboxylic acid (12.5 mg, 0.028 mmol) and tetrahydro-2H-pyran-4-amine (4.2 mg, 0.042 mmol), and was obtained as a colorless oil (7 mg, 44.1%). ¹H NMR (400 MHz, CD₃OD) δ ppm 1.52-1.63 (m, 2H), 1.64 (d, J=7.08 Hz, 3H), 1.87-2.02 (m, 4H), 2.05-2.16 (m, 2H), 2.72 (s, 3H), 2.93-3.01 (m, 1H), 3.02-3.10 (m, 1H), 3.40 (td, J=5.80, 2.56 Hz, 2H), 3.51-3.59 (m, 2H), 3.60-3.65 (m, 1H), 3.66-3.72 (m, 1H), 3.74-3.87 (m, 2H), 3.92-3.98 (m, 2H), 4.03 (tt, J=10.49, 4.39 Hz, 1H), 4.28 (q, J=6.83 Hz, 1H), 7.00-7.07 (m, 2H), 7.21-7.30 (m, 2H); ESI-MS m/z [M+H]⁺ 456.15.

Example 54

N-(3-(azetidin-1-yl)propyl)-6-(1-(4-fluorophenyl)ethyl)-3-methyl-5-((2-(pyrrolidin-1-yl)ethyl)amino)pyrazine-2-carboxamide

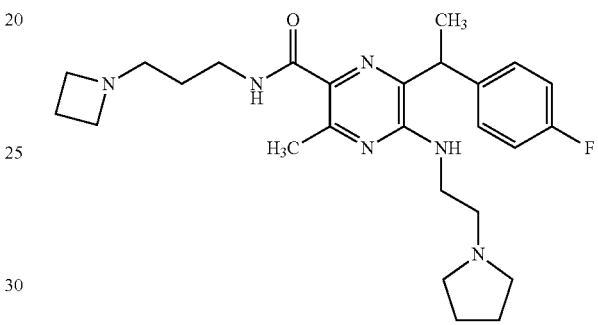

A TFA salt of the title compound was prepared like EXAMPLE 42, using 6-(1-(4-fluorophenyl)ethyl)-3-methyl-5-((2-(pyrrolidin-1-yl)ethyl)amino)pyrazine-2-carboxylic acid (12.5 mg, 0.028 mmol) and azetidine (2.9 mg, 0.050 mmol), and was obtained as a colorless oil (5.8 mg, 29.7%). ¹H NMR (400 MHz, CD₃OD) δ ppm 1.67 (d, J=6.83 Hz, 3H), 1.87 (quin, J=7.08 Hz, 2H), 1.91-2.00 (m, 2H), 2.03-2.13 (m, 2H), 2.37-2.49 (m, 1H), 2.56-2.69 (m, 1H), 2.74 (s, 3H), 2.88-2.96 (m, 1H), 2.99-3.08 (m, 1H), 3.20-3.26 (m, 2H), 3.33-3.43 (m, 2H), 3.46 (t, J=6.71 Hz, 2H), 3.54-3.61 (m, 1H), 3.66 (ddd, J=10.98, 7.32, 4.15 Hz, 1H), 3.79 (td, J=5.74, 3.42 Hz, 2H), 4.08 (q, J=9.84 Hz, 2H), 4.23-4.31 (m, 3H), 6.97-7.04 (m, 2H), 7.24-7.31 (m, 2H); ESI-MS m/z [M+H]⁺ 469.2.

Example 55: 6-(1-(4-fluorophenyl)ethyl)-3-methyl-5-((2-(pyrrolidin-1-yl)methyl)amino)pyrazine-2-carboxylic acid

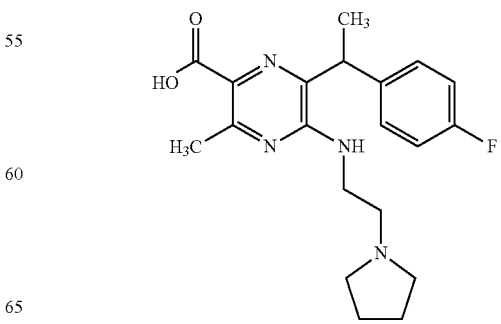

A small amount of crude 6-(1-(4-fluorophenyl)ethyl)-3-methyl-5-((2-(pyrrolidin-1-yl)ethyl)amino)pyrazine-2-carboxylic acid (PREPARATION 11) was purified by preparative HPLC (Phenomenex Gemini® C18, 5 μm, 30 mm ID×150 mm) using a gradient of 10-50% ACN (0.035% TFA) in water (0.05% TFA) to give the title compound for in vitro pharmacological tests. $^1$H NMR (500 MHz, CD$_3$OD) δ ppm 1.67 (d, J=6.83 Hz, 3H), 1.87-1.99 (m, 2H), 2.04-2.15 (m, 2H), 2.71 (s, 3H), 2.90-2.98 (m, 1H), 3.00-3.09 (m, 1H), 3.35-3.46 (m, 2H), 3.56-3.70 (m, 2H), 3.74-3.87 (m, 2H), 4.25 (q, J=6.83 Hz, 1H), 6.97-7.06 (m, 2H), 7.25-7.33 (m, 2H); ESI-MS m/z [M+H]$^+$ 373.1.

Example 56

6-(1-(4-fluorophenyl)ethyl)-N-(cis-3-methoxycyclobutyl)-3-methyl-5-((2-(pyrrolidin-1-yl)ethyl)amino)pyrazine-2-carboxamide

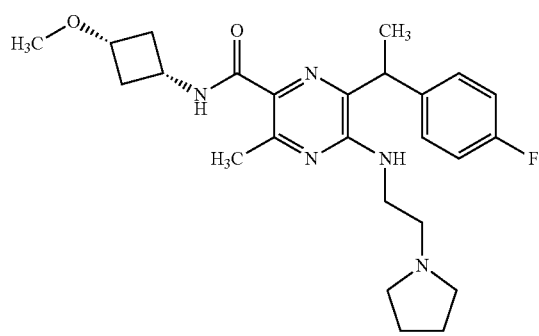 [SMILES: CO[C@H]1C[C@@H](NC(=O)c2nc(C(C)c3ccc(F)cc3)c(NCCN3CCCC3)nc2C)C1]

To a solution of 6-(1-(4-fluorophenyl)ethyl)-3-methyl-5-((2-(pyrrolidin-1-yl)ethyl)amino)pyrazine-2-carboxylic acid (40 mg, 0.070 mmol), (1s,3s)-3-methoxycyclobutan-1-amine hydrochloride (11.53 mg, 0.084 mmol) and DIPEA (73.0 μL, 0.419 mmol) in NMP (0.5 mL) was added T3P (59.6 μL, 0.105 mmol). The reaction mixture was stirred at 35° C. for 18 hours and then MeOH (0.5 mL) was added to quench the reaction. The reaction mixture was purified by preparative HPLC (Shimadzu, Phenomenex Gemini® column) using a gradient of 10-60% ACN (0.035% TFA) in water (0.05% TFA) to give a TFA salt of the title compound as a light-orange semisolid (30.7 mg, 97%). $^1$H NMR (500 MHz, CD$_3$OD) δ ppm 1.65 (d, J=6.83 Hz, 3H), 1.82-2.00 (m, 4H), 2.07 (br s, 2H), 2.70 (s, 3H), 2.72-2.83 (m, 2H), 2.86-2.96 (m, 1H), 2.98-3.08 (m, 1H), 3.27 (d, J=0.98 Hz, 3H), 3.34-3.46 (m, 2H), 3.54-3.63 (m, 1H), 3.64-3.70 (m, 1H), 3.70-3.76 (m, 1H), 3.81 (q, J=5.94 Hz, 2H), 4.06 (t, J=8.05 Hz, 1H), 4.29 (q, J=7.00 Hz, 1H), 7.03 (t, J=8.28 Hz, 2H), 7.28 (dd, J=8.42, 5.49 Hz, 2H). ESI-MS m/z [M+H]$^+$ 456.25.

Example 57

N-cyclopentyl-6-(1-(4-fluorophenyl)ethyl)-3-methyl-5-((2-(pyrrolidin-1-yl)ethyl)amino)pyrazine-2-carboxamide

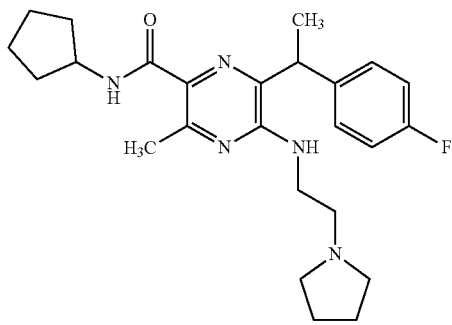 [SMILES: Cc1nc(NCCN2CCCC2)c(C(C)c2ccc(F)cc2)nc1C(=O)NC1CCCC1]

To a solution of 6-(1-(4-fluorophenyl)ethyl)-3-methyl-5-((2-(pyrrolidin-1-yl)ethyl)amino)pyrazine-2-carboxylic acid (25 mg, 0.067 mmol), cyclopentanamine (6.9 mg, 0.081 mmol) and DIPEA (70.0 μL, 0.403 mmol) in NMP (0.5 mL) was added T3P (30.6 μL, 0.101 mmol). The reaction mixture was stirred at 35° C. for 18 hours and then MeOH (0.5 mL) was added to quench the reaction. The reaction mixture was purified by preparative HPLC (Phenomenex Gemini® C18, 5 μm, 30 mm ID×150 mm) using a gradient of 10-100% aq ACN (80%, 10 mM NH$_4$HCO$_3$) in water (10 mM NH$_4$HCO$_3$) to give the title compound (16 mg, 55%). ESI-MS m/z [M+H]$^+$ 440.3.

Example 58

(6-(1-(4-fluorophenyl)ethyl)-3-methyl-5-((2-(pyrrolidin-1-yl)ethyl)amino)pyrazin-2-yl)(piperidin-1-yl)methanone

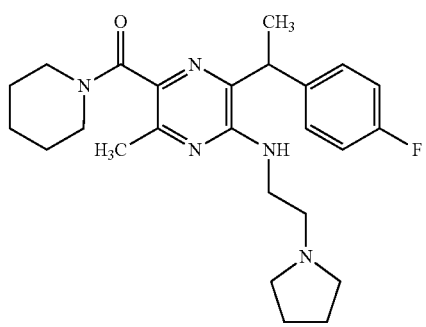 [SMILES: Cc1nc(NCCN2CCCC2)c(C(C)c2ccc(F)cc2)nc1C(=O)N1CCCCC1]

The title compound (17 mg, 57%) was prepared like EXAMPLE 57, using 6-(1-(4-fluorophenyl)ethyl)-3-methyl-5-((2-(pyrrolidin-1-yl)ethyl)amino)pyrazine-2-carboxylic acid (25 mg, 0.067 mmol, 1 eq) and piperidine (7 mg, 0.081 mmol). ESI-MS m/z [M+H]$^+$ 440.3.

Example 59

N,N-diethyl-6-(1-(4-fluorophenyl)ethyl)-3-methyl-5-((2-(pyrrolidin-1-yl)ethyl)amino)pyrazine-2-carboxamide

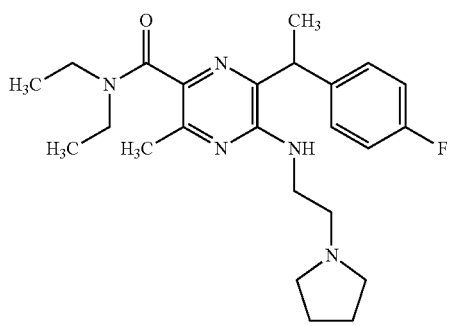 [SMILES: CCN(CC)C(=O)c1nc(C(C)c2ccc(F)cc2)c(NCCN2CCCC2)nc1C]

The title compound (13 mg, 45%) was prepared like EXAMPLE 57, using 6-(1-(4-fluorophenyl)ethyl)-3-methyl-5-((2-(pyrrolidin-1-yl)ethyl)amino)pyrazine-2-carboxylic acid (25 mg, 0.067 mmol, 1 eq) and diethylamine (6 mg, 0.81 mmol). ESI-MS m/z [M+H]$^+$ 428.3.

Example 60

(3,3-difluoropyrrolidin-1-yl)(6-(1-(4-fluorophenyl)ethyl)-3-methyl-5-((2-(pyrrolidin-1-yl)ethyl)amino)pyrazin-2-yl)methanone

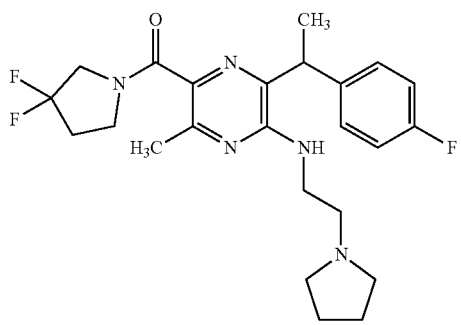 [SMILES: Cc1nc(NCCN2CCCC2)c(C(C)c2ccc(F)cc2)nc1C(=O)N1CCC(F)(F)C1]

The title compound (18 mg, 57%) was prepared like EXAMPLE 57, using 6-(1-(4-fluorophenyl)ethyl)-3-methyl-5-((2-(pyrrolidin-1-yl)ethyl)amino)pyrazine-2-carboxylic acid (25 mg, 0.067 mmol, 1 eq) and 3,3-difluoropyrrolidine (9 mg, 0.081 mmol). ESI-MS m/z [M+H]$^+$ 462.2.

Example 61

6-(1-(4-fluorophenyl)ethyl)-3-methyl-5-((2-(pyrrolidin-1-yl)ethyl)amino)-N-((R)-tetrahydrofuran-3-yl)pyrazine-2-carboxamide

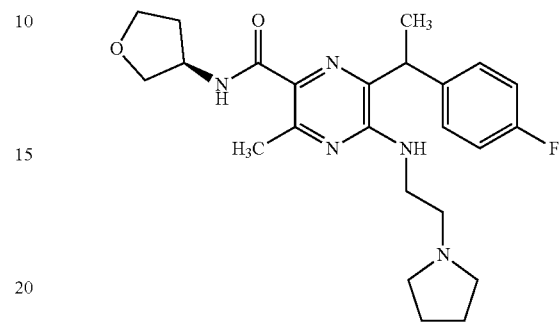

The title compound (13 mg, 42%) was prepared like EXAMPLE 57, using 6-(1-(4-fluorophenyl)ethyl)-3-methyl-5-((2-(pyrrolidin-1-yl)ethyl)amino)pyrazine-2-carboxylic acid (25 mg, 0.067 mmol, 1 eq) and (R)-tetrahydrofuran-3-amine (7 mg, 0.081 mmol). ESI-MS m/z [M+H]$^+$ 442.2.

Example 62

N-cyclopropyl-6-(1-(4-fluorophenyl)ethyl)-3-methyl-5-((2-(pyrrolidin-1-yl)ethyl)amino)pyrazine-2-carboxamide

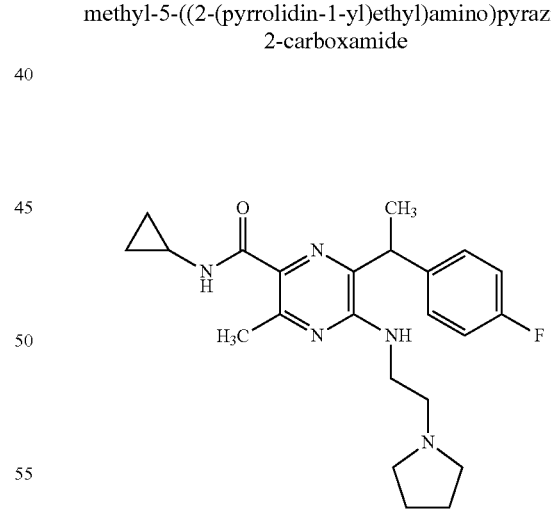

The title compound (20 mg, 71%) was prepared like EXAMPLE 57, using 6-(1-(4-fluorophenyl)ethyl)-3-methyl-5-((2-(pyrrolidin-1-yl)ethyl)amino)pyrazine-2-carboxylic acid (25 mg, 0.067 mmol, 1 eq) and cyclopropanamine (5 mg, 0.081 mmol). ESI-MS m/z [M+H]$^+$ 412.2.

Example 63

N-ethyl-6-(1-(4-fluorophenyl)ethyl)-N,3-dimethyl-5-((2-(pyrrolidin-1-yl)ethyl)amino)pyrazine-2-carboxamide

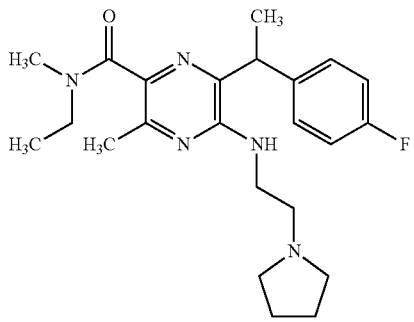 [SMILES: CCN(C)C(=O)c1nc(C(C)c2ccc(F)cc2)c(NCCN2CCCC2)nc1C]

The title compound (14 mg, 49%) was prepared like EXAMPLE 57, using 6-(1-(4-fluorophenyl)ethyl)-3-methyl-5-((2-(pyrrolidin-1-yl)ethyl)amino)pyrazine-2-carboxylic acid (25 mg, 0.067 mmol, 1 eq) and N-methyl-ethanamine (5 mg, 0.081 mmol). ESI-MS m/z [M+H]$^+$ 414.2.

Example 64

N-(cis-3-fluorocyclobutyl)-6-(1-(4-fluorophenyl)ethyl)-3-methyl-5-((2-(pyrrolidin-1-yl)ethyl)amino)pyrazine-2-carboxamide

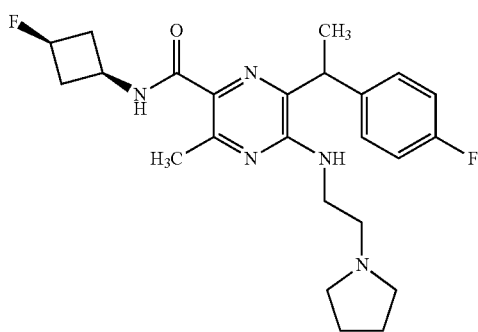 [SMILES: Cc1nc(NCCN2CCCC2)c(C(C)c2ccc(F)cc2)nc1C(=O)N[C@H]1C[C@@H](F)C1]

The title compound (20 mg, 68%) was prepared like EXAMPLE 57, using 6-(1-(4-fluorophenyl)ethyl)-3-methyl-5-((2-(pyrrolidin-1-yl)ethyl)amino)pyrazine-2-carboxylic acid (25 mg, 0.067 mmol, 1 eq) and cis-3-fluorocyclobutan-1-amine (10 mg, 0.081 mmol). ESI-MS m/z [M+H]$^+$ 444.2.

Example 65

N-cyclopropyl-6-(1-(4-fluorophenyl)ethyl)-N,3-dimethyl-5-((2-(pyrrolidin-1-yl)ethyl)amino)pyrazine-2-carboxamide

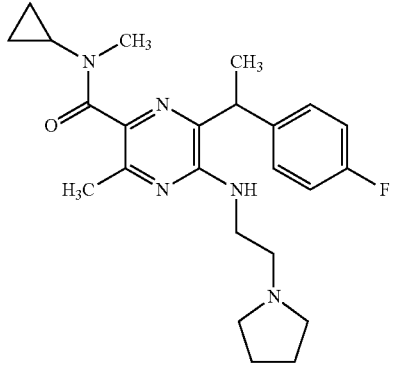 [SMILES: Cc1nc(NCCN2CCCC2)c(C(C)c2ccc(F)cc2)nc1C(=O)N(C)C1CC1]

The title compound (13 mg, 45%) was prepared like EXAMPLE 57, using 6-(1-(4-fluorophenyl)ethyl)-3-methyl-5-((2-(pyrrolidin-1-yl)ethyl)amino)pyrazine-2-carboxylic acid (25 mg, 0.067 mmol, 1 eq) and N-methylcyclopropanamine (9 mg, 0.081 mmol). ESI-MS m/z [M+H]$^+$ 426.2.

Example 66

(6-(1-(4-fluorophenyl)ethyl)-3-methyl-5-((2-(pyrrolidin-1-yl)ethyl)amino)pyrazin-2-yl)((S)-3-fluoropyrrolidin-1-yl)methanone

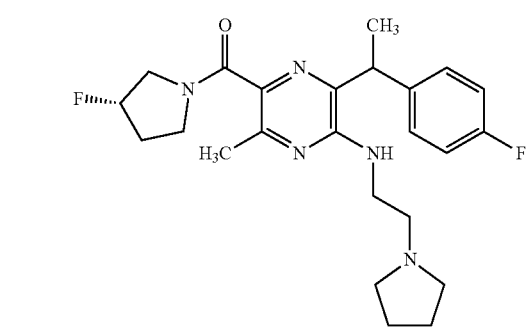 [SMILES: Cc1nc(NCCN2CCCC2)c(C(C)c2ccc(F)cc2)nc1C(=O)N1CC[C@H](F)C1]

The title compound (19 mg, 64%) was prepared like EXAMPLE 57, using 6-(1-(4-fluorophenyl)ethyl)-3-methyl-5-((2-(pyrrolidin-1-yl)ethyl)amino)pyrazine-2-carboxylic acid (25 mg, 0.067 mmol, 1 eq) and (S)-3-fluoropyrrolidine (7 mg, 0.081 mmol). ESI-MS m/z [M+H]$^+$ 444.2.

Example 67

6-(1-(4-fluorophenyl)ethyl)-N-isopropyl-N,3-dimethyl-5-((2-(pyrrolidin-1-yl)ethyl)amino)pyrazine-2-carboxamide

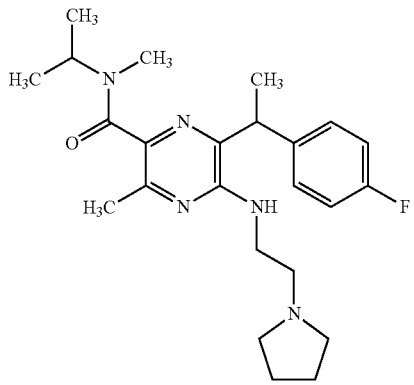 [SMILES: Cc1nc(NCCN2CCCC2)c(C(C)c2ccc(F)cc2)nc1C(=O)N(C)C(C)C]

The title compound (18 mg, 61%) was prepared like EXAMPLE 57, using 6-(1-(4-fluorophenyl)ethyl)-3-methyl-5-((2-(pyrrolidin-1-yl)ethyl)amino)pyrazine-2-carboxylic acid (25 mg, 0.067 mmol, 1 eq) and N-methylpropan-2-amine (6 mg, 0.081 mmol). ESI-MS m/z [M+H]$^+$ 428.3.

Example 68

(6-(1-(4-fluorophenyl)ethyl)-3-methyl-5-((2-(pyrrolidin-1-yl)ethyl)amino)pyrazin-2-yl)((S)-3-methoxypyrrolidin-1-yl)methanone

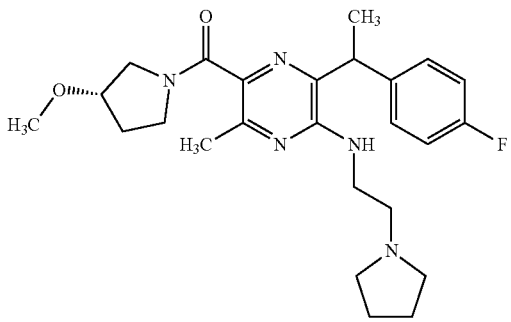 [SMILES: CO[C@H]1CCN(C(=O)c2nc(C(C)c3ccc(F)cc3)c(NCCN3CCCC3)nc2C)C1]

The title compound (15 mg, 48%) was prepared like EXAMPLE 57, using 6-(1-(4-fluorophenyl)ethyl)-3-methyl-5-((2-(pyrrolidin-1-yl)ethyl)amino)pyrazine-2-carboxylic acid (25 mg, 0.067 mmol, 1 eq) and (S)-3-methoxypyrrolidine (11 mg, 0.081 mmol). ESI-MS m/z [M+H]$^+$ 456.3.

Example 69

6-(1-(4-fluorophenyl)ethyl)-3-methyl-5-((2-(pyrrolidin-1-yl)ethyl)amino)-N-((S)-tetrahydrofuran-3-yl)pyrazine-2-carboxamide

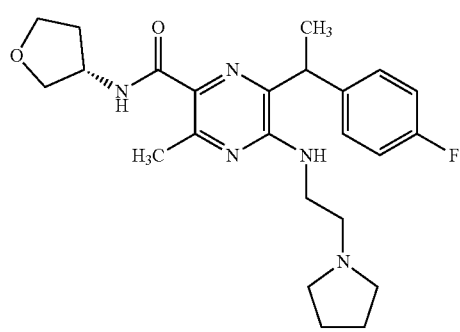 [SMILES: Cc1nc(NCCN2CCCC2)c(C(C)c2ccc(F)cc2)nc1C(=O)N[C@H]1CCOC1]

The title compound (17 mg, 58%) was prepared like EXAMPLE 57, using 6-(1-(4-fluorophenyl)ethyl)-3-methyl-5-((2-(pyrrolidin-1-yl)ethyl)amino)pyrazine-2-carboxylic acid (25 mg, 0.067 mmol, 1 eq) and (S)-tetrahydrofuran-3-amine (7 mg, 0.081 mmol). ESI-MS m/z [M+H]$^+$ 442.2.

Example 70

(6-(1-(4-fluorophenyl)ethyl)-3-methyl-5-((2-(pyrrolidin-1-yl)ethyl)amino)pyrazin-2-yl)(morpholino)methanone

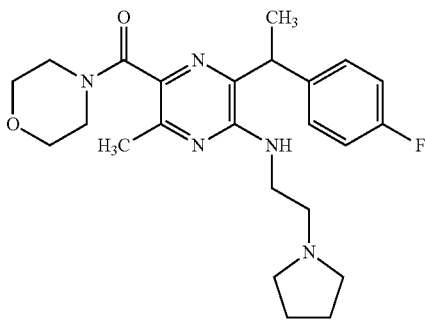 [SMILES: Cc1nc(NCCN2CCCC2)c(C(C)c2ccc(F)cc2)nc1C(=O)N1CCOCC1]

The title compound (9.8 mg, 33%) was prepared like EXAMPLE 57, using 6-(1-(4-fluorophenyl)ethyl)-3-methyl-5-((2-(pyrrolidin-1-yl)ethyl)amino)pyrazine-2-carboxylic acid (25 mg, 0.067 mmol, 1 eq) and morpholine (7 mg, 0.081 mmol). ESI-MS m/z [M+H]$^+$ 442.2.

Example 71

6-(1-(4-fluorophenyl)ethyl)-N-(trans-3-methoxycyclobutyl)-3-methyl-5-((2-(pyrrolidin-1-yl)ethyl)amino)pyrazine-2-carboxamide

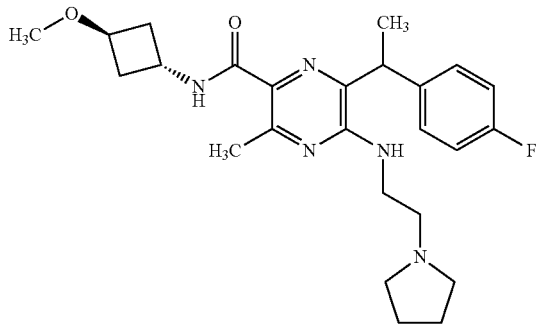 [SMILES: CO[C@H]1C[C@H](NC(=O)c2nc(C(C)c3ccc(F)cc3)c(NCCN3CCCC3)nc2C)C1]

The title compound (16 mg, 53%) was prepared like EXAMPLE 57, using 6-(1-(4-fluorophenyl)ethyl)-3-methyl-5-((2-(pyrrolidin-1-yl)ethyl)amino)pyrazine-2-carboxylic acid (25 mg, 0.067 mmol, 1 eq) and trans-3-methoxycyclobutan-1-amine (11 mg, 0.081 mmol). ESI-MS m/z [M+H]$^+$ 456.3.

Example 72

(6-(1-(4-fluorophenyl)ethyl)-3-methyl-5-((2-(pyrrolidin-1-yl)ethyl)amino)pyrazin-2-yl)((R)-3-methoxypyrrolidin-1-yl)methanone

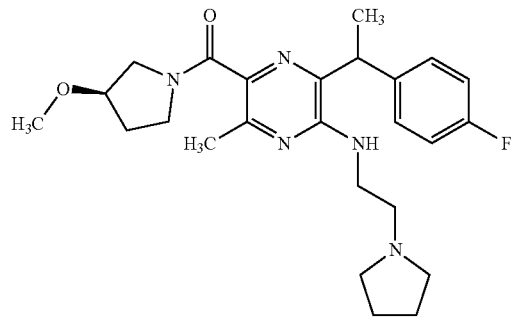 [SMILES: CO[C@@H]1CCN(C(=O)c2nc(C(C)c3ccc(F)cc3)c(NCCN3CCCC3)nc2C)C1]

The title compound (14 mg, 45%) was prepared like EXAMPLE 57, using 6-(1-(4-fluorophenyl)ethyl)-3-methyl-5-((2-(pyrrolidin-1-yl)ethyl)amino)pyrazine-2-carboxylic acid (25 mg, 0.067 mmol, 1 eq) and (R)-3-methoxypyrrolidine (11 mg, 0.081 mmol). ESI-MS m/z [M+H]$^+$ 456.2.

Example 73

N-(3,3-difluorocyclobutyl)-6-(1-(4-fluorophenyl)ethyl)-3-methyl-5-((2-(pyrrolidin-1-yl)ethyl)amino)pyrazine-2-carboxamide

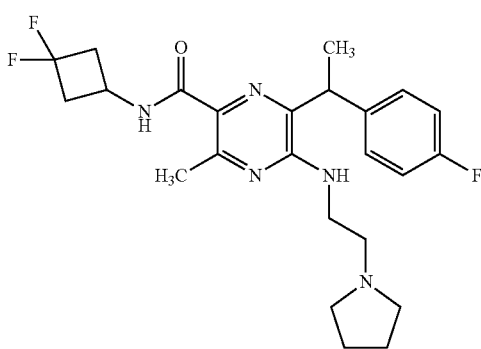 [SMILES: Cc1nc(NCCN2CCCC2)c(C(C)c2ccc(F)cc2)nc1C(=O)NC1CC(F)(F)C1]

The title compound (15 mg, 48%) was prepared like EXAMPLE 57, using 6-(1-(4-fluorophenyl)ethyl)-3-methyl-5-((2-(pyrrolidin-1-yl)ethyl)amino)pyrazine-2-carboxylic acid (25 mg, 0.067 mmol, 1 eq) and 3,3-difluorocyclobutan-1-amine (9 mg, 0.081 mmol). ESI-MS m/z [M+H]$^+$ 462.2.

Example 74

(6-(1-(4-fluorophenyl)ethyl)-3-methyl-5-((2-(pyrrolidin-1-yl)ethyl)amino)pyrazin-2-yl)((R)-3-fluoropyrrolidin-1-yl)methanone

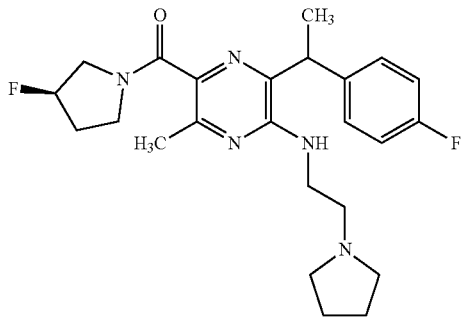

The title compound (15 mg, 49%) was prepared like EXAMPLE 57, using 6-(1-(4-fluorophenyl)ethyl)-3-methyl-5-((2-(pyrrolidin-1-yl)ethyl)amino)pyrazine-2-carboxylic acid (25 mg, 0.067 mmol, 1 eq) and (R)-3-fluoropyrrolidine (7 mg, 0.081 mmol). ESI-MS m/z [M+H]$^+$ 444.2.

Example 75

(6-(1-(4-fluorophenyl)ethyl)-3-methyl-5-((2-(pyrrolidin-1-yl)ethyl)amino)pyrazin-2-yl)(pyrrolidin-1-yl)methanone

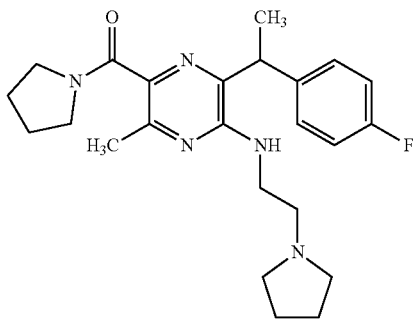 [SMILES: Cc1nc(NCCN2CCCC2)c(C(C)c2ccc(F)cc2)nc1C(=O)N1CCCC1]

The title compound (7.3 mg, 25%) was prepared like EXAMPLE 57, using 6-(1-(4-fluorophenyl)ethyl)-3-methyl-5-((2-(pyrrolidin-1-yl)ethyl)amino)pyrazine-2-carboxylic acid (25 mg, 0.067 mmol, 1 eq) and pyrrolidine (6 mg, 0.081 mmol). ESI-MS m/z [M+H]$^+$ 426.2.

Example 76

N-(trans-3-fluorocyclobutyl)-6-(1-(4-fluorophenyl)ethyl)-3-methyl-5-((2-(pyrrolidin-1-yl)ethyl)amino)pyrazine-2-carboxamide

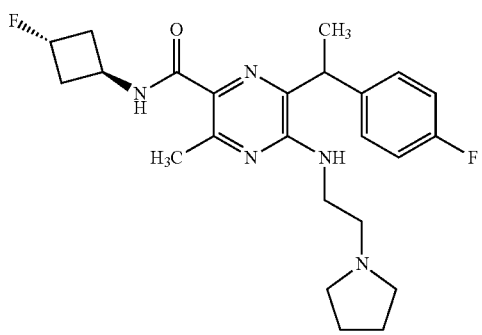 [SMILES: Cc1nc(NCCN2CCCC2)c(C(C)c2ccc(F)cc2)nc1C(=O)N[C@H]1C[C@H](F)C1]

The title compound (15 mg, 50%) was prepared like EXAMPLE 57, using 6-(1-(4-fluorophenyl)ethyl)-3-methyl-5-((2-(pyrrolidin-1-yl)ethyl)amino)pyrazine-2-carboxylic acid (25 mg, 0.067 mmol, 1 eq) and trans-3-fluorocyclobutan-1-amine (10 mg, 0.081 mmol). ESI-MS m/z [M+H]$^+$ 444.2.

Example 77

6-(1-(4-fluorophenyl)ethyl)-3-(methoxymethyl)-5-((2-(pyrrolidin-1-yl)ethyl)amino)pyrazine-2-carboxamide

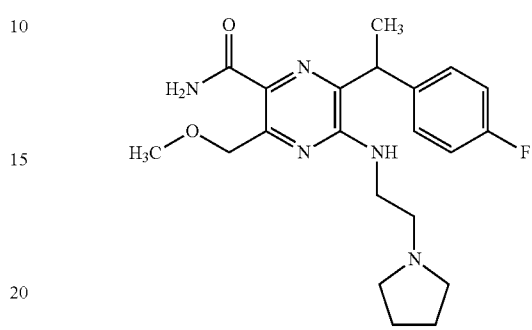

To a solution of 6-(1-(4-fluorophenyl)ethyl)-3-(methoxymethyl)-5-((2-(pyrrolidin-1-yl)ethyl)amino)pyrazine-2-carboxylic acid (33 mg, 0.047 mmol) in DMF (0.5 mL) were added HATU (17.77 mg, 0.047 mmol) and DIPEA (24.49 μL, 0.140 mmol). The mixture was stirred at room temperature for 5 minutes and then ammonium hydroxide (14.56 μL, 0.374 mmol) was added. The reaction mixture was stirred at room temperature for 2 days and then purified by preparative HPLC (Phenomenex Gemini® C18, 5 μm, 30 mm ID×150 mm) using a gradient of 10-50% ACN (0.035% TFA) in water (0.05% TFA) to give a TFA salt of the title compound as a white film (11.7 mg, 48.6%). $^1$H NMR (400 MHz, CD$_3$OD) δ ppm 1.70 (d, J=6.90 Hz, 3H), 2.01-2.20 (m, 4H), 3.06-3.18 (m, 2H), 3.35-3.44 (m, 2H), 3.51 (s, 3H), 3.67-3.80 (m, 4H), 4.33 (q, J=6.82 Hz, 1H), 5.02-5.13 (m, 2H), 6.99-7.08 (m, 2H), 7.27-7.37 (m, 2H).

Example 78

N-(2-(azetidin-1-yl)ethyl)-3-(4-fluorobenzyl)-5,6-dimethylpyrazin-2-amine

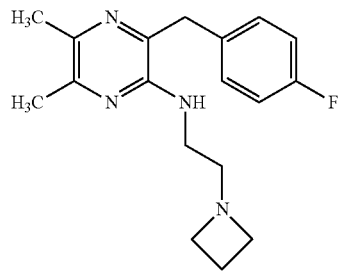 [SMILES: Cc1nc(Cc2ccc(F)cc2)c(NCCN2CCC2)nc1C]

133

Step A: 3-(4-fluorobenzyl)-5,6-dimethylpyrazin-2-yl trifluoromethanesulfonate

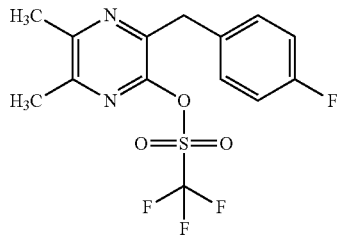 [SMILES: Cc1nc(Cc2ccc(F)cc2)c(OS(=O)(=O)C(F)(F)F)nc1C]

A solution of 3-(4-fluorobenzyl)-5,6-dimethylpyrazin-2-ol (83.0 mg, 0.357 mmol) in DCM (3.57 mL) at 0° C. was treated with DIPEA (187 μL, 1.07 mmol) and trifluoromethanesulfonic anhydride (121 μL, 0.715 mmol). The reaction mixture was stirred at 0° C. for 15 min and then quenched with saturated aq NH$_4$Cl and extracted with DCM. The organic phase was dried over Na$_2$SO$_4$, filtered, and concentrated under reduced pressure to give the title compound (130 mg) which was used without further purification. ESI-MS m/z [M+H]$^+$ 365.1.

Step B: N-(2-(azetidin-1-yl)ethyl)-3-(4-fluorobenzyl)-5,6-dimethylpyrazin-2-amine To a 5 mL microwave vial equipped with stir bar and charged with a solution of 3-(4-fluorobenzyl)-5,6-dimethylpyrazin-2-yl trifluoromethanesulfonate (130 mg, 0.357 mmol) and 2-(azetidin-1-yl)ethanamine (71.5 mg, 0.714 mmol) in toluene (1.78 mL) was added cesium carbonate (233 mg, 0.714 mmol), BINAP (22.2 mg, 0.0357 mmol), and Pd$_2$(dba)$_3$ (32.7 mg, 0.0357 mmol). The vial was sealed, and the reaction mixture was stirred at 100° C. in a heating block overnight and then poured into water and extracted with EtOAc. The organic phase was dried over Na$_2$SO$_4$, filtered, and concentrated under reduced pressure. The residue was taken up in methanol and filtered through a hydrophilic PTFE 0.45 μm Millipore® filter, rinsing with methanol. The filtrate was purified by preparative HPLC (Phenomenex Gemini® C18, 5 μm, 30 mm ID×150 mm) using a gradient of 10-50% ACN (0.035% TFA) in water (0.05% TFA). The product-containing fraction was concentrated under reduced pressure and then taken up in methanol and filtered through a basic Agilent PL-HCO$_3$ MP SPE cartridge (200 mg) to remove TFA. The filtrate was evaporated to give the title compound as a colorless film (0.7 mg, 0.6%). $^1$H NMR (500 MHz, CD$_3$OD) δ ppm 2.08 (quin, J=7.2 Hz, 2H), 2.37 (s, 6H), 2.58 (t, J=6.6 Hz, 2H), 3.21 (t, J=7.1 Hz, 4H), 3.33-3.36 (m, 2H), 4.00 (s, 2H), 6.94-7.04 (m, 2H), 7.14-7.25 (m, 2H); ESI-MS m/z [M+H]$^+$ 315.25.

134

Example 79

3-(4-fluorobenzyl)-5,6-dimethyl-N-(1-methylpiperidin-4-yl)pyrazin-2-amine

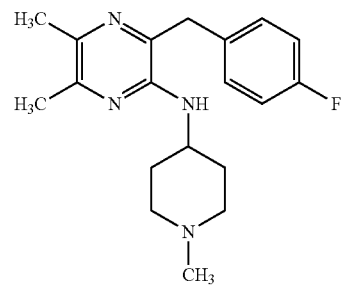 [SMILES: Cc1nc(Cc2ccc(F)cc2)c(NC2CCN(C)CC2)nc1C]

A mixture of 3-chloro-5,6-dimethyl-N-(1-methylpiperidin-4-yl)pyrazin-2-amine (30 mg, 0.118 mmol), 2-(4-fluorobenzyl)-4,4,5,5-tetramethyl-1,3,2-dioxaborolane (50.0 mg, 0.212 mmol), PdCl$_2$(dppf) (8.62 mg, 0.012 mmol) and Na$_2$CO$_3$ (2N, 118 μL, 0.236 mmol) in dioxane (0.6 mL) was heated at 110° C. for 16 hours. The reaction mixture was purified by preparative HPLC (Phenomenex Gemini® C18, 5 μm, 30 mm ID×150 mm) using a gradient of 10-50% ACN (0.035% TFA) in water (0.05% TFA) followed by a second purification by preparative HPLC (Phenomenex Gemini® C18, 5 μm, 30 mm ID×150 mm) using a gradient of 10-70% aq ACN (80%, 10 mM NH$_4$HCO$_3$) in water (10 mM NH$_4$HCO$_3$) to give the title compound as a brown oil (14 mg, 36.2%). $^1$H NMR (400 MHz, CD$_3$OD) δ ppm 1.25 (d, J=9.28 Hz, 2H), 1.83-1.90 (m, 2H), 2.11 (t, J=10.01 Hz, 2H), 2.21 (s, 3H), 2.36 (s, 3H), 2.39 (s, 3H), 2.42-2.57 (m, 2H), 3.77 (d, J=7.32 Hz, 1H), 3.82-3.91 (m, 1H), 3.98 (s, 2H), 6.94-7.01 (m, 2H), 7.11-7.18 (m, 2H); ESI-MS m/z [M+H]$^+$ 329.25.

Example 80

3-(4-fluorobenzyl)-5,6-dimethyl-N-(2-(pyrrolidin-1-yl)ethyl)pyrazin-2-amine

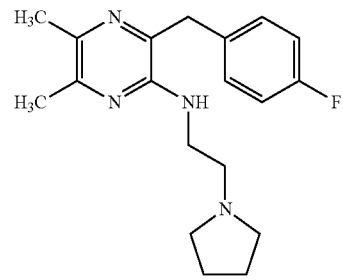 [SMILES: Cc1nc(Cc2ccc(F)cc2)c(NCCN2CCCC2)nc1C]

The title compound was prepared like EXAMPLE 79, using 3-chloro-5,6-dimethyl-N-(2-(pyrrolidin-1-yl)ethyl)pyrazin-2-amine (25 mg, 0.098 mmol, 1.0 eq) and 2-(4-fluorobenzyl)-4,4,5,5-tetramethyl-1,3,2-dioxaborolane (41.7 mg, 0.176 mmol) to give the title compound as a brown oil (13 mg, 40.3%). $^1$H NMR (400 MHz, CD$_3$OD) δ ppm 1.77 (dt, J=7.08, 3.30 Hz, 4H), 2.35 (s, 6H), 2.53 (br s, 4H), 2.64 (t, J=6.59 Hz, 2H), 3.49 (t, J=6.59 Hz, 2H), 3.99 (s, 2H), 6.91-7.01 (m, 2H), 7.13-7.22 (m, 2H); ESI-MS m/z [M+H]⁺ 329.20.

Example 81

(R)-3-(4-fluorobenzyl)-5,6-dimethyl-N-(1-methylpyrrolidin-3-yl)pyrazin-2-amine

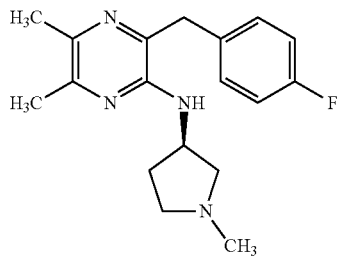 [SMILES: Cc1nc(Cc2ccc(F)cc2)c(N[C@@H]2CCN(C)C2)nc1C]

The title compound was prepared like EXAMPLE 79, using (R)-3-chloro-5,6-dimethyl-N-(1-methylpyrrolidin-3-yl)pyrazin-2-amine (20 mg, 0.083 mmol, 1.0 eq) and 2-(4-fluorobenzyl)-4,4,5,5-tetramethyl-1,3,2-dioxaborolane (35.3 mg, 0.150 mmol) to give the title compound as a brown oil (12 mg, 45.9%). ¹H NMR (400 MHz, CD₃OD) δ ppm 1.57 (dddd, J=13.18, 8.30, 6.83, 4.88 Hz, 1H), 2.24-2.31 (m, 1H), 2.34 (s, 3H), 2.35 (d, J=2.44 Hz, 6H), 2.38 (dd, J=10.25, 4.39 Hz, 1H), 2.48 (dt, J=9.28, 7.32 Hz, 1H), 2.68 (td, J=8.79, 5.86 Hz, 1H), 2.83 (dd, J=10.25, 6.83 Hz, 1H), 4.01 (s, 2H), 4.51 (ddt, J=9.03, 6.83, 4.76, 4.76 Hz, 1H), 6.94-7.02 (m, 2H), 7.14-7.23 (m, 2H); ESI-MS m/z [M+H]⁺ 315.20.

Example 82

5,6-dimethyl-3-(3-methylbenzyl)-N-(1-methylpiperidin-4-yl)pyrazin-2-amine

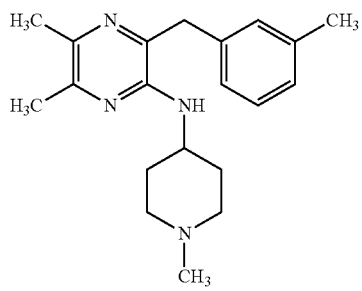

The title compound was prepared like EXAMPLE 79, using 3-chloro-5,6-dimethyl-N-(1-methylpiperidin-4-yl)pyrazin-2-amine (20 mg, 0.079 mmol, 1.0 eq) and 4,4,5,5-tetramethyl-2-(3-methylbenzyl)-1,3,2-dioxaborolane (36.4 mg, 0.157 mmol) to give the title compound as a brown oil (3.1 mg, 12.2%). ¹H NMR (400 MHz, CD₃OD) δ ppm 1.40 (d, J=8.79 Hz, 2H), 1.84 (d, J=9.76 Hz, 2H), 2.19 (br s, 2H), 2.22 (s, 3H), 2.28 (s, 3H), 2.35 (s, 3H), 2.37 (s, 3H), 2.42-2.76 (m, 2H), 3.88 (br s, 1H), 4.00 (s, 2H), 6.96 (d, J=7.32 Hz, 1H), 7.00-7.07 (m, 2H), 7.13-7.20 (m, 1H); ESI-MS m/z [M+H]⁺ 325.20.

Example 83

5,6-dimethyl-3-(3-methylbenzyl)-N-(2-(pyrrolidin-1-yl)ethyl)pyrazin-2-amine

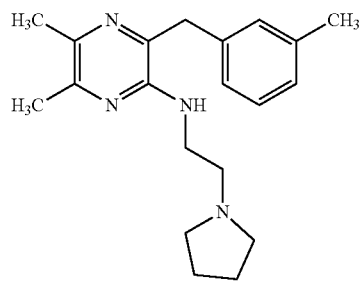

The title compound was prepared like EXAMPLE 79, using 3-chloro-5,6-dimethyl-N-(2-(pyrrolidin-1-yl)ethyl)pyrazin-2-amine (30 mg, 0.118 mmol, 1.0 eq) and 4,4,5,5-tetramethyl-2-(3-methylbenzyl)-1,3,2-dioxaborolane (49.2 mg, 0.212 mmol) to give the title compound as a brown oil (14 mg, 36.6%). ¹H NMR (400 MHz, CD₃OD) δ ppm 1.72-1.79 (m, 4H), 2.27 (s, 3H), 2.36 (d, J=4.39 Hz, 6H), 2.50 (br s, 4H), 2.61 (t, J=6.35 Hz, 2H), 3.48 (t, J=6.35 Hz, 2H), 3.98 (s, 2H), 6.92-7.03 (m, 3H), 7.10-7.17 (m, 1H); ESI-MS m/z [M+H]⁺ 325.25.

Example 84

(R)-5,6-dimethyl-3-(3-methylbenzyl)-N-(1-methylpyrrolidin-3-yl)pyrazin-2-amine

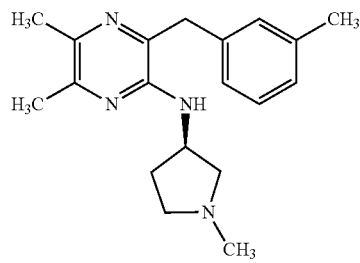

The title compound was prepared like EXAMPLE 79, using (R)-3-chloro-5,6-dimethyl-N-(1-methylpyrrolidin-3-yl)pyrazin-2-amine (20 mg, 0.083 mmol, 1.0 eq) and 4,4,5,5-tetramethyl-2-(3-methylbenzyl)-1,3,2-dioxaborolane (34.7 mg, 0.150 mmol) to give the title compound as a brown oil (8 mg, 31.0%). ¹H NMR (400 MHz, CD₃OD) δ ppm 1.46-1.55 (m, 1H), 2.20-2.25 (m, 1H), 2.27 (s, 3H), 2.30 (d, J=4.39 Hz, 1H), 2.32 (s, 3H), 2.36 (d, J=7.32 Hz, 6H), 2.44-2.53 (m, 1H), 2.61 (td, J=8.79, 5.86 Hz, 1H), 2.85 (dd, J=10.25, 6.83 Hz, 1H), 3.99 (s, 2H), 4.48 (ddt, J=8.79, 6.96, 4.58, 4.58 Hz, 1H), 6.96 (d, J=7.32 Hz, 1H), 7.00-7.04 (m, 2H), 7.11-7.17 (m, 1H); ESI-MS m/z [M+H]⁺ 311.20.

Example 85

3-(1-(4-fluorophenyl)ethyl)-6-methyl-N-(2-(pyrrolidin-1-yl)ethyl)pyrazin-2-amine

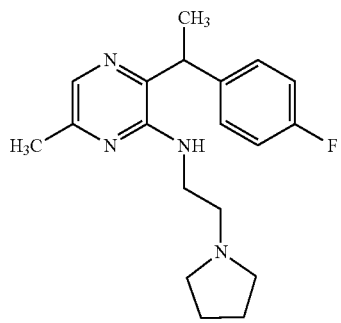 [SMILES: Cc1cnc(C(C)c2ccc(F)cc2)c(NCCN2CCCC2)n1]

and

Example 86

3-(1-(4-fluorophenyl)ethyl)-5-methyl-N-(2-(pyrrolidin-1-yl)ethyl)pyrazin-2-amine

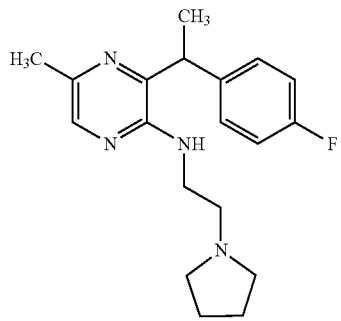 [SMILES: Cc1cnc(NCCN2CCCC2)c(C(C)c2ccc(F)cc2)n1]

Step A: 3-chloro-5-methyl-N-(2-(pyrrolidin-1-yl)ethyl)pyrazin-2-amine and 3-chloro-6-methyl-N-(2-(pyrrolidin-1-yl)ethyl)pyrazin-2-amine

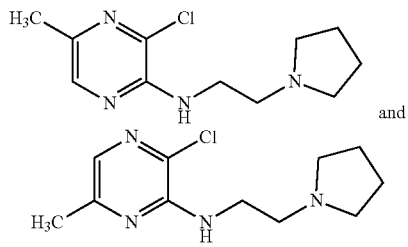

To a solution of 2,3-dichloro-5-methylpyrazine (100 mg, 0.61 mmol) in dioxane (2.5 mL) were added DIPEA (214 µL, 1.23 mmol) and 2-(pyrrolidin-1-yl)ethan-1-amine (77 mg, 0.68 mmol). The resulting solution was heated at 100° C. overnight and then purified by silica gel chromatography (NH column) to give a mixture of the title compounds (39 mg, 27%). ESI-MS m/z [M+H]$^+$ 241.1.

Step B: 3-(1-(4-fluorophenyl)vinyl)-5-methyl-N-(2-(pyrrolidin-1-yl)ethyl)pyrazin-2-amine and 3-(1-(4-fluorophenyl)vinyl)-6-methyl-N-(2-(pyrrolidin-1-yl)ethyl)pyrazin-2-amine

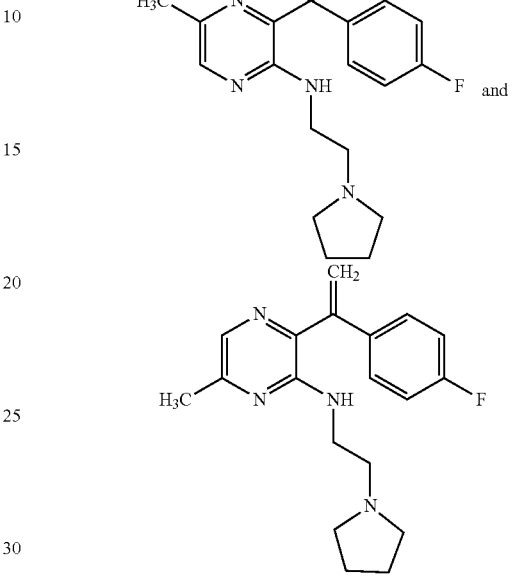

A mixture of 3-chloro-5-methyl-N-(2-(pyrrolidin-1-yl)ethyl)pyrazin-2-amine and 3-chloro-6-methyl-N-(2-(pyrrolidin-1-yl)ethyl)pyrazin-2-amine (35.0 mg, 0.145 mmol), 2-(1-(4-fluorophenyl)vinyl)-4,4,5,5-tetramethyl-1,3,2-dioxaborolane (72.1 mg, 0.291 mmol), Pd(dppf)Cl$_2$ (10.64 mg, 0.015 mmol) and Na$_2$CO$_3$ (145 µL, 0.291 mmol) in dioxane (1.5 mL) was degassed by N$_2$ and then heated in a sealed tube at 110° C. for 16 hours. Following reaction, the mixture was purified by silica gel column chromatography (NH column) using a gradient of 5-50% EtOAc in heptane to give a crude mixture of the title compounds (70 mg). ESI-MS m/z [M+H]$^+$ 327.1.

Step C: 3-(1-(4-fluorophenyl)ethyl)-6-methyl-N-(2-(pyrrolidin-1-yl)ethyl)pyrazin-2-amine and 3-(1-(4-fluorophenyl)ethyl)-5-methyl-N-(2-(pyrrolidin-1-yl)ethyl)pyrazin-2-amine A mixture of 3-(1-(4-fluorophenyl)vinyl)-5-methyl-N-(2-(pyrrolidin-1-yl)ethyl)pyrazin-2-amine and 3-(1-(4-fluorophenyl)vinyl)-6-methyl-N-(2-(pyrrolidin-1-yl)ethyl)pyrazin-2-amine (70 mg, crude) and palladium on carbon (11.41 mg, 0.107 mmol) in EtOAc (1.1 mL) was stirred under H$_2$ atmosphere (balloon) at room temperature for 5 hours. The reaction mixture was then purified by preparative HPLC (Phenomenex Gemini® C18, 5 µm, 30 mm ID×150 mm) using a gradient of 10-50% ACN (0.035% TFA) in water (0.05% TFA) to give two regioisomers. The major regioisomer was assigned as the TFA salt of 3-(1-(4-fluorophenyl)ethyl)-6-methyl-N-(2-(pyrrolidin-1-yl)ethyl)pyrazin-2-amine and was obtained as a colorless oil (19 mg, 40.0%). $^1$H NMR (400 MHz, CD$_3$OD) δ ppm 1.62 (d, J=6.88 Hz, 3H), 1.88-2.03 (m, 2H), 2.06-2.19 (m, 2H), 2.38 (s, 3H), 2.94-3.14 (m, 2H), 3.36-3.43 (m, 2H), 3.60-3.84 (m, 4H), 4.24 (q, J=6.91 Hz, 1H), 6.95-7.10 (m, 2H), 7.19-7.29

(m, 2H), 7.78 (s, 1H); ESI-MS m/z [M+H]⁺ 329.20. The minor regioisomer was assigned as the TFA salt of 3-(1-(4-fluorophenyl)ethyl)-5-methyl-N-(2-(pyrrolidin-1-yl)ethyl)pyrazin-2-amine and was obtained as a colorless oil (1.2 mg, 2.5%). ¹H NMR (400 MHz, CD₃OD) δ ppm 1.63 (d, J=6.97 Hz, 3H), 1.93-2.17 (m, 4H), 2.42 (s, 3H), 2.92-3.10 (m, 2H), 3.35-3.41 (m, 2H), 3.55-3.77 (m, 4H), 4.25 (q, J=6.91 Hz, 1H), 7.01 (t, J=8.71 Hz, 2H), 7.22-7.31 (m, 2H), 7.82 (s, 1H); ESI-MS m/z [M+H]⁺ 329.2.

Example 87

N-(2-(azetidin-1-yl)ethyl)-6-isopropyl-3-(3-methylbenzyl)pyrazin-2-amine

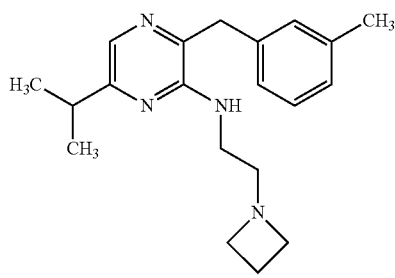 [SMILES: Cc1cccc(Cc2ncc(C(C)C)nc2NCCN2CCC2)c1]

A 10 mL microwave vial was charged with 3-chloro-5-isopropyl-2-(3-methylbenzyl)pyrazine (28 mg, 0.107 mmol), 2-(azetidin-1-yl)ethanamine (0.022 g, 0.215 mmol), DIPEA (0.014 g, 0.107 mmol) and KF (6.2 mg, 0.107 mmol) in DMSO (3 mL). The reaction mixture was heated at 100° C. for 5 hours in a Biotage® microwave reactor and then filtered and purified by preparative HPLC (Waters SunFire® C18, 5 μm, 30 mm ID×75 mm column) using a gradient of 10-35% ACN (0.035% TFA) in water (0.05% TFA). The product-containing fractions were combined to give a TFA salt of the title compound as a light-grey oil (1.2 mg, 3%). ¹H NMR (400 MHz, CD₃OD) δ ppm 1.30 (d, J=6.82 Hz, 6H), 2.29 (s, 3H), 2.30-2.39 (m, 1H), 2.46-2.57 (m, 1H), 2.91-3.01 (m, 1H), 3.41 (t, J=5.56 Hz, 2H), 3.66 (t, J=5.68 Hz, 2H), 3.94-4.03 (m, 4H), 4.04-4.13 (m, 2H), 6.97 (d, J=7.58 Hz, 1H), 7.01-7.06 (m, 2H), 7.13-7.20 (m, 1H), 7.69 (s, 1H); ESI-MS m/z [M+H]⁺ 325.2.

Example 88

N-(2-(azetidin-1-yl)ethyl)-6-ethoxy-3-(3-methylbenzyl)pyrazin-2-amine

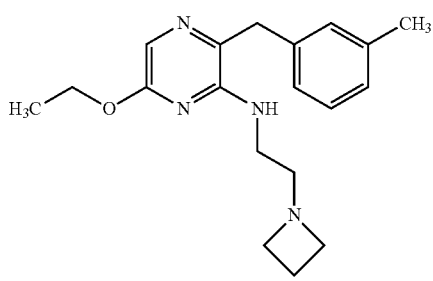 [SMILES: CCOc1cnc(Cc2cccc(C)c2)c(NCCN2CCC2)n1]

To a mixture of N-(2-(azetidin-1-yl)ethyl)-6-chloro-3-(3-methylbenzyl)pyrazin-2-amine (30 mg, 94.69 μmol) in EtOH (500 μL) was added EtONa (1 M in EtOH, 473.44 μL) at 20° C. The mixture was heated to 100° C. and stirred for 4 hours. The mixture was then diluted with EtOAc (20 mL) and saturated aq NH₄Cl solution (20 mL). The aqueous layer was separated and extracted with EtOAc (15 mL×3). The combined organic layers were dried over Na₂SO₄, filtered and concentrated in vacuo. The crude product was purified by preparative HPLC (Phenomenex Gemini® 10 μm, 25 mm ID×150 mm) using a gradient of 56-86% ACN in water (0.05% NH₄OH) to give the title compound as a red oil (16.4 mg, 53%). ¹H NMR (400 MHz, CDCl₃) δ ppm 1.39 (t, J=7.1 Hz, 3H), 2.03 (quin, J=6.9 Hz, 2H), 2.32 (s, 3H), 2.51 (t, J=6.0 Hz, 2H), 3.09 (t, J=7.1 Hz, 4H), 3.25 (q, J=5.7 Hz, 2H), 3.97 (s, 2H), 4.29 (q, J=7.1 Hz, 2H), 4.89 (br s, 1H), 6.95-7.09 (m, 3H), 7.16-7.22 (m, 1H), 7.42 (s, 1H); ESI-MS m/z [M+H]⁺ 327.0.

Example 89

N-(2-(azetidin-1-yl)ethyl)-3-benzyl-6-ethylpyrazin-2-amine

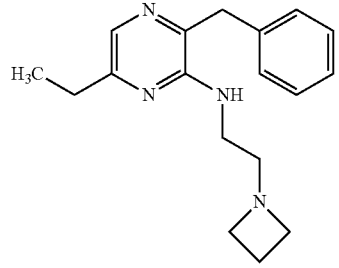 [SMILES: CCc1cnc(Cc2ccccc2)c(NCCN2CCC2)n1]

To a solution of 3-benzyl-6-ethylpyrazin-2-yl trifluoromethanesulfonate (30 mg, 86.63 μmol) in NMP (750 μL) were added Et₃N (8.77 mg, 86.63 μmol, 12.01 μL) and 2-(azetidin-1-yl)ethanamine (10.41 mg, 103.96 μmol). The mixture was stirred at 80° C. for 1 hour and then concentrated in vacuo. The residue was purified by preparative HPLC (Phenomenex Synergi™ C18, 4 μm, 21.2 mm ID×250 mm) using a gradient of 15-45% ACN in water (0.05% HCl) to give and HCl salt of the title compound as a yellow solid (9.0 mg, 31%). ¹H NMR (400 MHz, CD₃OD) δ ppm 1.35 (t, J=7.28 Hz, 3H), 2.40 (d, J=7.53 Hz, 1H), 2.57 (d, J=8.53 Hz, 1H), 2.81-2.96 (m, 2H), 3.51 (br s, 2H), 3.79-3.89 (m, 2H), 4.10 (d, J=9.03 Hz, 2H), 4.24 (br s, 2H), 4.38 (s, 2H), 7.29-7.48 (m, 5H), 7.72 (s, 1H); ESI-MS m/z [M+H]⁺ 296.9.

Example 90

N-(2-(azetidin-1-yl)ethyl)-6-cyclopropyl-3-(3-methylbenzyl)pyrazin-2-amine

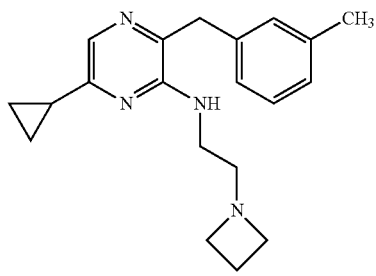 [SMILES: Cc1cccc(Cc2ncc(C3CC3)nc2NCCN2CCC2)c1]

An HCl salt of the title compound was prepared like EXAMPLE 89, using 6-cyclopropyl-3-(3-methylbenzyl)pyrazin-2-yl trifluoromethanesulfonate instead of 3-benzyl-6-ethylpyrazin-2-yl trifluoromethanesulfonate. Intermediate 6-cyclopropyl-3-(3-methylbenzyl)pyrazin-2-yl trifluoromethanesulfonate was prepared like PREPARATION 23, using 2-(tert-butoxycarbonylamino)-2-cyclopropyl-acetic acid instead of 2-(tert-butoxycarbonylamino)butanoic acid. $^1$H NMR (400 MHz, CD$_3$OD) δ ppm 1.18 (d, J=6.02 Hz, 4H), 2.18-2.27 (m, 1H), 2.29-2.44 (m, 4H), 2.51-2.63 (m, 1H), 3.40-3.51 (m, 2H), 3.76 (br s, 2H), 4.07 (q, J=9.20 Hz, 2H), 4.21 (d, J=4.02 Hz, 2H), 4.31 (s, 2H), 7.10 (d, J=7.53 Hz, 1H), 7.17 (br s, 2H), 7.24-7.31 (m, 1H), 7.79 (s, 1H); ESI-MS m/z [M+H]$^+$ 323.0.

Example 91

N-(1,3-dimethylpiperidin-4-yl)-3-(4-fluorobenzyl)-5-(trifluoromethyl)pyrazin-2-amine

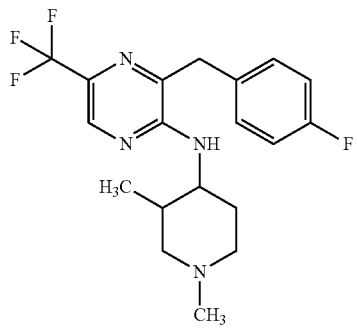 [SMILES: CC1CN(C)CCC1Nc1ncc(C(F)(F)F)nc1Cc1ccc(F)cc1]

Step A: tert-butyl 4-((3-(4-fluorobenzyl)-5-(trifluoromethyl)pyrazin-2-yl)amino)-3-methylpiperidine-1-carboxylate

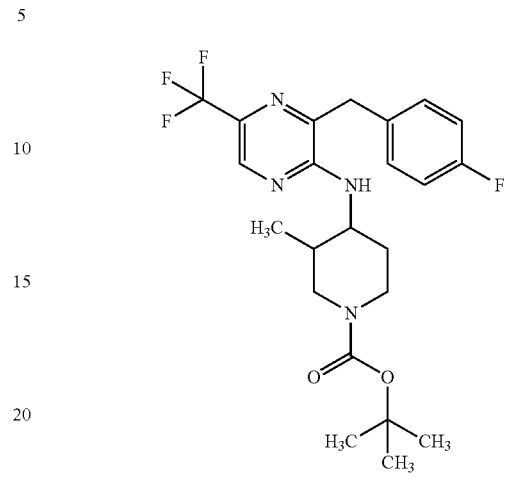

To a 40 mL vial were added PdCl$_2$(dppf)$_3$ (0.034 g, 0.046 mmol), Na$_2$CO$_3$ (0.098 g, 0.922 mmol), 2-(4-fluorobenzyl)-4,4,5,5-tetramethyl-1,3,2-dioxaborolane (0.196 g, 0.830 mmol), tert-butyl 4-((3-chloro-5-(trifluoromethyl)pyrazin-2-yl)amino)-3-methylpiperidine-1-carboxylate (0.182 g, 0.461 mmol) and dioxane (4.61 mL). The resulting orange suspension was degassed with N$_2$ and heated at 110° C. overnight. The mixture was then treated with water and extracted with EtOAc. The organic layers were dried over anhydrous MgSO$_4$ and concentrated to give the title compound as a tan film, which was used without further purification. ESI-MS m/z [M+H]$^+$ 469.4.

Step B: 3-(4-fluorobenzyl)-N-(3-methylpiperidin-4-yl)-5-(trifluoromethyl)pyrazin-2-amine

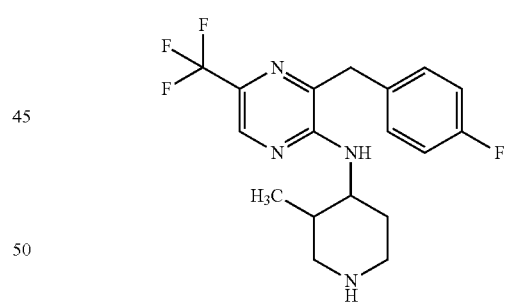

To a 125 mL pear flask were added tert-butyl 4-((3-(4-fluorobenzyl)-5-(trifluoromethyl)pyrazin-2-yl)amino)-3-methylpiperidine-1-carboxylate (0.216 g, 0.461 mmol), hydrogen chloride (0.461 mL, 1.844 mmol) and dioxane (3 mL). The resulting tan solution was stirred at 50° C. for 3 hours and then concentrated to dryness to give the title compound as a tan solid, which was used without further purification. ESI-MS m/z [M+H]$^+$ 369.4.

Step C: N-(1,3-dimethylpiperidin-4-yl)-3-(4-fluorobenzyl)-5-(trifluoromethyl)pyrazin-2-amine A 125 mL pear flask was charged with 3-(4-fluorobenzyl)-N-(3-methylpiperidin-4-yl)-5-(trifluoromethyl)pyrazin-2- amine (170 mg, 0.461 mmol), formaldehyde (0.071 mL, 0.913 mmol) and methanol (3 mL). To the resulting tan solution was added sodium cyanotrihydroborate (57.4 mg, 0.913 mmol). The mixture was stirred at room temperature overnight and then filtered and purified by preparative HPLC (Phenomenex Gemini® C18, 5 μm, 30 mm ID×150 mm) using a gradient of 10-50% ACN (0.035% TFA) in water (0.05% TFA) to give a TFA salt of the title compound as a mixture of cis and trans isomers (9.2 mg, 4.02%). $^1$H NMR (400 MHz, CD$_3$OD) δ ppm 0.77 (d, J=6.60 Hz, 3H), 1.68-1.86 (m, 1H), 2.04-2.15 (m, 1H), 2.16-2.26 (m, 1H), 2.82-2.89 (m, 4H), 3.12 (s, 1H), 3.44-3.57 (m, 2H), 3.97-4.07 (m, 1H), 4.04-4.07 (m, 1H), 4.09-4.21 (m, 2H), 6.94-7.07 (m, 2H), 7.17-7.28 (m, 2H), 8.23-8.28 (m, 1H); ESI-MS m/z [M+H]$^+$ 383.4.

Example 92

N-(1,3-dimethylpiperidin-4-yl)-3-(4-fluorobenzyl)-6-(trifluoromethyl)pyrazin-2-amine

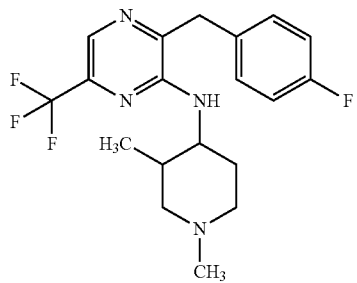 [SMILES: CC1CN(C)CCC1Nc1nc(C(F)(F)F)cnc1Cc1ccc(F)cc1]

Step A: tert-butyl 4-((3-(4-fluorobenzyl)-6-(trifluoromethyl)pyrazin-2-yl)amino)-3-methylpiperidine-1-carboxylate

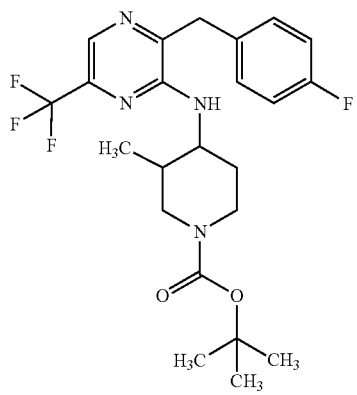 [SMILES: CC1CN(C(=O)OC(C)(C)C)CCC1Nc1nc(C(F)(F)F)cnc1Cc1ccc(F)cc1]

To a 30 mL microwave vial were added 3-chloro-2-(4-fluorobenzyl)-5-(trifluoromethyl)pyrazine (0.105 g, 0.361 mmol), tert-butyl 4-amino-3-methylpiperidine-1-carboxylate hydrogen chloride (0.091 g, 0.361 mmol), (R)-2,2'-bis(diphenylphosphanyl)-1,1'-binaphthalene (0.022 g, 0.036 mmol), (dba)$_3$Pd$_2$ (0.033 g, 0.036 mmol), cesium carbonate (0.235 g, 0.723 mmol) and toluene (3.61 mL). The resulting tan suspension was degassed with N$_2$ and heated at 80° C. for 2 days. The mixture was then treated with water and extracted with EtOAc. The organic layers were washed with brine, dried over anhydrous MgSO$_4$ and concentrated to give the title compound, which was used without further purification. ESI-MS m/z [M+H]$^+$ 469.5.

Step B: 3-(4-fluorobenzyl)-N-(3-methylpiperidin-4-yl)-6-(trifluoromethyl)pyrazin-2-amine

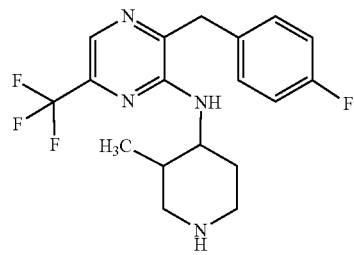 [SMILES: CC1CNCCC1Nc1nc(C(F)(F)F)cnc1Cc1ccc(F)cc1]

To a 125 mL pear flask were added tert-butyl 4-((3-(4-fluorobenzyl)-6-(trifluoromethyl)pyrazin-2-yl)amino)-3-methylpiperidine-1-carboxylate (0.169 g, 0.361 mmol) and hydrogen chloride (0.361 mL, 1.444 mmol) in dioxane (3 mL). The resulting tan solution was stirred at 50° C. for 3 hours and then concentrated to dryness to give the title compound, which was used without further purification. ESI-MS m/z [M+H]$^+$ 369.4.

Step C: N-(1,3-dimethylpiperidin-4-yl)-3-(4-fluorobenzyl)-6-(trifluoromethyl)pyrazin-2-amine A 125 mL pear flask was charged with 3-(4-fluorobenzyl)-N-(3-methylpiperidin-4-yl)-6-(trifluoromethyl)pyrazin-2-amine (133 mg, 0.361 mmol) and formaldehyde (0.055 mL, 0.715 mmol) in methanol (3 mL). To the resulting tan solution was added sodium cyanotrihydroborate (44.9 mg, 0.715 mmol). The mixture was stirred at room temperature overnight and then filtered and purified by preparative HPLC (Phenomenex Gemini® C18, 5 μm, 30 mm ID×150 mm) using a gradient of 10-50% ACN (0.035% TFA) in water (0.05% TFA) to give a TFA salt of the title compound (11.5 mg, 6.42%). $^1$H NMR (400 MHz, CD$_3$OD) δ ppm 0.81 (d, J=6.60 Hz, 3H), 1.71-1.88 (m, 1H), 2.02-2.14 (m, 1H), 2.18-2.27 (m, 1H), 2.87 (s, 5H), 3.12-3.22 (m, 1H), 3.46-3.59 (m, 2H), 3.95-4.06 (m, 1H), 4.08-4.24 (m, 2H), 6.95-7.10 (m, 2H), 7.17-7.32 (m, 2H), 8.01-8.08 (m, 1H); ESI-MS m/z [M+H]$^+$ 383.3.

Example 93

3-(4-fluorobenzyl)-N-(2-(pyrrolidin-1-yl)ethyl)-6-(trifluoromethyl)pyrazin-2-amine

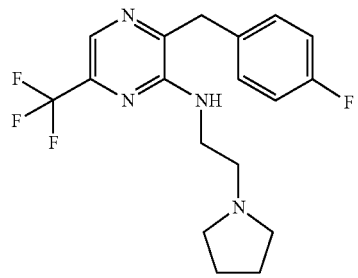 [SMILES: Fc1ccc(Cc2ncc(C(F)(F)F)nc2NCCN2CCCC2)cc1]

To a 40 mL vial were added 3-chloro-2-(4-fluorobenzyl)-5-(trifluoromethyl)pyrazine (0.081 g, 0.279 mmol), 2-(pyrrolidin-1-yl)ethan-1-amine (0.038 g, 0.334 mmol), (R)-2,2'-bis(diphenylphosphanyl)-1,1'-binaphthalene (0.017 g, 0.028 mmol), Pd₂(dba)₃ (0.026 g, 0.028 mmol), cesium carbonate (0.182 g, 0.557 mmol) and toluene (4 mL). The resulting tan suspension was degassed with N₂ and heated at 90° C. overnight. The mixture was subsequently stirred at room temperature for 3 hours, filtered and purified by preparative HPLC (Phenomenex Gemini® C18, 5 μm, 30 mm ID×150 mm) using a gradient of 10-50% ACN (0.035% TFA) in water (0.05% TFA) to give the title compound (9.3 mg, 6.9%). ¹H NMR (400 MHz, CD₃OD) δ ppm 1.90-2.02 (m, 2H), 2.07-2.17 (m, 2H), 3.02-3.13 (m, 2H), 3.39-3.46 (m, 2H), 3.65-3.77 (m, 2H), 3.79-3.87 (m, 2H), 4.09-4.16 (m, 2H), 6.98-7.07 (m, 2H), 7.19-7.28 (m, 2H), 8.08-8.14 (m, 1H); ESI-MS m/z [M+H]⁺ 369.3.

Example 94

3-(1-(4-fluorophenyl)ethyl)-N-(2-(pyrrolidin-1-yl)ethyl)-6-(trifluoromethyl)pyrazin-2-amine

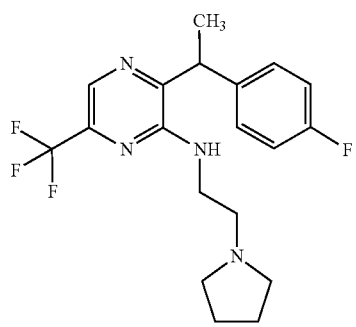

To a 20 mL vial were added 3-chloro-2-(1-(4-fluorophenyl)ethyl)-5-(trifluoromethyl)pyrazine (487 mg, 1.6 mmol), 2-(pyrrolidin-1-yl)ethan-1-amine (201 mg, 1.760 mmol), DIPEA (0.557 mL, 3.20 mmol) and dioxane (2 mL). The resulting orange solution was heated at 110° C. overnight and then purified by preparative HPLC (Phenomenex Gemini® C18, 5 μm, 30 mm ID×150 mm) using a gradient of 40-90% aq ACN (80%, 10 mM NH₄HCO₃) in water (10 mM NH₄HCO₃) to give the title compound (82.8 mg, 13.5%). ¹H NMR (400 MHz, CD₃OD) δ ppm 1.64 (d, J=6.90 Hz, 3H) 1.90-2.14 (m, 4H) 2.87-3.10 (m, 2H) 3.33-3.45 (m, 2H) 3.54-3.71 (m, 2H) 3.73-3.83 (m, 2H) 4.29-4.43 (m, 1H) 7.01 (s, 2H) 7.23-7.32 (m, 2H) 8.17-8.27 (m, 1H); ESI-MS m/z [M+H]⁺ 383.5.

Example 95

N-(trans-3-ethyl-1-methylpiperidin-4-yl)-3-(4-fluorobenzyl)-5-(trifluoromethyl)pyrazin-2-amine

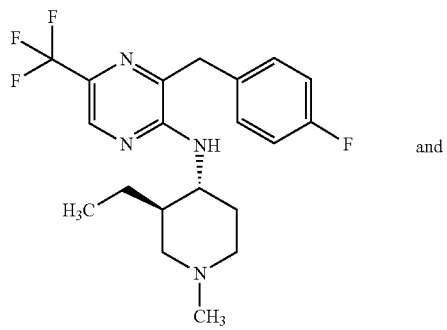

and

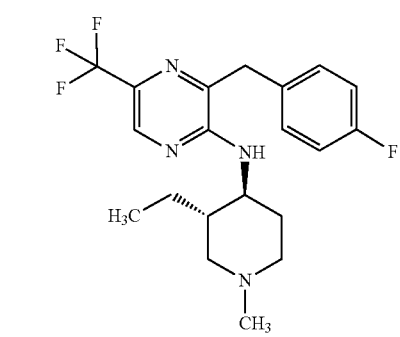

Step A: tert-butyl trans-3-ethyl-4-((3-(4-fluorobenzyl)-5-(trifluoromethyl)pyrazin-2-yl)amino)piperidine-1-carboxylate

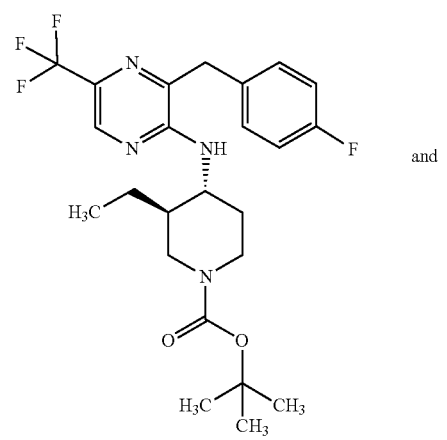

and

147

-continued

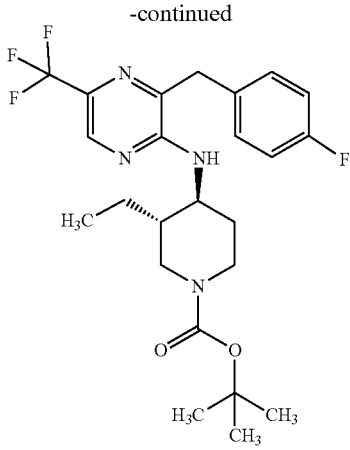

To a 40 mL vial were added (dppf)$_2$PdCl$_1$ (0.034 g, 0.046 mmol), Na$_2$CO$_3$ (0.098 g, 0.922 mmol), 2-(4-fluorobenzyl)-4,4,5,5-tetramethyl-1,3,2-dioxaborolane (0.196 g, 0.830 mmol), tert-butyl trans-4-((3-chloro-5-(trifluoromethyl)pyrazin-2-yl)amino) ethylpiperidine-1-carboxylate (0.188 g, 0.461 mmol) and dioxane (4.61 mL). The resulting orange suspension was degassed with N$_2$ and heated at 110° C. overnight. The reaction mixture was then treated with water and extracted with EtOAc. The organic phase was washed with brine, dried over anhydrous MgSO$_4$ and concentrated to give the title compound as a tan syrup. ESI-MS m/z [M+H]$^+$ 483.4.

Step B: trans-N-(3-ethylpiperidin-4-yl)-3-(4-fluorobenzyl)-5-(trifluoromethyl)pyrazin-2-amine

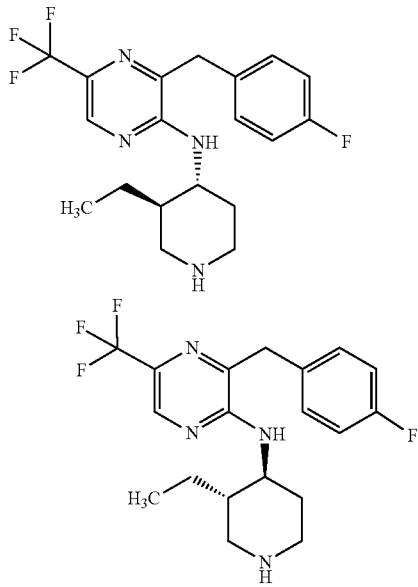

To a 125 mL pear flask were added tert-butyl trans-3-ethyl-4-((3-(4-fluorobenzyl)-5-(trifluoromethyl)pyrazin-2-yl)amino)piperidine-1-carboxylate (0.222 g, 0.461 mmol) and hydrogen chloride (0.461 mL, 1.844 mmol) in dioxane (3 mL). The resulting tan solution was stirred at 50° C. for 3 hours and then concentrated to dryness to give the title compound as a tan film. ESI-MS m/z [M+H]$^+$ 383.4.

148

Step C: N-(trans-3-ethyl-1-methylpiperidin-4-yl)-3-(4-fluorobenzyl)-5-(trifluoromethyl)pyrazin-2-amine To a 125 mL pear flask were added trans-N-(3-ethylpiperidin-4-yl)-3-(4-fluorobenzyl)-5-(trifluoromethyl)pyrazin-2-amine (176 mg, 0.461 mmol), formaldehyde (0.071 mL, 0.913 mmol) and methanol (3 mL). To the resulting tan solution was added sodium cyanotrihydroborate (57.4 mg, 0.913 mmol). The resulting mixture was stirred at room temperature overnight and then filtered and purified by preparative HPLC (Phenomenex Gemini® C18, 5 µm, 30 mm ID×150 mm) using a gradient of 10-50% ACN (0.035% TFA) in water (0.05% TFA) to give a TFA salt of the title compound (25.6 mg, 10.9%). $^1$H NMR (400 MHz, CD$_3$OD) δ ppm 0.66-0.87 (m, 4H), 0.94-1.07 (m, 1H), 1.84-2.02 (m, 2H), 2.12-2.30 (m, 1H), 2.68-2.81 (m, 1H), 2.84-2.91 (m, 4H), 3.07-3.23 (m, 1H), 3.42-3.59 (m, 1H), 4.15-4.37 (m, 2H), 4.45-4.58 (m, 1H), 7.09 (s, 2H), 7.19-7.31 (m, 2H), 8.31-8.38 (m, 1H); ESI-MS m/z [M+H]$^+$ 397.5.

Example 96

5-((2-(azetidin-1-yl)ethyl)amino)-6-(4-fluorobenzyl)-3-methylpyrazine-2-carbonitrile

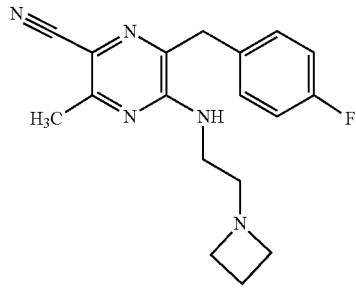 [SMILES: Cc1nc(NCCN2CCC2)c(Cc2ccc(F)cc2)nc1C#N]

A 5 mL microwave vial equipped with stir bar was charged with a solution of 5-((2-(azetidin-1-yl)ethyl)amino)-6-chloro-3-methylpyrazine-2-carbonitrile (50.0 mg, 0.199 mmol) and 2-(4-fluorobenzyl)-4,4,5,5-tetramethyl-1,3,2-dioxaborolane (56.3 mg, 0.238 mmol) in dioxane (1.32 mL) and with 2 M aqueous Na$_2$CO$_3$ (497 µL, 0.993 mmol). Next, PdCl$_2$(dppf) (14.5 mg, 0.020 mmol) was added. The mixture was sparged with nitrogen and the vial was sealed. The reaction mixture was stirred at 100° C. overnight in a heated reaction block and then allowed to cool to room temperature and filtered through a hydrophilic PTFE 0.45 µm Millipore® filter, rinsing with methanol. The filtrate was purified by preparative HPLC (Phenomenex Gemini® C18, 5 µm, 30 mm ID×150 mm) using a gradient of 10-100% aq ACN (80%, 10 mM NH$_4$HCO$_3$) in water (10 mM NH$_4$HCO$_3$) followed by a gradient of 10-40% ACN (0.035% TFA) in water (0.05% TFA). The product-containing fractions were evaporated and dried under vacuum to give a TFA salt of the title compound as an off-white solid (25.0 mg, 29%). $^1$H NMR (500 MHz, CD$_3$OD) δ ppm 2.34-2.45 (m, 1H), 2.54 (s, 4H), 3.43 (t, J=5.9 Hz, 2H), 3.72 (t, J=5.6 Hz, 2H), 4.01 (s, 2H), 4.05 (d, J=9.8 Hz, 2H), 4.16-4.27 (m, 2H), 7.02 (t, J=8.8 Hz, 2H), 7.19-7.28 (m, 2H); ESI-MS m/z [M+H]$^+$ 326.20.

Example 97

(R)-3-methyl-6-(3-methylbenzyl)-5-((1-methylpyrrolidin-3-yl)amino)pyrazine-2-carbonitrile

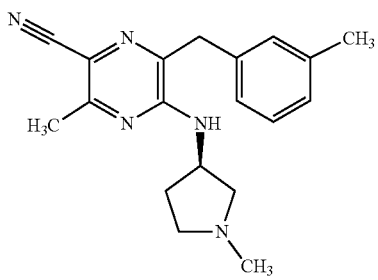 [SMILES: Cc1cccc(Cc2nc(C#N)c(C)nc2N[C@@H]2CCN(C)C2)c1]

A 5 mL microwave vial equipped with stir bar was charged with a solution of (R)-6-chloro-3-methyl-5-((1-methylpyrrolidin-3-yl)amino)pyrazine-2-carbonitrile (93 mg, 0.37 mmol) and 4,4,5,5-tetramethyl-2-(3-methylbenzyl)-1,3,2-dioxaborolane (129 mg, 0.555 mmol) in dioxane (1.85 mL). The solution was treated with 2 M aqueous $Na_2CO_3$ (555 µL, 1.11 mmol). The vial was evacuated and re-filled with nitrogen three times. Next $PdCl_2(dppf)$ (27.1 mg, 0.037 mmol) was added and the vial was evacuated and re-filled with nitrogen two more times. The vial was sealed, and the reaction mixture was stirred at 110° C. in a Biotage® microwave reactor for 2 hours and then concentrated under reduced pressure. The resulting residue was taken up in methanol and filtered through a hydrophilic PTFE 0.45 µm Millipore® filter. The filtrate was purified by preparative HPLC (Phenomenex Gemini® C18, 5 µm, 30 mm ID×150 mm) using a gradient of 10-100% aq ACN (80%, 10 mM $NH_4CO_3$) in water (10 mM $NH_4HCO_3$) followed by a gradient of 10-60% ACN (0.035% TFA) in water (0.05% TFA). The product-containing fractions were evaporated. The product was taken up in methanol and filtered through an Agilent PL-$HCO_3$ 500 mg basic cartridge to remove TFA. The filtrate was evaporated to give the title compound as a yellow oil (37.4 mg, 31%). $^1$H NMR (500 MHz, $CD_3OD$) δ ppm 1.62 (dddd, J=13.2, 8.2, 6.6, 4.6 Hz, 1H), 2.23-2.32 (m, 4H), 2.34 (s, 3H), 2.39-2.53 (m, 5H), 2.70 (td, J=8.9, 5.6 Hz, 1H), 2.80 (dd, J=10.2, 6.8 Hz, 1H), 4.02 (s, 2H), 4.59 (ddt, J=9.0, 7.0, 4.4, 4.4 Hz, 1H), 6.96-7.07 (m, 3H), 7.12-7.19 (m, 1H); ESI-MS m/z [M+H]$^+$ 322.20.

Example 98

(R)-6-(3-methoxybenzyl)-3-methyl-5-((1-methylpyrrolidin-3-yl)amino)pyrazine-2-carbonitrile

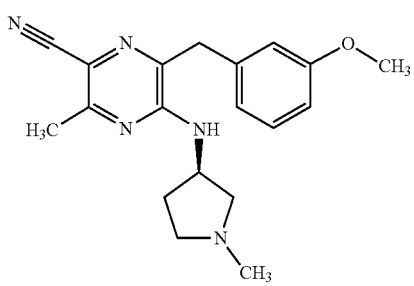 [SMILES: COc1cccc(Cc2nc(C#N)c(C)nc2N[C@@H]2CCN(C)C2)c1]

The title compound was prepared like EXAMPLE 97, using (R)-6-chloro-3-methyl-5-((1-methylpyrrolidin-3-yl)amino)pyrazine-2-carbonitrile (81 mg, 0.32 mmol, 1 eq), 2-(3-methoxybenxyl)-4,4,5,5-tetramethyl-1,3,2-dioxaborolane (119 mg, 0.480 mmol), $PdCl_2$ (dppf) (23.4 mg, 0.032 mmol) in dioxane (1.6 mL) and 2 M aqueous $Na_2CO_3$ (0.480 mL, 0.960 mmol) to give the title compound as an orange oil (34.9 mg, 32%). $^1$H NMR (500 MHz, $CD_3OD$) δ ppm 1.58-1.70 (m, 1H), 2.29 (dtd, J=13.7, 8.3, 8.3, 5.4 Hz, 1H), 2.35 (s, 3H), 2.41-2.53 (m, 5H), 2.72 (td, J=8.9, 5.6 Hz, 1H), 2.81 (dd, J=10.2, 6.8 Hz, 1H), 3.74 (s, 3H), 4.03 (s, 2H), 4.60 (ddt, J=8.8, 6.9, 4.6, 4.6 Hz, 1H), 6.75-6.82 (m, 3H), 7.18 (t, J=7.8 Hz, 1H); ESI-MS m/z [M+H]$^+$ 338.20.

Example 99

5-(4-fluorobenzyl)-N,N-dimethyl-6-((2-(pyrrolidin-1-yl)ethyl)amino)nicotinamide

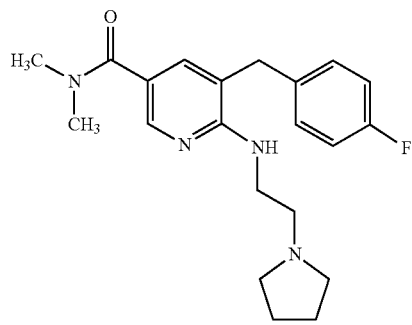 [SMILES: CN(C)C(=O)c1cnc(NCCN2CCCC2)c(Cc2ccc(F)cc2)c1]

An 8 mL vial was charged with 5-(4-fluorobenzyl)-6-((2-(pyrrolidin-1-yl)ethyl)amino)nicotinic acid (61.5 6 mg, 0.179 mmol), dimethylamine (0.179 mL, 0.358 mmol), HATU (74.9 mg, 0.197 mmol) and DIPEA (0.094 mL, 0.537 mmol) in DMF (2 mL). The resulting brown solution was stirred at room temperature overnight and then purified by preparative HPLC (Phenomenex Gemini® 30 mm ID×100 mm) using a gradient of 10-100% aq ACN (80%, 10 mM $NH_4HCO_3$) in water (10 mM $NH_4HCO_3$) to give the title compound (26.3 mg, 39.7%). $^1$H NMR (400 MHz, $CD_3OD$) δ ppm 1.78 (s, 4H), 2.53 (s, 4H), 2.68 (s, 2H), 3.05 (s, 6H), 3.56 (s, 2H), 3.83 (s, 2H), 7.03 (s, 2H), 7.18-7.27 (m, 3H), 8.09 (d, J=2.26 Hz, 1H); ESI-MS m/z [M+H]$^+$ 371.4.

Example 100

5-(4-fluorobenzyl)-6-((2-(pyrrolidin-1-yl)ethyl)amino)nicotinamide

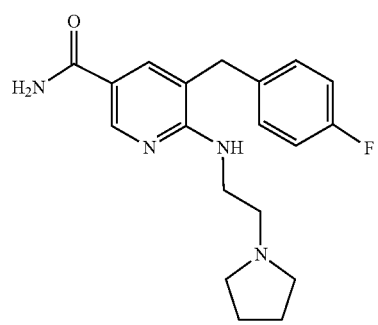 [SMILES: NC(=O)c1cnc(NCCN2CCCC2)c(Cc2ccc(F)cc2)c1]

The title compound (32.4 mg, 52.9%) was prepared like EXAMPLE 99, using 5-(4-fluorobenzyl)-6-((2-(pyrrolidin-1-yl)ethyl)amino)nicotinic acid (61.5 mg, 0.179 mmol, 1 eq) and ammonium chloride (19.15 mg, 0.358 mmol). $^1$H NMR (400 MHz, CDCl$_3$) δ ppm 1.76 (br s, 4H) 2.44-2.59 (m, 4H), 2.65-2.74 (m, 2H), 3.47-3.60 (m, 2H), 3.78-3.88 (m, 2H), 6.98 (s, 2H), 7.12-7.19 (m, 2H), 7.70-7.79 (m, 1H), 8.46-8.53 (m, 1H); ESI-MS m/z [M+H]$^+$ 343.4.

Example 101

5-(4-fluorobenzyl)-N-methyl-6-((2-((pyrrolidin-1-yl)ethyl)amino)nicotinamide

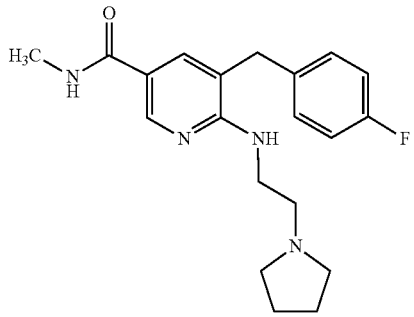 [SMILES: CNC(=O)c1cnc(NCCN2CCCC2)c(Cc2ccc(F)cc2)c1]

The title compound (26.3 mg, 41.2%) was prepared like EXAMPLE 99, using 5-(4-fluorobenzyl)-6-((2-(pyrrolidin-1-yl)ethyl)amino)nicotinic acid (61.5 mg, 0.179 mmol, 1 eq) and methanamine (0.179 mL, 0.358 mmol). $^1$H NMR (400 MHz, CD$_3$OD) δ ppm 1.76 (s, 4H), 2.50 (s, 4H), 2.66 (s, 2H), 2.86 (s, 3H), 3.55 (s, 2H), 3.84 (s, 2H), 6.93-7.08 (m, 2H), 7.15-7.24 (m, 2H), 7.57-7.66 (m, 1H), 8.40-8.47 (m, 1H); ESI-MS m/z [M+H]$^+$ 357.3.

Example 102

6-((1,3-dimethylpiperidin-4-yl)amino)-5-(4-fluorobenzyl)nicotinamide

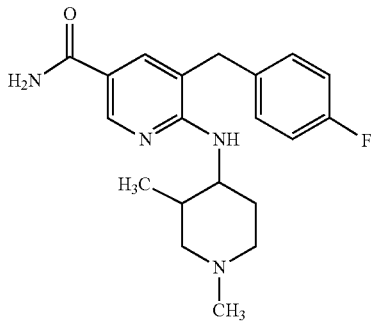 [SMILES: CC1CN(C)CCC1Nc1ncc(C(N)=O)cc1Cc1ccc(F)cc1]

To a 100 mL round-bottomed flask was added 6-((1,3-dimethylpiperidin-4-yl)amino)-5-(4-fluorobenzyl)nicotinic acid (41.8 mg, 0.117 mmol), ammonium chloride (12.52 mg, 0.234 mmol), HATU (66.7 mg, 0.176 mmol) and DIPEA (0.082 mL, 0.468 mmol) in DMF (2 mL). The resulting brown solution was stirred at room temperature overnight and then purified by preparative HPLC (Gemini® 30 mm ID×100 mm) using a gradient of 10-100% aq ACN (80%, 10 mM NH$_4$HCO$_3$) in water (10 mM NH$_4$HCO$_3$) to give the title compound as a mixture of cis and trans isomers (15.1 mg, 36.2%). $^1$H NMR (400 MHz, CD$_3$OD) δ ppm 0.67 (d, J=6.51 Hz, 3H), 1.32-1.49 (m, 1H), 1.58-1.72 (m, 1H), 1.74-1.84 (m, 1H), 1.88-2.01 (m, 1H), 2.06-2.17 (m, 1H), 2.26 (s, 3H), 2.79-2.91 (m, 2H), 3.62-3.76 (m, 1H), 3.88 (s, 2H), 7.02 (s, 2H), 7.17-7.27 (m, 2H), 7.68-7.79 (m, 1H), 8.48 (d, J=2.29 Hz, 1H); ESI-MS m/z [M+H]$^+$ 357.4.

Example 103

3-(1-(4-fluorophenyl)ethyl)-N-(2-(pyrrolidin-1-yl)ethyl)-6-(trifluoromethyl)pyridin-2-amine

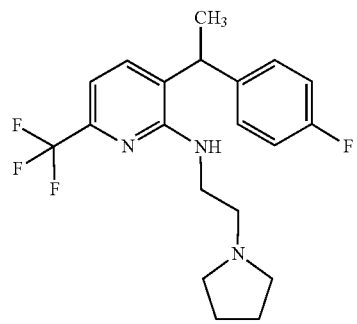 [SMILES: CC(c1ccc(F)cc1)c1ccc(C(F)(F)F)nc1NCCN1CCCC1]

Step A: 3-(1-(4-fluorophenyl)vinyl)-N-(2-(pyrrolidin-1-yl)ethyl)-6-(trifluoromethyl)pyridin-2-amine

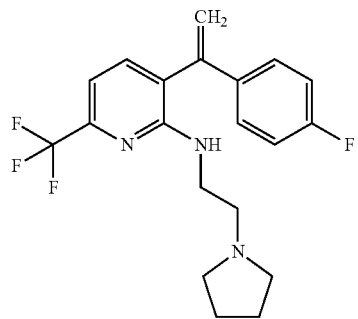 [SMILES: C=C(c1ccc(F)cc1)c1ccc(C(F)(F)F)nc1NCCN1CCCC1]

To a 8 mL microwave vial were added 3-bromo-N-(2-(pyrrolidin-1-yl)ethyl)-6-(trifluoromethyl)pyridin-2-amine (0.1 g, 0.278 mmol), 2-(1-(4-fluorophenyl)vinyl)-4,4,5,5-tetramethyl-1,3,2-dioxaborolane (0.103 g, 0.417 mmol), PdCl$_2$(dppf)$_2$ (0.041 g, 0.056 mmol) and Na$_2$CO$_3$ (0.088 g, 0.834 mmol) in dioxane (2.224 mL) and water (0.556 mL). The resulting orange suspension was degassed with N$_2$ and heated at 100° C. for 6 hours. The reaction mixture was next treated with water and extracted with EtOAc. The organic layers were washed with brine, dried over MgSO$_4$ and concentrated to give the title compound as a tan syrup which was used without further purification. ESI-MS m/z [M+H]$^+$ 380.5.

Step B: 3-(1-(4-fluorophenyl)ethyl)-N-(2-(pyrrolidin-1-yl)ethyl)-6-(trifluoromethyl)pyridin-2-amine To a 125 mL pear flask were added 3-(1-(4-fluorophenyl)vinyl)-N-(2-(pyrrolidin-1-yl)ethyl)-6-(trifluoromethyl)pyridin-2-amine (105 mg, 0.278 mmol) and palladium on carbon 10% (29.6 mg, 0.028 mmol) in methanol (4 mL). The resulting black suspension was stirred at room temperature under hydrogen atmosphere (balloon) overnight. The reaction mixture was subsequently filtered and purified by preparative HPLC (Phenomenex Gemini® C18, 5 μm, 30 mm ID×150 mm) using a gradient of 10-50% ACN (0.035% TFA) in water (0.05% TFA) to give a TFA salt of the title compound (22.9 mg, 16.6%). $^1$H NMR (400 MHz, CD$_3$OD) δ ppm 1.54 (d, J=7.03 Hz, 3H), 1.83-2.08 (m, 4H), 2.87-3.05 (m, 2H), 3.28-3.37 (m, 2H), 3.49-3.74 (m, 4H), 4.04-4.15 (m, 1H), 6.93-7.00 (m, 2H), 7.00-7.05 (m, 1H), 7.12-7.23 (m, 2H), 7.53 (s, 1H); ESI-MS m/z [M+H]$^+$ 382.5.

Example 104

3-(4-fluorobenzyl)-N-(2-(pyrrolidin-1-yl)ethyl)-6-(trifluoromethyl)pyridin-2-amine

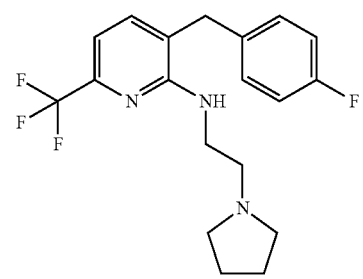 [SMILES: Fc1ccc(Cc2ccc(C(F)(F)F)nc2NCCN2CCCC2)cc1]

To a 8 mL microwave vial were added 3-bromo-N-(2-(pyrrolidin-1-yl)ethyl)-6-(trifluoromethyl)pyridin-2-amine (0.1 g, 0.278 mmol), 2-(4-fluorobenzyl)-4,4,5,5-tetramethyl-1,3,2-dioxaborolane (0.098 g, 0.417 mmol), PdCl$_2$(dppf)$_2$ (0.041 g, 0.056 mmol) and Na$_2$CO$_3$ (0.088 g, 0.834 mmol) in dioxane (2.22 mL) and water (0.560 mL). The resulting orange suspension was degassed with N$_2$ and then heated at 100° C. for 6 hours. The mixture was then filtered and purified by HPLC (Phenomenex Gemini® C18, 5 μm, 30 mm ID×150 mm) using a gradient of 10-50% ACN (0.035% TFA) in water (0.05% TFA) to give a TFA salt of the title compound (25.4 mg, 19.0%). $^1$H NMR (400 MHz, CD$_3$OD) δ ppm 1.94-2.07 (m, 2H), 2.10-2.22 (m, 2H), 3.05-3.18 (m, 2H), 3.42-3.51 (m, 2H), 3.71-3.81 (m, 2H), 3.81-3.86 (m, 2H), 3.90 (s, 2H), 6.98-7.03 (m, 1H), 7.08 (s, 2H), 7.20-7.26 (m, 2H), 7.27-7.32 (m, 1H); ESI-MS m/z [M+H]$^+$ 368.4.

Example 105

3-(1-(4-fluorophenyl)ethyl)-N-(2-(pyrrolidin-1-yl)ethyl)pyridin-2-amine

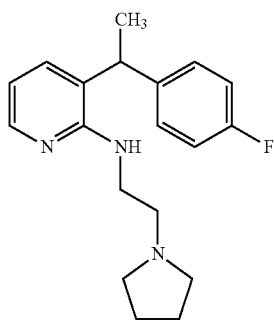 [SMILES: CC(c1ccc(F)cc1)c1cccnc1NCCN1CCCC1]

Step A: 3-iodo-N-(2-(pyrrolidin-1-yl)ethyl)pyridin-2-amine

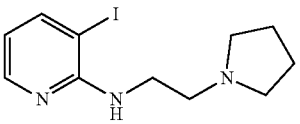 [SMILES: Ic1cccnc1NCCN1CCCC1]

To a solution of 2-fluoro-3-iodopyridine (200 mg, 896.92 μmol) and 2-pyrrolidin-1-ylethanamine (153.63 mg, 1.35 mmol) in dioxane (2 mL) was added DIPEA (1.56 mL, 8.97 mmol) at room temperature. The reaction mixture was stirred at 60° C. for 16 hours. Four reactions on the same scale (200 mg×4) were combined for work-up. The reaction mixture was poured into water (20 mL) and extracted with DCM (30 mL×2). The combined organic layers were washed with brine (20 mL), dried over anhydrous Na$_2$SO$_4$, filtered and concentrated in vacuo. The resulting concentrate was purified by silica gel column chromatography, using a gradient of petroleum ether/EtOAc (1:0 to 1:1) to give the title compound as a yellow oil (487 mg, 42%). $^1$H NMR (400 MHz, CDCl$_3$) δ ppm 1.77-1.82 (m, 4H), 2.55-2.60 (m, 4H), 2.75 (t, J=6.3 Hz, 2H), 3.51 (td, J=6.2, 5.0 Hz, 2H), 5.58 (br s, 1H), 6.30 (dd, J=7.5, 4.9 Hz, 1H), 7.81 (dd, J=7.5, 1.5 Hz, 1H), 8.06 (dd, J=4.9, 1.8 Hz, 1H); ESI-MS m/z [M+H]$^+$ 318.0.

Step B: (E)-3-(1-(4-fluorophenyl)-2-(trimethylsilyl)vinyl)-N-(2-(pyrrolidin-1-yl)ethyl)pyridin-2-amine

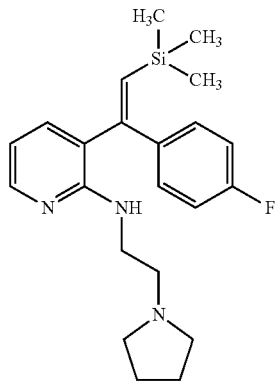 [SMILES: C[Si](C)(C)/C=C(\c1ccc(F)cc1)c1cccnc1NCCN1CCCC1]

To a round bottom flask containing 3-iodo-N-(2-(pyrrolidin-1-yl)ethyl)pyridin-2-amine (300 mg, 945.87 µmol) and (Z)-(2-(4-fluorophenyl)-2-(4,4,5,5-tetramethyl-1,3,2-dioxaborolan-2-yl)vinyl)trimethylsilane (454.42 mg, 1.42 mmol) in dioxane (3 mL) were added PdCl$_2$(dppf) (138.42 mg, 189.17 µmol) and 2 M Na$_2$CO$_3$ (1.18 mL). The suspension was degassed with N$_2$ several times. The mixture was stirred at 100° C. for 16 hours under N$_2$ and then purified by silica gel column chromatography, using a gradient of petroleum ether/EtOAc (1:0 to 1:2) to give the title compound as a black-brown oil (340 mg, 93.7%). $^1$H NMR (400 MHz, CDCl$_3$) δ ppm −0.03−−0.01 (m, 9H), 1.73 (br t, J=3.4 Hz, 4H), 2.42 (br s, 4H), 2.56 (t, J=6.0 Hz, 2H), 3.36-3.42 (m, 2H), 5.24 (br s, 1H), 6.02 (s, 1H), 6.52 (dd, J=7.2, 5.0 Hz, 1H), 6.96-7.03 (m, 2H), 7.16-7.24 (m, 3H), 8.04 (dd, J=5.1, 1.8 Hz, 1H); ESI-MS m/z [M+H]$^+$ 384.3.

Step C: 3-(1-(4-fluorophenyl)vinyl)-N-(2-(pyrrolidin-1-yl)ethyl)pyridin-2-amine

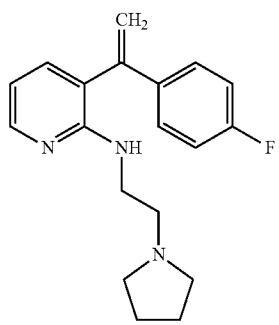 [SMILES: C=C(c1ccc(F)cc1)c1cccnc1NCCN1CCCC1]

To a round bottom flask containing (E)-3-(1-(4-fluorophenyl)-2-(trimethylsilyl)vinyl)-N-(2-(pyrrolidin-1-yl)ethyl)pyridin-2-amine (340 mg, 886.40 µmol) in DCM (2 mL) was added TFA (4 mL). The reaction mixture was stirred at 25° C. for 16 hours and then concentrated in vacuo. The resulting residue was dissolved in DCM (20 mL) and adjusted to pH 8~9 by addition of saturated aq Na$_2$CO$_3$. The organic layers were separated, dried over Na$_2$SO$_4$, and concentrated under reduced pressure to give the title compound as a black-brown oil (210 mg, 68.4%). $^1$H NMR (400 MHz, CDCl$_3$) δ ppm 1.69 (br s, 4H), 2.45 (br s, 4H), 2.63 (br s, 2H), 3.44 (br d, J=5.7 Hz, 2H), 4.87 (br s, 1H), 5.34 (d, J=0.7 Hz, 1H), 5.71 (d, J=0.9 Hz, 1H), 6.62 (dd, J=7.3, 5.1 Hz, 1H), 7.00 (t, J=8.7 Hz, 2H), 7.28-7.34 (m, 3H), 8.13 (dd, J=5.1, 2.0 Hz, 1H); ESI-MS m/z [M+H]$^+$ 312.2.

Step D: 3-(1-(4-fluorophenyl)ethyl)-N-(2-(pyrrolidin-1-yl)ethyl)pyridin-2-amine

To a round bottom flask containing 3-(1-(4-fluorophenyl)vinyl)-N-(2-(pyrrolidin-1-yl)ethyl)pyridin-2-amine (200 mg, 642.27 µmol) in MeOH (5 mL) was added Pd/C (60 mg, 10% purity, wet basis). The suspension was degassed under vacuum, purged with H$_2$ several times and stirred at 25° C. for 16 hours under H$_2$ (15 psi). The mixture was purified by preparative HPLC (Phenomenex Gemini® C18, 10 µm, 50 mm ID×250 mm) using a gradient of 5-35% ACN in water (0.05% HCl) to give an HCl salt of the title compound as a yellow solid (35 mg, 51.3%). $^1$H NMR (400 MHz, CDCl$_3$) δ ppm 1.93-1.98 (m, 3H), 2.16 (br s, 4H), 2.88-3.19 (m, 2H), 3.52-3.81 (m, 4H), 3.95-4.12 (m, 1H), 4.37-4.54 (m, 1H), 4.75-4.93 (m, 1H), 6.87-7.01 (m, 3H), 7.31 (br d, J=0.7 Hz, 2H), 7.76 (br d, J=6.2 Hz, 1H), 7.96 (br d, J=1.5 Hz, 1H), 8.38 (br s, 1H), 11.75 (br s, 1H), 14.95 (br s, 1H); ESI-MS m/z [M+H]$^+$ 314.3.

Example 106

5-(1-(4-fluorophenyl)ethyl)-6-((2-(pyrrolidin-1-yl)ethyl)amino)nicotinamide

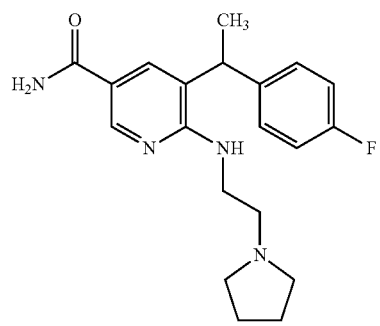 [SMILES: CC(c1ccc(F)cc1)c1cc(C(N)=O)cnc1NCCN1CCCC1]

Step A: methyl 5-bromo-6-((2-(pyrrolidin-1-yl)ethyl)amino)nicotinate

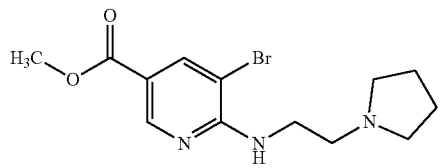 [SMILES: COC(=O)c1cnc(NCCN2CCCC2)c(Br)c1]

To a solution of methyl 5-bromo-6-chloro-pyridine-3-carboxylate (2 g, 7.98 mmol) and 2-pyrrolidin-1-ylethanamine (1 g, 8.78 mmol) in DCM (20 mL) was added DIPEA (3.1 g, 23.95 mmol, 4.17 mL) at 25° C. The mixture was stirred at 25° C. for 16 hours and then poured into water (20 mL) and extracted with DCM (30 mL×2). The combined organic layers were washed with brine (20 mL), dried over Na$_2$SO$_4$ and concentrated in vacuo. The product was purified by column chromatography (SiO₂) eluting with a gradient of petroleum ether/EtOAc (1:0 to 1:2). The product-containing fractions were concentrated to give the title compound as a yellow oil (940.0 mg, 35%). $^1$H NMR (400 MHz, CDCl₃) δ ppm 1.77-1.84 (m, 4H), 2.54-2.61 (m, 4H), 2.76 (t, J=6.1 Hz, 2H), 3.56-3.64 (m, 2H), 3.87 (s, 3H), 6.18 (br s, 1H), 8.18 (d, J=1.8 Hz, 1H), 8.70 (d, J=2.0 Hz, 1H); ESI-MS m/z [M+H]⁺ 328.0.

Step B: methyl (E)-5-(1-(4-fluorophenyl)-2-(trimethylsilyl)vinyl)-6-((2-(pyrrolidin-1-yl)ethyl)amino)nicotinate

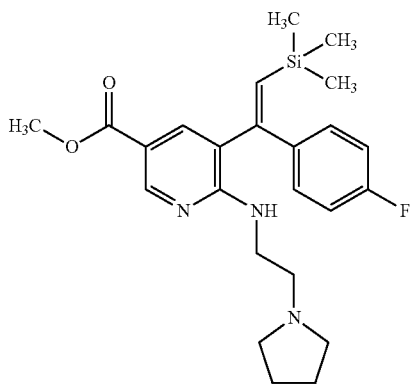 [SMILES: COC(=O)c1cnc(NCCN2CCCC2)c(/C(=C/[Si](C)(C)C)c2ccc(F)cc2)c1]

To a round bottom flask containing methyl 5-bromo-6-((2-(pyrrolidin-1-yl)ethyl)amino)nicotinate (700 mg, 2.13 mmol) and (Z)-(2-(4-fluorophenyl)-2-(4,4,5,5-tetramethyl-1,3,2-dioxaborolan-2-yl)vinyl)trimethylsilane (1.02 g, 3.20 mmol) in dioxane (8 mL) was added PdCl₂(dppf) (312.12 mg, 426.6 μmol) and 2 M Na₂CO₃ (2.67 mL). The suspension was degassed under vacuum and purged with N₂ several times. The mixture was stirred at 100° C. for 16 hours under N₂ and then poured into water (20 mL) and extracted with DCM (30 mL×2). The combined organic layers were washed with brine (20 mL), dried over Na₂SO₄, filtered and concentrated in vacuo. The product was purified by column chromatography (SiO₂) eluting with a gradient of petroleum ether/EtOAc (1:0 to 1:2). The product-containing fractions were concentrated to give the title compound as black-brown oil (780.0 mg, 79%). $^1$H NMR (400 MHz, CDCl₃) δ ppm −0.01 (s, 9H), 1.71-1.75 (m, 4H), 2.41 (br s, 4H), 2.55 (t, J=6.0 Hz, 2H), 3.41-3.45 (m, 2H), 3.87 (s, 3H), 5.67-5.74 (m, 1H), 6.04 (s, 1H), 6.97-7.03 (m, 2H), 7.19-7.24 (m, 2H), 7.78 (d, J=2.2 Hz, 1H), 8.71 (d, J=2.2 Hz, 1H); ESI-MS m/z [M+H]⁺ 442.3.

Step C: methyl 5-(1-(4-fluorophenyl)vinyl)-6-((2-(pyrrolidin-1-yl)ethyl)amino)nicotinate

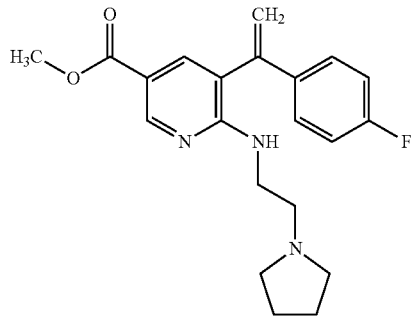

To a round bottom flask containing methyl (E)-5-(1-(4-fluorophenyl)-2-(trimethylsilyl)vinyl)-6-((2-(pyrrolidin-1-yl)ethyl)amino)nicotinate (780 mg, 1.77 mmol) in DCM (4 mL) was added TFA (8.0 mL). The reaction mixture was stirred at 25° C. for 16 hours and then concentrated in vacuo. The concentrate was dissolved in DCM (20 mL) and the mixture adjusted to pH 8~9 by adding saturated aq Na₂CO₃. The organic layer was separated and concentrated in vacuo to give the title compound as a yellow oil (640.0 mg, 94%). $^1$H NMR (400 MHz, CDCl₃) δ ppm 1.63 (dt, J=6.7, 3.2 Hz, 4H), 2.31 (br s, 4H), 2.51 (t, J=6.0 Hz, 2H), 3.40-3.46 (m, 2H), 3.88 (s, 3H), 5.37 (br s, 1H), 5.39 (s, 1H), 5.73 (s, 1H), 6.97-7.04 (m, 2H), 7.27-7.32 (m, 2H), 7.90 (d, J=2.2 Hz, 1H), 8.80 (d, J=2.2 Hz, 1H); ESI-MS m/z [M+H]⁺ 370.2.

Step D: methyl 5-(1-(4-fluorophenyl)ethyl)-6-((2-(pyrrolidin-1-yl)ethyl)amino)nicotinate

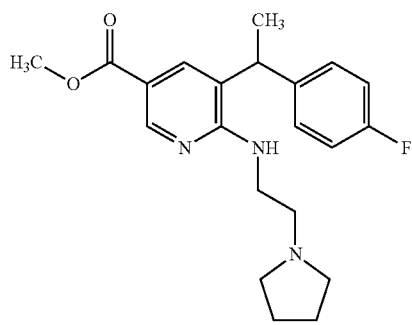

To a round bottom flask containing methyl 5-(1-(4-fluorophenyl)vinyl)-6-((2-(pyrrolidin-1-yl)ethyl)amino)nicotinate (640 mg, 1.73 mmol) in MeOH (5 mL) was added Pd/C (100 mg, 10%, wet basis). The suspension was degassed under vacuum, purged with H₂ several times and stirred at 25° C. for 16 hours under H₂ (15 psi). The mixture was then diluted with MeOH (30 mL) and filtered through a pad of Celite®. The filtrate was concentrated in vacuo to give the title compound as yellow oil (460.0 mg, 67%). $^1$H NMR (400 MHz, CDCl₃) δ ppm 1.61 (d, J=7.0 Hz, 3H), 1.73 (br d, J=2.5 Hz, 4H), 2.37 (br s, 2H), 2.41-2.77 (m, 4H), 3.34-3.49 (m, 2H), 3.83-3.89 (m, 1H), 3.90 (s, 3H), 5.53 (br s, 1H), 6.92-7.01 (m, 2H), 7.08-7.16 (m, 2H), 8.03 (d, J=1.5 Hz, 1H), 8.73 (d, J=2.0 Hz, 1H); ESI-MS m/z [M+H]⁺ 372.2.

Step E: 5-(1-(4-fluorophenyl)ethyl)-6-((2-(pyrrolidin-1-yl)ethyl)amino)nicotinic acid

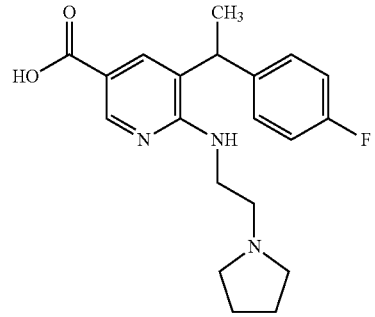 [SMILES: CC(c1ccc(F)cc1)c1cc(C(=O)O)cnc1NCCN1CCCC1]

To a pressure vessel containing methyl 5-(1-(4-fluorophenyl)ethyl)-6-((2-(pyrrolidin-1-yl)ethyl)amino)nicotinate (100 mg, 269.22 μmol) in dioxane (0.5 mL) was added NH$_3$·H$_2$O (3.70 mL, 25.97 mmol, 27% aq.). The reaction mixture was stirred at 110° C. for 16 hours and then quenched by addition of water (5 mL) and extracted with EtOAc (8 mL×3). The aqueous phase was concentrated in vacuo to give the title compound as a white solid (50 mg, 51%), which was used without further purification.

Step F: 5-(1-(4-fluorophenyl)ethyl)-6-((2-(pyrrolidin-1-yl)ethyl)amino)nicotinamide To a round bottom flask containing 5-(1-(4-fluorophenyl) ethyl)-6-((2-(pyrrolidin-1-yl)ethyl)amino)nicotinic acid (50 mg, 139.89 μmol) and NH$_4$C$_1$ (11.22 mg, 209.84 μmol) in DMF (1 mL) were added HATU (106.38 mg, 279.78 μmol) and DIPEA (73.10 μL, 419.67 μmol). The reaction mixture was stirred at 25° C. for 16 hours and then quenched by addition of water (10 mL) and extracted with EtOAc (10 mL×3). The combined organic layers were washed with brine (5 mL), dried over Na$_2$SO$_4$, filtered and concentrated in vacuo. The product was purified by preparative HPLC (Phenomenex Gemini® 10 μm, 25 mm ID×150 mm) using a gradient of 35%-65% ACN in water (0.05% NH$_4$OH). The product-containing fractions were combined and lyophilized to give the title compound as a white solid (8.0 mg, 6.33%). $^1$H NMR (400 MHz, CDCl$_3$) δ ppm 1.61-1.66 (m, 3H), 1.74 (br s, 4H), 2.32-2.51 (m, 5H), 2.63-2.76 (m, 1H), 3.35-3.53 (m, 2H), 3.82-3.94 (m, 1H), 5.45-5.54 (m, 1H), 6.90-7.01 (m, 2H), 7.14 (dd, J=5.4, 2.1 Hz, 2H), 7.28 (br d, J=3.3 Hz, 2H), 8.00 (br d, J=2.2 Hz, 1H), 8.41-8.52 (m, 1H); ESI-MS m/z [M+H]$^+$ 357.3.

Example 107

N-(1-(azetidin-1-yl)propan-2-yl)-3-(4-fluorobenzyl) pyrazin-2-amine

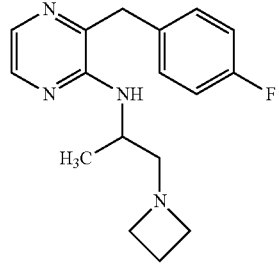 [SMILES: CC(CN1CCC1)Nc1nccnc1Cc1ccc(F)cc1]

A mixture of 2-chloro-3-(4-fluorobenzyl)pyrazine (25 mg, 0.112 mmol), 1-(azetidin-1-yl)propan-2-amine (26 mg, 0.23 mmol) and cesium carbonate (110 mg, 0.337 mmol) in DMSO (0.5 mL) was stirred at 120° C. for 24 hours. The mixture was filtered and purified by preparative HPLC (Phenomenex Gemini® 30 mm ID×100 mm) using a gradient of 10-100% aq ACN (80%, 10 mM NH$_4$HCO$_3$) in water (10 mM NH$_4$HCO$_3$). The product was re-purified by preparative HPLC (Phenomenex Gemini®) eluting with a gradient of 10-100% ACN (0.035% TFA) in water (0.05% TFA) to give a TFA salt of the title compound (3.0 mg, 9%). $^1$H NMR (400 MHz, CD$_3$OD) δ ppm 3.01 1.22-1.27 (m, 3H), 1.22-1.27 (m, 3H), 2.05-2.20 (m, 2H), 3.12-3.21 (m, 1H), 3.35-3.46 (m, 3H), 3.51-3.60 (m, 1H), 3.64-3.72 (m, 1H), 3.82-3.89 (m, 1H), 4.20-4.26 (m, 2H), 4.21-4.25 (m, 2H), 6.97-7.06 (m, 2H), 7.13-7.20 (m, 2H), 7.13-7.19 (m, 2H), 7.26-7.29 (m, 1H), 8.11-8.18 (m, 2H), 8.29-8.30 (m, 1H); ESI-MS m/z [M+H]$^+$ 301.2.

Example 108

N-(1-(azetidin-1-ylmethyl)cyclopropyl)-3-(4-fluorobenzyl)pyrazin-2-amine

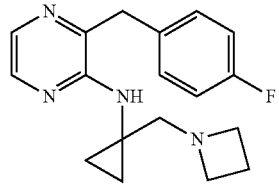 [SMILES: Fc1ccc(Cc2nccnc2NC2(CN3CCC3)CC2)cc1]

A mixture of 2-chloro-3-(4-fluorobenzyl)pyrazine (25 mg, 0.112 mmol), 1-(azetidin-1-ylmethyl)cyclopropan-1-amine (28 mg, 0.23 mmol) and cesium carbonate (110 mg, 0.337 mmol) in DMSO (0.5 mL) was stirred at 120° C. for 24 hours. The mixture was filtered and purified by preparative HPLC (Gemini® 30 mm ID×100 mm) using a gradient of 10-100% aq ACN (80%, 10 mM NH$_4$HCO$_3$) in water (10 mM NH$_4$HCO$_3$) to give the title compound (5.8 mg, 17%). $^1$H NMR (400 MHz, CD$_3$OD) δ ppm 0.39-0.44 (m, 2H), 0.40-0.44 (m, 2H), 0.63-0.67 (m, 2H), 1.89-1.96 (m, 2H), 2.85-2.90 (m, 2H), 3.45-3.48 (m, 2H), 3.55-3.60 (m, 2H), 4.16-4.20 (m, 2H), 6.96-7.02 (m, 2H), 7.12-7.18 (m, 2H), 7.94-7.98 (m, 1H), 8.04-8.06 (m, 1H); ESI-MS m/z [M+H]$^+$ 313.1.

Example 109

3-(4-fluorobenzyl)-N-((1-methylpyrrolidin-2-yl)methyl)pyrazin-2-amine

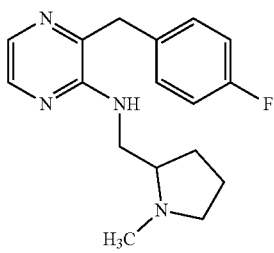 [SMILES: CN1CCCC1CNc1nccnc1Cc1ccc(F)cc1]

The title compound was prepared like EXAMPLE 108, using (1-methylpyrrolidin-2-yl)methanamine (26 mg, 0.23 mmol, 2.0 eq) and was obtained as a white solid (7.7 mg, 23%). $^1$H NMR (400 MHz, CD$_3$OD) δ ppm 1.67-1.80 (m, 2H), 1.91-1.99 (m, 1H), 2.07-2.15 (m, 1H), 2.21-2.24 (m, 3H), 2.39-2.45 (m, 1H), 2.58-2.64 (m, 1H), 3.20-3.27 (m, 1H), 3.66-3.74 (m, 1H), 4.12-4.19 (m, 1H), 4.27-4.33 (m, 1H), 4.48-4.56 (m, 1H), 6.95-7.02 (m, 2H), 7.06-7.12 (m, 2H), 7.90-7.94 (m, 1H), 8.03-8.06 (m, 1H); ESI-MS m/z [M+H]$^+$ 301.2.

Example 110

3-(4-fluorobenzyl)-N-((1-methylazetidin-2-yl)methyl)pyrazin-2-amine

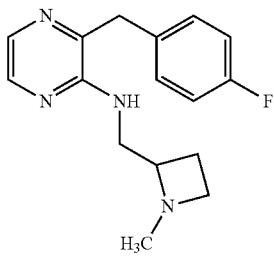 [SMILES: CN1CCC1CNc1nccnc1Cc1ccc(F)cc1]

The title compound was prepared like EXAMPLE 108, using (1-methylazetidin-2-yl)methanamine (67.5 mg, 0.674 mmol, 10 eq) and was obtained as a gray film (1.5 mg, 7.78%). $^1$H NMR (400 MHz, CD$_3$OD) δ ppm 1.73-1.86 (m, 1H), 2.07-2.20 (m, 1H), 2.35 (s, 3H), 3.24 (quin, J=6.05 Hz, 1H), 3.36-3.42 (m, 1H), 3.56 (dt, J=10.42, 7.28 Hz, 1H), 3.61-3.75 (m, 2H), 4.23-4.37 (m, 2H), 6.95-7.06 (m, 2H), 7.09-7.17 (m, 2H), 7.84 (d, J=2.64 Hz, 1H), 8.02 (d, J=2.64 Hz, 1H); ESI-MS m/z [M+H]$^+$ 287.2.

Example 111

3-(4-fluorobenzyl)-N-(1-(pyrrolidin-1-yl)propan-2-yl)pyrazin-2-amine

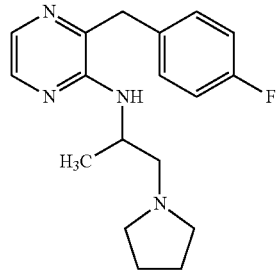 [SMILES: CC(CN1CCCC1)Nc1nccnc1Cc1ccc(F)cc1]

The title compound was prepared like EXAMPLE 108, using 2-chloro-3-(4-fluorobenzyl)pyrazine (20 mg, 0.090 mmol, 1 eq) and 1-(pyrrolidin-1-yl)propan-2-amine (17.28 mg, 0.135 mmol) and was obtained as a white film (1.5 mg, 5.31%). $^1$H NMR (400 MHz, CD$_3$OD) δ ppm 1.03 (d, J=6.53 Hz, 3H), 1.56-1.65 (m, 4H), 2.31-2.46 (m, 5H), 2.50-2.61 (m, 1H), 3.96 (s, 2H), 4.06-4.18 (m, 1H), 6.85-6.96 (m, 2H), 7.06-7.13 (m, 2H), 7.56 (d, J=3.01 Hz, 1H), 7.83 (d, J=2.76 Hz, 1H); ESI-MS m/z [M+H]$^+$ 315.3.

Example 112

3-(4-fluorobenzyl)-N-((1-methylpiperidin-2-yl)methyl)pyrazin-2-amine

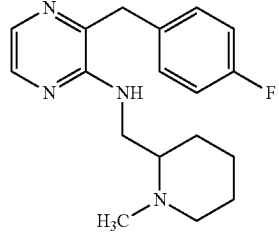 [SMILES: CN1CCCCC1CNc1nccnc1Cc1ccc(F)cc1]

The title compound (3.8 mg, 11%) was prepared like EXAMPLE 108, using (1-methylpiperidin-2-yl)methanamine (29 mg, 0.23 mmol, 2). ESI-MS m/z [M+H]$^+$ 315.3.

Example 113

N-(trans-1,2-dimethylpiperidin-4-yl)-3-(4-fluorobenzyl)pyrazin-2-amine

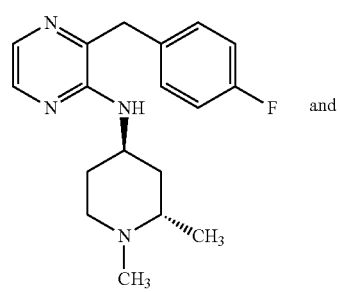

and

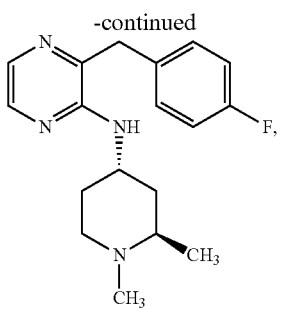

and

Example 114

N-(cis-1,2-dimethylpiperidin-4-yl)-3-(4-fluorobenzyl)pyrazin-2-amine

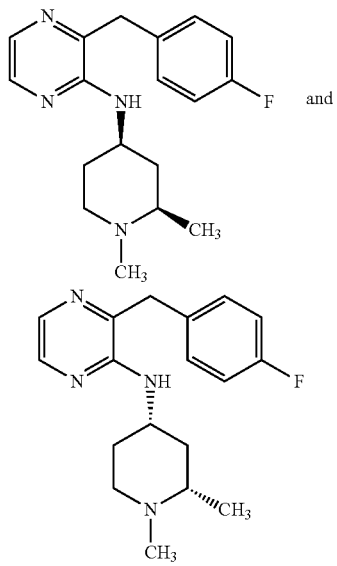

Step A: tert-butyl 4-((3-(4-fluorobenzyl)pyrazin-2-yl)amino)-2-methylpiperidine-1-carboxylate

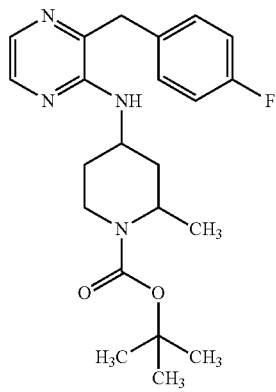 [SMILES: CC1CC(Nc2nccnc2Cc2ccc(F)cc2)CCN1C(=O)OC(C)(C)C]

A mixture of 2-chloro-3-(4-fluorobenzyl)pyrazine (200 mg, 791.39 μmol), tert-butyl 4-amino-2-methylpiperidine-1-carboxylate (203.52 mg, 949.67 μmol), Pd(OAc)$_2$ (8.88 mg, 639.57 μmol), BINAP (24.64 mg, 39.57 μmol) and Cs$_2$CO$_3$ (360.99 mg, 1.11 mmol) in toluene (10 mL) was stirred at 100° C. for 16 hours under N$_2$. The mixture was purified by silica gel column chromatography, using petroleum ether/EtOAc (3:1) as eluent. The title compound was obtained as a brown oil (180 mg, 56.8%). ESI-MS m/z [M+H]$^+$ 401.2.

Step B: 3-(4-fluorobenzyl)-N-(2-methylpiperidin-4-yl)pyrazin-2-amine

To a solution of tert-butyl 4-((3-(4-fluorobenzyl)pyrazin-2-yl)amino)-2-methylpiperidine-1-carboxylate (150 mg, 329.97 μmol) in DCM (10 mL) under N$_2$ was added TFA (564.37 mg, 4.95 mmol, 366.47 μL). The mixture was stirred at 25° C. for 5 hours and then concentrated. Ethyl acetate (10 mL) was added. The mixture was adjusted to pH 9 with saturated aq Na$_2$CO$_3$ (3 mL), extracted with EtOAc (20 mL×3) and purified by silica gel column chromatography using DCM/MeOH (7:1) as eluent. The title compound was obtained as a light-yellow oil (90 mg, 90.8%). ESI-MS m/z [M+H]$^+$ 301.1.

Step C: N-(1,2-dimethylpiperidin-4-yl)-3-(4-fluorobenzyl)pyrazin-2-amine

To a solution of 3-(4-fluorobenzyl)-N-(2-methylpiperidin-4-yl)pyrazin-2-amine (87 mg, 289.64 μmol) in MeOH (8 mL) was added formaldehyde (94.02 mg, 1.16 mmol, 86.26 μL, 37% aq). The mixture was stirred at 25° C. for 30 minutes. Next, NaBH(OAc)$_3$ (306.93 mg, 1.45 mmol) was added. The mixture was stirred at 25° C. for 1 hour and then poured into water (5 mL) and extracted with DCM (10 mL×3). The combined organic phases were dried over anhydrous Na$_2$SO$_4$, concentrated under reduced pressure and purified by silica gel column chromatography using DCM/MeOH (7:1) as eluent. The title compound was obtained as a light-yellow oil (62.6 mg, 68.7%). ESI-MS m/z [M+H]+ 315.2.

Step D: N-(trans-1,2-dimethylpiperidin-4-yl)-3-(4-fluorobenzyl)pyrazin-2-amine and N-(cis-1,2-dimethylpiperidin-4-yl)-3-(4-fluorobenzyl)pyrazin-2-amine N-(1,2-dimethylpiperidin-4-yl)-3-(4-fluorobenzyl)pyrazin-2-amine (62.6 mg, 199.11 μmol) was purified by preparative HPLC (Phenomenex Gemini® C18, 10 μm, ID 25 mm×150 mm) using a gradient of 46-76% ACN in water (0.05% NH4OH) to give two isomers, which were assigned arbitrarily. The later-eluting isomer was assigned as N-(trans-1,2-dimethylpiperidin-4-yl)-3-(4-fluorobenzyl)pyrazin-2-amine (6 mg, 7.76%) and was obtained as a yellow oil. $^1$H NMR (400 MHz, CDCl$_3$) δ ppm 0.99 (d, J=6.02 Hz, 3H), 1.53-1.57 (m, 2H), 1.83 (br s, 4H), 2.16 (s, 3H), 2.55 (dt, J=11.80, 3.76 Hz, 1H), 4.07 (s, 2H), 4.18 (dt, J=7.34, 3.73 Hz, 1H), 4.32 (br d, J=7.03 Hz, 1H), 7.04 (t, J=8.66 Hz, 2H), 7.20 (dd, J=8.41, 5.40 Hz, 2H), 7.79 (d, J=2.76 Hz, 1H), 7.96 (d, J=2.76 Hz, 1H); ESI-MS m/z [M+H]+ 315.2. The early-eluting isomer was assigned as N-(cis-1,2-dimethylpiperidin-4-yl)-3-(4-fluorobenzyl)pyrazin-2-amine (40 mg, 63.3%) and was obtained as a yellow oil. $^1$H NMR (400 MHz, CDCl$_3$) δ ppm 0.97 (q, J=11.71 Hz, 1H), 1.09 (d, J=6.27 Hz, 3H), 1.27 (qd, J=12.30, 4.02 Hz, 1H), 1.91 (dt, J=4.14, 2.20 Hz, 2H), 2.04 (ddd, J=11.11, 6.09, 2.38 Hz, 1H), 2.19 (td, J=12.30, 2.51 Hz, 1H), 2.28 (s, 3H), 2.87 (dt, J=11.92, 3.45 Hz, 1H), 3.81-3.92 (m, 1H), 4.00 (s, 2H), 4.05 (br d, J=7.78 Hz, 1H), 6.97-7.03 (m, 2H), 7.15 (dd, J=8.41, 5.40 Hz, 2H), 7.78 (d, J=2.76 Hz, 1H), 7.94 (d, J=2.76 Hz, 1H); ESI-MS m/z [M+H]+ 315.2.

Example 115

3-(4-fluorobenzyl)-N-(trans-3-fluoropiperidin-4-yl)pyrazin-2-amine

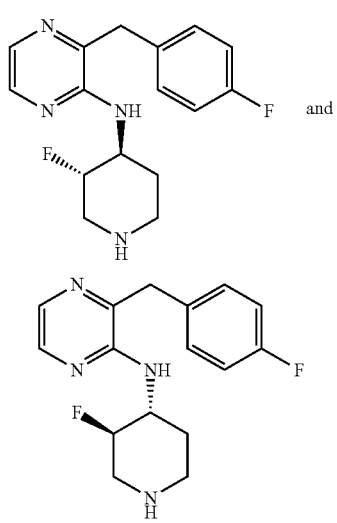

Step A: tert-butyl trans-3-fluoro-4-((3-(4-fluorobenzyl)pyrazin-2-yl)amino)piperidine-1-carboxylate

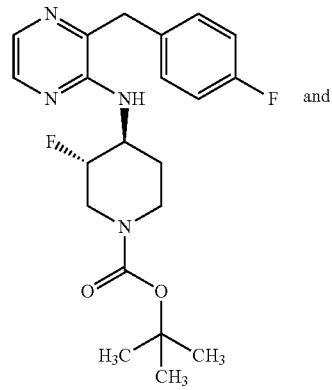

and

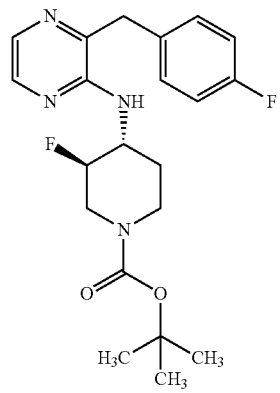

The title compound was prepared like STEP A of EXAMPLE 113 and EXAMPLE 114, using 2-chloro-3-(4-fluorobenzyl)pyrazine (130 mg, 514.40 μmol, 1.0 eq), tert-butyl trans-4-amino-3-fluoropiperidine-1-carboxylate (134.73 mg, 617.29 μmol), Pd(OAc)$_2$ (5.77 mg, 25.72 μmol), BINAP (16.02 mg, 25.72 μmol) and Cs$_2$CO$_3$ (234.64 mg, 720.17 μmol) in toluene (10 mL) and was obtained as a brown solid (131 mg, 52.1%). ESI-MS m/z [M+H]+ 405.2.

Step B: 3-(4-fluorobenzyl)-N-(trans-3-fluoropiperidin-4-yl)pyrazin-2-amine

The title compound was prepared like STEP B of EXAMPLE 113 and EXAMPLE 114, using tert-butyl trans-3-fluoro-4-((3-(4-fluorobenzyl)pyrazin-2-yl)amino)piperidine-1-carboxylate (90 mg, 184.03 μmol, 1.0 eq) and TFA (225.0 μL) in DCM (8 mL) and was obtained as a light-yellow oil (51 mg, 91.1%). $^1$H NMR (400 MHz, CDCl$_3$) δ ppm 2.09-2.17 (m, 1H), 2.67-2.82 (m, 3H), 3.04-3.15 (m, 1H), 4.08 (s, 2H), 4.13-4.32 (m, 3H), 6.99-7.07, (m, 2H), 7.19 (dd, J=8.60, 5.29 Hz, 2H), 7.84 (d, J=2.87 Hz, 1H), 7.97 (d, J=2.87 Hz, 1H); ESI-MS m/z [M+H]+ 305.1.

Example 116

N-(trans-3-fluoro-1-methylpiperidin-4-yl)-3-(4-fluorobenzyl)pyrazin-2-amine

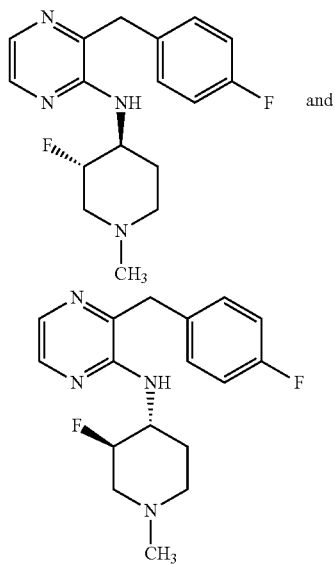

The title compound was prepared like STEP C of EXAMPLE 113 and EXAMPLE 114, using 3-(4-fluorobenzyl)-N-(trans-3-fluoropiperidin-4-yl)pyrazin-2-amine (32 mg, 105.15 µmol, 1 eq), formaldehyde (34.13 mg, 420.59 µmol, 37% aq) and NaBH(OAc)$_3$ (111.42 mg, 525.73 µmol) in MeOH (5 mL) and was obtained as a light-yellow oil (30 mg, 89.6%). $^1$H NMR (400 MHz, CDCl$_3$) δ ppm 1.23-1.33 (m, 2H), 1.92 (br s, 1H), 2.11-2.24 (m, 2H), 2.27 (s, 3H), 2.43 (br d, J=3.31 Hz, 1H), 2.69-2.84 (m, 1H), 4.07 (s, 2H), 4.19 (br d, J=6.39 Hz, 1H), 4.22-4.43 (m, 1H), 6.97-7.08 (m, 2H), 7.18 (br t, J=6.28 Hz, 2H), 7.83 (br d, J=1.10 Hz, 1H), 7.97 (br s, 1H); ESI-MS m/z [M+H]$^+$ 319.1.

Example 117

3-(1-(4-fluorophenyl)ethyl)-N-(2-(3-fluoropyrrolidin-1-yl)ethyl)pyrazin-2-amine

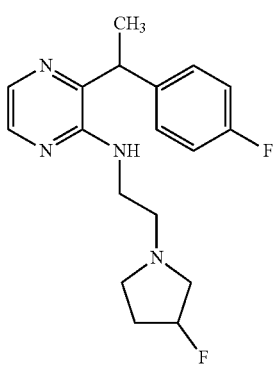 [SMILES: CC(c1ccc(F)cc1)c1nccnc1NCCN1CCC(F)C1]

A mixture of 2-(3-fluoropyrrolidin-1-yl)ethan-1-amine hydrochloride (19.24 mg, 0.114 mmol), 2-chloro-3-(1-(4-fluorophenyl)ethyl)pyrazine (27 mg, 0.114 mmol) and DIPEA (59.8 µL, 0.342 mmol) in dioxane (228 µL) was heated at 100° C. for 5 hours and then purified by preparative HPLC (Phenomenex Gemini® 30 mm ID×100 mm) using a gradient of 10-100% aq ACN (80%, 10 mM NH$_4$HCO$_3$) in water (10 mM NH$_4$HCO$_3$). The title compound was obtained as a white film (2.7 mg, 7.12%). $^1$H NMR (400 MHz, CD$_3$OD) δ ppm 1.62 (dd, J=7.03, 1.13 Hz, 3H), 1.87-2.06 (m, 1H), 2.09-2.27 (m, 1H), 2.30-2.38 (m, 1H), 2.45-2.63 (m, 2H), 2.65-2.74 (m, 1H), 2.75-2.98 (m, 2H), 3.41-3.51 (m, 2H), 4.17-4.28 (m, 1H), 5.03-5.26 (m, 1H), 6.96-7.06 (m, 2H), 7.19-7.26 (m, 2H), 7.77 (quin, J=2.82 Hz, 1H), 7.90 (dd, J=2.70, 1.69 Hz, 1H); ESI-MS m/z [M+H]$^+$ 333.1.

Example 118

N-(2-(3,3-difluoropyrrolidin-1-yl)ethyl)-3-(1-(4-fluorophenyl)ethyl)pyrazin-2-amine

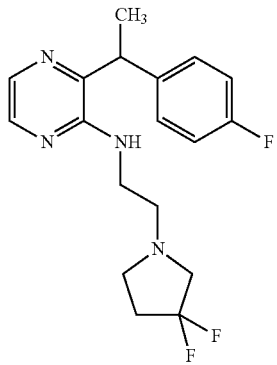 [SMILES: CC(c1ccc(F)cc1)c1nccnc1NCCN1CCC(F)(F)C1]

A TFA salt of the title compound was prepared like EXAMPLE 117, using 2-chloro-3-(1-(4-fluorophenyl)ethyl)pyrazine (40 mg, 0.169 mmol, 1 eq) and 2-(3,3-difluoropyrrolidin-1-yl)ethan-1-amine hydrochloride (41.0 mg, 0.220 mmol) and was obtained as a colorless oil (6 mg, 7.64%). $^1$H NMR (400 MHz, CD$_3$OD) δ ppm 1.60 (d, J=7.03 Hz, 3H), 2.11-2.29 (m, 2H), 2.47-2.57 (m, 1H), 2.59-2.71 (m, 3H), 2.72-2.92 (m, 2H), 3.35-3.46 (m, 2H), 4.17 (q, J=6.90 Hz, 1H), 6.95-7.04 (m, 2H), 7.17-7.24 (m, 2H), 7.76 (d, J=2.89 Hz, 1H), 7.88 (d, J=2.89 Hz, 1H); ESI-MS m/z [M+H]$^+$ 351.1.

Example 119

3-(1-(4-fluorophenyl)ethyl)-N-(2-(pyrrolidin-1-yl)ethyl)pyrazin-2-amine

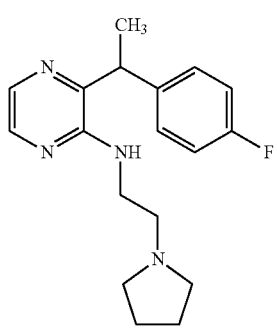

Step A: 3-(1-(4-fluorophenyl)vinyl)-N-(2-(pyrrolidin-1-yl)ethyl)pyrazin-2-amine

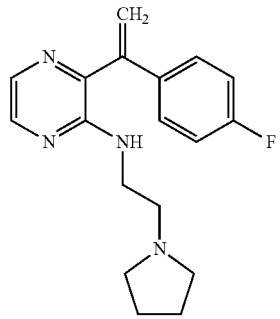

A mixture of 3-chloro-N-(2-(pyrrolidin-1-yl)ethyl)pyrazin-2-amine (150 mg, 0.662 mmol), 2-(1-(4-fluorophenyl)vinyl)-4,4,5,5-tetramethyl-1,3,2-dioxaborolane (295 mg, 1.191 mmol), Pd(dppf)Cl$_2$ (48.4 mg, 0.066 mmol) and Na$_2$CO$_3$ (662 µL, 1.323 mmol) in dioxane (3.3 mL) was degassed with N$_2$ and then heated in a sealed tube at 110° C. for 16 hours. The mixture was subsequently purified by silica gel column chromatography (NH column) using a gradient of 5-80% EtOAc in heptane to give the title compound as a light brown solid (170 mg, 82%). ESI-MS m/z [M+H]$^+$ 313.1.

Step B: 3-(1-(4-fluorophenyl)ethyl)-N-(2-(pyrrolidin-1-yl)ethyl)pyrazin-2-amine

A mixture of 3-(1-(4-fluorophenyl)vinyl)-N-(2-(pyrrolidin-1-yl)ethyl)pyrazin-2-amine (170 mg, 0.544 mmol) and 10% palladium on carbon (17.37 mg, 0.163 mmol) in EtOAc (0.27 mL) was stirred under H$_2$ atmosphere (balloon) at room temperature for 6 hours. The mixture was then purified by silica gel chromatography (NH column) using a gradient of 5-50% EtOAc in heptane to give the title compound as a light-yellow oil (109 mg, 63.7%). $^1$H NMR (400 MHz, CDCl$_3$) δ ppm 1.56 (d, J=6.97 Hz, 3H), 1.61-1.68 (m, 4H), 2.18-2.27 (m, 2H), 2.31-2.41 (m, 3H), 2.52-2.81 (m, 1H), 3.07-3.34 (m, 3H), 3.91 (q, J=6.97 Hz, 1H), 5.08 (br s, 1H), 6.80-6.94 (m, 2H), 7.02-7.14 (m, 2H), 7.75 (d, J=2.84 Hz, 1H), 7.84 (d, J=2.84 Hz, 1H); ESI-MS m/z [M+H]$^+$ 315.1.

Example 120

3-(1-phenylethyl)-N-(2-(pyrrolidin-1-yl)ethyl)pyrazin-2-amine

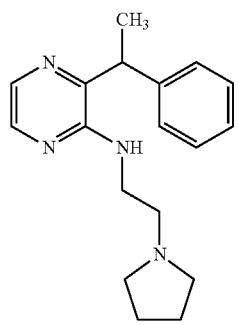 [SMILES: CC(c1ccccc1)c1nccnc1NCCN1CCCC1]

The title compound was prepared like EXAMPLE 119, starting with 3-chloro-N-(2-(pyrrolidin-1-yl)ethyl)pyrazin-2-amine (100 mg, 0.441 mmol, 1 eq) and 4,4,5,5-tetramethyl-2-(1-phenylvinyl)-1,3,2-dioxaborolane (183 mg, 0.794 mmol). The resulting intermediate, 3-(1-phenylvinyl)-N-(2-(pyrrolidin-1-yl)ethyl)pyrazin-2-amine (79 mg, 60.8%), was reduced to give a TFA salt of the title compound as a light orange oil (71 mg, 64.5% last step). $^1$H NMR (400 MHz, CD$_3$OD) δ ppm 1.65 (d, J=6.90 Hz, 3H), 1.98 (br s, 4H), 2.90-3.30 (m, 3H), 3.37-3.53 (m, 1H), 3.60-3.70 (m, 1H), 3.71-3.79 (m, 1H), 4.26 (q, J=7.03 Hz, 1H), 7.18-7.25 (m, 3H), 7.27-7.33 (m, 2H), 7.90 (d, J=2.89 Hz, 1H), 7.97 (d, J=2.64 Hz, 1H).

Example 121

(R)-3-(1-(4-fluorophenyl)ethyl)-N-(2-(pyrrolidin-1-yl)ethyl)pyrazin-2-amine

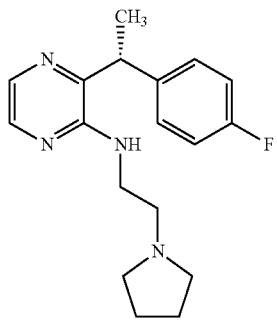 [SMILES: C[C@H](c1ccc(F)cc1)c1nccnc1NCCN1CCCC1]

and

Example 122

(S)-3-(1-(4-fluorophenyl)ethyl)-N-(2-(pyrrolidin-1-yl)ethyl)pyrazin-2-amine

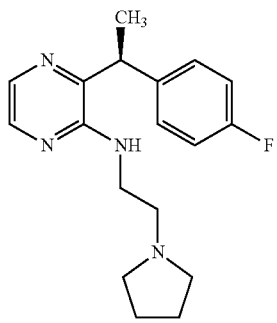 [SMILES: C[C@@H](c1ccc(F)cc1)c1nccnc1NCCN1CCCC1]

Racemate 3-(1-(4-fluorophenyl)ethyl)-N-(2-(pyrrolidin-1-yl)ethyl)pyrazin-2-amine (95 mg) was resolved by chiral SFC (Cellulose-2 column, 3 µm, 4.6 mm ID×150 mm) using CO$_2$/EtOH (0.05% DEA) to give the title enantiomers. The early-eluting enantiomer was assigned R-stereochemical configuration (39.9 mg, 42% recovery rate); ESI-MS m/z [M+H]$^+$ 315.1. The later-eluting enantiomer was assigned S-stereochemical configuration (40.7 mg, 43% recovery rate); ESI-MS m/z [M+H]$^+$ 315.1.

Example 123

3-(1-(4-fluorophenyl)ethyl)-5-(oxazol-2-yl)-N-(2-(pyrrolidin-1-yl)ethyl)pyrazin-2-amine

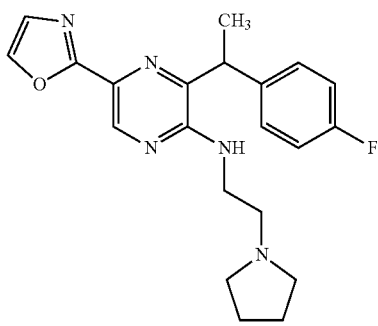 [SMILES: CC(c1ccc(F)cc1)c1nc(-c2ncco2)cnc1NCCN1CCCC1]

To a microwave tube containing 6-(1-(4-fluorophenyl)ethyl)-5-((2-(pyrrolidin-1-yl)ethyl)amino)pyrazine-2-carboxamide (120 mg, 335.74 μmol) was added 2-chloro-1,1-dimethoxyethane (3.18 g, 25.56 mmol, 2.92 mL). The mixture was stirred at 130° C. for 1 hour in a microwave reactor and then purified by preparative HPLC (Phenomenex Gemini® 10 μm, 25 mm ID×150 mm) using a gradient of 10-40% ACN in water (0.05% HCl) to give an HCl salt of the title compound as a yellow solid (9.7 mg, 70.2%). $^1$H NMR (400 MHz, CD$_3$OD) δ ppm 1.74 (br d, J=6.6 Hz, 3H), 1.92-2.11 (m, 4H), 2.94 (br s, 1H), 3.04 (br s, 1H), 3.39-3.53 (m, 2H), 3.64 (br d, J=7.9 Hz, 2H), 3.79-3.97 (m, 2H), 4.51 (br d, J=6.6 Hz, 1H), 7.02 (br t, J=8.6 Hz, 2H), 7.34-7.42 (m, 2H), 7.86 (s, 1H), 8.37 (s, 1H), 8.81 (s, 1H); ESI-MS m/z [M+H]$^+$ 382.1.

Example 124

3-(1-(4-fluorophenyl)ethyl)-5-(1-methyl-1H-imidazol-2-yl)-N-(2-(pyrrolidin-1-yl)ethyl)pyrazin-2-amine

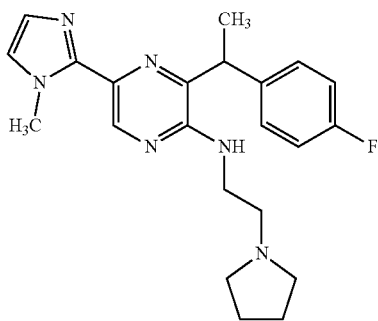 [SMILES: CC(c1ccc(F)cc1)c1nc(-c2nccn2C)cnc1NCCN1CCCC1]

To a round bottom flask charged with 6-(1-(4-fluorophenyl)ethyl)-5-(2-(pyrrolidin-1-yl)ethyl)amino)pyrazine-2-carboxamide (30 mg, 83.93 μmol) were added POCl$_3$ (825.00 mg, 5.38 mmol, 0.5 mL) and 2,2-dimethoxy-N-methylethanamine (463.50 mg, 3.89 mmol, 0.5 mL). The reaction mixture was stirred at 100° C. for 2 hours and then quenched by addition of water (20 mL). The aqueous phase was adjusted to pH 8 with aq NaHCO$_3$ and extracted with EtOAc (30 mL×2). The organic layers were combined, washed with brine and purified by preparative HPLC (Phenomenex Gemini® 10 μm, 25 mm ID×150 mm) using a gradient of 15-45% ACN in water (0.05% HCl) to give an HCl salt of the title compound as a black-brown solid (4.9 mg, 13.5%). $^1$H NMR (400 MHz, CD$_3$OD) δ ppm 1.70 (d, J=6.8 Hz, 3H), 1.94-2.13 (m, 4H), 2.90-2.99 (m, 1H), 3.00-3.10 (m, 1H), 3.40-3.52 (m, 2H), 3.59-3.73 (m, 2H), 3.84-3.91 (m, 2H), 4.10 (s, 3H), 4.53 (q, J=6.9 Hz, 1H), 7.04 (t, J=8.7 Hz, 2H), 7.33-7.39 (m, 2H), 7.62 (dd, J=9.7, 2.0 Hz, 2H), 8.59 (s, 1H); ESI-MS m/z [M+H]$^+$ 395.3.

Example 125

3-(1-(4-fluorophenyl)ethyl)-N-(2-(pyrrolidin-1-yl)ethyl)-5-(thiazol-2-yl)pyrazin-2-amine

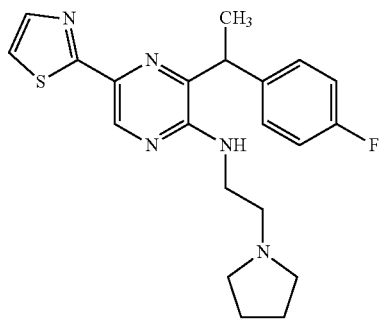 [SMILES: CC(c1ccc(F)cc1)c1nc(-c2nccs2)cnc1NCCN1CCCC1]

Step A: 6-(1-(4-fluorophenyl)ethyl)-5-((2-(pyrrolidin-1-yl)ethyl)amino)pyrazine-2-carbothioamide

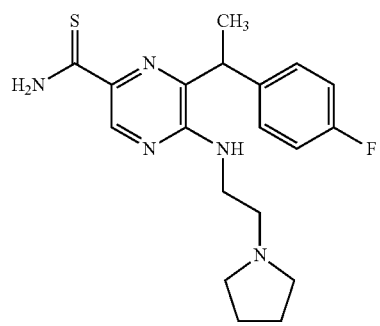 [SMILES: CC(c1ccc(F)cc1)c1nc(C(N)=S)cnc1NCCN1CCCC1]

To a microwave tube charged with 6-(1-(4-fluorophenyl)ethyl)-5-((2-(pyrrolidin-1-yl)ethyl)amino)pyrazine-2-carboxamide (0.1 g, 279.78 μmol) in THF (1 mL) was added Lawsson's reagent (169.74 mg, 419.67 μmol). The mixture was stirred at 130° C. for 1 hour in a microwave reactor and then purified by preparative HPLC (Phenomenex Gemini® 10 μm, 25 mm ID×150 mm) using a gradient of 10-40% ACN in water (0.05% HCl). The title compound was obtained as a yellow gum (14 mg, 12.0%). $^1$H NMR (400 MHz, CDCl$_3$) δ ppm 1.65 (d, J=6.8 Hz, 3H), 1.76-1.81 (m, 2H), 1.90 (br s, 2H), 2.36 (br d, J=5.1 Hz, 2H), 2.42-2.54 (m, 3H), 2.71 (ddd, J=12.2, 7.6, 4.7 Hz, 1H), 3.37 (ddt, J=13.0, 8.4, 4.3, 4.3 Hz, 1H), 3.43-3.54 (m, 1H), 4.03 (q, J=7.0 Hz, 1H), 5.90 (br s, 1H), 6.98 (br t, J=8.7 Hz, 2H), 7.08-7.17 (m, 2H), 7.37 (br s, 1H), 8.99 (br s, 1H), 9.28 (s, 1H); ESI-MS m/z [M+H]$^+$ 374.1.

Step B: 3-(1-(4-fluorophenyl)ethyl)-N-(2-(pyrrolidin-1-yl)ethyl)-5-(thiazol-2-yl)pyrazin-2-amine To a microwave tube charged with 6-(1-(4-fluorophenyl)ethyl)-5-((2-(pyrrolidin-1-yl)ethyl)amino)pyrazine-2-carbothioamide (14 mg, 37.48 μmol) was added 2-chloro-1,1-dimethoxyethane (355.47 mg, 2.85 mmol, 326.12 μL). The mixture was stirred at 120° C. for 1 hour in a microwave reactor and then purified by preparative HPLC (Phenomenex Gemini® 10 μm, 25 mm ID×150 mm) using a gradient of 20-50% ACN in water (0.05% HCl) to give an HCl salt of the title compound as a yellow solid (7.5 mg, 45.6%). $^1$H NMR (400 MHz, CD$_3$OD) δ ppm 1.70 (d, J=6.5 Hz, 3H), 1.98 (br s, 2H), 2.08 (br s, 2H), 2.88-3.09 (m, 2H), 3.45 (br s, 2H), 3.64 (br s, 2H), 3.87 (br s, 2H), 4.47 (br d, J=6.5 Hz, 1H), 7.03 (br t, J=8.3 Hz, 2H), 7.34-7.41 (m, 2H), 7.85 (d, J=3.0 Hz, 1H), 8.07 (d, J=3.0 Hz, 1H), 8.79 (s, 1H); ESI-MS m/z [M+H]$^+$ 398.0.

Example 126

3-(1-(4-fluorophenyl)ethyl)-5-(5-methyloxazol-2-yl)-N-(2-(pyrrolidin-1-yl)ethyl)pyrazin-2-amine

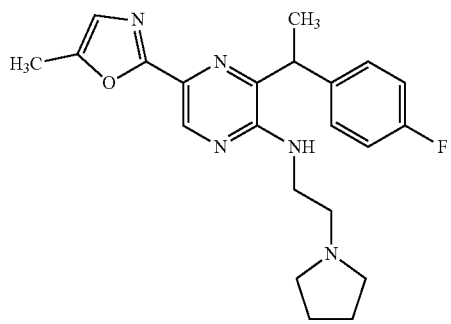 [SMILES: Cc1cnc(-c2cnc(NCCN3CCCC3)c(C(C)c3ccc(F)cc3)n2)o1]

To a round bottom flask charged with 6-(1-(4-fluorophenyl)ethyl)-N-(2-oxopropyl)-5-((2-(pyrrolidin-1-yl)ethyl)amino)pyrazine-2-carboxamide (30 mg, 72.55 μmol) was added POCl$_3$ (0.3 mL, 3.23 mmol). The mixture was stirred at 120° C. for 16 hours and then evacuated to remove POCl$_3$. The residue was dissolved in EtOAc (30 mL), washed with saturated aq NaHCO$_3$ and brine, and purified by preparative HPLC (Phenomenex Gemini® 10 μm, 25 mm ID×150 mm) using a gradient of 15-45% ACN in water (0.05% HCl) to give an HCl salt of the title compound as a yellow solid (9.3 mg, 29.0%). $^1$H NMR (400 MHz, CD$_3$OD) δ ppm 1.72 (d, J=6.8 Hz, 3H), 1.92-2.13 (m, 5H), 2.55 (d, J=0.9 Hz, 3H), 2.85-2.96 (m, 1H), 3.02 (br d, J=11.0 Hz, 1H), 3.38-3.51 (m, 2H), 3.57-3.69 (m, 2H), 3.77-3.96 (m, 2H), 4.48 (q, J=6.6 Hz, 1H), 7.01 (t, J=8.7 Hz, 2H), 7.37 (dd, J=8.6, 5.3 Hz, 2H), 7.48 (s, 1H), 8.76 (s, 1H); ESI-MS m/z [M+H]$^+$ 396.2.

Example 127

3-(1-(4-fluorophenyl)ethyl)-5-(5-methylthiazol-2-yl)-N-(2-(pyrrolidin-1-yl)ethyl)pyrazin-2-amine

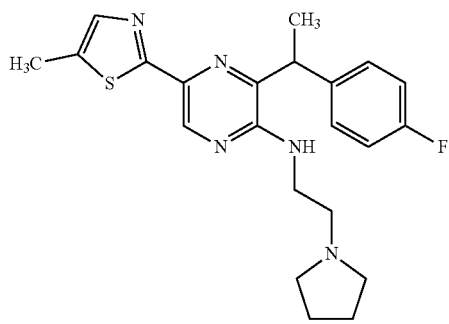 [SMILES: Cc1cnc(-c2cnc(NCCN3CCCC3)c(C(C)c3ccc(F)cc3)n2)s1]

To a microwave tube charged with 6-(1-(4-fluorophenyl)ethyl)-N-(2-oxopropyl)-5-((2-(pyrrolidin-1-yl)ethyl)amino)pyrazine-2-carboxamide (80 mg, 193.48 μmol) in THF (1 mL) was added Lawsson's reagent (140.86 mg, 348.26 μmol). The mixture was stirred at 120° C. for 1 hour in a microwave reactor and then purified by preparative HPLC (Phenomenex Gemini® 10 μm, 25 mm ID×150 mm) using a gradient of 25-55% ACN in water (0.05% HCl) to give an HCl salt of the title compound as a yellow solid (12.1 mg, 22.2%). $^1$H NMR (400 MHz, CD$_3$OD) δ ppm 1.69 (d, J=6.8 Hz, 3H), 1.93-2.02 (m, 2H), 2.04-2.13 (m, 2H), 2.60 (d, J=0.9 Hz, 3H), 2.88-3.07 (m, 2H), 3.37-3.50 (m, 2H), 3.58-3.69 (m, 2H), 3.82-3.89 (m, 2H), 4.46 (q, J=6.9 Hz, 1H), 7.02 (t, J=8.7 Hz, 2H), 7.36 (dd, 5.4 Hz, 2H), 7.86 (d, J=1.1 Hz, 1H), 8.75 (s, 1H); ESI-MS m/z [M+H]$^+$ 412.2.

Example 128

5-(1,5-dimethyl-1H-imidazol-2-yl)-3-(1-(4-fluorophenyl)ethyl)-N-(2-(pyrrolidin-1-yl)ethyl)pyrazin-2-amine

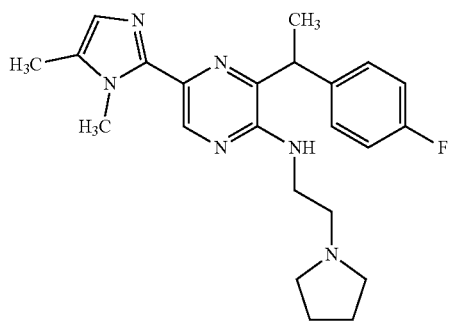 [SMILES: Cc1cnc(-c2cnc(NCCN3CCCC3)c(C(C)c3ccc(F)cc3)n2)n1C]

Step A: 6-(1-(4-fluorophenyl)ethyl)-N-(prop-2-yn-1-yl)-5-((2-(pyrrolidin-1-yl)ethyl)amino)pyrazine-2-carboxamide

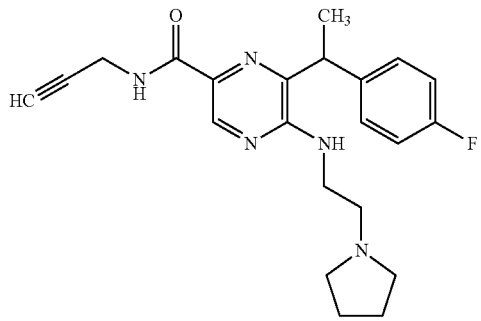 [SMILES: C#CCNC(=O)c1cnc(NCCN2CCCC2)c(C(C)c2ccc(F)cc2)n1]

To a round bottom flask charged with 6-(1-(4-fluorophenyl)ethyl)-5-((2-(pyrrolidin-1-yl)ethyl)amino)pyrazine-2-carboxylic acid (0.2 g, 558.02 μmol) and 2-propynylamine (46.10 mg, 837.03 μmol, 53.61 μL) in DMF (2 mL) were added DIPEA (216.36 mg, 1.67 mmol, 291.59 μL) and HATU (424.35 mg, 1.12 mmol). The mixture was stirred at 25° C. for 16 hours and then purified by preparative TLC, using DCM/MeOH (10:1) as eluent, to give the title compound as a yellow gum (0.18 g, 79.9%). $^1$H NMR (400 MHz, CD$_3$OD) δ ppm 1.69 (d, J=6.8 Hz, 3H), 1.80-1.89 (m, 4H), 2.61 (t, J=2.4 Hz, 1H), 2.72 (br s, 4H), 2.77-2.94 (m, 2H), 3.58-3.65 (m, 2H), 4.18-4.22 (m, 2H), 4.24-4.31 (m, 1H), 6.98-7.05 (m, 2H), 7.24-7.31 (m, 2H), 8.59 (s, 1H); ESI-MS m/z [M+H]$^+$ 396.2.

Step B: 5-(1,5-dimethyl-1H-imidazol-2-yl)-3-(1-(4-fluorophenyl)ethyl)-N-(2-(pyrrolidin-1-yl)ethyl)pyrazin-2-amine To a round bottom flask charged with 6-(1-(4-fluorophenyl)ethyl)-N-(prop-2-yn-1-yl)-5-((2-(pyrrolidin-1-yl)ethyl)amino)pyrazine-2-carboxamide (80 mg, 202.29 μmol) and CH$_3$NH$_2$ (30% in EtOH, 2.02 mmol, 0.5 mL) in toluene (0.5 mL) was added zinc; trifluoromethanesulfonate (147.08 mg, 404.58 μmol). The mixture was stirred at 120° C. for 16 hours and then purified by preparative HPLC (YMC-Actus ODS-AQ® 5 μm, 30 mm ID×150 mm) using a gradient of 15-37% ACN in water (0.05% HCl) to give an HCl salt of the title compound as a yellow semi-solid (6.1 mg, 6.7%). $^1$H NMR (400 MHz, CD$_3$OD) δ ppm 1.69 (d, J=7.0 Hz, 3H), 1.97-2.14 (m, 4H), 2.89-3.00 (m, 1H), 3.01-3.12 (m, 1H), 3.30 (s, 3H), 3.40-3.51 (m, 2H), 3.59-3.73 (m, 2H), 3.87 (t, J=5.3 Hz, 2H), 3.97 (s, 3H), 4.53 (q, J=6.8 Hz, 1H), 7.04 (t, J=8.8 Hz, 2H), 7.33-7.40 (m, 3H), 8.53 (s, 1H); ESI-MS m/z [M+H]$^+$ 409.3.

Example 129

3-(1-(4-fluorophenyl)ethyl)-6-methyl-5-(5-methyloxazol-2-yl)-N-(2-(pyrrolidin-1-yl)ethyl)pyrazin-2-amine

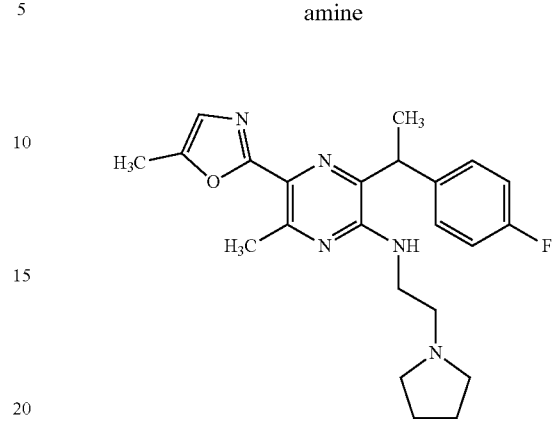

A solution of 6-(1-(4-fluorophenyl)ethyl)-3-methyl-N-(2-oxopropyl)-5-((2-(pyrrolidin-1-yl)ethyl)amino)pyrazine-2-carboxamide (10 mg, 0.023 mmol) and POCl$_3$ (0.2 mL, 2.146 mmol) was heated at 90° C. for 30 minutes and then evacuated to remove POCl$_3$. The residue was dissolved in EtOAc (10 mL), washed with saturated aq NaHCO$_3$ and brine, and purified by preparative HPLC (Phenomenex Gemini® C18, 5 μm, 30 mm ID×150 mm) using a gradient of 10-50% ACN (0.035% TFA) in water (0.05% TFA) to give a TFA salt of the title compound as colorless oil (2.5 mg, 20.4%). ESI-MS m/z [M+H]$^+$ 410.2.

Example 130

N-(2-(azetidin-1-yl)ethyl)-3-ethyl-6-(3-methylbenzyl)-1,2,4-triazin-5-amine

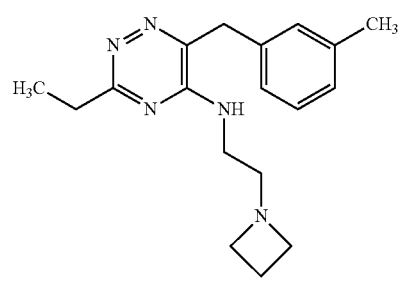 [SMILES: CCc1nnc(Cc2cccc(C)c2)c(NCCN2CCC2)n1]

A mixture of 3-ethyl-6-(3-methylbenzyl)-5-(methylthio)-1,2,4-triazine (30.0 mg, 109 μmol), 2-(azetidin-1-yl)ethanamine (54.4 mg, 544 μmol) and DIPEA (42.2 mg, 326 μmol) in DMSO (250 μL) was stirred at 100° C. for 16 hours. The reaction mixture was purified by preparative HPLC (Xtimate® C18, 5 μm, 25 mm ID×150 mm) using a gradient of 22-52% ACN in water (0.05% NH$_4$OH) to give the title compound as a light-yellow gum (10.0 mg, 29%). $^1$H NMR (400 MHz, DMSO-d$_6$) δ ppm 1.21 (t, J=7.6 Hz, 3H), 1.91 (quin, J=6.9 Hz, 2H), 2.25 (s, 3H), 2.43-2.48 (m, 2H), 2.65 (q, J=7.7 Hz, 2H), 3.04 (t, J=6.9 Hz, 4H), 3.28 (q, J=6.4 Hz, 2H), 4.04 (s, 2H), 6.98-7.10 (m, 3H), 7.14-7.20 (m, 1H), 7.30 (br t, J=5.2 Hz, 1H); ESI-MS m/z [M+H]$^+$ 312.2.

Example 131

N-(trans-1,3-dimethylpiperidin-4-yl)-6-(4-fluorobenzyl)-3-methyl-1,2,4-triazin-5-amine

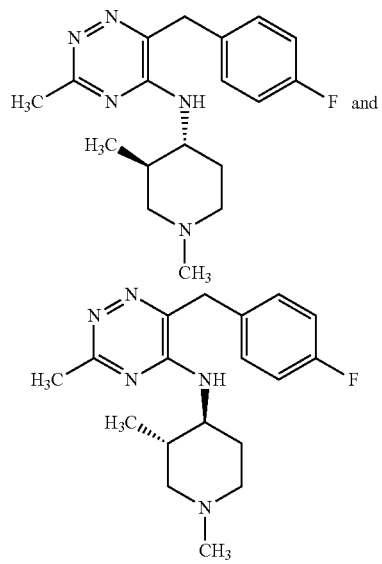

Step A: tert-butyl trans-4-((6-(4-fluorobenzyl)-3-methyl-1,2,4-triazin-5-yl)amino)-3-methylpiperidine-1-carboxylate

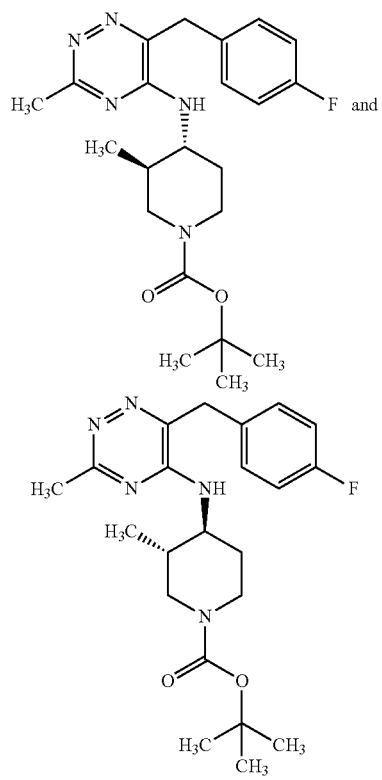

A mixture of DIPEA (0.391 mL, 2.238 mmol), tert-butyl trans-4-amino-3-methylpiperidine-1-carboxylate (0.224 g, 1.044 mmol) and 6-(4-fluorobenzyl)-3-methyl-5-(methylthio)-1,2,4-triazine (0.186 g, 0.746 mmol) in DMSO (1.24 mL) was heated at 100° C. for 16 hours. UPLC showed less than 15% conversion so the reaction mixture was heated at 120° C. for an additional 24 hours. The reaction mixture was then diluted with water, extracted with EtOAc, dried over anhydrous $Na_2SO_4$, filtered, and concentrated in vacuo to give the title compound (0.422 g, crude) which was used without further purification.

Step B: N-(trans-1,3-dimethylpiperidin-4-yl)-6-(4-fluorobenzyl)-3-methyl-1,2,4-triazin-5-amine To a mixture of tert-butyl trans-4-((6-(4-fluorobenzyl)-3-methyl-1,2,4-triazin-5-yl)amino)-3-methylpiperidine-1-carboxylate (0.422 g, 1.016 mmol) in dioxane (5.08 mL) was added HCl in dioxane (2.54 mL, 10.16 mmol). The mixture was stirred at room temperature for 24 hours and then concentrated in vacuo. The resulting amine intermediate was taken up in MeOH (5 mL). Formaldehyde (0.030 g, 1.016 mmol) and sodium cyanoborohydride (0.064 g, 1.016 mmol) were added. The reaction mixture was stirred for 24 hours at room temperature and then concentrated in vacuo. The concentrate was dispersed in MeOH, filtered, and purified by preparative HPLC (Xtimate® C18, 5 μm, 25 mm ID×150 mm) using a gradient of 22-52% ACN in water (0.05% $NH_4OH$) to give the title compound (0.111 g, 33.2%). $^1$H NMR (400 MHz, DMSO-$d_6$) δ ppm 0.53-0.64 (m, 3H), 1.46-1.58 (m, 1H), 1.59-1.69 (m, 1H), 1.69-1.85 (m, 2H), 1.85-1.98 (m, 1H), 2.11-2.21 (m, 3H), 2.31-2.40 (m, 3H), 2.70-2.82 (m, 2H), 3.17 (d, J=5.23 Hz, 2H), 3.55-3.70 (m, 1H), 4.02-4.12 (m, 2H), 4.13-4.23 (m, 1H), 6.95-7.02 (m, 1H), 7.06-7.15 (m, 2H), 7.23-7.34 (m, 2H).

Example 132

N-(2-(azetidin-1-yl)ethyl)-6-(1-(4-fluorophenyl)ethyl)-3-methyl-1,2,4-triazin-5-amine

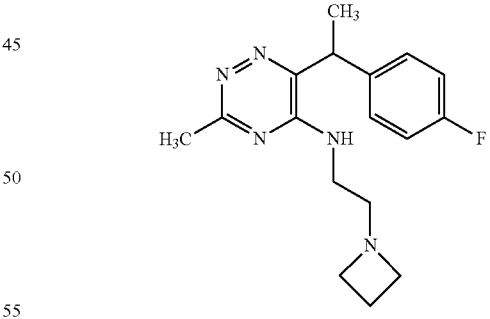

A mixture of 6-(1-(4-fluorophenyl)ethyl)-3-methyl-5-(methylthio)-1,2,4-triazine (800 mg, 3.04 mmol), 2-(azetidin-1-yl)ethanamine (800 mg, 7.99 mmol) and DIPEA (1.18 g, 9.11 mmol, 1.59 mL) in DMSO (5 mL) was stirred at 100° C. for 30 hours. The reaction mixture was purified by preparative HPLC (Phenomenex Gemini® 10 μm, 25 mm ID×150 mm) using a gradient of 25-55% ACN in water (0.05% $NH_4OH$) to give the title compound as a light-yellow gum (345.0 mg, 35%). $^1$H NMR (400 MHz, $CD_3OD$) δ ppm 1.65 (d, J=7.1 Hz, 3H), 2.04 (quin, J=7.2 Hz, 2H), 2.45 (s, 3H), 2.49-2.58 (m, 2H), 3.15 (td, J=7.2, 4.0 Hz, 4H), 3.37 (t, J=6.4 Hz, 2H), 4.29 (q, J=6.8 Hz, 1H), 6.97-7.05 (m, 2H), 7.23-7.29 (m, 2H); ESI-MS m/z [M+H]+ 316.0.

Example 133

(R)-N-(2-(azetidin-1-yl)ethyl)-6-(1-(4-fluorophenyl)ethyl)-3-methyl-1,2,4-triazin-5-amine

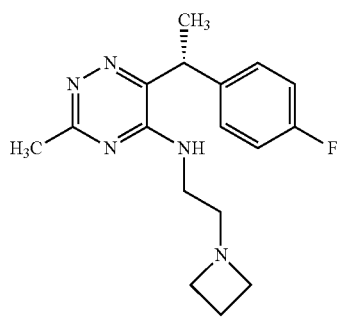 [SMILES: Cc1nnc([C@H](C)c2ccc(F)cc2)c(NCCN2CCC2)n1]

and

Example 134

(S)-N-(2-(azetidin-1-yl)ethyl)-6-(1-(4-fluorophenyl)ethyl)-3-methyl-1,2,4-triazin-5-amine

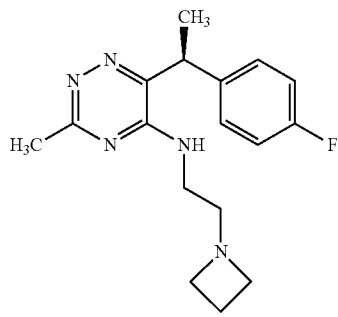 [SMILES: Cc1nnc([C@@H](C)c2ccc(F)cc2)c(NCCN2CCC2)n1]

N-(2-(azetidin-1-yl)ethyl)-6-(1-(4-fluorophenyl)ethyl)-3-methyl-1,2,4-triazin-5-amine (345 mg) was purified by chiral SFC (OZ column, 85 mL/minute, 15% IPA+0.1% DEA). The first eluting enantiomer was assigned R-stereochemical configuration, and the second eluting enantiomer was assigned S-stereochemical configuration.

Example 135

N-(2-(azetidin-1-yl)ethyl)-6-(4-fluorobenzyl)-3-methyl-1,2,4-triazin-5-amine

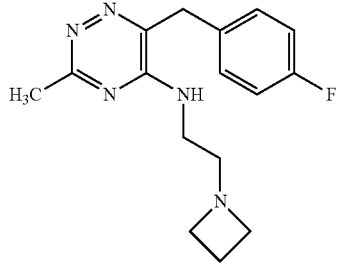 [SMILES: Cc1nnc(Cc2ccc(F)cc2)c(NCCN2CCC2)n1]

The title compound was prepared like EXAMPLE 132 in which a mixture of 6-(4-fluorobenzyl)-3-methyl-5-(methylthio)-1,2,4-triazine (15 mg, 60.17 μmol), 2-(azetidin-1-yl)ethanamine (30.13 mg, 300.83 μmol) and DIPEA (23.33 mg, 180.50 μmol, 31.52 μL) in DMSO (100 μL) was stirred at 100° C. for 16 hours. $^1$H NMR (400 MHz, CD$_3$OD) δ ppm 2.09 (quin, J=7.3 Hz, 2H), 2.46 (s, 3H), 2.64 (t, J=6.5 Hz, 2H), 3.25 (t, J=7.3 Hz, 4H), 3.45 (t, J=6.5 Hz, 2H), 4.11 (s, 2H), 6.96-7.08 (m, 2H), 7.18-7.31 (m, 2H); ESI-MS m/z [M+H]+ 302.1.

Example 136

N-(2-(azetidin-1-yl)ethyl)-3-ethyl-6-(4-fluorobenzyl)-1,2,4-triazin-5-amine

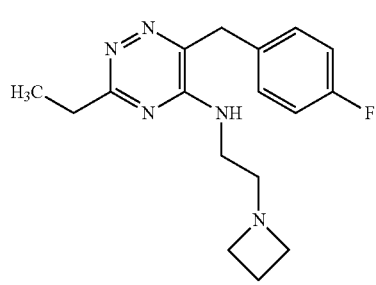 [SMILES: CCc1nnc(Cc2ccc(F)cc2)c(NCCN2CCC2)n1]

The title compound was prepared like EXAMPLE 132, using 3-ethyl-6-(4-fluorobenzyl)-5-(methylthio)-1,2,4-triazine instead of 6-(1-(4-fluorophenyl)ethyl)-3-methyl-5-(methylthio)-1,2,4-triazine. $^1$H NMR (400 MHz, CD$_3$OD) δ ppm 1.31 (t, J=7.5 Hz, 3H), 2.08 (quin, J=7.0 Hz, 2H), 2.62 (t, J=6.3 Hz, 2H), 2.75 (q, J=7.5 Hz, 2H), 3.22 (t, J=7.3 Hz, 4H), 3.46 (t, J=6.3 Hz, 2H), 4.11 (s, 2H), 7.03 (br t, J=8.5 Hz, 2H), 7.20-7.29 (m, 2H); ESI-MS m/z [M+H]+ 316.2.

Example 137

6-(4-fluorobenzyl)-3-methyl-N-(1-methylpiperidin-4-yl)-1,2,4-triazin-5-amine

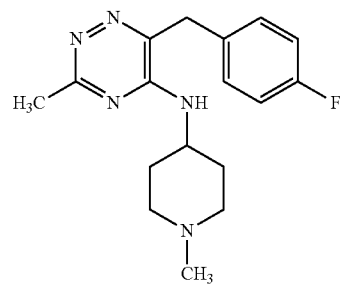 [SMILES: Cc1nnc(Cc2ccc(F)cc2)c(NC2CCN(C)CC2)n1]

An HCl salt of the title compound was prepared like EXAMPLE 132, using 6-(4-fluorobenzyl)-3-methyl-5-(methylthio)-1,2,4-triazine (40.00 mg, 160.44 μmol, 1.0 eq) and 1-methylpiperidin-4-amine (100.00 mg, 875.73 μmol) and was obtained as a light-yellow solid (7.30 mg, 12.9%). $^1$H NMR (400 MHz, CD$_3$OD) δ ppm 2.08-2.30 (m, 4H), 2.62 (s, 3H), 2.91 (s, 3H), 3.15-3.28 (m, 2H), 3.64 (br d, J=13.0 Hz, 2H), 4.21 (s, 2H), 4.55-4.73 (m, 1H), 7.04-7.12 (m, 2H), 7.27-7.35 (m, 2H); ESI-MS m/z [M+H]$^+$ 316.2.

Example 138

N-(2-(azetidin-1-yl)ethyl)-3-cyclopropyl-6-(4-fluorobenzyl)-1,2,4-triazin-5-amine

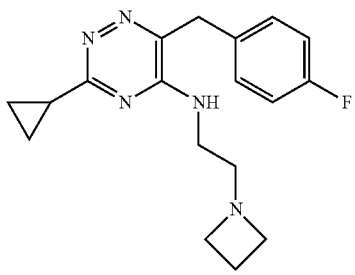 [SMILES: Fc1ccc(Cc2nnc(C3CC3)nc2NCCN2CCC2)cc1]

The title compound was prepared like EXAMPLE 132 in which a mixture of 3-cyclopropyl-6-(4-fluorobenzyl)-5-(methylthio)-1,2,4-triazine (24 mg, 87.16 μmol), 2-(azetidin-1-yl)ethanamine (43.65 mg, 435.80 μmol) and DIPEA (33.79 mg, 261.48 μmol, 45.66 μL) in DMSO (100 μL) was stirred at 100° C. for 16 hours. $^1$H NMR (400 MHz, CD$_3$OD) δ ppm 0.98-1.08 (m, 4H), 2.00-2.18 (m, 3H), 2.58 (t, J=6.8 Hz, 2H), 3.22 (t, J=7.0 Hz, 4H), 3.35-3.42 (m, 2H), 4.09 (s, 2H), 6.97-7.07 (m, 2H), 7.24 (dd, J=8.5, 5.0 Hz, 2H); ESI-MS m/z [M+H]$^+$ 328.2.

Example 139

(R)-6-(1-(4-fluorophenyl)ethyl)-3-methyl-N-(1-methylpiperidin-4-yl)-1,2,4-triazin-5-amine

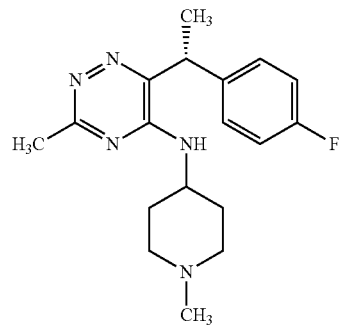 [SMILES: Cc1nnc([C@H](C)c2ccc(F)cc2)c(NC2CCN(C)CC2)n1]

and

Example 140

(S)-6-(1-(4-fluorophenyl)ethyl)-3-methyl-N-(1-methylpiperidin-4-yl)-1,2,4-triazin-5-amine

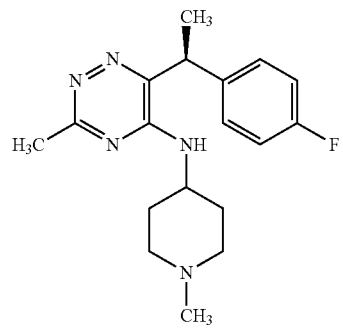 [SMILES: Cc1nnc([C@@H](C)c2ccc(F)cc2)c(NC2CCN(C)CC2)n1]

The title compounds were prepared like EXAMPLE 132 in which a mixture of 6-(1-(4-fluorophenyl)ethyl)-3-methyl-5-(methylthio)-1,2,4-triazine (250 mg, 189.88 μmol), 1-methylpiperidin-4-amine (433.65 mg, 3.80 mmol) and DIPEA (73.62 mg, 569.64 μmol, 99.49 μL) in DMSO (500 μL) was stirred at 130° C. for 16 hours. Preparative HPLC purification gave racemic 6-(1-(4-fluorophenyl)ethyl)-3-methyl-N-(1-methylpiperidin-4-yl)-1,2,4-triazin-5-amine (30 mg, 91.07 μmol), which was resolved by chiral SFC (AD column 10 μm, 30 mm ID×250 mm, 30% IPA+0.1% NH$_4$OH) to give two enantiomers. The early-eluting enantiomer was assigned R-stereochemical configuration. $^1$H NMR (400 MHz, CD$_3$OD) δ ppm 1.66 (d, J=6.8 Hz, 4H), 1.71-1.87 (m, 2H), 2.15 (br d, J=13.2 Hz, 1H), 2.47 (s, 3H), 2.62 (s, 3H), 2.69-2.87 (m, 2H), 2.97-3.13 (m, 1H), 3.14-3.24 (m, 1H), 4.13-4.22 (m, 1H), 4.45 (q, J=6.8 Hz, 1H), 6.99-7.07 (m, 2H), 7.24-7.30 (m, 2H); ESI-MS m/z [M+H]$^+$ 330.0. The later-eluting enantiomer was assigned S-stereochemical configuration. $^1$H NMR (400 MHz, CD$_3$OD) δ ppm 1.43-1.58 (m, 1H), 1.66 (d, J=7.1 Hz, 5H), 2.02 (br d, J=13.7 Hz, 1H), 2.20-2.39 (m, 5H), 2.46 (s, 3H), 2.85 (br s, 2H), 3.99-4.09 (m, 1H), 4.42 (q, J=6.9 Hz, 1H), 4.60 (br s, 1H), 7.03 (t, J=8.7 Hz, 2H), 7.26 (dd, J=8.7, 5.4 Hz, 2H); ESI-MS m/z [M+H]$^+$ 330.0.

Example 141

6-((R)-1-(4-fluorophenyl)ethyl)-3-methyl-N-((R)-1-methylpyrrolidin-3-yl)-1,2,4-triazin-5-amine

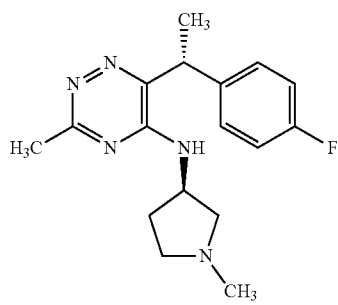 [SMILES: Cc1nnc([C@H](C)c2ccc(F)cc2)c(N[C@@H]2CCN(C)C2)n1]

and

Example 142

6-((S)-1-(4-fluorophenyl)ethyl)-3-methyl-N-((R)-1-methylpyrrolidin-3-yl)-1,2,4-triazin-5-amine

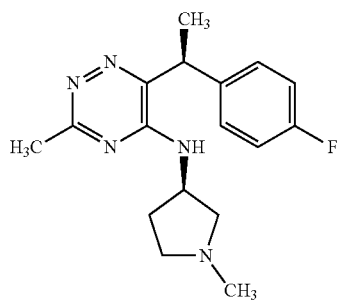 [SMILES: Cc1nnc([C@@H](C)c2ccc(F)cc2)c(N[C@@H]2CCN(C)C2)n1]

Step A: mixture of tert-butyl (R)-3((6-((R)-1-(4-fluorophenyl)ethyl)-3-methyl-1,2,4-triazin-5-yl)amino)pyrrolidine-1-carboxylate and tert-butyl (R)-3-((6-((S)-1-(4-fluorophenyl)ethyl)-3-methyl-1,2,4-triazin-5-yl)amino)pyrrolidine-1-carboxylate

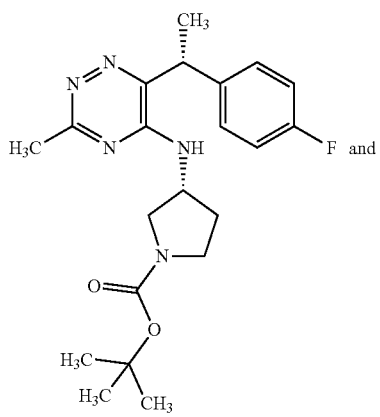

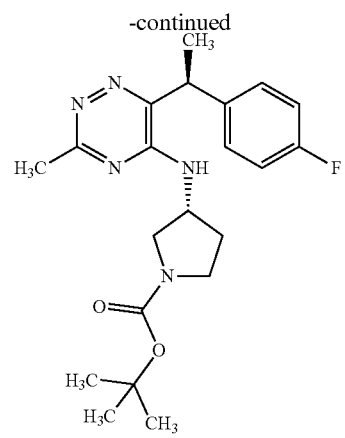

The title compounds were prepared like EXAMPLE 132 in which a mixture of 6-(1-(4-fluorophenyl)ethyl)-3-methyl-5-(methylthio)-1,2,4-triazine (100 mg, 379.75 tert-butyl (3R)-3-aminopyrrolidine-1-carboxylate (5.91 mmol) and DIPEA (147.24 mg, 1.14 mmol, 198.97 μL) in DMSO (1 mL) was stirred at 130° C. for 30 hours. The reaction mixture was purified by preparative HPLC (Phenomenex Gemini® 10 μm, 25 mm ID×150 mm) using a gradient of 45-75% ACN in water (0.05% NH$_4$OH) to give a mixture of the title compounds as a white solid (35.0 mg, 22%). $^1$H NMR (400 MHz, CDCl$_3$) δ ppm 1.47 (br s, 9H), 1.67 (br dd, J=12.2, 7.2 Hz, 1H), 1.74 (br d, J=7.1 Hz, 3H), 2.10 (br s, 1H), 2.58 (s, 3H), 3.01 (br s, 1H), 3.18-3.28 (m, 1H), 3.19-3.62 (m, 1H), 3.34 (br s, 1H), 3.41 (br s, 1H), 3.51 (br s, 1H), 4.09 (br s, 1H), 4.42-4.66 (m, 2H), 7.01-7.09 (m, 2H), 7.14-7.22 (m, 2H).

Step B: Mixture of 6-((R)-1-(4-fluorophenyl)ethyl)-3-methyl-N-((R)-pyrrolidin-3-yl)-1,2,4-triazin-5-amine and 6-((S)-1-(4-fluorophenyl)ethyl)-3-methyl-N-((R)-pyrrolidin-3-yl)-1,2,4-triazin-5-amine

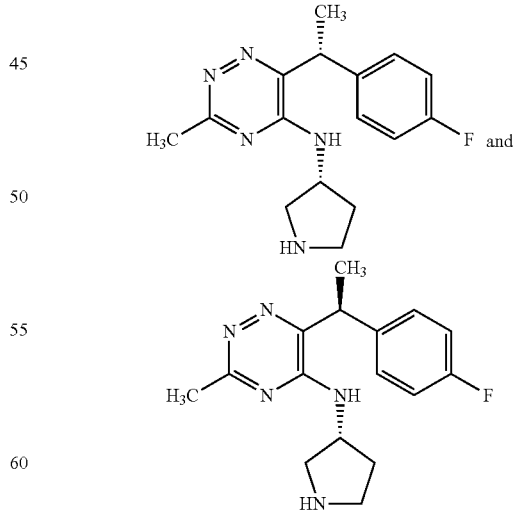

To a round bottom flask charged with a mixture of tert-butyl (R)-3-((6-((R)-1-(4-fluorophenyl)ethyl)-3-methyl-1,2,4-triazin-5-yl)amino)pyrrolidine-1-carboxylate and tert-butyl (R)-3-((6-((S)-1-(4-fluorophenyl)ethyl)-3- methyl-1,2,4-triazin-5-yl)amino)pyrrolidine-1-carboxylate (35 mg, 87.18 μmol) in EtOAc (2 mL) was added 4 M HCl in EtOAc (218 μL). The reaction mixture was stirred at 20° C. for 10 hours and then concentrated in vacuo. The crude material was dissolved in water (2 mL) and then acidified to pH 8~9 with saturated aq NaHCO₃ (1 mL). The mixture was stirred at 20° C. for 10 minutes and extracted with EtOAc (20 mL×2). The combined organic layers were dried over Na₂SO₄, filtered and concentrated in vacuo to give the title compound as a light-yellow gum, which was used without further purification. ESI-MS m/z [M+H]⁺ 302.0.

Step C: 6-((R)-1-(4-fluorophenyl)ethyl)-3-methyl-N-((R)-1-methylpyrrolidin-3-yl)-1,2,4-triazin-5-amine and 6-((S)-1-(4-fluorophenyl)ethyl)-3-methyl-N-((R)-1-methylpyrrolidin-3-yl)-1,2,4-triazin-5-amine To a round bottom flask charged with a mixture of 6-((R)-1-(4-fluorophenyl)ethyl)-3-methyl-N-((R)-pyrrolidin-3-yl)-1,2,4-triazin-5-amine and 6-((S)-1-(4-fluorophenyl)ethyl)-3-methyl-N-((R)-pyrrolidin-3-yl)-1,2,4-triazin-5-amine (30 mg, 99.6 μmol) in DCM (2 mL) were added formaldehyde (29.89 mg, 398.19 μmol, 40% q) and NaBH(OAc)₃ (84.39 mg, 398.19 μmol). The reaction mixture was stirred at 20° C. for 1 hour and then quenched with water (5 mL) and saturated aq NaHCO₃ (2 mL) and extracted with DCM (10 mL×2). The combined organic layers were washed with brine (30 mL×3), dried over Na₂SO₄, filtered and concentrated in vacuo. The product was purified by preparative HPLC (Phenomenex Gemini® 10 μm, 25 mm ID×150 mm) using a gradient of 25-55% ACN in water (0.05% NH₄OH) to give a pair of diastereoisomers. The early-eluting diastereoisomer was assigned as 6-((R)-1-(4-fluorophenyl)ethyl)-3-methyl-N-((R)-1-methylpyrrolidin-3-yl)-1,2,4-triazin amine and was obtained as a light-yellow gum (8.0 mg, 25%). ¹H NMR (400 MHz, CD₃OD) δ ppm 1.66 (d, J=6.8 Hz, 3H), 1.70-1.81 (m, 1H), 2.24 (dd, J=10.3, 4.5 Hz, 1H), 2.30-2.39 (m, 4H), 2.44-2.55 (m, 4H), 2.69-2.80 (m, 2H), 4.40 (q, J=6.8 Hz, 1H), 4.54-4.64 (m, 1H), 6.99-7.07 (m, 2H), 7.24-7.31 (m, 2H); ESI-MS m/z [M+H]⁺ 316.2. The later-eluting diastereoisomer was assigned as 6-((S)-1-(4-fluorophenyl)ethyl)-3-methyl-N-((R)-1-methylpyrrolidin-3-yl)-1,2,4-triazin-5-amine. ¹H NMR (400 MHz, CD₃OD) δ ppm 1.38-1.49 (m, 1H), 1.65 (d, J=6.8 Hz, 3H), 2.15-2.27 (m, 1H), 2.34-2.43 (m, 4H), 2.45 (s, 3H), 2.54 (dd, J=10.1, 4.2 Hz, 1H), 2.68-2.79 (m, 2H), 4.37 (q, J=7.0 Hz, 1H), 4.55-4.65 (m, 1H), 7.02 (t, J=8.7 Hz, 2H), 7.23-7.29 (m, 2H); ESI-MS m/z [M+H]⁺ 316.2.

Example 143

N-(2-(azetidin-1-yl)ethyl)-3-methyl-6-(1-phenylethyl)-1,2,4-triazin-5-amine

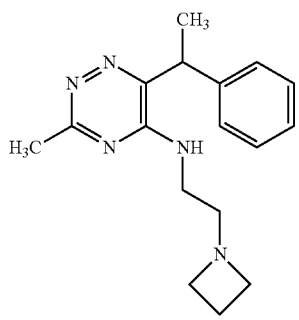 [SMILES: Cc1nnc(C(C)c2ccccc2)c(NCCN2CCC2)n1]

The title compound was prepared like EXAMPLE 132 in which a mixture of 3-methyl-5-methylsulfanyl-6-(1-phenylethyl)-1,2,4-triazine (220 mg, 896.71 μmol, prepared like PREPARATION 46), 2-(azetidin-1-yl)ethanamine (300.88 mg, 3.00 mmol) and DIPEA (354.63 mg, 2.74 mmol, 479.22 μL) in DMSO (1.2 mL) was stirred at 100° C. for 40 hours. The reaction mixture was purified by preparative HPLC (Phenomenex Gemini® 10 μm, 25 mm ID×150 mm) using a gradient of 20-50% ACN in water (0.05% NH₄OH) to give the title compound as a light-yellow gum (89.8 mg, 33%). ¹H NMR (400 MHz, CD₃OD) δ ppm 1.67 (d, J=7.0 Hz, 3H), 2.03 (quin, J=7.2 Hz, 2H), 2.47 (s, 3H), 2.48-2.57 (m, 2H), 3.04-3.18 (m, 4H), 3.36 (t, J=6.3 Hz, 2H), 4.28 (q, J=6.9 Hz, 1H), 7.14-7.36 (m, 5H); ESI-MS m/z [M+H]⁺ 298.2.

Example 144

(R)-N-(2-(azetidin-1-yl)ethyl)-3-methyl-6-(1-phenylethyl)-1,2,4-triazin-5-amine

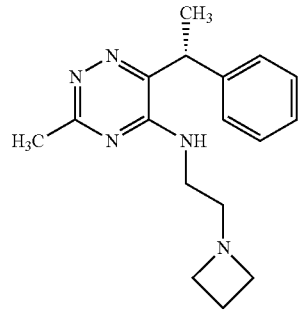 [SMILES: Cc1nnc([C@H](C)c2ccccc2)c(NCCN2CCC2)n1]

and

Example 145

(S)-N-(2-(azetidin-1-yl)ethyl)-3-methyl-6-(1-phenylethyl)-1,2,4-triazin-5-amine

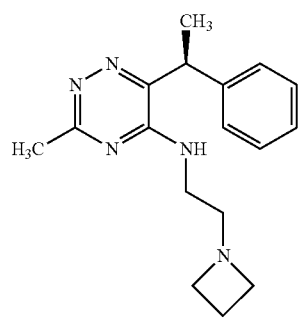 [SMILES: Cc1nnc([C@@H](C)c2ccccc2)c(NCCN2CCC2)n1]

Racemate N-(2-(azetidin-1-yl)ethyl)-3-methyl-6-(1-phenylethyl)-1,2,4-triazin-5-amine (89 mg) was resolved by chiral SFC (OZ column, 95 mL/minute, 10% IPA+0.1% DEA) to give two enantiomers. The early-eluting enantiomer was assigned R-stereochemical configuration and the later-eluting enantiomer was assigned S-stereochemical configuration.

Example 146

6-((R)-1-(4-fluorophenyl)ethyl)-3-methyl-N-((S)-1-methylpyrrolidin-3-yl)-1,2,4-triazin-5-amine

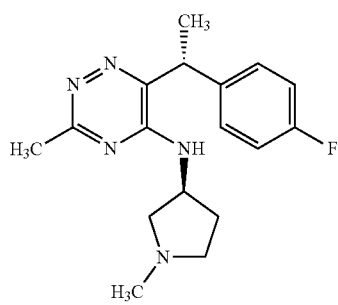 [SMILES: Cc1nnc([C@H](C)c2ccc(F)cc2)c(N[C@H]2CCN(C)C2)n1]

and

Example 147

6-((S)-1-(4-fluorophenyl)ethyl)-3-methyl-N-((S)-1-methylpyrrolidin-3-yl)-1,2,4-triazin-5-amine

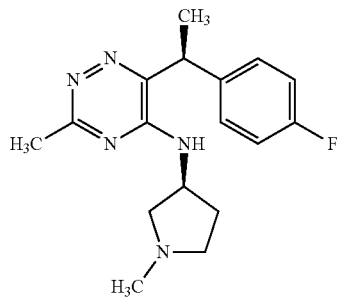 [SMILES: Cc1nnc([C@@H](C)c2ccc(F)cc2)c(N[C@H]2CCN(C)C2)n1]

A mixture of PyBroP® (2.278 g, 4.89 mmol), 6-(1-(4-fluorophenyl)ethyl)-3-methyl-1,2,4-triazin-5(4H)-one (1.036 g, 4.44 mmol), and (S)-1-methylpyrrolidin-3-amine (0.534 g, 5.33 mmol) in DCM (17.77 mL) was sonicated to dissolve the reactants. DIPEA (1.939 mL, 11.10 mmol) was added. The reaction mixture was stirred at room temperature for 26 hours and then concentrated, taken up in MeOH, filtered and purified by preparative HPLC to give a pair of diastereoisomers. The early-eluting diastereoisomer was assigned as 6-((R)-1-(4-fluorophenyl)ethyl)-3-methyl-N-((S)-1-methylpyrrolidin-3-yl)-1,2,4-triazin-5-amine and was obtained as a light-orange semisolid (0.23 g, 16.4%). $^1$H NMR (500 MHz, DMSO-$d_6$) δ ppm 1.43-1.61 (m, 3H), 1.62-1.79 (m, 1H), 2.06-2.23 (m, 5H), 2.27-2.43 (m, 4H), 2.50-2.58 (m, 1H), 2.59-2.67 (m, 1H), 4.32-4.47 (m, 1H), 4.56-4.73 (m, 1H), 6.99-7.18 (m, 3H), 7.25-7.39 (m, 2H); ESI-MS m/z [M+H]$^+$ 316.10. The later-eluting diastereoisomer was assigned as 64-((S)-1-(4-fluorophenyl)ethyl)-3-methyl-N-((S)-1-methylpyrrolidin-3-yl)-1,2,4-triazin-5-amine and was obtained as light-orange semisolid (0.107 g, 7.64%). $^1$H NMR (500 MHz, DMSO-$d_6$) δ ppm 1.46-1.66 (m, 4H) 1.93-2.13 (m, 1H) 2.23 (s, 3H) 2.28-2.36 (m, 4H) 2.36-2.44 (m, 1H) 2.55 (td, J=8.42, 5.61 Hz, 1H) 2.61-2.72 (m, 1H) 4.28-4.43 (m, 1H) 4.57-4.70 (m, 1H) 6.98-7.13 (m, 2H) 7.17 (d, J=6.83 Hz, 1H) 7.24-7.37 (m, 2H); ESI-MS m/z [M+H]$^+$ 316.10.

Example 148

N-(2-(azetidin-1-yl)ethyl)-3-methyl-6-(3-methylbenzyl)-1,2,4-triazin-5-amine

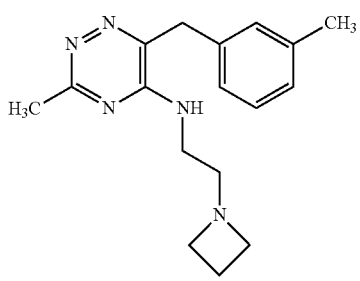

A mixture of 3-methyl-6-(3-methylbenzyl)-5-(methylthio)-1,2,4-triazine (28.0 mg, 110 μmol), 2-(azetidin-1-yl)ethanamine (54.9 mg, 548 μmol) and DIPEA (42.5 mg, 329 μmol) in DMSO (250 μL) was stirred at 100° C. for 16 hours. The reaction mixture was purified by preparative HPLC (Xtimate® C18, 5 μm, 25 mm ID×150 mm) using a gradient of 20-50% ACN in water (0.05% NH$_4$OH) to give the title compound as a light-yellow gum (2.0 mg, 6.1%). $^1$H NMR (400 MHz, CD$_3$OD) δ ppm 2.05 (br t, J=7.0 Hz, 2H), 2.29 (s, 3H), 2.47 (s, 2H), 2.42-2.50 (m, 1H), 2.57 (br t, J=6.0 Hz, 2H), 3.17 (br t, J=6.8 Hz, 4H), 3.42 (br t, J=6.0 Hz, 2H), 4.10 (s, 2H), 6.97-7.10 (m, 3H), 7.12-7.24 (m, 1H); ESI-MS m/z [M+H]$^+$ 298.2.

Example 149

3-methyl-N-((R)-1-methylpyrrolidin-3-yl)-6-((R)-1-phenylethyl)-1,2,4-triazin-5-amine

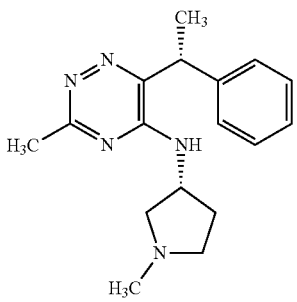 [SMILES: Cc1nnc([C@H](C)c2ccccc2)c(N[C@@H]2CCN(C)C2)n1]

and

Example 150

3-methyl-N-((R)-1-methylpyrrolidin-3-yl)-6-((S)-1-phenylethyl)-1,2,4-triazin-5-amine

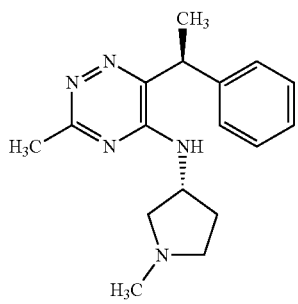 [SMILES: Cc1nnc([C@@H](C)c2ccccc2)c(N[C@@H]2CCN(C)C2)n1]

To a solution of 3-methyl-6-(1-phenylethyl)-1,2,4-triazin-5(4H)-one (0.093 g, 0.432 mmol) and DBU (0.130 mL, 0.864 mmol) in ACN (2.88 mL) was added PyBOP (0.304 g, 0.583 mmol). The resulting mixture was stirred at room temperature for 30 minutes and then heated to 80° C. for 30 minutes and allowed to cool to room temperature. Next, (R)-1-methylpyrrolidin-3-amine (0.104 g, 1.037 mmol) was added. The reaction mixture was heated to 80° C. for 1 hour and then diluted with DMF and MeOH, filtered, and purified by preparative HPLC (Xtimate® C18, 5 μm, 25 mm ID×150 mm) using a gradient of 20-50% ACN in water (0.05% NH$_4$OH) to give the title compound as a mixture of two diastereoisomers that were separated by chiral SFC. The early-eluting diastereoisomer was assigned as 3-methyl-N-((R)-1-methylpyrrolidin-3-yl)-6-((R)-1-phenylethyl)-1,2,4-triazin-5-amine and was obtained as a yellow film (6.1 mg, 4.7%). $^1$H NMR (500 MHz, CD$_3$OD) δ ppm 1.32-1.35 (m, 1H), 1.68 (d, J=5.6 Hz, 3H), 1.85 (t, J=0.4 Hz, 1H), 2.35 (s, 3H), 2.35-2.34 (m, 1H), 2.47 (s, 3H), 2.48-2.47 (m, 1H), 3.31-3.30 (m, 1H), 3.32-3.30 (m, 1H), 4.34-4.32 (m, 1H), 4.60-4.59 (m, 1H), 7.31-7.25 (m, 2h), 7.25-7.23 (m, 3H); ESI-MS m/z [M+H]$^+$ 298.4. The later-eluting diastereoisomer was assigned as 3-methyl-N-((R) methylpyrrolidin-3-yl)-6-((S)-1-phenylethyl)-1,2,4-triazin-5-amine and was obtained as a yellow-orange film (5.2 mg, 4.0%). $^1$H NMR (500 MHz, CD$_3$OD) δ ppm 1.65-1.64 (m, 1H), 1.68 (d, J=6.56 Hz, 3H), 1.82 (t, J=0.4 Hz, 1H), 2.25-2.15 (m, 1H), 2.29 (s, 3H), 2.29-2.28(m, 1H), 2.47 (s, 3H), 2.48-2.47 (m, 1H), 2.65-2.64 (m, 1H), 2.70-2.69 (m, 1H), 3.32-3.30 (m, 1H), 4.34-4.32 (m, 1H), 4.60-4.59 (m, 1H), 7.31-7.25 (m, 2h), 7.25-7.23 (m, 3H); ESI-MS m/z [M+H]$^+$ 298.4.

Example 151

3-methyl-N-((S)-1-methylpyrrolidin-3-yl)-6-((R)-1-phenylethyl)-1,2,4-triazin-5-amine

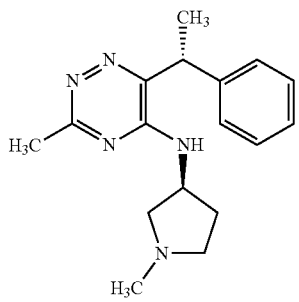 [SMILES: Cc1nnc([C@H](C)c2ccccc2)c(N[C@H]2CCN(C)C2)n1]

and

Example 152

3-methyl-N-((S)-1-methylpyrrolidin-3-yl)-6-((S)-1-phenylethyl)-1,2,4-triazin-5-amine

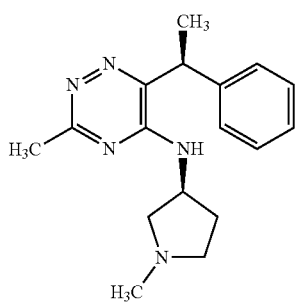 [SMILES: Cc1nnc([C@@H](C)c2ccccc2)c(N[C@H]2CCN(C)C2)n1]

The title compounds were prepared like EXAMPLE 149 and EXAMPLE 150, using 3-methyl-6-(1-phenylethyl)-1,2,4-triazin-5(4H)-one (0.150 g, 0.697 mmol) and (5)-1-methylpyrrolidin-3-amine (0.168 g, 1.672 mmol) to give two diastereomers. The early-eluting diastereoisomer was assigned as 3-methyl-N-((S)-1-methylpyrrolidin-3-yl)-6-((R)-1-phenylethyl)-1,2,4-triazin-5-amine. $^1$H NMR (500 MHz, CD$_3$OD) δ ppm 1.67 (d, J=6.83 Hz, 3H) 1.69-1.77 (m, 1H), 2.16 (dd, J=10.25, 4.88 Hz, 1H), 2.26-2.38 (m, 4H), 2.42-2.48 (m, 3H), 2.51 (ddd, J=9.40, 7.93, 6.59 Hz, 1H), 2.63-2.72 (m, 1H), 2.75 (dd, J=10.25, 6.83 Hz, 1H), 4.31-4.42 (m, 1H), 4.49-4.61 (m, 1H), 7.14-7.36 (m, 5H); ESI-MS m/z [M+H]$^+$ 298.2. The later-eluting diastereoisomer was assigned as 3-methyl-N-((S)-1-methylpyrrolidin-3-yl)-6-((S)-1-phenylethyl)-1,2,4-triazin-5-amine. $^1$H NMR (500 MHz, CD$_3$OD) δ ppm 1.29-1.43 (m, 1H), 1.68 (d, J=7.32 Hz, 3H), 2.08-2.24 (m, 1H), 2.31-2.42 (m, 4H), 2.46 (s, 3H), 2.52 (dd, J=10.01, 4.15 Hz, 1H), 2.68 (td, J=8.91, 5.13 Hz, 1H), 2.72-2.79 (m, 1H), 4.34 (q, J=6.83 Hz, 1H), 4.52-4.64 (m, 1H), 7.17-7.34 (m, 5H); ESI-MS m/z [M+H]$^+$ 298.2.

Example 153

3-methyl-N-(1-methylpiperidin-4-yl)-6-(1-phenylethyl)-1,2,4-triazin-5-amine

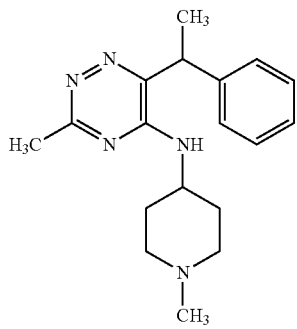 [SMILES: Cc1nnc(C(C)c2ccccc2)c(NC2CCN(C)CC2)n1]

The title compound (0.177 g, 60%) was prepared like EXAMPLE 149 and EXAMPLE 150, using 3-methyl-6-(1-phenylethyl)-1,2,4-triazin-5(4H)-one (3-methyl-6-(1-phenylethyl)-1,2,4-triazin-5(4H)-one (0.204 g, 0.948 mmol, 1 eq) and 1-methylpiperidin-4-amine (0.260 g, 2.275 mmol). $^1$H NMR (500 MHz, DMSO-$d_6$) δ ppm 1.41-1.48 (m, 2H), 1.51-1.56 (m, 1H), 1.55-1.62 (m, 3H), 1.69-1.76 (m, 2H), 1.76-1.83 (m, 1H), 1.83-1.91 (m, 1H), 1.91-2.02 (m, 1H), 2.07-2.08 (m, 2H), 2.10 (s, 3H), 2.35 (s, 3H), 2.57-2.70 (m, 1H), 2.93-3.07 (m, 2H), 3.73-3.90 (m, 1H), 4.56 (q, J=7.16 Hz, 1H), 4.50-4.64 (m, 1H), 6.65 (d, J=5.86 Hz, 1H), 7.12-7.22 (m, 1H), 7.23-7.35 (m, 4H).

Example 154

(S)-3-methyl-N-(1-methylpiperidin-4-yl)-6-(1-phenylethyl)-1,2,4-triazin-5-amine

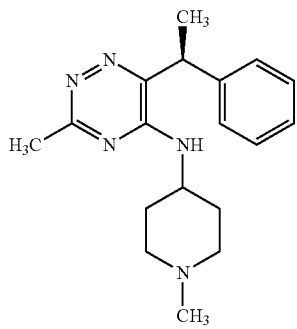 [SMILES: Cc1nnc([C@@H](C)c2ccccc2)c(NC2CCN(C)CC2)n1]

and

Example 155

(R)-3-methyl-N-(1-methylpiperidin-4-yl)-6-(1-phenylethyl)-1,2,4-triazin-5-amine

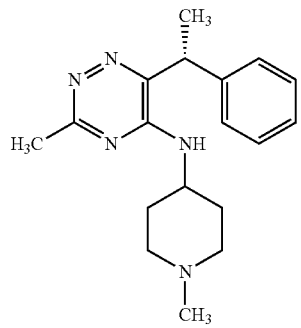

Racemate 3-methyl-N-(1-methylpiperidin-4-yl)-6-(1-phenylethyl)-1,2,4-triazin-5-amine (0.177 g) was separated by chiral SFC to provide two enantiomers. The early-eluting enantiomer was assigned as (R)-3-methyl-N-(1-methylpiperidin-4-yl)-6-(1-phenylethyl)-1,2,4-triazin-5-amine (37 mg, 21% recovery rate). $^1$H NMR (500 MHz, CD$_3$OD) δ ppm 1.34-1.49 (m, 1H), 1.52-1.64 (m, 2H), 1.67 (d, J=6.83 Hz, 3H), 1.91-2.02 (m, 1H), 2.09-2.19 (m, 1H), 2.20-2.34 (m, 4H), 2.42-2.51 (m, 3H), 2.61-2.83 (m, 1H), 3.91-4.07 (m, 1H), 4.31-4.44 (m, 1H), 7.18-7.27 (m, 3H), 7.27-7.38 (m, 2H); ESI-MS m/z [M+H]$^+$ 312.2. The later-eluting enantiomer was assigned as (S)-3-methyl-N-(1-methylpiperidin-4-yl)-6-(1-phenylethyl)-1,2,4-triazin-5-amine (38 mg, 21% recovery rate). $^1$H NMR (500 MHz, CD$_3$OD) δ ppm 1.33-1.49 (m, 1H), 1.53-1.64 (m, 2H), 1.65-1.70 (m, 3H), 1.92-2.01 (m, 1H), 2.10-2.18 (m, 1H), 2.25 (s, 4H), 2.46 (s, 3H), 2.64-2.82 (m, 1H), 3.33-3.37 (m, 5H), 3.93-4.04 (m, 1H), 4.33-4.40 (m, 1H), 7.20-7.27 (m, 3H), 7.27-7.36 (m, 2H); ESI-MS m/z [M+H]$^+$ 312.3.

Example 156

6-(1-(4-fluorophenyl)ethyl)-3-methyl-N-(2-(pyrrolidin-1-yl)ethyl)-1,2,4-triazin-5-amine

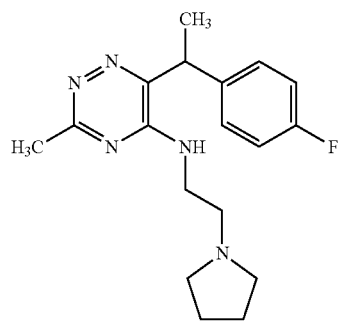 [SMILES: Cc1nnc(C(C)c2ccc(F)cc2)c(NCCN2CCCC2)n1]

To a 10 mL round-bottomed flask were added 6-(1-(4-fluorophenyl)ethyl)-3-methyl-1,2,4-triazin-5(4H)-one (0.1 g, 0.429 mmol), PyBroP® (0.220 g, 0.472 mmol), 2-(pyrrolidin-1-yl)ethan-1-amine (0.059 g, 0.514 mmol) and DCM (4.30 mL). To the resulting yellow solution was added DIPEA (0.187 mL, 1.072 mmol). The reaction mixture was stirred at room temperature overnight and then filtered and purified by preparative HPLC (Phenomenex Gemini® C18, 5 μm, 30 mm ID×150 mm) using a gradient of 10-50% ACN (0.035% TFA) in water (0.05% TFA) to give a TFA salt of the title compound (83.7 mg, 44.0%). $^1$H NMR (400 MHz, CD$_3$OD) δ ppm 1.66 (d, J=7.03 Hz, 3H), 1.75 (s, 4H), 2.40-2.49 (m, 7H), 2.50-2.69 (m, 2H), 3.46-3.62 (m, 2H), 4.26-4.36 (m, 1H), 7.01 (s, 2H), 7.21-7.30 (m, 2H); ESI-MS m/z [M+H]$^+$ 330.5.

Example 157

(R)-6-(1-(4-fluorophenyl)ethyl)-3-methyl-N-(2-(pyrrolidin-1-yl)ethyl)-1,2,4-triazin-5-amine

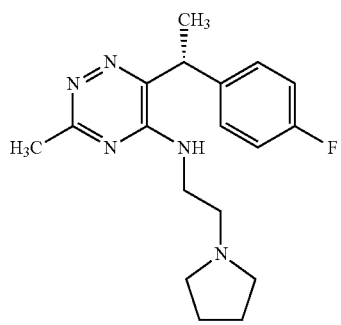 [SMILES: Cc1nnc([C@H](C)c2ccc(F)cc2)c(NCCN2CCCC2)n1]

and

Example 158

(S)-6-(1-(4-fluorophenyl)ethyl)-3-methyl-N-(2-(pyrrolidin-1-yl)ethyl)-1,2,4-triazin-5-amine

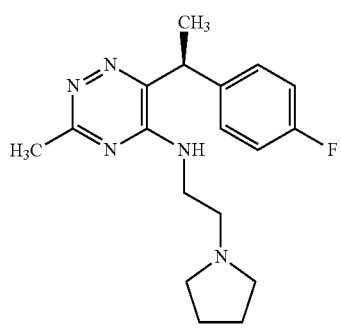 [SMILES: Cc1nnc([C@@H](C)c2ccc(F)cc2)c(NCCN2CCCC2)n1]

Racemate 6-(1-(4-fluorophenyl)ethyl)-3-methyl-N-(2-(pyrrolidin-1-yl)ethyl)-1,2,4-triazin-5-amine (488.9 mg, 1.484 mmol, scaled-up using the same procedure as in EXAMPLE 156) was resolved by chiral SFC to give two enantiomers. The early-eluting enantiomer was assigned R-stereochemical configuration (212.7 mg, 43.5%). $^1$H NMR (400 MHz, CD$_3$OD) δ ppm 1.94-2.07 (m, 2H), 2.10-2.22 (m, 2H), 3.05-3.18 (m, 2H), 3.42-3.51 (m, 2H), 3.71-3.81 (m, 2H), 3.81-3.86 (m, 2H), 3.90 (s, 2H), 6.98-7.03 (m, 1H), 7.08 (s, 2H), 7.20-7.26 (m, 2H), 7.27-7.32 (m, 1H); ESI-MS m/z [M+H]$^+$ 330.5. The later-eluting enantiomer was assigned S-stereochemical configuration (218.1 mg, 44.6%). $^1$H NMR (400 MHz, CD$_3$OD) δ ppm 1.94-2.07 (m, 2H), 2.10-2.22 (m, 2H), 3.05-3.18 (m, 2H), 3.42-3.51 (m, 2H), 3.71-3.81 (m, 2H), 3.81-3.86 (m, 2H), 3.90 (s, 2H), 6.98-7.03 (m, 1H), 7.08 (s, 2H), 7.20-7.26 (m, 2H), 7.27-7.32 (m, 1H); ESI-MS m/z [M+H]+330.5.

Table 1 lists biological assay data (SSTR4 activity, SSTR4 binding, and SSTR1 binding) for some of the compounds shown in the examples, where larger pEC$_{50}$ and pIC$_{50}$ values represent higher activity or potency. The compounds shown in Table 1 were tested in accordance with a cell-based assay which measures the inhibition of forskolin stimulated cAMP in cells overexpressing SSTR4 (reported as pEC$_{50}$). Many of the compounds shown in Table 1 were also tested in accordance with membrane-based assays which measure competitive binding of the compounds to SSTR4 and SSTR1 (reported as pIC$_{50}$). These assays are described in the section entitled Biological Activity, above.

TABLE 1

Biological Assay Data

| EXAMPLE No. | SSTR4 Activity pEC$_{50}$ | SSTR4 Binding pIC$_{50}$ | SSTR1 Binding pIC$_{50}$ |
| --- | --- | --- | --- |
| 1 | 6.78 | — | — |
| 2 | 7.17 | — | — |
| 3 | 6.34 | — | — |
| 4 | 7.20 | 7.42 | 5.81 |
| 5 | 6.48 | — | — |
| 6 | 7.31 | 7.64 | 5.71 |
| 7 | 6.18 | — | — |
| 8 | 7.50 | 6.85 | 5.71 |
| 9 | 7.09 | — | — |
| 10 | 7.57 | 6.42 | 5.50 |
| 11 | 7.54 | 6.67 | 5.46 |
| 12 | 7.82 | 6.79 | 5.25 |
| 13 | 7.93 | 6.79 | 5.39 |
| 14 | 8.21 | 7.11 | 5.23 |
| 15 | 7.92 | 7.16 | 5.36 |
| 16 | 8.21 | 7.29 | 5.46 |
| 17 | 7.93 | 6.79 | 5.10 |
| 18 | 7.92 | 6.78 | 5.05 |
| 19 | 8.27 | 7.30 | 5.24 |
| 20 | 6.15 | — | — |
| 21 | 8.29 | 7.61 | 5.55 |
| 22 | 8.43 | 7.11 | 4.98 |
| 23 | 7.60 | 7.20 | 4.88 |
| 24 | 7.73 | 7.34 | 5.29 |
| 25 | 8.26 | 6.95 | 5.19 |
| 26 | 5.74 | — | — |
| 27 | 7.70 | 7.27 | 5.02 |
| 28 | 8.33 | 6.41 | 5.78 |
| 29 | — | — | — |
| 30 | 7.31 | 6.04 | 4.91 |
| 31 | 6.48 | — | — |
| 32 | 6.10 | — | — |
| 33 | 7.15 | 5.33 | 4.99 |
| 34 | 6.27 | — | — |
| 35 | 5.92 | — | — |
| 36 | 6.65 | — | — |
| 37 | 7.21 | 6.31 | 5.34 |
| 38 | 7.24 | 5.79 | 5.58 |
| 39 | 8.37 | 7.38 | 4.57 |
| 40 | 8.93 | 7.66 | 5.05 |
| 41 | 8.68 | 7.63 | 4.88 |
| 42 | 7.90 | 6.86 | 5.00 |
| 43 | 7.90 | 7.40 | 5.01 |
| 44 | 8.32 | 7.17 | 4.93 |
| 45 | 7.42 | 6.89 | 4.74 |
| 46 | 7.14 | 6.31 | 4.84 |
| 47 | 7.32 | — | — |
| 48 | 9.11 | 7.93 | 5.02 |
| 49 | 9.01 | 7.78 | 5.59 |
| 50 | 9.13 | 8.25 | 5.48 |
| 51 | 8.51 | 7.74 | 7.09 |
| 52 | 8.73 | 7.79 | 5.79 |
| 53 | 8.53 | 7.60 | 5.80 |
| 54 | 7.63 | 6.92 | 4.62 |
| 55 | 7.86 | — | — |

TABLE 1-continued

Biological Assay Data

| EXAMPLE No. | SSTR4 Activity pEC$_{50}$ | SSTR4 Binding pIC$_{50}$ | SSTR1 Binding pIC$_{50}$ |
|---|---|---|---|
| 56 | 8.12 | — | — |
| 57 | 7.39 | — | — |
| 58 | 8.57 | 7.88 | 5.46 |
| 59 | 8.88 | 7.54 | 5.53 |
| 60 | 8.31 | 7.39 | 5.80 |
| 61 | 7.80 | 7.69 | 5.82 |
| 62 | 8.37 | 7.84 | 5.85 |
| 63 | 8.87 | 7.74 | 5.27 |
| 64 | 7.86 | 7.47 | 5.90 |
| 65 | 8.79 | 7.77 | 5.47 |
| 66 | 8.38 | 7.44 | 5.46 |
| 67 | 8.77 | 8.00 | 5.44 |
| 68 | 9.17 | 7.50 | 5.45 |
| 69 | 8.06 | 6.87 | 5.62 |
| 70 | 9.16 | 7.75 | 5.14 |
| 71 | 8.37 | 7.50 | 5.61 |
| 72 | 8.47 | 7.19 | 5.32 |
| 73 | 8.01 | 7.32 | 5.96 |
| 74 | 8.49 | 7.20 | 5.36 |
| 75 | 8.69 | 7.56 | 5.28 |
| 76 | 8.11 | — | — |
| 77 | 8.05 | 6.89 | 5.39 |
| 78 | 7.90 | 7.11 | 4.55 |
| 79 | 6.64 | — | — |
| 80 | 7.72 | — | — |
| 81 | 6.62 | — | — |
| 82 | 6.97 | — | — |
| 83 | 8.11 | — | — |
| 84 | 7.34 | — | — |
| 85 | 7.88 | 6.48 | 4.99 |
| 86 | 7.10 | — | — |
| 87 | 8.30 | 7.98 | 5.43 |
| 88 | 7.79 | 6.98 | 5.35 |
| 89 | 7.80 | — | — |
| 90 | 8.88 | 8.40 | 5.15 |
| 91 | 6.18 | — | — |
| 92 | 6.94 | — | — |
| 93 | 7.11 | — | — |
| 94 | 6.82 | — | — |
| 95 | 6.13 | — | — |
| 96 | 7.56 | 7.21 | 4.96 |
| 97 | 7.44 | — | — |
| 98 | 7.11 | — | — |
| 99 | 6.97 | — | — |
| 100 | 7.02 | — | — |
| 101 | 6.78 | — | — |
| 102 | 6.40 | — | — |
| 103 | 7.65 | 6.05 | 5.47 |
| 104 | 7.26 | 6.29 | 5.30 |
| 105 | 7.03 | 5.93 | 5.16 |
| 106 | 7.84 | 6.60 | 5.42 |
| 107 | 5.00 | — | — |
| 108 | 5.00 | — | — |
| 109 | 6.30 | — | — |
| 110 | 5.69 | — | — |
| 111 | 5.00 | — | — |
| 112 | 6.26 | — | — |
| 113 | 6.09 | — | — |
| 114 | 6.24 | — | — |
| 115 | 6.66 | — | — |
| 116 | 5.00 | — | — |
| 117 | 6.65 | — | — |
| 118 | 5.00 | — | — |
| 119 | 8.06 | 6.82 | 4.92 |
| 120 | 7.26 | 6.67 | 5.05 |
| 121 | 8.36 | 7.40 | 5.86 |
| 122 | 6.24 | — | — |
| 123 | 7.68 | 6.91 | 5.48 |
| 124 | 7.44 | 6.61 | 5.46 |
| 125 | 7.37 | 7.42 | 5.91 |
| 126 | 7.53 | 6.96 | 5.58 |
| 127 | 6.65 | — | — |
| 128 | 7.09 | — | — |
| 129 | 8.00 | 7.45 | 5.64 |
| 130 | 8.10 | — | — |
| 131 | 7.16 | 5.76 | 4.36 |
| 132 | 8.71 | 7.55 | 4.32 |
| 133 | 7.37 | 6.68 | 4.52 |
| 134 | 8.66 | 7.71 | 4.82 |
| 135 | 6.89 | — | — |
| 136 | 7.46 | 6.90 | 5.15 |
| 137 | 6.85 | — | — |
| 138 | 7.79 | 7.05 | 5.30 |
| 139 | 6.67 | — | — |
| 140 | 7.70 | 7.06 | 4.92 |
| 141 | 7.67 | 7.03 | 4.59 |
| 142 | 6.92 | — | — |
| 143 | 8.37 | 7.31 | 5.00 |
| 144 | 7.42 | 6.22 | 4.73 |
| 145 | 8.76 | 7.60 | 4.84 |
| 146 | 7.56 | 7.04 | 5.00 |
| 147 | 6.65 | — | — |
| 148 | 8.00 | 7.37 | 4.82 |
| 149 | 7.40 | 6.76 | 4.89 |
| 150 | 6.44 | — | — |
| 151 | 6.50 | — | — |
| 152 | 7.57 | 6.69 | 5.00 |
| 153 | 7.32 | — | — |
| 154 | 7.00 | — | — |
| 155 | 7.50 | 6.60 | 5.00 |
| 156 | 8.28 | 7.13 | 5.29 |
| 157 | 6.51 | — | — |
| 158 | 8.17 | 7.62 | 5.28 |

As used in this specification and the appended claims, singular articles such as "a," "an," and "the," may refer to a single object or to a plurality of objects unless the context clearly indicates otherwise. Thus, for example, reference to a composition containing "a compound" may include a single compound or two or more compounds. The above description is intended to be illustrative and not restrictive. Many embodiments will be apparent to those of skill in the art upon reading the above description. Therefore, the scope of the invention should be determined with reference to the appended claims and includes the full scope of equivalents to which such claims are entitled. The disclosures of all articles and references cited in the disclosure, including patents, patent applications and publications, are herein incorporated by reference in their entirety and for all purposes.

What is claimed is:

1. A compound of Formula 1,

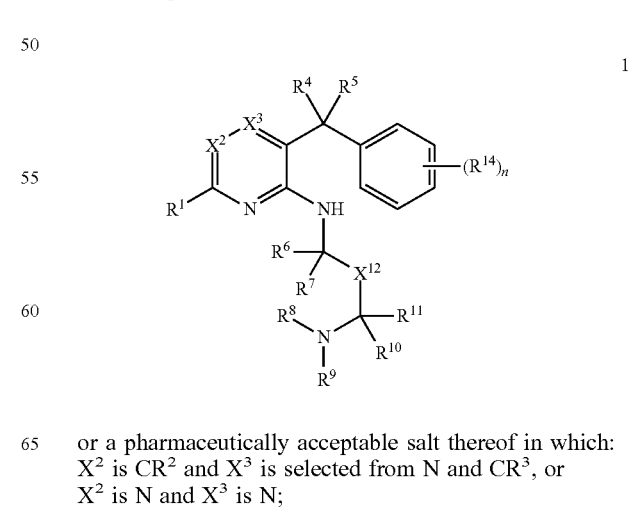

or a pharmaceutically acceptable salt thereof in which:
$X^2$ is $CR^2$ and $X^3$ is selected from N and $CR^3$, or
$X^2$ is N and $X^3$ is N;

$R^1$ and $R^2$ are each independently selected from hydrogen, halo, cyano, $R^a$, —$OR^b$, —$C(O)R^b$, —$C(O)OR^b$, —$C(O)N(R^c)R^b$ and —$C(O)N(R^c)OR^b$, or $R^1$ and $R^2$, together with the carbon atoms to which they are attached, form a benzene ring which is unsubstituted or substituted with from 1 to 4 optional substituents independently selected from halo, hydroxy, cyano, amino, and $C_{1-4}$ alkyl which at each occurrence is independently unsubstituted or substituted with from 1 to 3 optional substituents independently selected from halo; and wherein:

$R^a$ is selected from $C_{1-4}$ alkyl, $C_{3-6}$ cycloalkyl, $C_{2-6}$ heterocyclyl and $C_{1-5}$ heteroaryl, each unsubstituted or substituted with from 1 to 3 optional substituents independently selected from halo, $C_{1-4}$ alkyl and $C_{1-4}$ alkoxy, wherein the $C_{1-4}$ alkyl and $C_{1-4}$ alkoxy optional substituents are each independently unsubstituted or substituted with from 1 to 3 optional substituents independently selected from halo;

$R^b$ is selected from hydrogen and from $C_{1-4}$ alkyl, $C_{3-6}$ cycloalkyl, $C_{2-6}$ heterocyclyl and $C_{1-5}$ heteroaryl, each unsubstituted or substituted with from 1 to 3 optional substituents independently selected from halo, $C_{1-4}$ alkyl and $C_{1-4}$ alkoxy, wherein the $C_{1-4}$ alkyl and $C_{1-4}$ alkoxy optional substituents are each independently unsubstituted or substituted with from 1 to 3 optional substituents independently selected from halo; and $R^c$ is selected from hydrogen and $C_{1-4}$ alkyl;

wherein for $R^a$ and $R^b$, the $C_{2-6}$ heterocyclyl substituent is a monocyclic ring with from 3 to 8 ring members in which 1 or 2 ring members are heteroatoms, each of the heteroatoms independently selected from N, O and S, and the Cis heteroaryl substituent is a monocyclic ring with 5 or 6 ring members in which 1 to 4 ring members are heteroatoms, each of the heteroatoms independently selected from N, O, and S, provided no more than one of the ring members is O or S;

$R^3$ is selected from hydrogen, halo, cyano and $C_{1-4}$ alkyl which is unsubstituted or substituted with from 1 to 3 optional substituents independently selected from halo;

$R^4$ and $R^5$ are each independently selected from hydrogen, halo and $C_{1-4}$ alkyl which is unsubstituted or substituted with from 1 to 3 optional substituents independently selected from halo, or $R^4$ and $R^5$, together with the carbon atom to which they are both attached, form a $C_{3-5}$ cycloalkylidene;

$X^{12}$ is selected from a bond and $CR^{12}R^{13}$, and (a) $R^6$ is selected from hydrogen, halo and $C_{1-4}$ alkyl;
$R^7$ and $R^8$, together with the carbon and nitrogen atoms to which they are respectively attached, form a $C_{3-5}$ heterocyclyl having 1 ring heteroatom;
$R^9$ is selected from hydrogen and $C_{1-4}$ alkyl; and
$R^{10}$, $R^{11}$, $R^{12}$ and $R^{13}$ are each independently selected from hydrogen, halo and $C_{1-4}$ alkyl; or (b) $R^6$ and $R^7$ are each independently selected from hydrogen, halo and $C_{1-4}$ alkyl, or $R^6$ and $R^7$, together with the carbon atom to which they are both attached, form a $C_{3-5}$ cycloalkylidene;
$R^8$ and $R^9$, together with the nitrogen atom to which they are both attached, form a $C_{3-5}$ heterocyclyl which has 1 ring heteroatom and is unsubstituted or substituted with 1 to 3 optional substituents independently selected from halo and $C_{1-4}$ alkyl; and
$R^{10}$, $R^{11}$, $R^{12}$ and $R^{13}$ are each independently selected from hydrogen, halo and $C_{1-4}$ alkyl; or (c) $R^6$ and $R^7$ are each independently selected from hydrogen, halo and $C_{1-4}$ alkyl;
$R^8$ is selected from hydrogen and $C_{1-4}$ alkyl;
$R^9$ and $R^{10}$, together with the nitrogen and carbon atoms to which they are respectively attached, form a $C_{3-5}$ heterocyclyl which has 1 ring heteroatom and is unsubstituted or substituted with from 1 to 3 optional substituents independently selected from halo and $C_{1-4}$ alkyl; and
$R^{11}$, $R^{12}$ and $R^{13}$ are each independently selected from hydrogen, halo and $C_{1-4}$ alkyl;

n is selected from 0, 1, 2, 3, 4 and 5; and each $R^{14}$ is independently selected from halo, $C_{1-4}$ alkyl and $C_{1-4}$ alkoxy, wherein the $C_{1-4}$ alkyl and $C_{1-4}$ alkoxy substituents are each independently unsubstituted or substituted with from 1 to 3 optional substituents independently selected from halo;

provided if $X^2$ is $CR^2$, $X^3$ is N, $X^{12}$ is a bond, n is 1, each of $R^1$, $R^4$, $R^5$, $R^6$, $R^7$, $R^8$, and $R^{11}$ is hydrogen, $R^9$ and $R^{10}$ together with the nitrogen and carbon atoms to which they are respectively attached form an unsubstituted pyrrolidin-2-yl, and $R^{14}$ is methoxy, then $R^2$ cannot be unsubstituted pyridin-3-yl or unsubstituted pyrimidin-5-yl.

2. The compound or pharmaceutically acceptable salt according to claim 1, wherein $R^1$ and $R^2$, together with the carbon atoms to which they are attached, form a benzene ring which is unsubstituted or substituted with from 1 to 4 optional substituents independently selected from halo, hydroxy, cyano, amino, and $C_{1-4}$ alkyl which at each occurrence is independently unsubstituted or substituted with from 1 to 3 optional substituents independently selected from halo.

3. The compound or pharmaceutically acceptable salt according to claim 1, wherein $R^1$ and $R^2$ are each independently selected from hydrogen, halo, cyano, $R^a$, —$OR^b$, —$C(O)RE$, —$C(O)OR^5$, —$C(O)N(R^c)R^b$ and —$C(O)N(R^e)OR^b$.

4. The compound or pharmaceutically acceptable salt according to claim 3, wherein:

$R^a$ is selected from $C_{1-4}$ alkyl, $C_{3-6}$ cycloalkyl, $C_{3-5}$ heterocyclyl and $C_{1-5}$ heteroaryl, each unsubstituted or substituted with from 1 to 3 optional substituents independently selected from halo, $C_{1-4}$ alkyl and $C_{1-4}$ alkoxy, wherein the $C_{1-4}$ alkyl and $C_{1-4}$ alkoxy optional substituents are each independently unsubstituted or substituted with from 1 to 3 optional substituents independently selected from halo;

$R^b$ is selected from hydrogen and from $C_{1-4}$ alkyl, $C_{3-6}$ cycloalkyl, $C_{3-5}$ heterocyclyl and $C_{1-5}$ heteroaryl, each unsubstituted or substituted with from 1 to 3 optional substituents independently selected from halo, $C_{1-4}$ alkyl and $C_{1-4}$ alkoxy, wherein the $C_{1-4}$ alkyl and $C_{1-4}$ alkoxy optional substituents are each independently unsubstituted or substituted with from 1 to 3 optional substituents independently selected from halo; and $R^c$ is selected from hydrogen and $C_{1-4}$ alkyl;

wherein for $R^a$ and $R^b$, the $C_{3-5}$ heterocyclyl substituent is a monocyclic ring with from 4 to 7 ring members in which 1 or 2 ring members are heteroatoms, each of the heteroatoms independently selected from N, O and S, and the Cis heteroaryl substituent is a monocyclic ring with 5 or 6 ring members in which 1 to 4 ring members are heteroatoms, each of the heteroatoms independently selected from N, O, and S, provided no more than one of the ring members is O or S.

5. The compound or pharmaceutically acceptable salt according to claim 4, wherein for $R^a$ and $R^b$ the $C_{3-5}$ heterocyclyl substituent is selected from azetidinyl, pyrrolidinyl, piperidinyl, tetrahydrofuranyl, tetrahydropyranyl, and morpholinyl.

6. The compound or pharmaceutically acceptable salt according to claim 4, wherein for $R^a$ and $R^b$ the $C_{1-5}$ heteroaryl substituent is selected from pyrazolyl, imidazolyl, isoxazolyl, oxazolyl, isothiazolyl and thiazolyl.

7. The compound or pharmaceutically acceptable salt according to claim 1, wherein $X^2$ is $CR^2$ and $X^3$ is N.

8. The compound or pharmaceutically acceptable salt according to claim 7, wherein $R^1$ is selected from hydrogen, $R^a$, —$OR^b$, —$C(O)R^b$, —$C(O)OR^b$ and —$C(O)N(R^c)R^b$, and wherein:
   $R^a$ is selected from $C_{1-4}$ alkyl and $C_{3-6}$ cycloalkyl, each unsubstituted or substituted with from 1 to 3 optional substituents independently selected from halo, $C_{1-4}$ alkyl and $C_{1-4}$ alkoxy, wherein the $C_{1-4}$ alkyl and $C_{1-4}$ alkoxy optional substituents are each independently unsubstituted or substituted with from 1 to 3 optional substituents independently selected from halo;
   $R^b$ is selected from hydrogen and from $C_{1-4}$ alkyl and $C_{3-6}$ cycloalkyl, each unsubstituted or substituted with from 1 to 3 optional substituents independently selected from halo, $C_{1-4}$ alkyl and $C_{1-4}$ alkoxy, wherein the $C_{1-4}$ alkyl and $C_{1-4}$ alkoxy optional substituents are each independently unsubstituted or substituted with from 1 to 3 optional substituents independently selected from halo; and
   $R^c$ is selected from hydrogen and $C_{1-4}$ alkyl.

9. The compound or pharmaceutically acceptable salt according to claim 7, wherein $R^4$ and $R^5$ are each independently selected from hydrogen and methyl.

10. The compound or pharmaceutically acceptable salt according to claim 7, wherein $X^{12}$ is a bond.

11. The compound or pharmaceutically acceptable salt according to claim 7, wherein $X^{12}$ is a bond, and
   $R^6$ and $R^7$ are each independently selected from hydrogen, halo and $C_{1-4}$ alkyl, or $R^6$ and $R^7$, together with the carbon atom to which they are both attached, form a $C_{3-5}$ cycloalkylidene;
   $R^8$ and $R^9$, together with the nitrogen atom to which they are both attached, form a $C_{3-5}$ heterocyclyl which has 1 ring heteroatom and is unsubstituted or substituted with from 1 to 3 optional substituents independently selected from halo and $C_{1-4}$ alkyl; and
   $R^{10}$ and $R^{11}$ are each independently selected from hydrogen, halo and $C_{1-4}$ alkyl.

12. The compound or pharmaceutically acceptable salt according to claim 11, wherein $R^6$ and $R^7$ are each independently selected from hydrogen and methyl, or together with the carbon atom to which they are both attached, form a cyclopropylidene.

13. The compound or pharmaceutically acceptable salt according to claim 11, wherein $R^8$ and $R^9$, together with the nitrogen atom to which they are both attached, form a $C_{3-5}$ heterocyclyl which is selected from azetidinyl and pyrrolidinyl, each unsubstituted or substituted with from 1 to 3 optional substituents independently selected from halo and $C_{1-4}$ alkyl.

14. The compound or pharmaceutically acceptable salt according to claim 13, wherein $R^8$ and $R^9$, together with the nitrogen atom to which they are both attached, form a $C_{3-5}$ heterocyclyl which is selected from azetidinyl and pyrrolidinyl, each unsubstituted or substituted with from 1 or 2 fluoro.

15. The compound or pharmaceutically acceptable salt according to claim 11, wherein $R^{10}$ and $R^{11}$ are each hydrogen.

16. The compound or pharmaceutically acceptable salt according to claim 11, wherein $X^{12}$ is a bond, and
   $R^6$ and $R^7$ are each independently selected from hydrogen, halo and $C_{1-4}$ alkyl;
   $R^8$ is selected from hydrogen and $C_{1-4}$ alkyl;
   $R^9$ and $R^{10}$, together with the nitrogen and carbon atoms to which they are respectively attached, form a $C_{3-5}$ heterocyclyl which has 1 ring heteroatom and is unsubstituted or substituted with from 1 to 3 optional substituents independently selected from halo and $C_{1-4}$ alkyl; and
   $R^{11}$ is selected from hydrogen, halo and $C_{1-4}$ alkyl.

17. The compound or pharmaceutically acceptable salt according to claim 16, wherein $R^6$ and $R^7$ are each hydrogen.

18. The compound or pharmaceutically acceptable salt according to claim 16, wherein $R^8$ is selected from hydrogen and methyl.

19. The compound or pharmaceutically acceptable salt according to claim 16, wherein $R^9$ and $R^{10}$, together with the nitrogen and carbon atoms to which they are respectively attached, form an azetidinyl, which is unsubstituted or substituted with from 1 to 3 optional substituents independently selected from halo and $C_{1-4}$ alkyl.

20. The compound or pharmaceutically acceptable salt according to claim 16, wherein $R^9$ and $R^{10}$, together with the nitrogen and carbon atoms to which they are respectively attached, form a pyrrolidinyl, which is unsubstituted or substituted with from 1 to 3 optional substituents independently selected from halo and $C_{1-4}$ alkyl.

21. The compound or pharmaceutically acceptable salt according to claim 16, wherein $R^9$ and $R^{10}$, together with the nitrogen and carbon atoms to which they are respectively attached, form a piperidinyl, which is unsubstituted or substituted with from 1 to 3 optional substituents independently selected from halo and $C_{1-4}$ alkyl.

22. The compound or pharmaceutically acceptable salt according to claim 16, wherein $R^{11}$ is hydrogen.

23. The compound or pharmaceutically acceptable salt according to claim 7, wherein $X^{12}$ is $CR^{12}R^{13}$.

24. The compound or pharmaceutically acceptable salt according to claim 23, wherein $X^{12}$ is $CR^{12}R^{13}$, and
   $R^6$ is selected from hydrogen, halo and $C_{1-4}$ alkyl;
   $R^7$ and $R^8$, together with the carbon and nitrogen atoms to which they are respectively attached, form a $C_{3-5}$ heterocyclyl having 1 ring heteroatom;
   $R^9$ is selected from hydrogen and $C_{1-4}$ alkyl; and
   $R^{10}$, $R^1$, $R^{12}$ and $R^{13}$ are each independently selected from hydrogen, halo and $C_{1-4}$ alkyl.

25. The compound or pharmaceutically acceptable salt according to claim 24, wherein $R^6$ is hydrogen.

26. The compound or pharmaceutically acceptable salt according to claim 24, wherein $R^7$ and $R^8$, together with the carbon and nitrogen atoms to which they are respectively attached, form a $C_{3-5}$ heterocyclyl selected from pyrrolidinyl and piperidinyl.

27. The compound or pharmaceutically acceptable salt according to claim 24, wherein $R^9$ is selected from hydrogen and methyl.

28. The compound or pharmaceutically acceptable salt according to claim 24, wherein $R^{10}$ and $R^{11}$ are each independently selected from hydrogen and methyl.

29. The compound or pharmaceutically acceptable salt according to claim 24, wherein $R^{12}$ and $R^{13}$ are each independently selected from hydrogen, fluoro, methyl and ethyl.

30. The compound or pharmaceutically acceptable salt according to claim 7, wherein each $R^{14}$ is independently selected from halo, methyl and methoxy, and wherein the methyl and methoxy substituents are each independently unsubstituted or substituted with from 1 to 3 optional substituents independently selected from halo.

31. The compound according to claim 1, which is selected from the following compounds:
3-benzyl-N-(2-(pyrrolidin-1-yl)ethyl) quinoxalin-2-amine;
N-(2-(azetidin-1-yl)ethyl)-3-benzyl-8-methylquinoxalin-2-amine;
N-(2-(azetidin-1-yl)ethyl)-3-benzyl-5-methylquinoxalin-2-amine;
N-(2-(azetidin-1-yl)ethyl)-3-(3-methoxybenzyl)-8-methylquinoxalin-2-amine;
N-(2-(azetidin-1-yl)ethyl)-3-(3-methoxybenzyl)-5-methylquinoxalin-2-amine;
N-(2-(azetidin-1-yl)ethyl)-8-methyl-3-(3-methylbenzyl) quinoxalin-2-amine;
8-methyl-3-(3-methylbenzyl)-N-(2-(pyrrolidin-1-yl) ethyl) quinolin-2-amine;
(R)-(6-(1-(4-fluorophenyl)ethyl)-5-((2-(pyrrolidin-1-yl) ethyl)amino)pyrazin-2-yl) (pyrrolidin-1-yl)methanone;
(R)-N-cyclobutyl-6-(1-(4-fluorophenyl)ethyl)-5-((2-(pyrrolidin-1-yl)ethyl)amino)pyrazine-2-carboxamide;
(6-((R)-1-(4-fluorophenyl)ethyl)-5-((2-(pyrrolidin-1-yl) ethyl)amino)pyrazin-2-yl)((S)-3-methoxypyrrolidin-1-yl)methanone;
(6-((R)-1-(4-fluorophenyl)ethyl)-5-((2-(pyrrolidin-1-yl) ethyl)amino)pyrazin-2-yl)((R)-3-methoxypyrrolidin-1-yl)methanone;
6-((R)-1-(4-fluorophenyl)ethyl)-5-((2-(pyrrolidin-1-yl) ethyl)amino)-N-((S)-tetrahydrofuran-3-yl)pyrazine-2-carboxamide;
6-((R)-1-(4-fluorophenyl)ethyl)-5-((2-(pyrrolidin-1-yl) ethyl)amino)-N-((R)-tetrahydrofuran-3-yl)pyrazine-2-carboxamide;
6-((R)-1-(4-fluorophenyl)ethyl)-N-(cis-3-methoxycyclobutyl)-5-((2-(pyrrolidin-1-yl)ethyl)amino)pyrazine-2-carboxamide;
6-((R)-1-(4-fluorophenyl)ethyl)-N-(trans-3-methoxycyclobutyl)-5-((2-(pyrrolidin-1-yl)ethyl)amino)pyrazine-2-carboxamide 2,2,2-trifluoroacetate;
(R)-(6-(1-(4-fluorophenyl)ethyl)-5-((2-(pyrrolidin-1-yl) ethyl)amino)pyrazin-2-yl) (morpholino) methanone;
(R)-N-cyclopropyl-6-(1-(4-fluorophenyl)ethyl)-N-methyl-5-((2-(pyrrolidin-1-yl)ethyl)amino)pyrazine-2-carboxamide;
(R)-6-(1-(4-fluorophenyl)ethyl)-5-((2-(pyrrolidin-1-yl) ethyl)amino)-N-(tetrahydro-2H-pyran-4-yl)pyrazine-2-carboxamide;
6-(1-(4-fluorophenyl)ethyl)-5-((2-(pyrrolidin-1-yl)ethyl) amino)pyrazine-2-carboxamide;
(S)-6-(1-(4-fluorophenyl)ethyl)-5-((2-(pyrrolidin-1-yl) ethyl)amino)pyrazine-2-carboxamide;
(R)-6-(1-(4-fluorophenyl)ethyl)-5-((2-(pyrrolidin-1-yl) ethyl)amino)pyrazine-2-carboxamide;
6-(1-(4-fluorophenyl)ethyl)-N-methyl-5-((2-(pyrrolidin-1-yl)ethyl)amino)pyrazine-2-carboxamide;
(S)-6-(1-(4-fluorophenyl)ethyl)-N-methyl-5-((2-(pyrrolidin-1-yl)ethyl)amino)pyrazine-2-carboxamide;
(R)-6-(1-(4-fluorophenyl)ethyl)-N-methyl-5-((2-(pyrrolidin-1-yl)ethyl)amino)pyrazine-2-carboxamide;
6-(1-(4-fluorophenyl)ethyl)-N,N-dimethyl-5-((2-(pyrrolidin-1-yl)ethyl)amino)pyrazine-2-carboxamide;
(S)-6-(1-(4-fluorophenyl)ethyl)-N,N-dimethyl-5-((2-(pyrrolidin-1-yl)ethyl)amino)pyrazine-2-carboxamide;
(R)-6-(1-(4-fluorophenyl)ethyl)-N,N-dimethyl-5-((2-(pyrrolidin-1-yl)ethyl)amino)pyrazine-2-carboxamide;
5-(1-(4-fluorophenyl)ethyl)-N,N-dimethyl-6-((2-(pyrrolidin-1-yl)ethyl)amino)pyrazine-2-carboxamide;
methyl (R)-6-(1-(4-fluorophenyl)ethyl)-5-((2-(pyrrolidin-1-yl)ethyl)amino)pyrazine-2-carboxylate;
6-((R)-1-(4-fluorophenyl)ethyl)-5-(((R)-1-methylpyrrolidin-3-yl)amino)pyrazine-2-carboxamide;
6-((S)-1-(4-fluorophenyl)ethyl)-5-(((R)-1-methylpyrrolidin-3-yl)amino)pyrazine-2-carboxamide;
6-((S)-1-(4-fluorophenyl)ethyl)-N,N-dimethyl-5-(((R)-1-methylpyrrolidin-3-yl)amino)pyrazine-2-carboxamide;
6-((R)-1-(4-fluorophenyl)ethyl)-N,N-dimethyl-5-(((R)-1-methylpyrrolidin-3-yl)amino)pyrazine-2-carboxamide;
6-((S)-1-(4-fluorophenyl)ethyl)-N-methyl-5-(((R)-1-methylpyrrolidin-3-yl)amino)pyrazine-2-carboxamide;
6-((R)-1-(4-fluorophenyl)ethyl)-N-methyl-5-(((R)-1-methylpyrrolidin-3-yl)amino)pyrazine-2-carboxamide;
5-((trans-3-ethyl-1-methylpiperidin-4-yl)amino)-6-(4-fluorobenzyl)-N-methylpyrazine-2-carboxamide;
5-(1-(4-fluorophenyl)ethyl)-6-((2-(pyrrolidin-1-yl)ethyl) amino)pyrazine-2-carboxamide;
5-(1-(4-fluorophenyl)ethyl)-N-methyl-6-((2-(pyrrolidin-1-yl)ethyl)amino)pyrazine-2-carboxamide;
N,N,3-trimethyl-6-(3-methylbenzyl)-5-((2-(pyrrolidin-1-yl)ethyl)amino)pyrazine-2-carboxamide;
N,3-dimethyl-6-(3-methylbenzyl)-5-((2-(pyrrolidin-1-yl) ethyl)amino)pyrazine-2-carboxamide;
3-methyl-6-(3-methylbenzyl)-5-((2-(pyrrolidin-1-yl) ethyl)amino)pyrazine-2-carboxamide;
6-(4-fluorobenzyl)-N,N,3-trimethyl-5-((2-(pyrrolidin-1-yl)ethyl)amino)pyrazine-2-carboxamide;
6-(4-fluorobenzyl)-N,3-dimethyl-5-((2-(pyrrolidin-1-yl) ethyl)amino)pyrazine-2-carboxamide;
6-(4-fluorobenzyl)-N,3-dimethyl-5-((2-(pyrrolidin-1-yl) ethyl)amino)pyrazine-2-carboxamide;
5-((trans-1,3-dimethylpiperidin-4-yl)amino)-6-(4-fluorobenzyl)-3-methylpyrazine-2-carboxamide;
5-((trans-1,3-dimethylpiperidin-4-yl)amino)-6-(4-fluorobenzyl)-N,3-dimethylpyrazine-2-carboxamide;
5-((trans-1,3-dimethylpiperidin-4-yl)amino)-6-(4-fluorobenzyl)-N,N,3-trimethylpyrazine-2-carboxamide;
6-(1-(4-fluorophenyl)ethyl)-N,N,3-trimethyl-5-((2-(pyrrolidin-1-yl)ethyl)amino)pyrazine-2-carboxamide;
6-(1-(4-fluorophenyl)ethyl)-N,3-dimethyl-5-((2-(pyrrolidin-1-yl)ethyl)amino)pyrazine-2-carboxamide;
6-(1-(4-fluorophenyl)ethyl)-3-methyl-5-((2-(pyrrolidin-1-yl)ethyl)amino)pyrazine-2-carboxamide;
N-(2-fluoroethyl)-6-(1-(4-fluorophenyl)ethyl)-3-methyl-5-((2-(pyrrolidin-1-yl)ethyl)amino)pyrazine-2-carboxamide;
6-(1-(4-fluorophenyl)ethyl)-N-(2-methoxyethyl)-3-methyl-5-((2-(pyrrolidin-1-yl)ethyl)amino)pyrazine-2-carboxamide;
6-(1-(4-fluorophenyl)ethyl)-3-methyl-5-((2-(pyrrolidin-1-yl)ethyl)amino)-N-(tetrahydro-2H-pyran-4-yl)pyrazine-2-carboxamide;
N-(3-(azetidin-1-yl) propyl)-6-(1-(4-fluorophenyl)ethyl)-3-methyl-5-((2-(pyrrolidin-1-yl)ethyl)amino)pyrazine-2-carboxamide;
6-(1-(4-fluorophenyl)ethyl)-3-methyl-5-((2-(pyrrolidin-1-yl)ethyl)amino)pyrazine-2-carboxylic acid;

6-(1-(4-fluorophenyl)ethyl)-N-(cis-3-methoxycyclobutyl)-3-methyl-5-(2-(pyrrolidin-1-yl)ethyl)amino)pyrazine-2-carboxamide;
N-cyclopentyl-6-(1-(4-fluorophenyl)ethyl)-3-methyl-5-((2-(pyrrolidin-1-yl)ethyl)amino)pyrazine-2-carboxamide;
(6-(1-(4-fluorophenyl)ethyl)-3-methyl-5-((2-(pyrrolidin-1-yl)ethyl)amino)pyrazin-2-yl)(piperidin-1-yl)methanone;
N,N-diethyl-6-(1-(4-fluorophenyl)ethyl)-3-methyl-5-((2-(pyrrolidin-1-yl)ethyl)amino)pyrazine-2-carboxamide;
(3,3-difluoropyrrolidin-1-yl) (6-(1-(4-fluorophenyl)ethyl)-3-methyl-5-((2-(pyrrolidin-1-yl)ethyl)amino)pyrazin-2-yl)methanone;
6-(1-(4-fluorophenyl)ethyl)-3-methyl-5-((2-(pyrrolidin-1-yl)ethyl)amino)-N-((R)-tetrahydrofuran-3-yl)pyrazine-2-carboxamide;
N-cyclopropyl-6-(1-(4-fluorophenyl)ethyl)-3-methyl-5-((2-(pyrrolidin-1-yl)ethyl)amino)pyrazine-2-carboxamide;
N-ethyl-6-(1-(4-fluorophenyl)ethyl)-N,3-dimethyl-5-((2-(pyrrolidin-1-yl)ethyl)amino)pyrazine-2-carboxamide;
N-(cis-3-fluorocyclobutyl)-6-(1-(4-fluorophenyl)ethyl)-3-methyl-5-((2-(pyrrolidin-1-yl)ethyl)amino)pyrazine-2-carboxamide;
N-cyclopropyl-6-(1-(4-fluorophenyl)ethyl)-N,3-dimethyl-5-((2-(pyrrolidin-1-yl)ethyl)amino)pyrazine-2-carboxamide;
(6-(1-(4-fluorophenyl)ethyl)-3-methyl-5-((2-(pyrrolidin-1-yl)ethyl)amino)pyrazin-2-yl)((S)-3-fluoropyrrolidin-1-yl)methanone;
6-(1-(4-fluorophenyl)ethyl)-N-isopropyl-N,3-dimethyl-5-((2-(pyrrolidin-1-yl)ethyl)amino)pyrazine-2-carboxamide;
(6-(1-(4-fluorophenyl)ethyl)-3-methyl-5-((2-(pyrrolidin-1-yl)ethyl)amino)pyrazin-2-yl)((S)-3-methoxypyrrolidin-1-yl)methanone;
6-(1-(4-fluorophenyl)ethyl)-3-methyl-5-((2-(pyrrolidin-1-yl)ethyl)amino)-N-((S)-tetrahydrofuran-3-yl)pyrazine-2-carboxamide;
(6-(1-(4-fluorophenyl)ethyl)-3-methyl-5-((2-(pyrrolidin-1-yl)ethyl)amino)pyrazin-2-yl) (morpholino) methanone;
6-(1-(4-fluorophenyl)ethyl)-N-(trans-3-methoxycyclobutyl)-3-methyl-5-((2-(pyrrolidin-1-yl)ethyl)amino)pyrazine-2-carboxamide;
(6-(1-(4-fluorophenyl)ethyl)-3-methyl-5-((2-(pyrrolidin-1-yl)ethyl)amino)pyrazin-2-yl)((R)-3-methoxypyrrolidin-1-yl)methanone;
N-(3,3-difluorocyclobutyl)-6-(1-(4-fluorophenyl)ethyl)-3-methyl-5-((2-(pyrrolidin-1-yl)ethyl)amino)pyrazine-2-carboxamide;
(6-(1-(4-fluorophenyl)ethyl)-3-methyl-5-((2-(pyrrolidin-1-yl)ethyl)amino)pyrazin-2-yl)((R)-3-fluoropyrrolidin-1-yl)methanone;
(6-(1-(4-fluorophenyl)ethyl)-3-methyl-5-((2-(pyrrolidin-1-yl)ethyl)amino)pyrazin-2-yl) (pyrrolidin-1-yl)methanone;
N-(trans-3-fluorocyclobutyl)-6-(1-(4-fluorophenyl)ethyl)-3-methyl-5-((2-(pyrrolidin-1-yl)ethyl)amino)pyrazine-2-carboxamide;
6-(1-(4-fluorophenyl)ethyl)-3-(methoxymethyl)-5-((2-(pyrrolidin-1-yl)ethyl)amino)pyrazine-2-carboxamide;
N-(2-(azetidin-1-yl)ethyl)-3-(4-fluorobenzyl)-5,6-dimethylpyrazin-2-amine;
3-(4-fluorobenzyl)-5,6-dimethyl-N-(1-methylpiperidin-4-yl)pyrazin-2-amine;
3-(4-fluorobenzyl)-5,6-dimethyl-N-(2-(pyrrolidin-1-yl)ethyl)pyrazin-2-amine;
(R)-3-(4-fluorobenzyl)-5,6-dimethyl-N-(1-methylpyrrolidin-3-yl)pyrazin-2-amine;
5,6-dimethyl-3-(3-methylbenzyl)-N-(1-methylpiperidin-4-yl)pyrazin-2-amine;
5,6-dimethyl-3-(3-methylbenzyl)-N-(2-(pyrrolidin-1-yl)ethyl)pyrazin-2-amine;
(R)-5,6-dimethyl-3-(3-methylbenzyl)-N-(1-methylpyrrolidin-3-yl)pyrazin-2-amine;
3-(1-(4-fluorophenyl)ethyl)-6-methyl-N-(2-(pyrrolidin-1-yl)ethyl)pyrazin-2-amine;
3-(1-(4-fluorophenyl)ethyl)-5-methyl-N-(2-(pyrrolidin-1-yl)ethyl)pyrazin-2-amine;
N-(2-(azetidin-1-yl)ethyl)-6-isopropyl-3-(3-methylbenzyl)pyrazin-2-amine;
N-(2-(azetidin-1-yl)ethyl)-6-ethoxy-3-(3-methylbenzyl)pyrazin-2-amine;
N-(2-(azetidin-1-yl)ethyl)-3-benzyl-6-ethylpyrazin-2-amine;
N-(2-(azetidin-1-yl)ethyl)-6-cyclopropyl-3-(3-methylbenzyl)pyrazin-2-amine;
N-(1,3-dimethylpiperidin-4-yl)-3-(4-fluorobenzyl)-5-(trifluoromethyl)pyrazin-2-amine;
N-(1,3-dimethylpiperidin-4-yl)-3-(4-fluorobenzyl)-6-(trifluoromethyl)pyrazin-2-amine;
3-(4-fluorobenzyl)-N-(2-(pyrrolidin-1-yl)ethyl)-6-(trifluoromethyl)pyrazin-2-amine;
3-(1-(4-fluorophenyl)ethyl)-N-(2-(pyrrolidin-1-yl)ethyl)-6-(trifluoromethyl)pyrazin-2-amine;
N-(trans-3-ethyl-1-methylpiperidin-4-yl)-3-(4-fluorobenzyl)-5-(trifluoromethyl)pyrazin-2-amine;
5-((2-(azetidin-1-yl)ethyl)amino)-6-(4-fluorobenzyl)-3-methylpyrazine-2-carbonitrile;
(R)-3-methyl-6-(3-methylbenzyl)-5-((1-methylpyrrolidin-3-yl)amino)pyrazine-2-carbonitrile;
(R)-6-(3-methoxybenzyl)-3-methyl-5-((1-methylpyrrolidin-3-yl)amino)pyrazine-2-carbonitrile;
5-(4-fluorobenzyl)-N,N-dimethyl-6-((2-(pyrrolidin-1-yl)ethyl)amino) nicotinamide;
5-(4-fluorobenzyl)-6-((2-(pyrrolidin-1-yl)ethyl)amino) nicotinamide;
5-(4-fluorobenzyl)-N-methyl-6-((2-(pyrrolidin-1-yl)ethyl)amino) nicotinamide;
6-((1,3-dimethylpiperidin-4-yl)amino)-5-(4-fluorobenzyl) nicotinamide;
3-(1-(4-fluorophenyl)ethyl)-N-(2-(pyrrolidin-1-yl)ethyl)-6-(trifluoromethyl) pyridin-2-amine;
3-(4-fluorobenzyl)-N-(2-(pyrrolidin-1-yl)ethyl)-6-(trifluoromethyl) pyridin-2-amine;
3-(1-(4-fluorophenyl)ethyl)-N-(2-(pyrrolidin-1-yl)ethyl) pyridin-2-amine;
5-(1-(4-fluorophenyl)ethyl)-6-((2-(pyrrolidin-1-yl)ethyl)amino) nicotinamide;
N-(1-(azetidin-1-yl)propan-2-yl)-3-(4-fluorobenzyl)pyrazin-2-amine;
N-(1-(azetidin-1-ylmethyl)cyclopropyl)-3-(4-fluorobenzyl)pyrazin-2-amine;
3-(4-fluorobenzyl)-N-((1-methylpyrrolidin-2-yl)methyl)pyrazin-2-amine;
3-(4-fluorobenzyl)-N-((1-methylazetidin-2-yl)methyl)pyrazin-2-amine;
3-(4-fluorobenzyl)-N-(1-(pyrrolidin-1-yl)propan-2-yl)pyrazin-2-amine;
3-(4-fluorobenzyl)-N-((1-methylpiperidin-2-yl)methyl)pyrazin-2-amine;

N-(trans-1,2-dimethylpiperidin-4-yl)-3-(4-fluorobenzyl)pyrazin-2-amine;
N-(cis-1,2-dimethylpiperidin-4-yl)-3-(4-fluorobenzyl)pyrazin-2-amine;
3-(4-fluorobenzyl)-N-(trans-3-fluoropiperidin-4-yl)pyrazin-2-amine;
N-(trans-3-fluoro-1-methylpiperidin-4-yl)-3-(4-fluorobenzyl)pyrazin-2-amine;
3-(1-(4-fluorophenyl)ethyl)-N-(2-(3-fluoropyrrolidin-1-yl)ethyl)pyrazin-2-amine;
N-(2-(3,3-difluoropyrrolidin-1-yl)ethyl)-3-(1-(4-fluorophenyl)ethyl)pyrazin-2-amine;
3-(1-(4-fluorophenyl)ethyl)-N-(2-(pyrrolidin-1-yl)ethyl)pyrazin-2-amine;
3-(1-phenylethyl)-N-(2-(pyrrolidin-1-yl)ethyl)pyrazin-2-amine;
(R)-3-(1-(4-fluorophenyl)ethyl)-N-(2-(pyrrolidin-1-yl)ethyl)pyrazin-2-amine;
(S)-3-(1-(4-fluorophenyl)ethyl)-N-(2-(pyrrolidin-1-yl)ethyl)pyrazin-2-amine;
3-(1-(4-fluorophenyl)ethyl)-5-(oxazol-2-yl)-N-(2-(pyrrolidin-1-yl)ethyl)pyrazin-2-amine;
3-(1-(4-fluorophenyl)ethyl)-5-(1-methyl-1H-imidazol-2-yl)-N-(2-(pyrrolidin-1-yl)ethyl)pyrazin-2-amine;
3-(1-(4-fluorophenyl)ethyl)-N-(2-(pyrrolidin-1-yl)ethyl)-5-(thiazol-2-yl)pyrazin-2-amine;
3-(1-(4-fluorophenyl)ethyl)-5-(5-methyloxazol-2-yl)-N-(2-(pyrrolidin-1-yl)ethyl)pyrazin-2-amine;
3-(1-(4-fluorophenyl)ethyl)-5-(5-methylthiazol-2-yl)-N-(2-(pyrrolidin-1-yl)ethyl)pyrazin-2-amine;
5-(1,5-dimethyl-1H-imidazol-2-yl)-3-(1-(4-fluorophenyl)ethyl)-N-(2-(pyrrolidin-1-yl)ethyl)pyrazin-2-amine;
3-(1-(4-fluorophenyl)ethyl)-6-methyl-5-(5-methyloxazol-2-yl)-N-(2-(pyrrolidin-1-yl)ethyl)pyrazin-2-amine;
N-(2-(azetidin-1-yl)ethyl)-3-ethyl-6-(3-methylbenzyl)-1,2,4-triazin-5-amine;
N-(trans-1,3-dimethylpiperidin-4-yl)-6-(4-fluorobenzyl)-3-methyl-1,2,4-triazin-5-amine;
N-(2-(azetidin-1-yl)ethyl)-6-(1-(4-fluorophenyl)ethyl)-3-methyl-1,2,4-triazin-5-amine;
(R)-N-(2-(azetidin-1-yl)ethyl)-6-(1-(4-fluorophenyl)ethyl)-3-methyl-1,2,4-triazin-5-amine;
(S)-N-(2-(azetidin-1-yl)ethyl)-6-(1-(4-fluorophenyl)ethyl)-3-methyl-1,2,4-triazin-S-amine;
N-(2-(azetidin-1-yl)ethyl)-6-(4-fluorobenzyl)-3-methyl-1,2,4-triazin-5-amine;
N-(2-(azetidin-1-yl)ethyl)-3-ethyl-6-(4-fluorobenzyl)-1,2,4-triazin-5-amine;
6-(4-fluorobenzyl)-3-methyl-N-(1-methylpiperidin-4-yl)-1,2,4-triazin-5-amine;
N-(2-(azetidin-1-yl)ethyl)-3-cyclopropyl-6-(4-fluorobenzyl)-1,2,4-triazin-5-amine;
(R)-6-(1-(4-fluorophenyl)ethyl)-3-methyl-N-(1-methylpiperidin-4-yl)-1,2,4-triazin-5-amine;
(S)-6-(1-(4-fluorophenyl)ethyl)-3-methyl-N-(1-methylpiperidin-4-yl)-1,2,4-triazin-5-amine;
6-((R)-1-(4-fluorophenyl)ethyl)-3-methyl-N-((R)-1-methylpyrrolidin-3-yl)-1,2,4-triazin-5-amine;
6-((S)-1-(4-fluorophenyl)ethyl)-3-methyl-N-((R)-1-methylpyrrolidin-3-yl)-1,2,4-triazin-5-amine;
N-(2-(azetidin-1-yl)ethyl)-3-methyl-6-(1-phenylethyl)-1,2,4-triazin-5-amine;
(R)-N-(2-(azetidin-1-yl)ethyl)-3-methyl-6-(1-phenylethyl)-1,2,4-triazin-5-amine;
(S)-N-(2-(azetidin-1-yl)ethyl)-3-methyl-6-(1-phenylethyl)-1,2,4-triazin-5-amine;
6-((R)-1-(4-fluorophenyl)ethyl)-3-methyl-N-((S)-1-methylpyrrolidin-3-yl)-1,2,4-triazin-5-amine;
6-((S)-1-(4-fluorophenyl)ethyl)-3-methyl-N-((S)-1-methylpyrrolidin-3-yl)-1,2,4-triazin-5-amine;
N-(2-(azetidin-1-yl)ethyl)-3-methyl-6-(3-methylbenzyl)-1,2,4-triazin-5-amine;
3-methyl-N-((R)-1-methylpyrrolidin-3-yl)-6-((R)-1-phenylethyl)-1,2,4-triazin-5-amine;
3-methyl-N-((R)-1-methylpyrrolidin-3-yl)-6-((S)-1-phenylethyl)-1,2,4-triazin-5-amine;
3-methyl-N-((S)-1-methylpyrrolidin-3-yl)-6-((R)-1-phenylethyl)-1,2,4-triazin-5-amine;
3-methyl-N-((S)-1-methylpyrrolidin-3-yl)-6-((S)-1-phenylethyl)-1,2,4-triazin-5-amine;
3-methyl-N-(1-methylpiperidin-4-yl)-6-(1-phenylethyl)-1,2,4-triazin-5-amine;
(S)-3-methyl-N-(1-methylpiperidin-4-yl)-6-(1-phenylethyl)-1,2,4-triazin-5-amine;
(R)-3-methyl-N-(1-methylpiperidin-4-yl)-6-(1-phenylethyl)-1,2,4-triazin-5-amine;
6-(1-(4-fluorophenyl)ethyl)-3-methyl-N-(2-(pyrrolidin-1-yl)ethyl)-1,2,4-triazin-5-amine;
(R)-6-(1-(4-fluorophenyl)ethyl)-3-methyl-N-(2-(pyrrolidin-1-yl)ethyl)-1,2,4-triazin-5-amine;
(S)-6-(1-(4-fluorophenyl)ethyl)-3-methyl-N-(2-(pyrrolidin-1-yl)ethyl)-1,2,4-triazin-5-amine; and
a pharmaceutically acceptable salt of any one of the aforementioned compounds.

32. A pharmaceutical composition comprising:
a compound or pharmaceutically acceptable salt as defined in claim 1; and
a pharmaceutically acceptable excipient.

33. A method of treating a disease, disorder or condition in a subject, the method comprising administering to the subject a compound or pharmaceutically acceptable salt as defined in claim 1, wherein the disease, disorder or condition is selected from Alzheimer's disease, depression, anxiety, schizophrenia, bipolar disorder, autism, epilepsy, pain, and hyperactivity disorder.

* * * * *